United States Patent
Paruch et al.

(10) Patent No.: US 11,584,742 B2
(45) Date of Patent: Feb. 21, 2023

(54) SUBSTITUTED AMINOTHIAZOLES AS INHIBITORS OF NUCLEASES

(71) Applicant: MASARYKOVA UNIVERZITA, Brno (CZ)

(72) Inventors: Kamil Paruch, Tisnov (CZ); Benoit Carbain, Brno (CZ); Stepan Havel, Cernozice (CZ); Jiri Damborsky, Brno (CZ); Jan Brezovsky, Brno (CZ); Lukas Daniel, Zlin (CZ); Alexandra Sisakova, Slanec (SK); Fedor Nikulenkov, Slapanice (CZ); Lumir Krejci, Brno (CZ)

(73) Assignee: MASARYKOVA UNIVERZITA, Brno (CZ)

( * ) Notice: Subject to any disclaimer, the term of this patent is extended or adjusted under 35 U.S.C. 154(b) by 8 days.

(21) Appl. No.: 17/047,004

(22) PCT Filed: Apr. 15, 2019

(86) PCT No.: PCT/EP2019/059689
§ 371 (c)(1),
(2) Date: Oct. 12, 2020

(87) PCT Pub. No.: WO2019/201865
PCT Pub. Date: Oct. 24, 2019

(65) Prior Publication Data
US 2022/0002282 A1    Jan. 6, 2022

(30) Foreign Application Priority Data
Apr. 17, 2018  (EP) .................................. 18167651

(51) Int. Cl.
*C07D 417/04*    (2006.01)
*C07D 277/46*    (2006.01)
*C07D 277/60*    (2006.01)
*C07D 417/12*    (2006.01)

(52) U.S. Cl.
CPC ......... *C07D 417/04* (2013.01); *C07D 277/46* (2013.01); *C07D 277/60* (2013.01); *C07D 417/12* (2013.01)

(58) Field of Classification Search
CPC .. C07D 417/04; C07D 277/46; C07D 277/60; C07D 417/12
See application file for complete search history.

(56) References Cited

U.S. PATENT DOCUMENTS

2022/0073507 A1 *   3/2022   Paruch ................ C07D 417/04

FOREIGN PATENT DOCUMENTS

| JP | H08248567 A | 9/1996 | | |
|---|---|---|---|---|
| WO | 2005072731 A1 | 8/2005 | | |
| WO | 2010075372 A1 | 7/2010 | | |
| WO | WO-2018036501 A1 * | 3/2018 | ............ | A61K 31/277 |
| WO | WO-2019201867 A1 * | 10/2019 | ............... | A61P 25/00 |

OTHER PUBLICATIONS

Chemical Abstracts STN Registry Database, Record for RN 358653-14-2, "2-Cyano-3-phenyl-N-(4-phenyl-2-thiazolyl)-2-propenamide", Entered into STN on Sep. 25, 2001. (Year: 2001).*
Dupre; Nature Chemical Biology 2008, 4, 119-125. (Year: 2008).*
Hengel; Cell Chemical Biology 2017, 24, 1101-1119. (Year: 2017).*
Hussein; Phosphorus, Sulfur, and Silicon, 2008, 183, 1722-1734. (Year: 2008).*
Shibata; Mol. Cell, 2014, 53, 7-18. (Year: 2014).*
National Center for Biotechnology Information. PubChem Compound Summary for CID 19195546. https://pubchem.ncbi.nlm.nih.gov/compound/19195546. Create Date Dec. 4, 2007. (Year: 2007).*
STN Registry Database, Record for RN 891595-83-8, "2-Cyano-3-(3,4-dihydroxyphenyl)-N-(4-phenyl-2-thiazolyl)-2-propenamide", Entered into STN Jul. 10, 2006. (Year: 2006).*
Chemical Abstracts STN Registry Database, Record for RN 1394801-15-0, Entered STN Sep. 18, 2012. (Year: 2012).*
Chemical Abstracts STN Registry Database, Record for RN 1013264-44-2, Entered STN Apr. 9, 2008. (Year: 2008).*
Chemical Abstracts STN Registry Database, Record for RN 1012954-81-2, Entered STN Apr. 8, 2008. (Year: 2008).*
Chemical Abstracts STN Registry Database, Record for RN 1004736-30-4, Entered STN Feb. 20, 2008. (Year: 2008).*
Chemical Abstracts STN Registry Database, Record for RN 733801-61-1, Entered STN Aug. 27, 2004. (Year: 2004).*
Irwin; J. Chem. Inf. Model. 2005, 45, 1, 177-182. https://doi.org/10.1021/ci049714+ (Year: 2005).*
Kaupp; Journal of Heterocyclic Chemistry 2003, 40, 963-971. DOI: 10.1002/jhet.5570400603 (Year: 2003).*
International Search Report and Written Opinion for corresponding PCT application No. PCT/EP2019/059689, dated May 28, 2019.

\* cited by examiner

Primary Examiner — Daniel R Carcanague
(74) *Attorney, Agent, or Firm* — Notaro, Michalos & Zaccaria P.C.

(57) ABSTRACT

Compounds represented by the structural formula (1) R1, R2, R3, R4, R5, R6 are inhibitors of nucleases, and are useful in particular in a method of treatment and/or prevention of proliferative diseases, neurodegenerative diseases, and other genomic instability associated diseases.

11 Claims, No Drawings

Specification includes a Sequence Listing.

SEQUENCE LISTING

<160> NUMBER OF SEQ ID NOS: 2

<210> SEQ ID NO 1
<211> LENGTH: 22
<212> TYPE: DNA
<213> ORGANISM: artificial
<220> FEATURE:
<223> OTHER INFORMATION: oligonucleotide 1 for HTS assay

<400> SEQUENCE: 1
ctaagttcgt caggattcca gc       22

<210> SEQ ID NO 2

```
<211> LENGTH: 40
<212> TYPE: DNA
<213> ORGANISM: artificial
<220> FEATURE:
<223> OTHER INFORMATION: olgonucleotide 2 for HTS assay

<400> SEQUENCE: 2
ctctatcact gttacaatgc tggaatcctg acgaacttag                40
```

SUBSTITUTED AMINOTHIAZOLES AS INHIBITORS OF NUCLEASES

FIELD OF THE INVENTION

The present invention relates to substituted aminothiazoles as inhibitors of nucleases, especially nuclease MRE11 and MRE11-containing complexes, pharmaceutical compositions containing the compounds, and methods of treatment using the compounds and compositions to treat diseases such as cancer and other genome instability associated diseases.

BACKGROUND ART

Despite intense development of new anticancer substances, the clinical treatment of most frequently diagnosed solid tumors needs to be improved and for some malignancies reasonably efficient therapies need to be developed, as they are practically non-existent. Early detection followed by surgery remains the main tool that enables significant expansion of life span for majority of patients. In most malignancies it may be necessary to modulate (preferably in a synergistic manner) several relevant biological pathways. Accordingly, the required phenotype (death of tumor cells) can be elicited by synthetic lethal modulation of properly chosen biological processes. Synthetic lethal interactions tend to form clusters; one significant network of such interactions encompasses the biological processes involved in the DNA damage/repair. Selective and efficient activity modulation of selected processes is therefore of significant importance and can lead to a new generation of modern anticancer drugs.

Maintenance of genomic integrity ensured by multifaceted cellular DNA damage response (DDR) is a fundamental biological phenomenon shared by all organisms. On one hand, the DDR network of genome surveillance, checkpoint and repair pathways counterbalances the potentially mutagenic effects of endogenous (oxidative and replicative lesions) and exogenous (e.g. ionizing or UV radiation, cigarette smoke) DNA damaging assaults. On the other hand, modulation of selected components can be exploited in efficient treatment of malignant diseases. It is likely that optimal synthetic lethal treatments will be different for particular tumor sub-populations; this approach is therefore compatible with the concept of personalized medicine.

Amongst the DNA repair processing enzymes, the MRE11-RAD50-NBS1 (MRN) complex plays an important role in preserving genomic integrity by acting as a DNA damage sensor of double strand breaks (DSB) and by promoting repair through non-homologous end-joining (NHEJ) or homologous recombination (*Nature Reviews* 2002, 3, 317; *Trends Biochem*. Sciences 2002, 27, 410). In response to DSB, MRN activates and recruits ATM (belonging to the phosphatidylinositol-3' kinase-related kinases (PIKKs) family) to damaged DNA sites. ATM initiates a signaling cascade leading to cell cycle arrest and DNA repair. MRE11 is the subunit core of the MRN complex and displays 3'-5' exonuclease activity, single-stranded and DNA-hairpin endonuclease activity. The MRE11-RAD50 complex functions include DNA binding, bridging the ends of DSBs and their processing. NBS1 does not possess any enzymatic activity; its role lies in signaling and interacting with other proteins (*DNA Repair* 2010, 9, 1299; *Cell* 2008, 135, 97). The significance of MRN complex is underlined by the fact that germline mutations of MRE11, NBS1 and RAD50 cause ataxia-telangiectasia-like disease (ATLD), Nijmegen breakage syndrome (NBS) and NBS-like disorder (NBSLD), respectively (*Cell* 1998, 93, 477; *Cell*, 1999, 99, 577; *Am. J. Hum. Genet*. 2009, 84, 605). ATLD, NBS and NBSLD have similar features as does ataxia-telangiectasia (AT), caused by mutations in the ATM gene, which include hypersensitivity to DSB-inducing agents, chromosome fragility, DNA damage-dependent cell-cycle arrest and high predisposition to cancer (*Cell* 1998, 93, 477; *Oncogene* 2007, 26, 7749; *Cell* 1999, 99, 577; *Am. J. Hum. Genet*. 2009, 84, 605). In addition, depletion of MRE11 leads to sensitization to poly(ADP-ribose) polymerase (PARP) inhibition (*Cancer Res*. 2011, 71, 2632). Furthermore, MRE11-deficient cells are also sensitive to topoisomerase poisons, suggesting a role of MRE11 in removal of TOP1/TOP2-lessions and in stimulating an effect of topo inhibitors (*Mol. Cell. Biol*. 2004, 24, 9682). Indeed, triapine (RNR inhibitor) was recently shown to block MRN-mediated recombination and sensitize ovarian cancer cells to PARP and topo inhibitors (*Mol. Cancer Res*. 2014, 12, 381; *Cancer Res*. 2012, 72, 2814). Therapeutic importance of MRE11 inhibitors in modern oncology is further supported by recently reported synthetically lethal genetic interactions for MRE11-FEN1 (*PLoS Genet*. 2013, 9, 1, e1003254) and MRE11-BRCA2 (*Cancer Res.,* 2012, 72, 2814). Defects in some DNA repair processes also manifest themselves in neuronal tissues and thus can be associated with human neurological disorders (*Cell* 2007, 130, 991). Mirin and two its structurally closely related analogs PFM01 and PFM03 (*Mol. Cell* 2014, 53, 1; WO 2010/075372) are essentially the only reported examples of (relatively weak) inhibitors of MRE11 nuclease.

DISCLOSURE OF THE INVENTION

The present invention provides novel substituted aminothiazole compounds, methods of preparing such compounds, pharmaceutical compositions comprising one or more of such compounds, methods of preparing pharmaceutical formulations comprising one or more of such compounds, and methods of treatment, prevention, inhibition or amelioration of one or more diseases, preferably diseases associated with MRE11 nuclease and/or MRE11-related DNA repair pathways using such compounds or pharmaceutical compositions.

The present invention provides compounds represented by general formula (1):

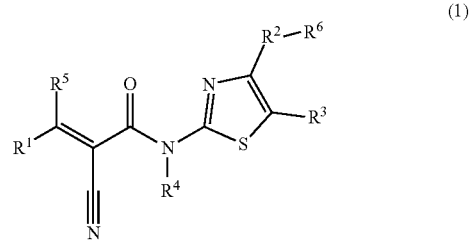

or a pharmaceutically acceptable salt, or solvate thereof, which are suitable for use in a method of treatment of cancer, premature aging and/or neurological diseases, more specifically of genome instability-related cancer, genome instability-related premature aging and/or genome instability-related neurological diseases, in particular MRE11-related cancer, MRE11-related premature aging and/or MRE11-related neurological diseases, wherein:

$R^1$ is selected from the group consisting of aryl; heteroaryl; heterocyclyl; alkyl; and cycloalkyl;

wherein each of the aryl, heteroaryl, heterocyclyl, cycloalkyl can be unsubstituted or optionally substituted with one or more moieties which can be the same or different, each moiety being independently selected from the group consisting of F, Cl, Br, I, OH, CN, $N_3$, =O, $O(C_1\text{-}C_6\text{-alkyl})$, =S, SH, $S(C_1\text{-}C_6\text{-alkyl})$, $S(O)C_1\text{-}C_6\text{-alkyl}$, $S(O)_2C_1\text{-}C_6\text{-alkyl}$, $CF_3$, $C_2F_5$, $OCF_3$, $OC_2F_5$, $NH_2$, $NH(C_1\text{-}C_6\text{-alkyl})$, $N(C_1\text{-}C_6\text{-alkyl})_2$ (such as $N(CH_3)_2$), =N—OH, =N—$O(C_1\text{-}C_6\text{-alkyl})$, $NO_2$, COOH, $COO(C_1\text{-}C_6\text{-alkyl})$, $CO(C_1\text{-}C_6\text{-alkyl})$, $CONH_2$, $CONH(C_1\text{-}C_6\text{-alkyl})$, $CON(C_1\text{-}C_6\text{-alkyl})_2$, $(C_1\text{-}C_6\text{-alkyl})\text{-}S(O)_2\text{—NH—}$, $(C_1\text{-}C_6\text{-alkyl})\text{-}S(O)_2\text{—N}(C_1\text{-}C_6\text{-alkyl})\text{-}$, $(C_1\text{-}C_6\text{-alkyl})\text{-NH—}(SO)_2\text{—}$, $(C_1\text{-}C_6\text{-alkyl})_2N\text{—}(SO)_2\text{—}$, $(C_1\text{-}C_6\text{-alkyl})\text{-CO—NH—}$, $(C_1\text{-}C_6\text{-alkyl})\text{-CO—N}(C_1\text{-}C_6\text{-alkyl})\text{-}$, $(C_1\text{-}C_6\text{-alkyl})\text{-OCO—NH—}$, $(C_1\text{-}C_6\text{-alkyl})\text{-OCO—N}(C_1\text{-}C_6\text{-alkyl})\text{-}$, $(C_1\text{-}C_6\text{-alkyl})\text{-CO—NH—CO—}$, $(C_1\text{-}C_6\text{-alkyl})\text{-CO—N}(C_1\text{-}C_6\text{-alkyl})\text{-CO—}$, $NH_2\text{—CO—NH—}$, $(C_1\text{-}C_6\text{-alkyl})\text{-NH—CO—NH—}$, $(C_1\text{-}C_6\text{-alkyl})_2N\text{—CO—NH—}$, $NH_2\text{—CO—N}(C_1\text{-}C_6\text{-alkyl})\text{-}$, $(C_1\text{-}C_6\text{-alkyl})\text{-NH—CO—N}(C_1\text{-}C_6\text{-alkyl})\text{-}$, $(C_1\text{-}C_6\text{-alkyl})_2N\text{—CO—N}(C_1\text{-}C_6\text{-alkyl})\text{-}$, $NH_2\text{—S}(O)_2\text{—NH—}$, $(C_1\text{-}C_6\text{-alkyl})\text{-NH—S}(O)_2\text{—NH—}$, $(C_1\text{-}C_6\text{-alkyl})_2N\text{—S}(O)_2\text{—NH—}$, $NH_2\text{—S}(O)_2\text{—N}(C_1\text{-}C_6\text{-alkyl})\text{-}$, $(C_1\text{-}C_6\text{-alkyl})\text{-NH—S}(O)_2\text{—N}(C_1\text{-}C_6\text{-alkyl})\text{-}$, $(C_1\text{-}C_6\text{-alkyl})_2N\text{—S}(O)_2\text{—N}(C_1\text{-}C_6\text{-alkyl})\text{-}$, $C_1\text{-}C_6\text{-alkyl}$, $O\text{—}C_1\text{-}C_6\text{-alkyl}$, O-phenyl, phenyl;

whereas the $C_1\text{-}C_6\text{-alkyl}$, O-phenyl, phenyl in these moieties can optionally be further substituted by one or more substituents selected independently from: F, Cl, Br, I, $C_1\text{-}C_6\text{-alkyl}$, OH, $O\text{—}C_1\text{-}C_6\text{-alkyl}$, SH, $SCH_3$, $S(O)C_1\text{-}C_6\text{-alkyl}$, $S(O)_2C_1\text{-}C_6\text{-alkyl}$, $CF_3$, $OCF_3$, $NH_2$, $NH(C_1\text{-}C_6\text{-alkyl})$, $N(C_1\text{-}C_6\text{-alkyl})_2$ (such as $N(CH_3)_2$), $NO_2$, COOH, $COO(C_1\text{-}C_6\text{-alkyl})$, $CONH_2$, $CONH(C_1\text{-}C_6\text{-alkyl})$, $CON(C_1\text{-}C_6\text{-alkyl})_2$, $NHC(O)C_1\text{-}C_6\text{-alkyl}$, or $NHC(O)NH_2$;

$R^2$ is selected from the group consisting of aryl; heteroaryl; cycloalkyl; heterocyclyl; and hydroxyalkyl residues;

wherein each of the hydroxyalkyl, aryl, cycloalkyl, heterocyclyl, heteroaryl, can be unsubstituted or optionally substituted with one or more moieties which can be the same or different, independently selected from the group consisting of F, Cl, Br, I, OH, CN, $N_3$, =O, $O(C_1\text{-}C_6\text{-alkyl})$, =S, SH, $S(C_1\text{-}C_6\text{-alkyl})$, $S(O)C_1\text{-}C_6\text{-alkyl}$, $S(O)_2C_1\text{-}C_6\text{-alkyl}$, $CF_3$, $C_2F_5$, $OCF_3$, $OC_2F_5$, $NH_2$, $NH(C_1\text{-}C_6\text{-alkyl})$, $N(C_1\text{-}C_6\text{-alkyl})_2$ (such as $N(CH_3)_2$), =N—OH, =N—$O(C_1\text{-}C_6\text{-alkyl})$, $NO_2$, COOH, $COO(C_1\text{-}C_6\text{-alkyl})$, $CO(C_1\text{-}C_6\text{-alkyl})$, $CONH_2$, $CONH(C_1\text{-}C_6\text{-alkyl})$, $CON(C_1\text{-}C_6\text{-alkyl})_2$, $(C_1\text{-}C_6\text{-alkyl})\text{-}S(O)_2\text{—NH—}$, $(C_1\text{-}C_6\text{-alkyl})\text{-}S(O)_2\text{—N}(C_1\text{-}C_6\text{-alkyl})\text{-}$, $(C_1\text{-}C_6\text{-alkyl})\text{-NH—}(SO)_2\text{—}$, $(C_1\text{-}C_6\text{-alkyl})_2N\text{—}(SO)_2\text{—}$, $(C_1\text{-}C_6\text{-alkyl})\text{-CO—NH—}$, $(C_1\text{-}C_6\text{-alkyl})\text{-CO—N}(C_1\text{-}C_6\text{-alkyl})\text{-}$, $(C_1\text{-}C_6\text{-alkyl})\text{-OCO—NH—}$, $(C_1\text{-}C_6\text{-alkyl})\text{-OCO—N}(C_1\text{-}C_6\text{-alkyl})\text{-}$, $(C_1\text{-}C_6\text{-alkyl})\text{-CO—NH—CO—}$, $(C_1\text{-}C_6\text{-alkyl})\text{-CO—N}(C_1\text{-}C_6\text{-alkyl})\text{-CO—}$, $NH_2\text{—CO—NH—}$, $(C_1\text{-}C_6\text{-alkyl})\text{-NH—CO—NH—}$, $(C_1\text{-}C_6\text{-alkyl})_2N\text{—CO—NH—}$, $NH_2\text{—CO—N}(C_1\text{-}C_6\text{-alkyl})\text{-}$, $(C_1\text{-}C_6\text{-alkyl})\text{-NH—CO—N}(C_1\text{-}C_6\text{-alkyl})\text{-}$, $(C_1\text{-}C_6\text{-alkyl})_2N\text{—CO—N}(C_1\text{-}C_6\text{-alkyl})\text{-}$, $NH_2\text{—S}(O)_2\text{—NH—}$, $(C_1\text{-}C_6\text{-alkyl})\text{-NH—S}(O)_2\text{—NH—}$, $(C_1\text{-}C_6\text{-alkyl})_2N\text{—S}(O)_2\text{—NH—}$, $NH_2\text{—S}(O)_2\text{—N}(C_1\text{-}C_6\text{-alkyl})\text{-}$, $(C_1\text{-}C_6\text{-alkyl})\text{-NH—S}(O)_2\text{—N}(C_1\text{-}C_6\text{-alkyl})\text{-}$, $(C_1\text{-}C_6\text{-alkyl})_2N\text{—S}(O)_2\text{—N}(C_1\text{-}C_6\text{-alkyl})\text{-}$, $C_1\text{-}C_6\text{-alkyl}$, $O\text{—}C_1\text{-}C_6\text{-alkyl}$, O-phenyl, phenyl;

whereas the $C_1\text{-}C_6\text{-alkyl}$, O-phenyl, phenyl in these moieties can optionally be further substituted by one or more substituents selected independently from: F, Cl, Br, $C_1\text{-}C_6\text{-alkyl}$, OH, $O\text{—}C_1\text{-}C_6\text{-alkyl}$, SH, $SCH_3$, $S(O)C_1\text{-}C_6\text{-alkyl}$, $S(O)_2C_1\text{-}C_6\text{-alkyl}$, $CF_3$, $OCF_3$, $NH_2$, $NH(C_1\text{-}C_6\text{-alkyl})$, $N(C_1\text{-}C_6\text{-alkyl})_2$ (such as $N(CH_3)_2$), $NO_2$, COOH, $COO(C_1\text{-}C_6\text{-alkyl})$, $CONH_2$, $CONH(C_1\text{-}C_6\text{-alkyl})$, $CON(C_1\text{-}C_6\text{-alkyl})_2$, $NHC(O)C_1\text{-}C_6\text{-alkyl}$, or $NHC(O)NH_2$, $R^6$ is selected from the group consisting of H; heterocyclyl; cycloalkyl; heteroaryl; aryl; heteroaryl; wherein each of the aryl, cycloalkyl, heterocyclyl, heteroaryl, can be unsubstituted or optionally substituted with one or more moieties which can be the same or different, independently selected from the group consisting of F, Cl, Br, $C_1\text{-}C_6\text{-alkyl}$, OH, $O\text{—}C_1\text{-}C_6\text{-alkyl}$, SH, $SCH_3$, $S(O)C_1\text{-}C_6\text{-alkyl}$, $S(O)_2C_1\text{-}C_6\text{-alkyl}$, $CF_3$, $OCF_3$, $NH_2$, $NH(C_1\text{-}C_6\text{-alkyl})$, $N(C_1\text{-}C_6\text{-alkyl})_2$ (such as $N(CH_3)_2$), $NO_2$, COOH, $COO(C_1\text{-}C_6\text{-alkyl})$, $CONH_2$, $CONH(C_1\text{-}C_6\text{-alkyl})$, $CON(C_1\text{-}C_6\text{-alkyl})_2$, $NHC(O)C_1\text{-}C_6\text{-alkyl}$, or $NHC(O)NH_2$;

$R^3$ is selected from the group consisting of H; aryl; heteroaryl; heterocyclyl; cycloalkyl; alkyl; and halogen;

wherein each of the aryl, cycloalkyl, alkyl or heteroaryl can be unsubstituted or optionally substituted with one or more moieties which can be the same or different, each moiety being independently selected from the group consisting of F, Cl, Br, I, OH, CN, $N_3$, =O, $O(C_1\text{-}C_6\text{-alkyl})$, =S, SH, $S(C_1\text{-}C_6\text{-alkyl})$, $S(O)C_1\text{-}C_6\text{-alkyl}$, $S(O)_2C_1\text{-}C_6\text{-alkyl}$, $CF_3$, $C_2F_5$, $OCF_3$, $OC_2F_5$, $NH_2$, $NH(C_1\text{-}C_6\text{-alkyl})$, $N(C_1\text{-}C_6\text{-alkyl})_2$ (such as $N(CH_3)_2$), =N—OH, =N—$O(C_1\text{-}C_6\text{-alkyl})$, $NO_2$, COOH, $COO(C_1\text{-}C_6\text{-alkyl})$, $CO(C_1\text{-}C_6\text{-alkyl})$, $CONH_2$, $CONH(C_1\text{-}C_6\text{-alkyl})$, $CON(C_1\text{-}C_6\text{-alkyl})_2$, $(C_1\text{-}C_6\text{-alkyl})\text{-}S(O)_2\text{—NH—}$, $(C_1\text{-}C_6\text{-alkyl})\text{-}S(O)_2\text{—N}(C_1\text{-}C_6\text{-alkyl})\text{-}$, $(C_1\text{-}C_6\text{-alkyl})\text{-NH—}(SO)_2\text{—}$, $(C_1\text{-}C_6\text{-alkyl})_2N\text{—}(SO)_2\text{—}$, $(C_1\text{-}C_6\text{-alkyl})\text{-CO—NH—}$, $(C_1\text{-}C_6\text{-alkyl})\text{-CO—N}(C_1\text{-}C_6\text{-alkyl})\text{-}$, $(C_1\text{-}C_6\text{-alkyl})\text{-OCO—NH—}$, $(C_1\text{-}C_6\text{-alkyl})\text{-OCO—N}(C_1\text{-}C_6\text{-alkyl})\text{-}$, $(C_1\text{-}C_6\text{-alkyl})\text{-CO—NH—CO—}$, $(C_1\text{-}C_6\text{-alkyl})\text{-CO—N}(C_1\text{-}C_6\text{-alkyl})\text{-CO—}$, $NH_2\text{—CO—NH—}$, $(C_1\text{-}C_6\text{-alkyl})\text{-NH—CO—NH—}$, $(C_1\text{-}C_6\text{-alkyl})_2N\text{—CO—NH—}$, $NH_2\text{—CO—N}(C_1\text{-}C_6\text{-alkyl})\text{-}$, $(C_1\text{-}C_6\text{-alkyl})\text{-NH—CO—N}(C_{1\text{-}6}\text{-alkyl})\text{-}$, $(C_1\text{-}C_6\text{-alkyl})_2N\text{—CO—N}(C_{1\text{-}6}\text{-alkyl})\text{-}$, $NH_2\text{—S}(O)_2\text{—NH—}$, $(C_1\text{-}C_6\text{-alkyl})\text{-NH—S}(O)_2\text{—NH—}$, $(C_1\text{-}C_6\text{-alkyl})_2N\text{—S}(O)_2\text{—NH—}$, $NH_2\text{—S}(O)_2\text{—N}(C_1\text{-}C_6\text{-alkyl})\text{-}$, $(C_1\text{-}C_6\text{-alkyl})\text{-NH—S}(O)_2\text{—N}(C_1\text{-}C_6\text{-alkyl})\text{-}$, $(C_1\text{-}C_6\text{-alkyl})_2N\text{—S}(O)_2\text{—N}(C_1\text{-}C_6\text{-alkyl})\text{-}$, $C_1\text{-}C_6\text{-alkyl}$, $O\text{—}C_1\text{-}C_6\text{-alkyl}$, O-phenyl, phenyl;

whereas the $C_1\text{-}C_6\text{-alkyl}$, O-phenyl, phenyl in these moieties can optionally be further substituted by one or more substituents selected independently from: F, Cl, Br, $C_1\text{-}C_6\text{-alkyl}$, OH, $O\text{—}C_1\text{-}C_6\text{-alkyl}$, SH, $SCH_3$, $S(O)C_1\text{-}C_6\text{-alkyl}$, $S(O)_2C_1\text{-}C_6\text{-alkyl}$, $CF_3$, $OCF_3$, $NH_2$, $NH(C_1\text{-}C_6\text{-alkyl})$, $N(C_1\text{-}C_6\text{-alkyl})_2$ (such as $N(CH_3)_2$), $NO_2$, COOH, $COO(C_1\text{-}C_6\text{-alkyl})$, $CONH_2$, $CONH(C_1\text{-}C_6\text{-alkyl})$, $CON(C_1\text{-}C_6\text{-alkyl})_2$, $NHC(O)C_1\text{-}C_6\text{-alkyl}$, or $NHC(O)NH_2$, $R^2$ and $R^3$ together with the carbon atoms to which they are bound may also form an aliphatic or aromatic ring structure, preferably a monocyclic or polycyclic ring structure having 5-10 ring atoms selected from C, N, O, S;

$R^4$ is selected from the group consisting of H and $C_1\text{-}C_6\text{-alkyl}$;

$R^5$ is selected from the group consisting of H and aryl.

In this description and unless indicated otherwise, the generic substituent groups have the following meanings:

"alkyl" means an aliphatic hydrocarbon group which may be straight or branched and contains 1 to 8 carbon atoms, preferably 1 to 6 carbon atoms, even more preferably 1 to 4 carbon atoms, in the chain. Examples of suitable alkyls are methyl, ethyl, propyl, isopropyl, butyl, isobutyl, tert-butyl, pentyl, isopentyl, hexyl;

"aryl" means a hydrocarbyl containing 6 to 14 carbon atoms, preferably 6 to 10 carbon atoms, said hydrocarbyl containing an aromatic monocyclic or polycyclic ring system. Aryls can preferably be monocyclic or bicyclic or tricyclic, condensed or non-condensed. Examples of suitable aryls are phenyl, benzyl, naphthyl, biphenyl. In some embodiments, aryl means an aromatic monocyclic or polycyclic ring system containing 6 to 14 carbon atoms, preferably 6 to 10 carbon atom;

"cycloalkyl" means an aliphatic monocyclic or polycyclic ring system comprising 3 to 10 carbon atoms, preferably 5 to 7 carbon atoms. Suitable examples include cyclopentyl, cyclohexyl, cycloheptyl, 1-decalinyl, norbornyl, adamantyl;

"heterocyclyl" means an aliphatic hydroheterocarbyl containing 3 to 10 carbon atoms, preferably 4 to 8 carbon atoms, and at least one heteroatom selected from the group consisting of nitrogen, oxygen and sulfur, said hydroheterocarbyl containing an aliphatic monocyclic or polycyclic ring system. Suitable examples include piperazinyl and morpholinyl. In some embodiments, heterocyclyl means an aliphatic monocyclic or polycyclic ring system containing 3 to 10 carbon atoms, preferably 4 to 8 carbon atoms, and at least one heteroatom selected from the group consisting of nitrogen, oxygen and sulfur;

"heteroaryl" means a hydroheterocarbyl containing 3 to 14 carbon atoms, preferably 3 to 7 carbon atoms, and at least one heteroatom selected from the group consisting of nitrogen, oxygen and sulfur; said hydrocarbyl containing an aromatic monocyclic or polycyclic ring system. Heteroaryls can preferably be monocyclic or bicyclic or tricyclic, condensed or non-condensed. Examples of suitable heteroaryls are pyridyl, pyrimidinyl, pyrazinyl, furanyl, thienyl, pyrazolyl, oxazolyl, thiazolyl, isothiazolyl, isoxazolyl, pyrrolyl, imidazolyl, benzimidazolyl, dihydrobenzimidazolyl, indolyl, indolinolyl, imidazopyridazinyl, benzoxazinyl, dihydrobenzoxazinyl, benzofuranyl. Especially preferred are heteroaryls containing at least one nitrogen atom. In some embodiments, heteroaryl means an aromatic monocyclic or polycyclic ring system containing 3 to 14 carbon atoms, preferably 3 to 7 carbon atoms, and at least one heteroatom selected from the group consisting of nitrogen, oxygen and sulfur.

The substituent =O can be present only on aliphatic moieties or in aliphatic parts of moieties.

Pharmaceutically acceptable salts are salts with acids or bases, or acid addition salts. The acids and bases can be inorganic or organic acids and bases commonly used in the art of formulation, such as hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, paratoluenesulfonate, primary, secondary and tertiary amides, ammonia. Solvates are structures containing molecules of a solvent, such as water (hydrates) or any other pharmaceutically acceptable solvent molecules.

$R^1$ is preferably selected from $C_6$-$C_{12}$ aryl and heteroaryl having 5 to 12 ring atoms, wherein said aryl or heteroaryl is monocyclic, bicyclic or tricyclic, and the rings may be condensed or non-condensed. The aryls and heteroaryls include condensed rings wherein one or more rings are aromatic and one or more rings are aliphatic. The aryl or heteroaryl may optionally be substituted by one or more substituents, independently selected from the group consisting of F, Cl, Br, OH, $C_1$-$C_6$ alkyl, O($C_1$-$C_4$ alkyl), phenyl, O-phenyl, $NH_2$, N($C_1$-$C_4$ alkyl)$_2$, $NO_2$, NHCO($C_1$-$C_4$ alkyl), $CF_3$, $OCF_3$, CN, S(O)$_2C_1$-$C_6$-alkyl, $SO_2NH(C_1$-$C_6$-alkyl), $SO_2N(C_1$-$C_6$-alkyl)$_2$.

More preferably, the aryl in R1 is phenyl, biphenyl or naphthyl.

More preferably, the substituents attached to the aryl or heteroaryl in R1 are selected from F, Cl, Br, $C_1$-$C_6$ alkyl, O($C_1$-$C_4$ alkyl), $NO_2$, NHCO($C_1$-$C_4$ alkyl), $CF_3$. CN, phenyl, OH; or the substituents may be selected from S(O)$_2C_1$-$C_6$-alkyl, $SO_2NH(C_1$-$C_6$-alkyl), $SO_2N(C_1$-$C_6$-alkyl)$_2$.

More preferably, $R^1$ is selected from $C_6$-$C_{12}$ aryl (preferably phenyl) and heteroaryl having 5 to 12 ring atoms, said aryl or heteroaryl is monocyclic, bicyclic or tricyclic, and the rings may be condensed or non-condensed. The aryls and heteroaryls include condensed rings wherein one or more rings are aromatic and one or more rings are aliphatic. The aryl or heteroaryl is substituted with one to three OH groups, preferably with two OH groups or one OH group and one group selected from CN, Cl, Br, F. Preferably, the OH groups are in vicinal positions. The aryl or heteroaryl may optionally be substituted by one or more further substituents, independently selected from the group consisting of F, Cl, Br, $C_1$-$C_6$ alkyl, O($C_1$-$C_4$ alkyl), phenyl, O-phenyl, $NH_2$, N($C_1$-$C_4$ alkyl)$_2$, $NO_2$, NHCO($C_1$-$C_4$ alkyl), $CF_3$, $OCF_3$, CN, S(O)$_2C_1$-$C_6$-alkyl, $SO_2NH(C_1$-$C_6$-alkyl), $SO_2N(C_1$-$C_6$-alkyl)$_2$; in particular selected from F, Cl, Br, $C_1$—C alkyl, O($C_1$-$C_4$ alkyl), $CF_3$, $OCF_3$.

Most preferably, $R^1$ is 3,4-dihydroxyphenyl.

$R^2$ is preferably selected from $C_6$-$C_{12}$ aryl and heteroaryl having 5 to 12 ring atoms, which may optionally be substituted by one or more substituents, independently selected from the group consisting of F, Cl, Br, $C_1$-$C_4$ linear or branched alkyl, $C_3$-$C_5$ cycloalkyl, O($C_1$-$C_4$ alkyl), phenyl, O-phenyl, $NH_2$, N($C_1$-$C_4$ alkyl)$_2$, $NO_2$, NHCO($C_1$-$C_4$ alkyl), $CF_3$, $OCF_3$, CN, S(O)$_2C_1$-$C_6$-alkyl, $SO_2NH(C_1$-$C_6$-alkyl), $SO_2N(C_1$-$C_6$-alkyl)$_2$; in particular selected from F, Cl, Br, $C_1$-$C_6$ alkyl, O($C_1$-$C_4$ alkyl), $CF_3$, $OCF_3$.

More preferably, $R^2$ is selected from phenyl, naphthyl, benzofuranyl, pyridyl, thiophenyl, pyridazinyl, which are unsubstituted or substituted with one to two substituents selected independently from O($C_1$-$C_4$ alkyl), OH, $C_1$-$C_4$ linear or branched alkyl, $C_3$-$C_5$ cycloalkyl, F, Br, Cl, $CF_3$, $OCF_3$.

$R^6$ is preferably selected from phenyl, morpholinyl, optionally substituted as described herein above.

$R^3$ is preferably selected from H, phenyl, methyl, ethyl, propyl, isopropyl, butyl, isobutyl, tert-butyl, F, Cl, Br, cyclopropyl, cyclobutyl, cyclopentyl, cyclohexyl, tetrahydropyranyl, tetrahydrofuranyl, piperidinyl, which are unsubstituted or substituted by one or more substituents, independently selected from the group consisting of F, Cl, Br, OH, $C_1$-$C_6$ alkyl, phenyl, $NH_2$, N($C_1$-$C_4$ alkyl)$_2$, $NO_2$, NHCO($C_1$-$C_4$ alkyl), $CF_3$, $OCF_3$, CN, $SO_2NH(C_1$-$C_6$-alkyl), $SO_2N(C_1$-$C_6$-alkyl)$_2$, S(O)$_2C_1$-$C_6$-alkyl.

$R^4$ is preferably selected from H, methyl, ethyl, isopropyl. For example, $R^4$ is H.

$R^5$ is preferably selected from H, phenyl. More preferably, $R^5$ is H.

In all preferred embodiments, the alkyls, O-phenyls and phenyls may optionally be further substituted by one or more substituents selected from F, Cl, Br, $C_1$-$C_6$-alkyl, OH, O—$C_1$-$C_6$-alkyl, SH, $SCH_3$, S(O)$C_1$-$C_6$-alkyl, S(O)$_2C_1$-$C_6$- alkyl, CF$_3$, OCF$_3$, NH$_2$, NH(C$_1$-C$_6$-alkyl), N(C$_1$-C$_6$-alkyl)$_2$ (such as N(CH$_3$)$_2$), NO$_2$, COOH, COO(C$_1$-C$_6$-alkyl), CONH$_2$, CONH(C$_1$-C$_6$-alkyl), CON(C$_1$-C$_6$-alkyl)$_2$, NHC(O)C$_1$-C$_6$-alkyl, or NHC(O)NH$_2$.

The compounds of the present invention can be in configuration (E) or (Z) on the double C—C bond. The (E) configuration is preferred.

It should be understood that the preferred and/or specific embodiments can be combined in any combinations, and they can be combined in any combinations with the most general embodiments of the substituent groups.

The compounds of the invention include, for example:
(E)-2-cyano-3-(3,4-dihydroxyphenyl)-N-(4-(4-methoxyphenyl)thiazol-2-yl)acrylamide
(E)-2-cyano-3-(3,4-dihydroxyphenyl)-N-(4-(naphthalen-2-yl)thiazol-2-yl)acrylamide
(E)-N-(4-([1,1'-biphenyl]-4-yl)thiazol-2-yl)-2-cyano-3-(3,4-dihydroxyphenyl)acrylamide
(E)-N-(4-(4-bromophenyl)thiazol-2-yl)-2-cyano-3-(3,5-dichloro-4-hydroxyphenyl)acrylamide
(E)-2-cyano-3-(3,4-dihydroxyphenyl)-N-(4-(3-hydroxy-4-methoxyphenyl)thiazol-2-yl)acrylamide
(E)-2-cyano-3-(3,4-dihydroxyphenyl)-N-(4-(2-hydroxypropan-2-yl)thiazol-2-yl)acrylamide
(E)-2-cyano-3-(3,5-dichloro-4-hydroxyphenyl)-N-(4-(p-tolyl)thiazol-2-yl)acrylamide
(E)-N-(4-(3-bromophenyl)thiazol-2-yl)-2-cyano-3-(3,4-dihydroxyphenyl)acrylamide
(E)-N-(4-(2-bromophenyl)thiazol-2-yl)-2-cyano-3-(3,4-dihydroxyphenyl)acrylamide
(E)-2-cyano-3-(3,4-dihydroxyphenyl)-N-(4-(3-(trifluoromethoxy)phenyl)thiazol-2-yl)acrylamide
(E)-2-cyano-3-(3,4-dihydroxyphenyl)-N-(4-(4-phenoxyphenyl)thiazol-2-yl)acrylamide
(E)-N-(4-(benzofuran-2-yl)thiazol-2-yl)-2-cyano-3-(3,4-dihydroxyphenyl)acrylamide
(E)-N-(4-((1S,3s)-adamantan-1-yl)thiazol-2-yl)-2-cyano-3-(3,4-dihydroxyphenyl)acrylamide
(E)-2-cyano-N-(5-cyclohexyl-4-(4-(trifluoromethoxy)phenyl)thiazol-2-yl)-3-(3,4-dihydroxyphenyl)acrylamide
(E)-2-cyano-3-(3,4-dihydroxyphenyl)-N-(4,5-diphenylthiazol-2-yl)acrylamide
(E)-2-cyano-3-(3,5-dimethyl-4-hydroxyphenyl)-N-(4-(4-(trifluoromethoxy)phenyl)thiazol-2-yl)acrylamide
(E)-2-cyano-3-(3,4-dihydroxyphenyl)-N-(4-(4-morpholinophenyl)thiazol-2-yl)acrylamide
(E)-2-cyano-3-(3,4-dihydroxyphenyl)-N-(4-(5-(trifluoromethyl)pyridin-2-yl)thiazol-2-yl)acrylamide
(E)-2-cyano-N-(4-(3-cyanophenyl)thiazol-2-yl)-3-(3,4-dihydroxyphenyl)acrylamide
(E)-4-(2-(2-cyano-3-(3,4-dihydroxyphenyl)acrylamido)thiazol-4-yl)-N,N-dimethylbenzamide
(E)-2-cyano-3-(3,4-dihydroxyphenyl)-N-(4-(4-(2-hydroxypropan-2-yl)phenyl)thiazol-2-yl)acrylamide
(E)-2-cyano-N-(4-(5-cyanothiophen-2-yl)thiazol-2-yl)-3-(3,4-dihydroxyphenyl)acrylamide
(E)-2-cyano-3-(3,4-dihydroxyphenyl)-N-(4-(thiophen-2-yl)thiazol-2-yl)acrylamide
(E)-2-cyano-N-(4-(3,5-difluorophenyl)thiazol-2-yl)-3-(3,4-dihydroxyphenyl)acrylamide
(E)-2-cyano-3-(3,4-dihydroxyphenyl)-N-(4-(pyridazin-3-yl)thiazol-2-yl)acrylamide
(E)-2-cyano-3-(3,4-dihydroxyphenyl)-N-(4-(4-fluorophenyl)thiazol-2-yl)acrylamide
(E)-2-cyano-3-(3,4-dihydroxyphenyl)-N-(4-(pyridin-4-yl)thiazol-2-yl)acrylamide
Methyl (E)-4-(2-(2-cyano-3-(3,4-dihydroxyphenyl)acrylamido)thiazol-4-yl)benzoate
(E/Z)-2-cyano-3-(3,4-dihydroxyphenyl)-3-phenyl-N-(4-phenylthiazol-2-yl)acrylamide
(E)-2-cyano-3-(3,4-dihydroxyphenyl)-N-(4,5,6,7-tetrahydrobenzo[d]thiazol-2-yl)acrylamide
(E)-2-cyano-3-(3,5-dibromo-4-hydroxyphenyl)-N-(4-phenylthiazol-2-yl)acrylamide
(E)-2-cyano-3-(3,5-dichloro-4-hydroxyphenyl)-N-(4-phenylthiazol-2-yl)acrylamide
(E)-2-cyano-3-(3,4-dihydroxyphenyl)-N-(5-methyl-4-phenylthiazol-2-yl)acrylamide
(E)-N-(5-chloro-4-phenylthiazol-2-yl)-2-cyano-3-(3,4-dihydroxyphenyl)acrylamide
(E)-N-(5-bromo-4-phenylthiazol-2-yl)-2-cyano-3-(3,4-dihydroxyphenyl)acrylamide
(E)-2-cyano-3-(3,4-dihydroxyphenyl)-N-(4-(4-ethynylphenyl)thiazol-2-yl)acrylamide
(E)-2-cyano-N-(4-(3-cyclopropyl-4-methoxyphenyl)thiazol-2-yl)-3-(3,4-dihydroxyphenyl)acrylamide
(E)-N-(4-(tert-butyl)thiazol-2-yl)-2-cyano-3-(3,4-dihydroxyphenyl)acrylamide
(E)-2-cyano-3-(5,6-dihydroxypyridin-3-yl)-N-(4-phenylthiazol-2-yl)acrylamide
(E)-3-(3-chloro-4-hydroxyphenyl)-2-cyano-N-(4-phenylthiazol-2-yl)acrylamide
(E)-3-(3-bromo-4-hydroxyphenyl)-2-cyano-N-(4-phenylthiazol-2-yl)acrylamide
(E)-2-cyano-3-(3-fluoro-4-hydroxy-5-methoxyphenyl)-N-(4-phenylthiazol-2-yl)acrylamide
(E)-4-(2-cyano-3-oxo-3-((4-phenylthiazol-2-yl)amino)prop-1-en-1-yl)benzoic acid
(E)-2-cyano-3-(1H-indazol-6-yl)-N-(4-phenylthiazol-2-yl)acrylamide
(E)-2-cyano-3-(2-fluorophenyl)-N-(4-phenylthiazol-2-yl)acrylamide
3-(3-acetamidophenyl)-2-cyano-N-(4-phenylthiazol-2-yl)acrylamide
(E)-2-cyano-3-(4-hydroxy-3-nitrophenyl)-N-(4-phenylthiazol-2-yl)acrylamide
(E)-2-cyano-3-(4-nitrophenyl)-N-(4-phenylthiazol-2-yl)acrylamide
(E)-3-(2-cyano-3-oxo-3-((4-phenylthiazol-2-yl)amino)prop-1-en-1-yl)benzoic acid
(E)-2-cyano-3-(6-hydroxy-[1,1'-biphenyl]-3-yl)-N-(4-phenylthiazol-2-yl)acrylamide
(E)-2-cyano-3-(3,5-difluoro-4-hydroxyphenyl)-N-(4-phenylthiazol-2-yl)acrylamide
(E)-2-cyano-3-(3,4-difluorophenyl)-N-(4-phenylthiazol-2-yl)acrylamide
(E)- and (Z)-2-cyano-3-(1H-imidazol-4-yl)-N-(4-phenylthiazol-2-yl)acrylamide
(E)-2-cyano-3-(2,3-dihydroxyphenyl)-N-(4-phenylthiazol-2-yl)acrylamide
(E)-2-cyano-3-(2-oxo-2,3-dihydro-1H-benzo[d]imidazol-5-yl)-N-(4-phenylthiazol-2-yl)acrylamide
(E)-2-cyano-3-(4-hydroxy-3-methylphenyl)-N-(4-phenylthiazol-2-yl)acrylamide
(E)-2-cyano-3-(2,4-dihydroxyphenyl)-N-(4-phenylthiazol-2-yl)acrylamide
(E)-N-(4-(5-bromothiophen-2-yl)thiazol-2-yl)-2-cyano-3-(3,4-dihydroxyphenyl) acrylamide
(E)-2-cyano-3-(3-oxo-3,4-dihydro-2H-benzo[b][1,4]oxazin-7-yl)-N-(4-phenylthiazol-2-yl)acrylamide
(E)-2-cyano-3-(3,5-di-tert-butyl-4-hydroxyphenyl)-N-(4-(4-(trifluoromethoxy)phenyl)thiazol-2-yl)acrylamide (E)-3-(4-acetamido-3-hydroxyphenyl)-2-cyano-N-(4-phenylthiazol-2-yl)acrylamide
(E)-N-(4-(4-(tert-butyl)phenyl)thiazol-2-yl)-2-cyano-3-(3,5-dichloro-4-hydroxyphenyl)acrylamide
(E)-2-cyano-3-(4-hydroxy-2-methylphenyl)-N-(4-phenylthiazol-2-yl)acrylamide
(E)-2-cyano-3-(2-fluoro-4-hydroxyphenyl)-N-(4-phenylthiazol-2-yl)acrylamide
(E)-2-cyano-3-(4-hydroxynaphthalen-1-yl)-N-(4-phenylthiazol-2-yl)acrylamide
2-cyano-3-(3-cyano-4-hydroxyphenyl)-N-(4-phenylthiazol-2-yl)propanamide
(E)-2-cyano-3-(3,4-dihydroxyphenyl)-N-(4-(5-methylthiophen-2-yl)thiazol-2-yl)acrylamide
(E)-2-cyano-3-(3,4-dihydroxyphenyl)-N-methyl-N-(4-phenylthiazol-2-yl)acrylamide
(E)-2-cyano-N-(4-phenylthiazol-2-yl)-3-(3-(trifluoromethyl)phenyl)acrylamide
(E)-2-cyano-3-(3,4-dihydroxyphenyl)-N-(4-(6-methylpyridin-3-yl)thiazol-2-yl)acrylamide
(E)-2-cyano-3-(3,4-dihydroxyphenyl)-N-(4-phenyl-5-(tetrahydro-2H-pyran-4-yl)thiazol-2-yl)acrylamide
(E)-3-(3-(tert-butyl)-4-hydroxy-5-methylphenyl)-2-cyano-N-(4-phenylthiazol-2-yl)acrylamide
(E)-3-(3-(tert-butyl)-4-hydroxyphenyl)-2-cyano-N-(4-phenylthiazol-2-yl)acrylamide
(E)-2-cyano-3-(3,4-dihydroxyphenyl)-N-(4-(3-fluorophenyl)thiazol-2-yl)acrylamide
(E)-2-cyano-3-(4-hydroxy-3,5-diisopropylphenyl)-N-(4-phenylthiazol-2-yl)acrylamide
(E)-2-cyano-3-(3,4-dihydroxyphenyl)-N-(4-phenyl-5-(pyrazin-2-yl)thiazol-2-yl)acrylamide
(E)-2-cyano-3-(3,4-dihydroxyphenyl)-N-(4-phenylthiazol-2-yl)acrylamide
(E)-2-cyano-3-(3,4-dihydroxyphenyl)-N-(4-(3-methylpyridin-2-yl)thiazol-2-yl)acrylamide
(E)-2-cyano-3-(2,6-di-tert-butylpyridine-4-yl)-N-(4-phenylthiazol-2-yl)acrylamide
(E)-2-cyano-3-(3,4-dihydroxyphenyl)-N-(4-(6-methoxypyridin-3-yl)thiazol-2-yl)acrylamide
(E)-2-cyano-3-(3,4-dihydroxyphenyl)-N-(4-(3-methoxypyridin-2-yl)thiazol-2-yl)acrylamide
(E)-2-cyano-3-(3,5-dichloro-4-hydroxyphenyl)-N-(4-(pyridin-2-yl)thiazol-2-yl)acrylamide
(E)-2-cyano-3-(3,4-dihydroxyphenyl)-N-(4-(4-(methylsulfonyl)phenyl)thiazol-2-yl)acrylamide
(E)-2-cyano-3-(3,4-dihydroxyphenyl)-N-(5-phenylthiazol-2-yl)acrylamide
(E)-N-(4-(4-(tert-butyl)-2,6-dimethylphenyl)thiazol-2-yl)-2-cyano-3-(3,4-dihydroxyphenyl)acrylamide
(E)-N-(4-(3-(tert-butyl)phenyl)thiazol-2-yl)-2-cyano-3-(3,4-dihydroxyphenyl)acrylamide
(E)-2-cyano-3-(4-hydroxy-3,5-dimethylphenyl)-N-(4-(pyridin-2-yl)thiazol-2-yl)acrylamide
(E)-2-cyano-3-(3,5-dibromo-4-hydroxyphenyl)-N-(4-(pyridin-2-yl)thiazol-2-yl)acrylamide
(E)-2-cyano-N-(4-(3-fluoropyridin-2-yl)thiazol-2-yl)-3-(4-hydroxy-3,5-dimethylphenyl)acrylamide
(E)-2-cyano-3-(3,5-dibromo-4-hydroxyphenyl)-N-(4-(3-fluoropyridin-2-yl)thiazol-2-yl)acrylamide
(E)-2-cyano-3-(3,5-dichloro-4-hydroxyphenyl)-N-(4-(3-fluoropyridin-2-yl)thiazol-2-yl)acrylamide
(E)-5-(2-cyano-3-oxo-3-((4-phenylthiazol-2-yl)amino)prop-1-en-1-yl)-2-hydroxybenzoic acid
(E)-5-(2-cyano-3-oxo-3-((4-phenylthiazol-2-yl)amino)prop-1-en-1-yl)-2-hydroxybenzamide
(E)-3-(2-bromo-4-hydroxyphenyl)-2-cyano-N-(4-phenylthiazol-2-yl)acrylamide
(E)-2-cyano-3-(3,4-dihydroxy-5-nitrophenyl)-N-(4-phenylthiazol-2-yl)acrylamide
methyl (E)-4-(2-cyano-3-oxo-3-((4-phenylthiazol-2-yl)amino)prop-1-en-1-yl)-2-hydroxybenzoate
(E)-4-(2-cyano-3-oxo-3-((4-phenylthiazol-2-yl)amino)prop-1-en-1-yl)-2-hydroxybenzoic acid
(E)-2-cyano-3-(4-hydroxy-3-(hydroxymethyl)phenyl)-N-(4-phenylthiazol-2-yl)acrylamide
(E)-N-(4-benzoylthiazol-2-yl)-2-cyano-3-(3,4-dihydroxyphenyl)acrylamide
(E)-2-cyano-3-(3,4-dihydroxyphenyl)-N-(5-(pyrazin-2-yl)thiazol-2-yl)acrylamide
(E)-2-cyano-3-(3,4-dihydroxyphenyl)-N-(5-(pyrazin-2-yl)-4-(pyridin-2-yl)thiazol-2-yl)acrylamide
(E)-2-cyano-3-(3,4-dihydroxyphenyl)-N-(4-(6-morpholinopyridin-2-yl)thiazol-2-yl)acrylamide
(E)-2-cyano-3-(3,4-dihydroxyphenyl)-N-(4-(6-morpholinopyridin-3-yl)thiazol-2-yl)acrylamide
(E)-3-(3-bromo-4,5-dihydroxyphenyl)-2-cyano-N-(4-phenylthiazol-2-yl)acrylamide
(E)-2-cyano-3-(3-fluoro-4,5-dihydroxyphenyl)-N-(4-phenylthiazol-2-yl)acrylamide
(E)-2-cyano-3-(3-cyano-4-hydroxy-5-methoxyphenyl)-N-(4-phenylthiazol-2-yl)acrylamide
(E)-2-cyano-3-(3-cyano-4,5-dihydroxyphenyl)-N-(4-phenylthiazol-2-yl)acrylamide
(E)-2-cyano-3-(3,4-dihydroxyphenyl)-N-(4-(3-fluoro-5-morpholinopyridin-2-yl)thiazol-2-yl)acrylamide
(E)-2-cyano-3-(3,5-dibromo-4-hydroxyphenyl)-N-(4-(3-fluoro-5-morpholinopyridin-2-yl)thiazol-2-yl)acrylamide
(E)-3-(3-bromo-4,5-dihydroxyphenyl)-2-cyano-N-(4-(3-fluoro-5-morpholinopyridin-2-yl)thiazol-2-yl)acrylamide
(E)-N-(4-benzylthiazol-2-yl)-2-cyano-3-(3,4-dihydroxyphenyl)acrylamide
(E)-N-(4-benzylthiazol-2-yl)-3-(3-bromo-4,5-dihydroxyphenyl)-2-cyanoacrylamide
(E)-N-(4-benzylthiazol-2-yl)-2-cyano-3-(3,5-dichloro-4-hydroxyphenyl)acrylamide
(E)-N-(4-benzylthiazol-2-yl)-2-cyano-3-(3,5-dibromo-4-hydroxyphenyl)acrylamide In general, the compounds described in this invention can be prepared through the general routes described below in Scheme 1. Aminothiazoles (3) can be prepared through the routes described in Scheme 2 and Scheme 3.

Briefly, condensation of appropriate bromoketone (2) with thiourea provides the corresponding aminothiazole (3), which reacts with ethyl cyanoacetate under basic conditions to afford the corresponding amide (4). Alternatively, amide (4) can be prepared in two steps from aminothiazole (3) via reaction with chloroacetyl chloride followed by reaction with potassium cyanide. Subsequent condensation with appropriate aldehyde or ketone provides the target compound (1).

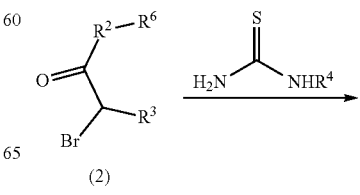

Scheme 1

-continued

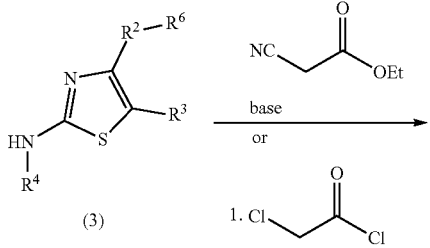

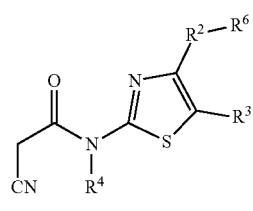

Scheme 2

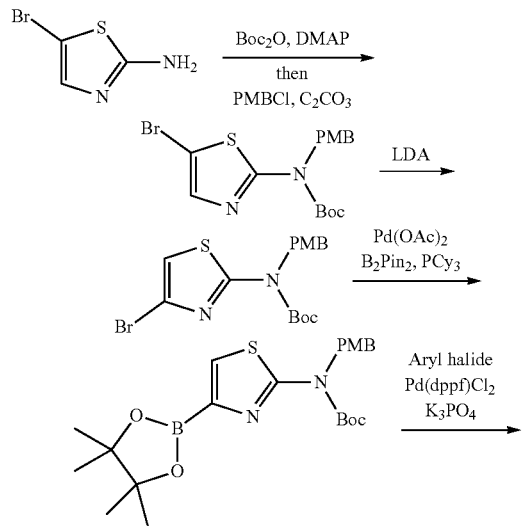

-continued

[scheme showing thiazole with PMB, Boc groups reacting with TFA to give 2-aminothiazole (3)]

Scheme 3

[scheme showing thiourea derivatives, Boc protection, coupling with R'-Br boronate, PMBCl/Cs2CO3, aryl halide/Pd(dppf)Cl2/K3PO4, then TFA to give compound (3)]

The compounds of Formula (1) act as inhibitors of nuclease MRE11, and are useful in the treatment and prevention of diseases associated with genome instability, e.g. cancer (in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia), premature aging and neurological diseases.

The present invention thus provides the compounds of formula (1) for use as medicaments. More specifically, it provides the compounds of formula (1) for use in the treatment and prevention of conditions selected from genome instability-associated diseases, e.g. cancer (in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia), premature aging and neurological diseases. In one embodiment, the present invention provides the compounds of formula (1) for use in the treatment of solid tumors with mutated BRCA-2. Tests for diagnosing BRCA-2 mutations are commercially available.

The present invention also provides a method for treatment, inhibition, amelioration or prevention of a condition selected from genome instability-associated diseases, e.g. cancer (in particular breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia), premature aging and neurological diseases in a patient suffering from such condition, comprising the step of administering at least one compound of formula (1) to said patient.

The present invention further includes pharmaceutical compositions comprising at least one compound of formula (1) and at least one pharmaceutically acceptable auxiliary compound. The auxiliary compounds may include, e.g., carriers, diluents, fillers, preservatives, stabilisers, binders, wetting agents, emulsifiers, buffers, etc. Suitable auxiliary compounds are well known to those skilled in the art of formulation. The pharmaceutical compositions are prepared by known methods, e.g., mixing, dissolving, etc.

The present invention may also provide novel compounds of general formula (1) as defined above, including the preferred embodiments, with the proviso that if $R^1$ is phenyl, then it is not substituted by two alkoxy substituents attached to the phenyl through oxygen atom.

EXAMPLES OF CARRYING OUT THE INVENTION

The present invention provides substituted aminothiazoles which are represented by structural Formula (1), or pharmaceutically acceptable salts, solvates, esters or prodrugs thereof, wherein the various moieties are as described above.

PREPARATIVE EXAMPLES

Materials and Methods

All commercially available reagents were used as supplied without further purification. The reaction solvents were purchased anhydrous and were stored under nitrogen. Unless noted otherwise, the reactions were carried out in oven-dried glassware under atmosphere of nitrogen. Column chromatography was carried out using silica gel (pore size 60 Å, 230-400 mesh particle size, 40-63 m particle size). Purification by preparative thin layer chromatography was performed using plates from Merck (PLC Silica gel 60 $F_{254}$, 1 mm). Reverse phase column chromatography was carried out using $C_{18}$-reversed phase silica gel (pore size 90 Å, 230-400 mesh particle size, 40-63 μm particle size). NMR spectra were obtained in indicated deuterated solvents; chemical shifts are quoted in parts per million (δ) referenced to the appropriate deuterated solvent employed. Multiplicities are indicated by s (singlet), d (doublet), t (triplet), q (quartet), p (pentet), sept (septet), m (multiplet) or (br) broad, or combinations thereof. Coupling constant values are given in Hz.

General Procedure A1: Bromination of Acetophenones with Bromine

To a cold solution (0° C.) of the substrate (i.e. appropriate acetophenone derivative) in $CH_2Cl_2$ (14 mL per 1 mmol of the substrate, unless stated otherwise) was added $Br_2$ (1 eq), the resulting mixture was allowed to warm to 25° C. and stirred for 1 h (unless stated otherwise). A saturated aqueous solution of $NaHCO_3$ (3 mL per 1 mmol of the substrate) was added and the mixture was extracted with $CH_2Cl_2$ (3 mL per 1 mmol of the substrate). The combined organic extracts were washed with a 10% aqueous solution of $Na_2S_2O_3$ (2 mL per 1 mmol of the substrate), brine (2 mL per 1 mmol of the substrate), dried over $MgSO_4$, filtered, and the solvent was evaporated in vacuo. The resulting product—the desired bromoketone—was used directly without further purification in the next step.

General Procedure A2: Bromination of Acetophenones with $CuBr_2$

To a solution of the appropriate acetophenone derivative in a mixture of $CHCl_3$ and ethyl acetate (1:1) (2 mL per 1 mmol of the substrate, unless stated otherwise), was added $CuBr_2$ (2 eq.) and the resulting mixture was refluxed for 2 h. The mixture was filtered through a HPLC filter and evaporated in vacuo. The product was dried under vacuum and used in the next step without further purification.

General Procedure A3: Bromination of Acetophenones with TMSOTf and NBS:

To a solution of the appropriate acetophenone derivative in $CH_2Cl_2$ (2 mL per 1 mmol of the substrate, unless stated otherwise), were added $NEt_3$ (1.2 eq) and TMSOTf (1.1 eq.) at 0° C. The mixture was allowed to warm to 25° C. and stirred for 16 h. The reaction mixture was then again cooled to 0° C. and NBS (1.1 eq.) was added. The mixture was stirred for 15-30 min at 0° C. The crude mixture was absorbed on silica and quickly filtered through a pad of silica gel (hexane:EtOAc; 1:1, unless stated otherwise) to provide the desired bromoacetophenone, which was used directly in the next step.

General Procedure A4: Bromination Acetophenones with $Br_2$ and HBr (47% in $H_2O$):

The appropriate acetophenone (1 eq) was added to a solution of HBr (47% in $H_2O$, 3 eq) and acetic acid (3 mL per 1 mmol of the substrate, unless stated otherwise) at 25° C. Then $Br_2$ (1.1 eq) was added dropwise at 25° C. and the resulting reaction mixture was stirred for 16 h at 25° C.

A saturated aqueous solution of $NaHCO_3$ was added until the pH was neutral and the mixture was extracted with EtOAc (3×10 mL per 1 mmol of the substrate). The combined organic extracts were dried over $MgSO_4$, filtered, and the solvent was evaporated in vacuo. The resulting product was used directly without further purification in the next step.

General Procedure B: Condensation of Bromoketones with Thiourea

A mixture of the substrate (i.e. appropriate bromoketone) (1 eq) and thiourea (1.5 eq) in EtOH (3 mL per 1 mmol of bromoketone, unless stated otherwise) was refluxed for 2 h (unless stated otherwise).

Work-Up 1:

A saturated aqueous solution of $NaHCO_3$ (3 mL per 1 mmol of bromoketone) was added to the mixture, which was then extracted with EtOAc (3×5 mL per 1 mmol of bromoketone). The combined organic extracts were washed with brine (3 mL per 1 mmol of bromoketone), dried over $MgSO_4$, filtered, and the solvent was evaporated in vacuo. If necessary, the product was purified by column chromatography on silica gel (unless stated otherwise) to provide the desired aminothiazole.

Work-Up 2:

The solvent was evaporated in vacuo. The resulting solid was triturated with EtOAc (1 mL per 1 mmol of bromoketone) and the mixture was filtered. The solid residue was dissolved in MeOH (1 mL per 1 mmol of bromoketone). A saturated aqueous solution of $NaHCO_3$ (3 mL per 1 mmol of bromoketone) was added and the mixture was extracted with EtOAc (3×5 mL per 1 mmol of bromoketone). The combined organic extracts were washed with brine (3 mL per 1 mmol of bromoketone), dried over $MgSO_4$, filtered, and the solvent was evaporated in vacuo. The product—the desired aminothiazole—was usually sufficiently pure and was used directly without further purification (unless stated otherwise) in the next step.

General Procedure C1: Amide Formation Using NaOEt or NaOMe

To a mixture of the appropriate aminothiazole (1 eq) and ethyl cyanoacetate (1.5 eq) in anhydrous EtOH or MeOH (2 mL per 1 mmol of aminothiazole, unless stated otherwise) was added a solution of NaOEt (21% in EtOH) (1.5 eq, unless stated otherwise) or NaOEt (1 mM in EtOH, freshly made from Na and anhydrous EtOH) at 25° C. The mixture was heated to 55° C. for 5 h (unless stated otherwise). A saturated aqueous solution of $NH_4Cl$ (10 mL per 1 mmol of aminothiazole) was added and the mixture was extracted with EtOAc (3×15 mL per 1 mmol of aminothiazole). The organic extracts were washed with water (10 mL per 1 mmol of aminothiazole), brine (10 mL per 1 mmol of aminothiazole), dried over $MgSO_4$, filtered, and the solvent was evaporated in vacuo. The residue was purified by column chromatography on silica gel (unless stated otherwise) to provide the desired amide.

General Procedure C2: Amide Formation with Chloroacetyl Chloride in Two Steps

Step 1: To a solution of the appropriate aminothiazole (1 eq) in anhydrous acetonitrile (1 mL per 1 mmol), was added $NEt_3$ (1 eq, unless stated otherwise) at 25° C. The mixture was heated to 80° C. and a solution of chloroacetyl chloride (1.5 eq.) in dry acetonitrile (0.5 mL per 1 mmol) was added. The reaction mixture was stirred at 80° C. for 2 h. A saturated aqueous solution of $NH_4Cl$ (10 mL per 1 mmol of aminothiazole) was added and the mixture was extracted with EtOAc (3×15 mL per 1 mmol of amonothiazole). Organic phases were combined and washed with brine (10 mL per 1 mmol of aminothiazole), dried over $MgSO_4$, filtered, and the solvent was evaporated in vacuo. The residue was quickly filtered through a pad of silica gel (hexane:EtOAc; 1:1, unless stated otherwise) to provide the corresponding chloroacetamide.

Step 2: The chloroacetamide was dissolved in anhydrous DMF (1 mL per 1 mmol) and KCN (1 eq, unless stated otherwise) was added and stirred at 25° C. for 6 h. Water (5 mL per 1 mmol) was added and the mixture was extracted with EtOAc (3×15 mL per 1 mmol). The combined organic extracts were dried over $MgSO_4$, filtered, and the solvent was evaporated in vacuo. The residue was purified by column chromatography to provide the desired cyanoacetamide.

General Procedure C3: Amide Formation Using NaH

To a solution of the appropriate aminothiazole (1 eq) in anhydrous THF:MeOH (5:1) (6 ml, per 1 mmol, unless stated otherwise), was added NaH (1.1 eq, 60% in mineral oil) at 0° C. The mixture was stirred at 55° C. and ethyl cyanoacetate (1.5 eq) was added. After 4 h, additional ethyl cyanoacetate (1.5 eq) was added and the mixture was refluxed for 14 h. The mixture was cooled to 25° C., a saturated aqueous solution of $NH_4Cl$ (20 ml, per 1 mmol of aminothiazole) was added and the mixture was extracted with EtOAc (3×20 ml, per 1 mmol of aminothiazole). Organic phases were combined and washed with brine (20 ml, per 1 mmol of aminothiazole), dried over $MgSO_4$, filtered, and the solvent was evaporated in vacuo. The residue was purified by column chromatography to provide the desired cyanoacetamide.

General Procedure D1: Condensation with Triethylamine as a Base

To a mixture of the appropriate aldehyde (0.95 eq) and cyanoacetamide (1 eq) in absolute EtOH (17 ml, per 1 mmol of aldehyde, unless stated otherwise) was added triethylamine (1 eq) and the mixture was stirred at 50° C. for 2 h (unless stated otherwise).

Work-Up 1:

When a precipitate appeared, the solvent was removed by filtration. The solid residue was dissolved in EtOAc (5 ml, per 0.05 mmol of aldehyde) and a saturated aqueous solution of $NH_4Cl$ (5 ml, per 0.05 mmol of aldehyde) was added. The mixture was extracted with EtOAc (3×5 ml, per 0.05 mmol of aldehyde). The combined organic extracts were washed with water (ca. 4 ml per 0.05 mmol of aldehyde), brine (ca. 4 ml, per 0.05 mmol of aldehyde), dried over $MgSO_4$, filtered, and the solvent was evaporated in vacuo. The resulting product—the desired acrylamide—was usually sufficiently pure and did not require additional purification (unless stated otherwise).

Work-Up 2:

When no precipitate appeared, a saturated aqueous solution of $NH_4Cl$ (5 ml, per 0.05 mmol of aldehyde) was added to the reaction mixture, which was then extracted with EtOAc (3×5 ml, per 0.05 mmol of aldehyde). The organic extracts were washed with water (4 ml, per 0.05 mmol of aldehyde), brine (4 ml, per 0.05 mmol of aldehyde), dried over $MgSO_4$, filtered, and the solvent was evaporated in vacuo. The residue was purified by column chromatography on silica gel and/or by reverse phase column chromatography on $C_{18}$ silica gel to provide the desired acrylamide.

General Procedure D2: Condensation with Piperidine as a Base

To a mixture of the appropriate aldehyde (1 eq) and cyanoacetamide (1 eq) in $CH_2Cl_2$ or $CH_3CN$ (10 ml, per 1 mmol of aldehyde, unless stated otherwise) was added piperidine (0.1 eq). The mixture was refluxed for 2 h (unless stated otherwise). A saturated aqueous solution of $NH_4Cl$ (5 ml, per 0.1 mmol of aldehyde) was added and the mixture was extracted with EtOAc (3×5 ml, per 0.1 mmol of aldehyde). The organic extracts were washed with water (5 ml, per 0.1 mmol of aldehyde), brine (5 mL per 0.1 mmol of aldehyde), dried over $MgSO_4$, filtered, and the solvent was evaporated in vacuo. The residue was purified by preparative TLC and/or by column chromatography on silica gel and/or by reverse phase column chromatography on $C_{18}$ silica gel (unless stated otherwise) to provide the desired acrylamide.

General Procedure E: Deprotection with TFA

Trifluoroacetic acid (4 mL per 1 mmol of the substrate unless stated otherwise) was added to a tert-butyl (substitutedthiazol-2-yl)carbamate (1 eq) and stirred at 70° C. for 2 h, then the solvent was evaporated under reduced pressure. The residue was quenched with a saturated aqueous solution of $NaHCO_3$ (30 mL per 1 mmol of the substrate) and extracted with $CH_2Cl_2$ or EtOAc (2×50 mL per 1 mmol of the substrate). The combined organic extracts were dried over $MgSO_4$, filtered, and concentrated under reduced pressure. The residue was purified by column chromatography to provide the desired deprotected compound.

Preparation of Individual Intermediates and Target Compounds as Examples

Preparative Example 1

2-bromo-1-phenylpropan-1-one

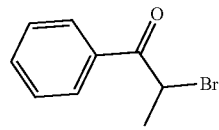

Prepared according to General procedure A1 from propiophenone (2.5 mL, 18.8 mmol) and bromine (964 μL, 18.8 mmol) in CH$_2$Cl$_2$ (25 mL); reaction time 1 h. The product was obtained as a colorless oil (3.873 g, 97%).

$^1$H NMR (500 MHz, CDCl$_3$) δ (ppm) 8.07-7.98 (m, 2H), 7.64-7.56 (m, 1H), 7.53-7.45 (m, 2H), 5.29 (q, J=6.6 Hz, 1H), 1.91 (d, J=6.6 Hz, 3H);

HRMS calcd for C$_9$H$_{10}$BrO [M+H]$^+$ 212.9910, found 212.9913.

Preparative Example 2

1-(4-((trimethylsilyl)ethynyl)phenyl)ethan-1-one

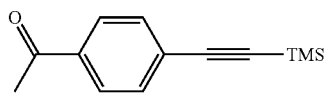

To a solution of 4-bromoacetophenone (1 g, 5 mmol) in anhydrous THF (6 mL) were added CuI (38 mg, 0.2 mmol), Et$_3$N (0.75 g, 1 mL, 7.5 mmol) and Pd(PPh$_3$)$_2$Cl$_2$ (70 mg, 0.1 mmol). A solution of trimethylsilylacetylene (0.52 g, 0.75 mL, 5.3 mmol) in anhydrous THF (2 mL) was added dropwise over 1 h, then the mixture was stirred at 25° C. for 4 h. The crude mixture was pre-adsorbed on silica gel and purified by column chromatography (hexane:EtOAc; 10:1). The product was isolated as a colorless oil (0.91 g, 85%).

$^1$H NMR (500 MHz, CDCl$_3$) δ (ppm) 7.91-7.82 (m, 2H), 7.53-7.47 (m, 2H), 2.56 (s, 3H), 0.23 (s, 9H);

$^{13}$C NMR (126 MHz, CDCl$_3$) δ (ppm) 197.5, 136.7, 132.3, 128.3, 128.2, 104.3, 98.3, 26.8, 0.1;

HRMS calcd for C$_{13}$H$_{17}$OSi [M+H]$^+$ 217.1043, found 217.1042.

Preparative Example 3

1-(3-bromo-4-methoxyphenyl)ethan-1-one

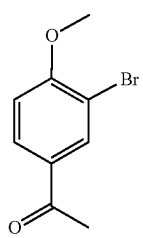

1-(4-methoxyphenyl)ethan-1-one (0.98 g, 6.5 mmol) and NBS (1.16 g, 6.5 mmol) were added to 20 mL of water. The mixture was stirred at 60° C. and 96% H$_2$SO$_4$ (0.7 mL, 13 mmol) was added dropwise. The resulting mixture was stirred at 60° C. for 5 h, then cooled to 25° C., and extracted with EtOAc (3×15 ml). The combined organic extracts were washed with a saturated aqueous solution of NaHCO$_3$ (50 mL), dried over MgSO$_4$, filtered, and the solvent was evaporated in vacuo. The product (670 mg, 45%) was obtained as a white solid.

$^1$H NMR (500 MHz, CDCl$_3$) δ (ppm) 8.18 (d, J=2.2 Hz, 1H), 7.93 (dd, J=8.6, 2.2 Hz, 1H), 6.95 (d, J=8.6 Hz, 1H), 3.98 (s, 3H), 2.57 (s, 3H);

$^{13}$C NMR (126 MHz, CDCl$_3$) δ (ppm) 195.8, 159.8, 134.1, 131.6, 129.7, 112.1, 111.3, 56.7, 26.5;

HRMS calcd for C$_9$H$_{10}$BrO$_2$ [M+H]$^+$ 228.9859, found 228.9858.

Preparative Example 4

1-(3-cyclopropyl-4-methoxyphenyl)ethan-1-one

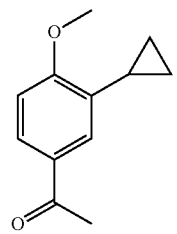

A mixture of 1-(3-bromo-4-methoxyphenyl)ethan-1-one (250 mg, 1.1 mmol), K$_3$PO$_4$ (250 mg, 1.2 mmol), cyclopropylboronic acid (103 mg, 1.2 mmol) and Pd(dppf)Cl$_2$ (36 mg, 0.05 mmol) in dioxane (5 mL) and H$_2$O (1 mL) was stirred at 90° C. for 16 h. The mixture was pre-adsorbed on silica gel and purified by column chromatography (hexane:EtOAc; 5:1) to afford the product as a colorless oil (0.13 g, 60%).

$^1$H NMR (500 MHz, CDCl$_3$) δ (ppm) 7.79 (dd, J=8.5, 2.3 Hz, 1H), 7.51 (d, J=2.3 Hz, 1H), 6.87 (d, J=8.5 Hz, 1H), 3.94 (s, 3H), 2.54 (s, 3H), 2.21-2.12 (m, 1H), 0.99-0.93 (m, 2H), 0.74-0.68 (m, 2H);

$^{13}$C NMR (126 MHz, CDCl$_3$) δ (ppm) 197.2, 162.5, 132.5, 130.3, 128.2, 125.6, 109.5, 56.0, 26.5, 9.7, 7.9;

HRMS calcd for C$_{12}$H$_5$O$_2$ [M+H]$^+$ 191.1067, found 191.1070.

Preparative Example 5

N-(3-formylphenyl)acetamide

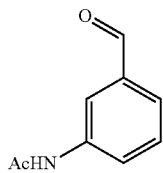

(3-nitrophenyl)methanol (0.67 g, 4.38 mmol) was dissolved in THF (5 ml), Pd/C (5 mg) was added and the mixture was stirred at 25° C. under H₂ for 4 h. The suspension was filtered through Celite and the solvent was evaporated in vacuo. To the residue were added THF (5 mL), Et₃N (1.8 g, 2.5 mL, 18 mmol) and Ac₂O (1.3 g, 1.25 mL, 13 mmol) and the mixture was stirred at 25° C. for 16 h. The mixture was poured into a saturated aqueous solution of NH₄Cl (10 mL) and extracted with EtOAc (3×10 mL). Organic fractions were combined, dried over MgSO₄, filtered, and the solvent was evaporated in vacuo. The diacetylated product was dissolved in THF/H₂O (4.5/0.5 mL) and LiOH (190 mg, 7.8 mmol) was added. The solution was stirred at 25° C. for 16 h, H₂O (20 mL) was added and the mixture was extracted with EtOAc (3×10 mL). Organic layers were combined, dried over MgSO₄, filtered, and the solvent was evaporated in vacuo. The desired intermediate (i.e. N-(3-(hydroxymethyl)phenyl)acetamide), purified by column chromatography (hexane:EtOAc; 1:2), was obtained as a white solid (490 mg, 3 mmol, 70%).

HRMS calcd for $C_9H_{12}NO_2$ [M+H]⁺ 166.0863, found 166.0865.

N-(3-(hydroxymethyl)phenyl)acetamide (100 mg, 0.6 mmol), PCC (390 mg, 1.8 mmol), and Celite (100 mg) were suspended in a mixture of CH₂Cl₂ (6 mL) and DMF (0.5 mL). The mixture was stirred at 25° C. for 2 h. The solvent was evaporated in vacuo and the residue was purified by column chromatography (hexane:EtOAc; 1:2). The product was obtained as a white solid (95 mg, 95%).

¹H NMR (500 MHz, CDCl₃) δ (ppm) 9.99 (s, 1H), 8.02-7.98 (m, 1H), 7.92-7.86 (m, 1H), 7.70 (s, 1H), 7.63 (d, J=7.6 Hz, 1H), 7.54-7.45 (m, 1H), 2.23 (s, 3H);

¹³C NMR (126 MHz, CDCl₃) δ (ppm) 192.2, 168.9, 139.1, 137.3, 130.0, 125.9, 125.8, 120.5, 24.8;

HRMS calcd for $C_9H_8NO_2$ [M-H]⁻ 162.0561, found 162.0560.

Preparative Example 6

6-hydroxy-[1,1'-biphenyl]-3-carbaldehyde

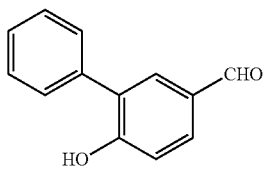 [SMILES: O=Cc1ccc(O)c(-c2ccccc2)c1]

A mixture of 3-bromo-4-hydroxybenzaldehyde (1 g, 5 mmol), K₂CO₃ (1.38 mg, 10 mmol), phenylboronic acid (0.66 g, 5.5 mmol), and Pd(dppf)Cl₂ (36 mg, 0.05 mmol) in degassed dioxane (8 mL) and water (2 mL) was stirred at 90° C. for 16 h. The mixture was poured into a saturated aqueous solution of NH₄Cl (30 mL) and extracted with EtOAc (3×10 mL). The combined organic fractions were washed with brine (20 mL), dried over MgSO₄, filtered and pre-absorbed on silica gel. The product, purified by column chromatography (hexane:EtOAc; 5:1), was isolated as a colorless oil (0.82 g, 85%).

¹H NMR (500 MHz, CDCl₃) δ (ppm) δ 9.92 (s, 1H), 7.85-7.81 (m, 2H), 7.57-7.52 (m, 2H), 7.51-7.44 (m, 3H), 7.13 (d, J=8.2 Hz, 1H), 5.94 (s, 1H);

¹³C NMR (126 MHz, CDCl₃) δ (ppm) 191.1, 158.3, 135.7, 132.8, 131.7, 130.5, 129.9, 129.3, 129.1, 128.9, 116.8;

HRMS calcd for $C_{13}H_{11}O_2$ [M+H]⁺ 199.0754, found 199.0750.

Preparative Example 7

Methyl 3-oxo-3,4-dihydro-2H-benzo[b][1,4]oxazine-7-carboxylate

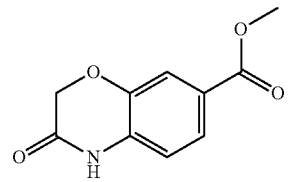

Methyl 3-hydroxy-4-nitrobenzoate (1.00 g, 5.0 mmol) was dissolved in THF (15 mL), Pd/C (10 mg) was added and the mixture was stirred under H₂ at 50° C. for 3 h. The mixture was filtered and the filtrate was concentrated in a vacuum. The residue was dissolved in DMF (15 mL), chloroacetyl chloride (0.70 g, 0.50 mL, 6.0 mmol) and K₂CO₃ (1.80 g, 13.0 mmol) were added and the mixture was stirred at 25° C. for 2 h. Then the mixture was poured into water (100 mL). The precipitate was filtered, washed with water (10 mL) and Et₂O (15 mL) and dried under vacuum. The product was obtained as a white solid (0.65 g, 65%).

¹H NMR (500 MHz, DMSO-d₆) δ (ppm) 11.04 (s, 1H), 7.58 (dd, J=8.2, 1.8 Hz, 1H), 7.43 (d, J=1.8 Hz, 1H), 6.98 (d, J=8.1 Hz, 1H), 4.64 (s, 2H), 3.81 (s, 3H);

¹³C NMR (126 MHz, DMSO-d₆) δ (ppm) 165.5, 164.9, 142.8, 131.8, 124.1, 124.0, 116.6, 115.7, 66.6, 52.0;

HRMS calcd for $C_{10}H_{10}NO_4$ [M+H]⁺ 208.0604, found 208.0606.

Preparative Example 8

7-(hydroxymethyl)-2H-benzo[b][1,4]oxazin-3(4H)-one

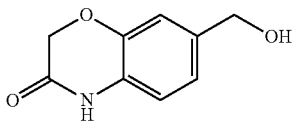

Methyl 3-oxo-3,4-dihydro-2H-benzo[b][1,4]oxazine-7-carboxylate (98 mg, 0.473 mmol) was dissolved in THF (5 mL). The solution was cooled to −78° C. and DIBAL (1M solution in Et₂O, 2 mL, 2 mmol) was added. The mixture was then stirred at 25° C. for 18 h. The mixture was poured into water (25 mL), NaHSO₄ (1 g, 8.3 mmol) was added and the resulting solution was extracted with EtOAc (3×10 mL). The combined organic fractions were washed with brine (20 mL), dried over MgSO₄, filtered, and the solvent was evaporated in vacuo. The residue was purified by column chromatography (hexane:EtOAc; 1:1 to 0:1). The product was obtained as a white solid (47 mg, 55%).

¹H NMR (500 MHz, DMSO-d₆) δ (ppm) 10.62 (s, 1H), 6.89-6.86 (m, 2H), 6.83 (d, J=8.4 Hz, 1H), 4.53 (s, 2H), 4.39 (s, 2H);

¹³C NMR (126 MHz, DMSO-d₆) δ (ppm) 164.7, 143.0, 137.8, 125.7, 120.3, 115.4, 114.3, 66.7, 62.3;

HRMS calcd for $C_{10}H_8NO_3$ [M−H]⁻ 178.051, found 178.051.

Preparative Example 9

3-oxo-3,4-dihydro-2H-benzo[b][1,4]oxazine-7-carbaldehyde

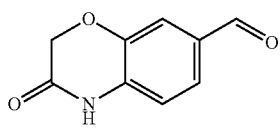 [SMILES: O=Cc1ccc2c(c1)OCC(=O)N2]

To a suspension of 7-(hydroxymethyl)-2H-benzo[b][1,4]oxazin-3(4H)-one (43 mg, 0.24 mmol) in $CH_2Cl_2$ (2 mL) and DMF (0.2 mL), were added Celite (103 mg) and PCC (103 mg, 0.48 mmol). The reaction mixture was stirred at 25° C. for 2 h. The solvent was removed in vacuo and the residue was purified by column chromatography (EtOAc). The product was obtained as a white solid (37 mg, 80%).

¹H NMR (500 MHz, DMSO-d₆) δ (ppm) 11.12 (s, 1H), 9.83 (s, 1H), 7.55 (dd, J=8.0, 1.7 Hz, 1H), 7.42 (d, J=1.7 Hz, 1H), 7.06 (d, J=8.0 Hz, 1H), 4.67 (s, 2H);

¹³C NMR (126 MHz, DMSO-d₆) δ (ppm) 191.3, 164.9, 143.3, 133.0, 131.7, 125.1, 116.1, 116.0, 66.6;

HRMS calcd for $C_9H_6NO$ [M−H]⁻ 176.0353, found 176.0355.

Preparative Example 10

Methyl 4-acetamido-3-hydroxybenzoate

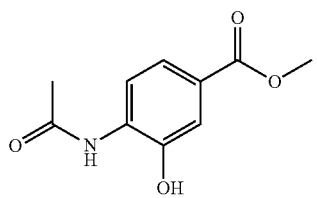

Methyl 3-hydroxy-4-nitrobenzoate (0.7 g, 3.5 mmol) was dissolved in THF (10 mL). Pd/C (10 mg) was added and the mixture was stirred under $H_2$ at 50° C. for 3 h, then it was filtered through Celite and the filtrate was concentrated in vacuo. The residue was dissolved in THF (10 mL), acetyl chloride (0.8 g, 0.75 mL, 10.5 mmol) and $Et_3N$ (1.4 g, 2 mL, 14 mmol) were added and the mixture was stirred at 25° C. for 16 h. The mixture was poured into water (15 mL) and extracted with EtOAc (3×10 mL). Organic phases were combined, dried over $MgSO_4$, filtered, and the solvent was evaporated in vacuo. The product was dissolved in MeOH (5 mL), $Et_3N$ (1.5 g, 2 mL, 14 mmol) was added, and solution was stirred at 25° C. for 16 h. The solvent was evaporated in vacuo and the residue was purified by column chromatography (hexane:EtOAc; 1:1) to afford the product as a yellow solid (0.52 g, 70%).

¹H NMR (500 MHz, DMSO-d₆) δ (ppm) 10.28 (s, 1H), 9.31 (s, 1H), 8.07 (d, J=8.4 Hz, 1H), 7.45 (d, J=1.9 Hz, 1H), 7.40 (dd, J=8.5, 1.9 Hz, 1H), 3.80 (s, 3H), 2.13 (s, 3H);

¹³C NMR (126 MHz, DMSO-d₆) δ (ppm) 169.2, 165.9, 146.6, 131.3, 124.5, 120.6, 120.4, 115.4, 51.8, 23.9;

HRMS calcd for $C_{10}H_{12}NO_4$ [M+H]⁺ 210.0761, found 210.0762.

Preparative Example 11

Methyl 4-acetamido-3-((tert-butyldimethylsilyl)oxy)benzoate

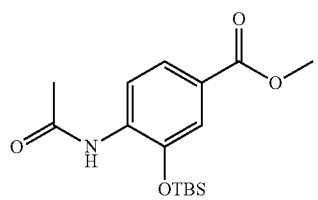 [SMILES: COC(=O)c1ccc(NC(C)=O)c(O[Si](C)(C)C(C)(C)C)c1]

Methyl 4-acetamido-3-hydroxybenzoate (0.5 g, 2.6 mmol) was dissolved in $CH_2Cl_2$. $Et_3N$ (0.5 g, 0.73 mL, 5.2 mmol), DMAP (31 mg, 0.26 mmol) and TBSCl (0.43 g, 2.8 mmol) were added and the mixture was stirred at 25° C. for 16 h. The solvent was evaporated in vacuo and the residue was purified by column chromatography (hexane:EtOAc; 7:3). The product was obtained as a white solid (0.6 g, 75%).

¹H NMR (500 MHz, CDCl₃) δ (ppm) 8.42 (d, J=8.5 Hz, 1H), 7.86 (s, 1H), 7.68 (dd, J=8.5, 1.9 Hz, 1H), 7.50 (d, J=1.8 Hz, 1H), 3.90 (s, 3H), 2.20 (s, 3H), 1.06 (s, 9H), 0.32 (s, 6H);

¹³C NMR (126 MHz, CDCl₃) δ (ppm) 168.2, 166.8, 143.5, 134.3, 125.2, 124.1, 119.2, 118.5, 52.3, 26.0, 25.1, 18.4, −4.1;

HRMS calcd for $C_{16}H_{26}NO_4Si$ [M+H]⁺ 324.1626, found 324.1630.

Preparative Example 12

N-(2-((tert-butyldimethylsilyl)oxy)-4-(hydroxymethyl)phenyl)acetamide

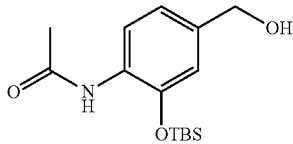 [SMILES: CC(=O)Nc1ccc(CO)cc1O[Si](C)(C)C(C)(C)C]

Methyl 4-acetamido-3-((tert-butyldimethylsilyl)oxy)benzoate (180 mg, 0.55 mmol) was dissolved in THF (3 mL) and the solution was cooled to 0° C. DIBAL (1M in THF, 1.95 mL, 1.95 mmol) was added and the mixture was stirred at 25° C. for 16 h. The mixture was poured into a saturated aqueous solution of $NH_4Cl$ (10 mL) and extracted with EtOAc (3×10 mL). The organic extracts were combined, dried over $MgSO_4$, filtered, and the solvent was evaporated in vacuo. The product, purified by column column chromatography (hexane:EtOAc; 7:3), was obtained as a brownish solid (70 mg, 45%).

¹H NMR (500 MHz, CDCl₃) δ (ppm) 8.28 (d, J=8.3 Hz, 1H), 7.67 (s, 1H), 6.94 (dd, J=8.3, 1.8 Hz, 1H), 6.87 (d, J=1.9 Hz, 1H), 4.60 (d, J=5.4 Hz, 2H), 2.17 (s, 3H), 1.68-1.62 (m, 1H), 1.06 (s, 9H), 0.28 (s, 6H);

¹³C NMR (126 MHz, CDCl₃) δ (ppm) 168.0, 144.2, 136.7, 129.4, 120.6, 120.3, 116.6, 65.3, 26.0, 25.0, 18.4, 4.1;

Preparative Example 13

N-(2-((tert-butyldimethylsilyl)oxy)-4-formylphenyl)acetamide

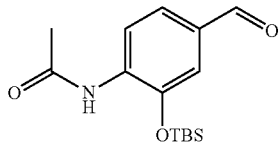 [SMILES: CC(=O)Nc1ccc(C=O)cc1O[Si](C)(C)C(C)(C)C]

To a solution of N-(2-((tert-butyldimethylsilyl)oxy)-4-(hydroxymethyl)phenyl)acetamide (65 mg, 0.22 mmol) in CH$_2$Cl$_2$ (2 mL) were added Celite (95 mg) and PCC (95 mg, 0.44 mmol). The reaction mixture was stirred at 25° C. for 2 h. The mixture was filtered through a pad of silica gel and the product was eluted with CH$_2$Cl$_2$. The solvent was evaporated in vacuo and the product was dried under vacuum. The product was obtained as a pale yellow solid (65 mg, 100%).

$^1$H NMR (500 MHz, CDCl$_3$) δ (ppm) 9.86 (s, 1H), 8.55 (d, J=8.3 Hz, 1H), 7.94 (s, 1H), 7.49 (dd, J=8.3, 1.8 Hz, 1H), 7.34 (d, J=1.7 Hz, 1H), 2.22 (s, 3H), 1.07 (s, 9H), 0.33 (s, 6H);

$^{13}$C NMR (126 MHz, CDCl$_3$) δ (ppm) 191.1, 168.3, 144.3, 135.9, 132.1, 126.8, 119.4, 115.8, 26.0, 25.2, 18.4, −4.1;

HRMS calcd for C$_{15}$H$_{24}$NO$_3$Si [M+H]$^+$ 294.152, found 294.1524.

Preparative Example 14

N-methoxy-N-methyl-2-(tetrahydro-2H-pyran-4-yl)acetamide

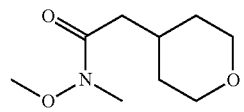

To a solution of ethyl 2-(tetrahydro-2H-pyran-4-yl)acetate (300 mg, 1.74 mmol) and N,O-dimethylhydroxylamine hydrochloride (200 mg, 2.1 mmol) in THF (2 mL) was added iPrMgCl.LiCl (1.3M in THF, 3.4 mL, 4.95 mmol) at −10° C. The reaction mixture was stirred at −5° C. for 1 h, then it was poured into a saturated aqueous solution of NH$_4$Cl (10 mL) and extracted with EtOAc (3×10 mL). The combined organic extracts were dried over MgSO$_4$, filtered, and the solvent was evaporated in vacuo. The residue was purified by column chromatography (hexane:EtOAc; 10:1). The product was obtained as a colorless oil (225 mg, 70%).

$^1$H NMR (500 MHz, CDCl$_3$) δ (ppm) 4.00-3.91 (m, 2H), 3.69 (s, 3H), 3.43 (td, J=11.8, 2.1 Hz, 2H), 3.19 (s, 3H), 2.37 (d, J=7.0 Hz, 2H), 2.17-2.06 (m, 1H), 1.73-1.64 (m, 2H), 1.42-1.30 (m, 2H);

$^{13}$C NMR (126 MHz, CDCl$_3$) δ (ppm) 174.4, 68.1, 61.4, 39.0, 33.3, 32.3, 31.8.

HRMS calcd for C$_{15}$H$_{26}$NO$_3$Si [M+H]$^+$ 296.1676, found 296.1679.

Preparative Example 15

1-phenyl-2-(tetrahydro-2H-pyran-4-yl)ethan-1-one

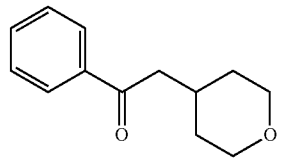 [SMILES: O=C(CC1CCOCC1)c1ccccc1]

To a solution of N-methoxy-N-methyl-2-(tetrahydro-2H-pyran-4-yl)acetamide (250 mg, 1.34 mmol) in THF (2 mL) was added PhLi (1.8M in THF, 0.74 mL, 1.34 mmol) at −78° C. The reaction mixture was stirred at −78° C. for 30 min, then it was poured into a saturated aqueous solution of NH$_4$Cl (10 mL) and extracted with EtOAc (3×10 mL). The combined organic extracts were dried over MgSO$_4$, filtered, and the solvent was evaporated in vacuo. The product, purified by column chromatography (hexane:EtOAc; 1:1), was obtained as a white solid (235 mg, 85%).

$^1$H NMR (500 MHz, CDCl$_3$) δ (ppm) 7.98-7.94 (m, 2H), 7.61-7.53 (m, 1H), 7.50-7.44 (m, 2H), 4.02-3.91 (m, 2H), 3.45 (td, J=11.8, 2.2 Hz, 2H), 2.90 (dd, J=6.7, 2.3 Hz, 2H), 2.34-2.20 (m, 1H), 1.76-1.66 (m, 2H), 1.48-1.33 (m, 2H);

$^{13}$C NMR (126 MHz, CDCl$_3$) δ (ppm) 199.4, 137.5, 133.3, 128.8, 128.3, 68.1, 45.6, 33.3, 31.6;

HRMS calcd for C$_{13}$H$_{17}$O$_2$ [M+H]$^+$ 205.1223, found 205.1221.

Preparative Example 16

(2,6-di-tert-butylpyridine-4-yl)methyl benzoate

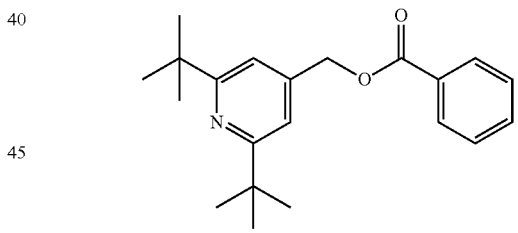

To a mixture of 2,6-di-tert-butyl-4-methylpyridine (577 mg, 2.81 mmol), NBS (525 mg, 2.95 mmol) and AIBN (138 mg, 0.843 mmol) was added CCl$_4$ (25 mL). The mixture was heated to reflux. After 1 h, additional AIBN (138 mg, 0.843 mmol) was added to the mixture and addition of the same amount of AIBN was repeated twice during 2 h. The mixture was cooled to 25° C., filtered and the filtrate was concentrated in vacuo. The residue was purified by column chromatography on silica gel (hexane), providing a mixture of the product (4-(bromomethyl)-2,6-di-tert-butylpyridine) with the starting material (ca. 1/1.3) as an amorphous solid (673 mg). This material was used as such in the next step.

The mixture containing 4-(bromomethyl)-2,6-di-tert-butylpyridine (320 mg) was dissolved in DMF (10 mL). Benzoic acid (275 mg, 2.252 mmol) and K$_2$CO$_3$ (342 mg, 2.48 mmol) were added and the mixture was stirred at 50° C. overnight. The solvent was evaporated in vacuo and the residue was diluted with EtOAc (25 mL). The organic phase was washed with H₂O (3×20 mL), then with brine (3×20 mL), dried over MgSO₄, filtered, and concentrated in vacuo. The residue was purified by column chromatography on silica gel (hexane:EtOAc; 1:0 to 10:1). The product was obtained as a colorless oil (364 mg).

¹H NMR (300 MHz, CDCl₃) δ (ppm) 8.13-8.08 (m, 2H), 7.62-7.56 (m, 1H), 7.50-7.44 (m, 2H), 7.14 (s, 2H), 5.33 (s, 2H), 1.36 (s, 18H);

¹³C NMR (126 MHz, CDCl₃) δ (ppm) 168.4, 166.5, 144.7, 133.3, 130.1, 129.9, 128.6, 114.2, 66.0, 37.8, 30.3.

Preparative Example 17

(2,6-di-tert-butylpyridine-4-yl)methanol

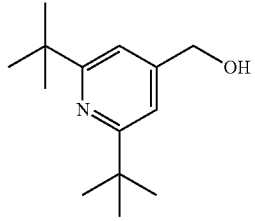 [SMILES: CC(C)(C)c1cc(CO)cc(C(C)(C)C)n1]

(2,6-di-tert-butylpyridine-4-yl)methyl benzoate (359 mg, 1.103 mmol) was dissolved in MeOH (10 mL) and the solution was cooled to 0° C. NaH (60% in mineral oil, 27 mg, 1.103 mmol) was added and the mixture was stirred and allowed to warm to 25° C. After 1 h, a saturated aqueous solution of ammonium chloride (20 mL) was added and the mixture was extracted with EtOAc (3×30 mL). The organic extracts were combined, washed with brine (40 mL), dried over MgSO₄, filtered and concentrated in vacuo. The residue was purified by column chromatography on silica gel (hexane:EtOAc; 1:0 to 5:1 to 4:1). The product was obtained as a white solid (199 mg, 82%).

¹H NMR (300 MHz, CDCl₃) δ (ppm) 7.08 (s, 2H), 4.69 (s, 2H), 1.35 (s, 18H);

¹³C NMR (126 MHz, CDCl₃) δ (ppm) 168.2, 149.4, 113.2, 64.9, 37.8, 30.3;

HRMS calcd for C₁₄H₂₄NO [M+H]⁺ 222.1852, found 222.1856.

Preparative Example 18

2,6-di-tert-butylisonicotinaldehyde

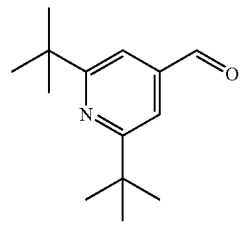 [SMILES: CC(C)(C)c1cc(C=O)cc(C(C)(C)C)n1]

A mixture of (2,6-di-tert-butylpyridine-4-yl)methanol (55 mg, 0.248 mmol), pyridinium chlorochromate (107 mg, 0.497 mmol) and Celite (110 mg) in CH₂Cl₂ (2 mL) was stirred at 25° C. for 4 h. The mixture was filtered through a pad of silica gel to afford the product as a colorless oil (40 mg, 73%).

¹H NMR (300 MHz, CDCl₃) δ (ppm) 10.05 (s, 1H), 7.51 (s, 2H), 1.39 (s, 18H);

¹³C NMR (126 MHz, CDCl₃) δ (ppm) 193.2, 169.9, 142.7, 114.7, 38.1, 30.2.

Preparative Example 19

2-cyclohexylacetaldehyde

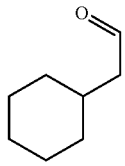

Methyl 2-cyclohexylacetate (1.04 g, 6.66 mmol) was dissolved in THF (5 mL). The solution was cooled to 0° C. and a solution of LiAlH₄ (1M in Et₂O, 13.3 mL, 13.3 mmol) was added and the mixture was stirred at 25° C. for 16 h. The resulting mixture was poured into water (20 mL) with H₂SO₄ (4 mL) and extracted with EtOAc (3×10 mL). The organic fractions were combined, washed with brine (20 mL), dried over MgSO₄, and concentrated in vacuo. The resulting crude alcohol was dissolved in CH₂Cl₂ (10 mL), then PCC (2.9 g, 13.32 mmol) and Celite (2.9 g) were added and the mixture was stirred at 25° C. for 2 h. The mixture was then loaded onto a short column of silica gel (50 mL) and the product was eluted with CH₂Cl₂. The product was obtained as a colorless oil (588 mg, 70%).

¹H NMR (300 MHz, CDCl₃) δ9.78 (t, J=2.4 Hz, 1H), 2.31 (dd, J=6.8, 2.4 Hz, 2H), 2.00-1.83 (m, 1H), 1.81-1.64 (m, 6H), 1.42-1.13 (m, 2H), 1.11-0.95 (m, 2H);

¹³C NMR (75 MHz, CDCl₃) δ203.1, 51.6, 33.5, 32.9, 26.3, 26.3.

Preparative Example 20

2-cyclohexyl-1-(4-(trifluoromethoxy)phenyl)ethan-1-ol

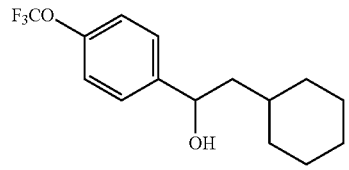 [SMILES: OC(CC1CCCCC1)c1ccc(OC(F)(F)F)cc1]

To a solution of 1-bromo-4-(trifluoromethoxy)benzene (486 mg, 0.3 mL, 2.0 mmol) in THF (3 mL) was added n-BuLi (2.5M in hexane, 435 μL, 6 mmol) at −78° C. and the reaction mixture was stirred at −78° C. for 1 h. A solution of 2-cyclohexylacetaldehyde (280 mg, 2.2 mmol) in THF (1 mL) was added and the mixture was stirred at 25° C. for 5 h. The reaction mixture was poured into a saturated aqueous solution of NH₄Cl (20 mL) and extracted with EtOAc (3×15 mL). The combined organic extracts were dried over MgSO₄, filtered, and the solvent was evaporated in vacuo. The residue was purified by column chromatography (hexane:EtOAc; 10:1). The product was obtained as a colorless oil (450 mg, 80%).

¹H NMR (500 MHz, CDCl₃) δ (ppm) 7.41-7.35 (m, 2H), 7.22-7.18 (m, 2H), 4.82 (dd, J=8.8, 4.9 Hz, 1H), 1.87-1.79 (m, 1H), 1.79-1.61 (m, 4H), 1.56-1.47 (m, 2H), 1.47-1.38 (m, 1H), 1.32-1.14 (m, 3H), 1.07-0.89 (m, 2H);

¹³C NMR (126 MHz, CDCl₃) δ (ppm) 148.7, 144.3, 127.4, 121.2, 120.7 (q, J=256.9 Hz), 71.6, 47.4, 34.5, 26.8, 26.5, 26.3;

¹⁹F NMR (471 MHz, CDCl₃) δ (ppm) −57.89.

Preparative Example 21

2-cyclohexyl-1-(4-(trifluoromethoxy)phenyl)ethan-1-one

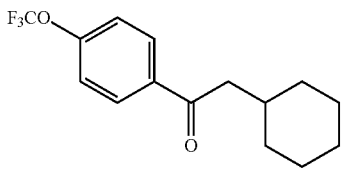 [SMILES: O=C(CC1CCCCC1)c1ccc(OC(F)(F)F)cc1]

To a solution of 2-cyclohexyl-1-(4-(trifluoromethoxy)phenyl)ethan-1-ol (300 mg, 1.04 mmol) in CH₂Cl₂ (3 mL) was added Celite (450 mg) and PCC (450 mg, 2.08 mmol) and the reaction mixture was stirred at 25° C. for 2 h. The mixture was loaded onto a short plug of silica gel and the product was eluted with CH₂Cl₂. The product was obtained as a white solid (250 mg, 80%).

¹H NMR (500 MHz, CDCl₃) δ (ppm) 8.06-7.96 (m, 2H), 7.31-7.27 (m, 2H), 2.82 (d, J=6.7 Hz, 2H), 2.06-1.92 (m, 1H), 1.82-1.62 (m, 4H), 1.36-1.25 (m, 3H), 1.23-1.11 (m, 1H), 1.10-0.96 (m, 2H);

¹³C NMR (126 MHz, CDCl₃) δ (ppm) 198.9, 152.7, 136.0, 130.4, 120.6, 120.6 (q, J=258.5 Hz), 46.5, 34.8, 33.7, 26.5, 26.45;

¹⁹F NMR (471 MHz, CDCl₃) δ (ppm) −57.62;

HRMS calcd for C₁₅H₁₈F₃O₂[M+H]⁺ 287.1253, found 287.1256.

Preparative Example 22

5-formyl-2-hydroxybenzamide

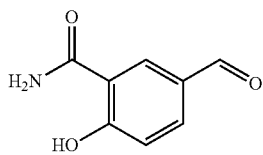 [SMILES: NC(=O)c1cc(C=O)ccc1O]

Methyl 5-formyl-2-hydroxybenzoate (200 mg, 1.11 mmol) was dissolved in MeOH (5 mL) in a pressure tube and NH₃ in MeOH (7 M, 1 ml) was added. The pressure tube was sealed, and the mixture was stirred at 50° C. for 16 hours. The solvent was evaporated and the residue was purified by column flash chromatography (hexane:EtOAc; 1:1 to 0:1). The product was obtained as a white solid (40 mg, 21%).

¹H NMR (500 MHz, DMSO-d₆) δ (ppm) 13.90 (s, 1H), 9.83 (s, 1H), 8.65 (s, 1H), 8.49 (d, J=2.1 Hz, 1H), 8.12 (s, 1H), 7.95 (dd, J=2.0, 8.6 Hz, 1H), 7.07 (d, J=8.6 Hz, 1H);

¹³C NMR (126 MHz, DMSO-d₆) δ (ppm) 190.5, 171.1, 166.1, 134.6, 131.5, 127.8, 118.3, 114.8;

HRMS calcd for C₈H₈NO₃ [M+H]⁺ 166.0499, found 166.0499.

Preparative Example 23

6-bromo-2,2-dimethyl-4H-benzo[d][1,3]dioxine

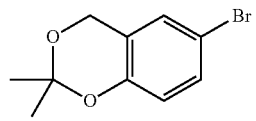

To a solution of 4-bromo-2-(hydroxymethyl)phenol (500 mg, 2.5 mmol) in acetone (3 mL) and THF (2 mL) cooled to 0° C., was portionwise added AlCl₃ (110 mg, 0.8 mmol) over 5 min. The mixture was stirred at 25° C. for 2 h and then poured into aqueous solution of NaOH (2 M, 10 mL) and extracted with EtOAc (3×10 ml). The organic fractions were combined, washed with brine (15 mL), filtered, and the solvent was evaporated in vacuo. The product, purified by column flash chromatography (hexane:EtOAc; 7:3), was obtained as a colorless oil (520 mg, 85%).

¹H NMR (500 MHz, CDCl₃) δ (ppm) 7.31-7.23 (m, 1H), 7.15-7.05 (m, 1H), 6.72 (d, J=8.7 Hz, 1H), 4.83 (d, J=0.9 Hz, 2H), 1.55 (s, 6H);

¹³C NMR (126 MHz, CDCl₃) δ (ppm) 150.6, 131.3, 127.6, 121.6, 119.2, 112.7, 100.1, 60.6, 24.9.

Preparative Example 24

6-bromo-2,2-dimethyl-4H-benzo[d][1,3]dioxine

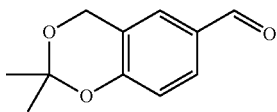

To a solution of 6-bromo-2,2-dimethyl-4H-benzo[d][1,3]dioxine (313 mg, 1.28 mmol) in THF (3 mL) cooled to −78° C., was added BuLi (2.5 M in hexane, 0.67 mL, 1.6 mmol). The mixture was stirred for 1 h at −78° C. A solution of DMF (0.19 g, 201 μL, 2.56 mmol) in THF (1 mL) was added to the mixture. The mixture was allowed to warm up to 0° C. over 2 h. The reaction mixture was poured into a saturated solution of NH₄Cl (20 mL) and extracted with EtOAc (3×10 mL). The organic fractions were combined, washed with brine (15 mL), and the solvent was evaporated in vacuo. The product, purified by column flash chromatography (hexane:EtOAc; 10:1), was obtained as a colorless oil (180 mg, 75%).

¹H NMR (500 MHz, CDCl₃) δ (ppm) 9.87 (d, J=1.4 Hz, 1H), 7.85-7.66 (m, 1H), 7.60-7.53 (m, 1H), 6.98-6.90 (m, 1H), 4.92 (s, 2H), 1.58 (s, 6H);

¹³C NMR (126 MHz, CDCl₃) δ (ppm) 190.9, 157.0, 130.7, 129.7, 127.1, 120.0, 118.0, 101.0, 60.8, 25.0;

HRMS calcd for C₁₁H₃O₃[M+H]⁺ 193.0859, found 193.0858.

Preparative Example 25

4-hydroxy-3-(hydroxymethyl)benzaldehyde

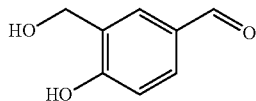

To a solution of 6-bromo-2,2-dimethyl-4H-benzo[d][1,3]dioxine_(180 mg, 0.93 mmol) in MeOH:H$_2$O (3 mL+1 mL) was added aqueous HCl (35%, 0.25 mL) and the mixture was stirred at 50° C. for 2 h. The solvent was removed in vacuo. The product was obtained as a white solid (120 mg, 85%), which was used in the next step without any further purification.

$^1$H NMR (500 MHz, DMSO-d$_6$) δ (ppm) 9.80 (d, J=2.6 Hz, 1H), 7.99-7.81 (m, 1H), 7.65 (dd, J=2.2, 8.3 Hz, 1H), 6.93 (dd, J=1.8, 8.2 Hz, 1H), 4.51 (s, 2H);

$^{13}$C NMR (126 MHz, DMSO-d$_6$) δ (ppm) 191.1, 160.0, 130.4, 129.7, 128.7, 128.2, 114.8, 57.6;

HRMS calcd for C$_8$H$_7$O$_3$[M−H]$^-$ 151.0401, found 151.0401.

Preparative Example 26 tert-butyl (4-methoxybenzyl)(thiazol-2-yl)carbamate

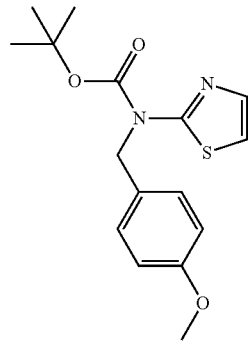 [SMILES: COc1ccc(CN(C(=O)OC(C)(C)C)c2nccs2)cc1]

Thiazol-2-amine (1.5 g, 10 mmol), Boc$_2$O (2.18 g, 10 mmol) and DMAP (12 mg, 0.1 mmol) were stirred in CH$_2$Cl$_2$ (10 mL) at 25° C. for 16 h. The solvent was removed in vacuo. The residue was dissolved in DMF (15 mL) and Cs$_2$CO$_3$ (3.25 g, 10 mmol) was added followed by PMBCl (1.56 g, 10 mmol). The mixture was stirred at 80° C. for 2 h, poured into water (50 mL), and extracted with Et$_2$O (3×30 mL). Organic fractions were combined, washed with brine (50 mL), dried over MgSO$_4$, filtered, and the solvent was evaporated in vacuo. The product, purified by column flash chromatography (hexane:EtOAc; 20:1 to 7:3), was obtained as a colorless wax (2.4 g, 75%).

$^1$H NMR (500 MHz, CDCl$_3$) δ (ppm) 7.45 (d, J=3.6 Hz, 1H), 7.35-7.30 (m, 2H), 6.95 (d, J=3.6 Hz, 1H), 6.88-6.81 (m, 2H), 5.30 (s, 2H), 3.79 (s, 3H), 1.54 (s, 9H);

$^{13}$C NMR (126 MHz, CDCl$_3$) δ (ppm) 162.0, 159.0, 153.3, 137.6, 130.2, 129.3, 114.3, 113.8, 83.5, 55.4, 49.8, 28.4;

HRMS calcd for C$_{16}$H$_{21}$N$_2$O$_3$S [M+H]$^+$ 321.1267, found 321.1264.

Preparative Example 27 tert-butyl (4-methoxybenzyl)(5-(pyrazin-2-yl)thiazol-2-yl)carbamate

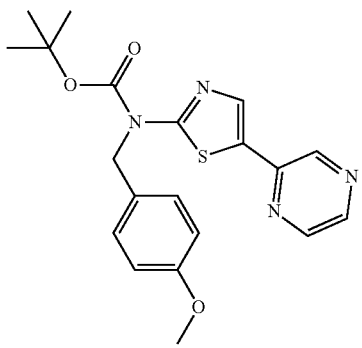 [SMILES: COc1ccc(CN(C(=O)OC(C)(C)C)c2ncc(-c3cnccn3)s2)cc1]

To a solution of diisopropylamine (0.38 g, 0.52 mL, 3.75 mmol) in THF (5 mL) at −78° C. was added BuLi (2.5 M in hexane, 1.5 mL, 3.75 mmol). The mixture was stirred at −78° C. for 10 min and then allowed to warm up to 0° C. The resulting solution was added to a solution of tert-butyl (4-methoxybenzyl)(thiazol-2-yl)carbamate (1.0 g, 3.1 mmol) and 2-isopropoxy-4,4,5,5-tetramethyl-1,3,2-dioxaborolane (0.75 g, 0.82 mL, 4 mmol) in anhydrous THF (5 mL) at −78° C. The mixture was stirred at −78° C. for 2 h and then allowed to warm up to 0° C. over 3 h. The reaction mixture was quenched with saturated aqueous solution of NH$_4$Cl (20 mL) and the mixture was extracted with EtOAc (3×20 mL). The combined organic extracts were dried over MgSO$_4$, filtered, concentrated under reduced pressure and dried under vacuum. The product, tert-butyl (4-methoxybenzyl)(5-(4,4,5,5-tetramethyl-1,3,2-dioxaborolan-2-yl)thiazol-2-yl)carbamate (1.4 g, 3.1 mmol), was used as such in the next step. n-Butanol (8 mL) and DIPEA (2 mL) were purged with argon for 5 min. To this solution were added Pd$_2$(dba)$_3$ (50 mg, 0.05 mmol) and SPhos (45 mg, 0.1 mmol) and the mixture was stirred at room temperature for 10 min. 2-chloropyrazine (0.35 g, 0.28 mL, 3.1 mmol), tert-butyl (4-methoxybenzyl)(5-(4,4,5,5-tetramethyl-1,3,2-dioxaborolan-2-yl)thiazol-2-yl)carbamate (1.4 g, 3.1 mmol) and K$_3$PO$_4$ (1.3 g, 6.2 mmol) were added. The resulting mixture was stirred at 100° C. for 3 h. The mixture was absorbed on silica-gel and purified by column flash chromatography (hexane:EtOAc; 10:1 to 1:1). The product was obtained as a white solid (0.7 g, 57%).

$^1$H NMR (300 MHz, CDCl$_3$) δ (ppm) 8.87 (d, J=1.6 Hz, 1H), 8.50-8.44 (m, 1H), 8.37 (d, J=2.6 Hz, 1H), 8.03 (s, 1H), 7.39-7.30 (m, 2H), 6.91-6.80 (m, 2H), 5.31 (s, 2H), 3.79 (s, 3H), 1.56 (s, 9H);

$^{13}$C NMR (75 MHz, CDCl$_3$) δ (ppm) 163.7, 159.2, 153.1, 148.2, 144.3, 142.1, 140.9, 136.9, 131.0, 129.9, 129.4, 113.9, 84.2, 55.4, 49.5, 28.4;

HRMS calcd for C$_{20}$H$_{23}$N$_4$O$_3$S [M+H]$^+$ 399.1485, found 399.1483.

Preparative Example 28

2-(pyrazin-2-yl)-1-(pyridin-2-yl)ethan-1-one

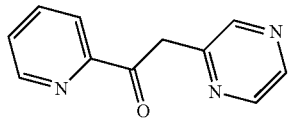 [SMILES: O=C(Cc1cnccn1)c1ccccn1]

To a solution of methyl picolinate (1.14 g, 1 mL, 8.3 mmol) and 2-methylpyrazine (0.78 g, 0.76 mL, 8.3 mmol) in THF (15 mL) was added NaH (60% in mineral oil, 0.5 g, 12 mmol). The mixture was refluxed for 16 h. Once cooled to room temperature, the mixture was poured into saturated aqueous solution of $NH_4Cl$ (30 mL) and extracted with EtOAc (3×30 mL). Organic fractions were combined, washed with brine (30 mL), dried over $MgSO_4$, and the solvent was evaporated in vacuo. The product, purified by column flash chromatography ($CH_2Cl_2$:MeOH; 10:1 to 5:1), was obtained as a yellow solid (1.3 g, 80%). ($^1$H NMR shows a mixture of the keto- and enol-forms in ratio ca. 1:1)

$^1$H NMR (500 MHz, $CDCl_3$) δ (ppm) 13.65 (s, 1H), 8.71 (ddd, J=0.9, 1.8, 4.8 Hz, 1H), 8.67-8.64 (m, 2H), 8.58 (d, J=1.1 Hz, 1H), 8.52 (dd, J=1.6, 2.6 Hz, 1H), 8.46 (d, J=2.6 Hz, 1H), 8.36-8.31 (m, 2H), 8.12-8.05 (m, 1H), 8.00-7.94 (m, 1H), 7.88-7.83 (m, 1H), 7.83-7.77 (m, 1H), 7.50 (ddd, J=1.2, 4.7, 7.5 Hz, 1H), 7.32 (ddd, J=1.2, 4.7, 7.5 Hz, 1H), 6.94 (s, 1H), 4.80 (s, 2H);

$^{13}$C NMR (126 MHz, $CDCl_3$) δ (ppm) 197.7, 162.0, 154.2, 152.9, 152.6, 152.1, 149.3, 149.3, 146.3, 145.2, 144.4, 142.9, 140.2, 140.0, 137.2, 137.2, 127.7, 124.4, 122.5, 120.5, 94.2, 44.5;

HRMS calcd for $C_{11}H_{10}N_3O$ $[M+H]^+$ 200.0818, found 200.0816.

Preparative Example 29

N-Bocthiourea

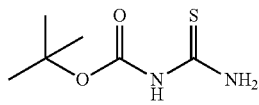

To a solution of thiourea (4.4 g, 57.8 mmol) in THF (300 mL) at 0° C. was added NaH (60% in mineral oil, 5.4 g, 0.133 mmol). The mixture was stirred 15 min, then a solution of di-tert-butyldicarbonate (13.25 g, 0.061 mmol) in THF (50 mL) was slowly added. The mixture was allowed to warm to room temperature and stirred for 2 h. $CH_2Cl_2$ (300 mL) was added and the organic phase was washed with a saturated aqueous solution of $NaHCO_3$ (2×200 mL), $H_2O$ (200 mL) and brine (200 mL), dried over $MgSO_4$, filtered, and the solvent was evaporated in vacuo. The crude residue was triturated with heptane (500 mL) and the precipitate was collected by filtration. The product was obtained as a white solid (3.243 g, 32%).

$^1$H NMR (300 MHz, DMSO-$d_6$) δ (ppm) 10.49 (s, 1H), 9.13 (s, 1H), 8.96 (s, 1H), 1.44 (s, 9H);

$^{13}$C NMR (75 MHz, DMSO-$d_6$) δ (ppm) 181.5, 152.2, 81.9, 27.6;

HRMS calcd for $C_6H_{11}N_2O_2S$ $[M-H]^-$ 175.0547, found 175.0548.

Preparative Example 30 tert-butyl (4-(6-methyl-4,8-dioxo-1,3,6,2-dioxazaborocan-2-yl)thiazol-2-yl)carbamate

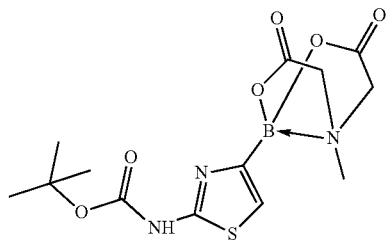 [SMILES: CC(C)(C)OC(=O)Nc1nc([B-]23OC(=O)C[N+]2(C)CC(=O)O3)cs1]

To a mixture of 2-(2-bromoacetyl)-6-methyl-1,3,6,2-dioxazaborocane-4,8-dione (1.13 g, 4.07 mmol) and N-Boc-thiourea (788 mg, 4.47 mmol) in $CH_3CN$ (50 mL) was added $NEt_3$ (1.23 g, 1.7 mL, 12.2 mmol) and the mixture was stirred at 70° C. for 50 min. The reaction mixture was diluted with EtOAc (100 mL) and washed with saturated aqueous solution of $NaHCO_3$ (50 mL). The aqueous phase was extracted with EtOAc (2×75 mL). The combined organic extracts were washed with brine (100 mL), dried over $MgSO_4$, filtered, and the solvent was evaporated in vacuo. The product, purified by flash column chromatography (hexane:EtOAc; 1:2 to 0:1), was obtained as a white solid (0.905 g, 63%).

$^1$H NMR (300 MHz, Chloroform-d) δ (ppm) 7.23 (s, 1H), 4.13 (d, J=17.0 Hz, 2H), 3.91 (d, J=16.8 Hz, 2H), 2.64 (s, 3H), 1.51 (s, 9H);

$^{13}$C NMR (75 MHz, Chloroform-d) δ (ppm) 168.8, 161.2, 152.4, 120.1, 82.8, 77.4, 62.1, 47.1, 28.3;

HRMS calcd for $C_{13}H_{19}BN_3O_6S$ $[M+H]^+$ 356.1085, found 356.1085.

Preparative Example 31 tert-butyl (4-methoxybenzyl)(4-(6-methyl-4,8-dioxo-1,3,6,2-dioxazaborocan-2-yl)thiazol-2-yl)carbamate

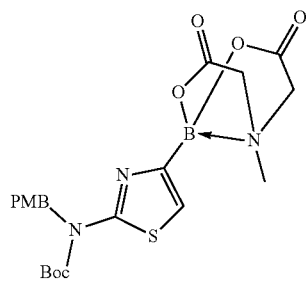

To a mixture of tert-butyl (4-(6-methyl-4,8-dioxo-1,3,6,2-dioxazaborocan-2-yl)thiazol-2-yl)carbamate (0.371 g, 1.045 mmol) and Cs$_2$CO$_3$ (0.851 g, 2.61 mmol) in CH$_3$CN (4 mL) was added 4-methoxybenzyl chloride (0.204 g, 0.177 mL, 1.31 mmol), and the resulting mixture was stirred at 80° C. for 1 h. The solvent was evaporated and the residue was purified by column chromatography (hexane:EtOAc:CH$_3$CN; 1:1:0 to 0:1:0 to 0:1:1). The product was obtained as a white solid (0.353 g, 71%).

$^1$H NMR (500 MHz, Chloroform-d) δ (ppm) 7.27 (s, 1H), 7.17-7.13 (m, 2H), 6.84-6.79 (m, 2H), 5.20 (s, 2H), 3.80 (d, J=16.2 Hz, 2H), 3.76 (s, 3H), 3.64 (d, J=16.2 Hz, 2H), 2.26 (s, 3H), 1.56 (s, 9H);

$^{13}$C NMR (126 MHz, Chloroform-d) δ (ppm) 167.5, 162.2, 158.8, 130.6, 128.1, 121.3, 114.0, 61.9, 55.5, 50.2, 46.2, 28.4;

HRMS calcd for C$_{21}$H$_{27}$BN$_3$O$_7$S [M+H]$^+$ 476.1661, found 476.1661.

Preparative Example 32 tert-butyl (4-methoxybenzyl)(4-(6-morpholinopyridin-2-yl)thiazol-2-yl)carbamate

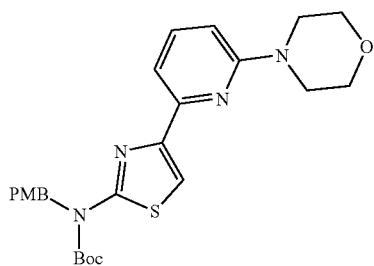

To a solution of tert-butyl (4-methoxybenzyl)(4-(6-methyl-4,8-dioxo-1,3,6,2-dioxazaborocan-2-yl)thiazol-2-yl)carbamate (160 mg, 0.337 mmol) in DME (6 mL) and H$_2$O (1.5 mL) were added 2-bromo-6-morpholinopyridine (90 mg, 0.37 mmol), K$_3$PO$_4$ (0.286 g, 1.35 mmol) and Pd(dppf)Cl$_2$ (25 mg, 0.034 mmol). The reaction mixture was stirred at 80° C. for 16 h, then diluted with water (10 mL), and extracted with EtOAc (2×20 mL). The combined organic extracts were washed with brine (10 mL), dried over MgSO$_4$, filtered, and concentrated under reduced pressure. The product, purified by flash column chromatography (hexane:EtOAc; 1:0 to 1:1), was obtained as a white solid (0.121 g, 74%).

$^1$H NMR (500 MHz, Chloroform-d) δ (ppm) 7.65 (s, 1H), 7.57 (t, J=7.8 Hz, 1H), 7.48 (d, J=7.4 Hz, 1H), 7.41 (d, J=8.7 Hz, 2H), 6.88-6.77 (m, 2H), 6.57 (d, J=8.3 Hz, 1H), 5.35 (s, 2H), 3.91-3.80 (m, 4H), 3.77 (s, 3H), 3.63-3.54 (m, 4H), 1.55 (s, 9H);

$^{13}$C NMR (126 MHz, Chloroform-d) δ (ppm) 161.1, 159.1, 159.0, 153.3, 151.1, 150.2, 138.5, 130.4, 129.7, 113.7, 112.1, 111.0, 106.1, 83.5, 67.0, 55.3, 49.8, 45.8, 28.4;

HRMS calcd for C$_{25}$H$_{31}$N$_4$O$_4$S [M+H]$^+$ 483.2061; Found 483.2061.

Preparative Example 33 tert-butyl (5-bromothiazol-2-yl)(4-methoxybenzyl)carbamate

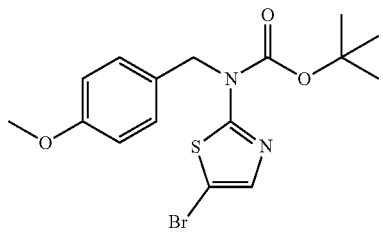 [SMILES: COc1ccc(CN(C(=O)OC(C)(C)C)c2ncc(Br)s2)cc1]

5-bromothiazol-2-amine hydrobromide (8.58 g, 33 mmol) was shaken with saturated aqueous solution of NaHCO$_3$ (50 mL) and EtOAc (3×50 mL). The combined organic extracts were washed with brine (50 mL), dried over MgSO$_4$, filtered, concentrated under reduced pressure and dried under high vacuum. The residue was dissolved in CH$_2$Cl$_2$ (40 mL). To the solution were added DMAP (40 mg, 0.33 mmol) and di-tert-butyl dicarbonate (8.0 g, 36.0 mmol). The mixture was stirred at 25° C. for 24 hours. The solvent was evaporated and the resulting tert-butyl (5-bromothiazol-2-yl)carbamate was directly used in the next step without purification.

tert-Butyl (5-bromothiazol-2-yl)carbamate was dissolved in DMF (40 mL). To the solution were added Cs$_2$CO$_3$ (18.0 g, 56.0 mmol) followed by 4-methoxybenzyl chloride (5.1 g, 33.0 mmol). The mixture was stirred at 80° C. for 1 h. The reaction mixture was cooled to 25° C., quenched with water (100 mL), and extracted with Et$_2$O (3×100 mL). The organic extracts were dried over MgSO$_4$, filtered, and concentrated under reduced pressure. The product, purified by flash column chromatography (hexane:EtOAc; 1:0 to 7:3), was obtained as a colorless oil (8.7 g, 66%).

$^1$H NMR (500 MHz, Chloroform-d) δ (ppm); 7.36 (s, 1H), 7.28-7.33 (m, 2H), 6.82-6.88 (m, 2H), 5.22 (s, 2H), 3.80 (s, 3H), 1.60 (s, 9H);

$^{13}$C NMR (126 MHz, Chloroform-d) δ (ppm) 161.6, 159.2, 153.3, 138.4, 129.8, 129.4, 113.9, 103.6, 84.1, 55.4, 49.0, 28.4;

HRMS calcd for C$_{16}$H$_{20}$BrN$_2$O$_3$S [M+H]$^+$ 399.0373, found 399.0371.

Preparative Example 34 tert-butyl (4-bromothiazol-2-yl)(4-methoxybenzyl)carbamate

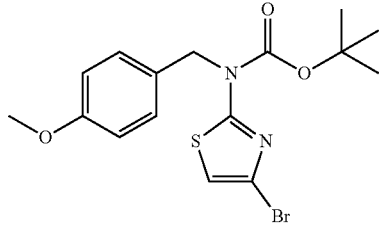 [SMILES: COc1ccc(CN(C(=O)OC(C)(C)C)c2nc(Br)cs2)cc1]

A solution of diisopropylamine (0.6 g, 0.84 mL, 6 mmol) in THF (5 mL) was cooled −78° C. BuLi (2.5 M in hexane, 2.4 mL, 6 mmol) was slowly added and the mixture was stirred at −78° C. for 10 min, and then allowed to warm to 0° C. Then, the resulting solution was added to a solution of tert-butyl (5-bromothiazol-2-yl)(4-methoxybenzyl)carbamate (2.0 g, 5 mmol) in THF (2 mL) at −78° C. and the mixture was stirred at −78° C. for 30 min. The reaction mixture was quenched with saturated solution of NH$_4$Cl (25 mL) and extracted with EtOAc (3×25 mL). The combined organic extracts were dried over MgSO$_4$, filtered, and concentrated under reduced pressure. The product, purified by flash column chromatography (hexane:EtOAc; 1:0 to 4:1), was obtained as a colorless oil (1.6 g, 80%).

$^1$H NMR (500 MHz, Chloroform-d) δ (ppm) 7.31-7.36 (m, 2H), 6.81-6.85 (m, 2H), 6.81 (s, 1H), 5.21 (s, 2H), 3.78 (s, 3H), 1.52 (s, 9H);

$^{13}$C NMR (126 MHz, Chloroform-d) δ (ppm) 161.9, 159.1, 153.0, 129.7, 129.6, 120.5, 113.8, 112.1, 84.1, 55.4, 49.7, 28.3;

HRMS calcd for C$_{16}$H$_{20}$BrN$_2$O$_3$S [M+H]$^+$ 401.0353, found 401.0359.

Preparative Example 35 tert-butyl (4-methoxybenzyl)(4-(4,4,5,5-tetramethyl-1,3,2-dioxaborolan-2-yl)thiazol-2-yl)carbamate

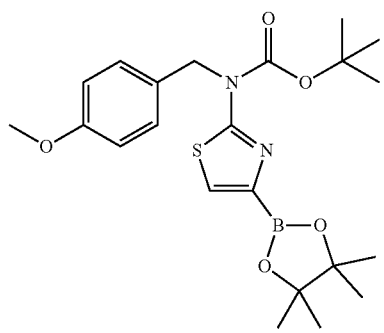 [SMILES: COc1ccc(CN(C(=O)OC(C)(C)C)c2nc(B3OC(C)(C)C(C)(C)O3)cs2)cc1]

Dioxane (25 mL) was added to a mixture of tert-butyl (4-bromothiazol-2-yl)(4-methoxybenzyl)carbamate (5.3 g, 13.25 mmol), Pd(OAc)$_2$ (60 mg, 0.26 mmol), PCy$_3$ (150 mg, 0.42 mmol), bis(pinacolato)diboron (4 g, 14.7 mmol), KOAc (3.3 g, 33 mmol). The reaction mixture was stirred at 90° C. for 2 h, then it was poured into water (30 ml) and extracted with EtOAc (3×20 mL). The organic fractions were combined, washed with brine (50 mL), dried over MgSO$_4$, filtered, and concentrated under reduced pressure to afford crude tert-butyl (4-methoxybenzyl)(4-(4,4,5,5-tetramethyl-1,3,2-dioxaborolan-2-yl)thiazol-2-yl)carbamate as a brownwish solid (5.92 g), which was directly used in the next step without further purification.

$^1$H NMR (500 MHz, Chloroform-d) δ (ppm) 7.64 (s, 1H), 7.28-7.31 (m, 2H), 6.75-6.84 (m, 2H), 5.37 (s, 2H), 3.78 (s, 3H), 1.48 (s, 9H), 1.36 (s, 12H);

$^{13}$C NMR (126 MHz, Chloroform-d) δ (ppm) 162.2, 158.9, 153.5, 130.7, 129.5, 128.1, 113.7, 84.3, 83.7, 55.4, 28.4, 25.1;

$^{11}$B NMR (96 MHz, Chloroform-d) δ (ppm) 30.80;

HRMS calcd for C$_2$H$_{32}$BN$_2$O$_5$S [M+H]$^+$ 447.2124, found 447.2128.

Preparative Example 36 tert-butyl (4-methoxybenzyl)(4-(6-morpholinopyridin-3-yl)thiazol-2-yl)carbamate

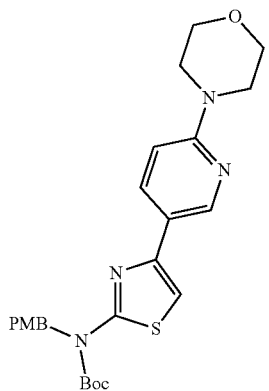

To a solution of tert-butyl (4-methoxybenzyl)(4-(4,4,5,5-tetramethyl-1,3,2-dioxaborolan-2-yl)thiazol-2-yl)carbamate (0.5 g, 1.12 mmol) in dioxane (4 mL) and H$_2$O (1 mL), were added 4-(5-bromopyridin-2-yl)morpholine (231 mg, 0.95 mmol) and K$_3$PO$_4$ (0.7 g 3.36 mmol). The mixture purged with Ar over 10 min, then Pd(dppf)Cl$_2$ (10 mg, 0.01 mmol) was added. The reaction mixture was stirred at 90° C. for 1 h, then it was absorbed on silica-gel and directly purified by column flash chromatography (hexane/EtOAc; 10:1 to 1:1). The product was obtained as a white foam (340 mg, 75%).

$^1$H NMR (500 MHz, Chloroform-d) δ (ppm) 8.78 (d, J=2.4 Hz, 1H), 7.98 (dd, J=2.4, 8.8 Hz, 1H), 7.45-7.38 (m, 2H), 6.98 (s, 1H), 6.88-6.79 (m, 2H), 6.69 (d, J=8.8 Hz, 1H), 5.34 (s, 2H), 3.90-3.83 (m, 4H), 3.79 (s, 3H), 3.57 (t, J=4.9 Hz, 4H), 1.57 (s, 9H);

$^{13}$C NMR (126 MHz, Chloroform-d) δ (ppm) 161.5, 159.1, 159.0, 153.4, 147.4, 146.1, 135.4, 130.4, 129.8, 121.8, 113.9, 106.7, 106.3, 83.7, 67.0, 55.4, 49.9, 46.0, 28.5;

HRMS calcd for C$_{25}$H$_{31}$N$_4$O$_4$S [M+H]$^+$ 483.2061, found 483.2063.

Preparative Example 37

3-bromo-4,5-dihydroxybenzaldehyde

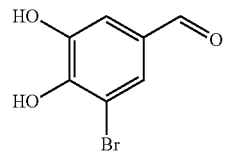

To a solution of 3-bromo-4-hydroxy-5-methoxybenzaldehyde (10.5 g, 45.45 mmol) in CH$_2$Cl$_2$ (20 mL) cooled to 0° C. was slowly added a solution of BBr$_3$ (1M in CH$_2$Cl$_2$, 0.1 mol, 100 mL). The mixture was stirred at 25° C. for 4 h, then it was cooled to 0° C., EtOH (20 mL) was slowly added, followed by water (30 mL). The mixture was concentrated under reduce pressure. To the residue was added water (50 mL) and the precipitate was collected by filtration and washed with Et$_2$O (100 mL). The product was obtained as an off-white solid (9.5 g, 97%).

¹H NMR (500 MHz, DMSO-d₆) δ (ppm) 10.47 (s, 1H), 10.39 (s, 1H), 9.70 (s, 1H), 7.56 (d, J=1.9 Hz, 1H), 7.25 (d, J=1.8 Hz, 1H);
¹³C NMR (126 MHz, DMSO-d₆) δ (ppm) 190.5, 149.3, 146.5, 129.1, 127.3, 112.8, 109.5;
HRMS calcd for C₇H₄BrO₃ [M–H]⁻ 214.9349, found 214.9348.

Preparative Example 38

3-fluoro-4,5-dihydroxybenzaldehyde

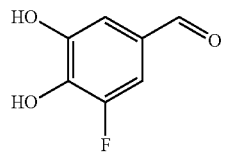

To a solution of 3-fluoro-4-hydroxy-5-methoxybenzaldehyde (535 mg, 3.14 mmol) in CH₂Cl₂ (5 mL) cooled to 0° C. was slowly added BBr₃ (1.7 g, 0.67 mL, 5.9 mol). The mixture was stirred at 25° C. for 30 min, then it was cooled to 0° C., EtOH (5 mL) was slowly added, followed by water (30 mL). The mixture was extracted with EtOAc (3×10 mL). The organic fractions were combined and the solvent was evaporated in vacuo. The residue was purified by column flash chromatography (CH₂Cl₂:MeOH; 10:1 to 5:1). The product was obtained as a white solid (0.4 g, 82%).

¹H NMR (500 MHz, DMSO-d₆) δ (ppm) 10.21 (s, 1H), 10.11 (s, 1H), 9.71 (d, J=1.5 Hz, 1H), 7.22 (dd, J=1.9, 10.4 Hz, 1H), 7.17-7.13 (m, 1H);
¹³C NMR (126 MHz, DMSO-d₆) δ (ppm) 190.7, 151.6 (d, J=239.9 Hz), 147.8 (d, J=5.5 Hz), 140.0 (d, J=14.4 Hz), 127.1 (d, J=7.2 Hz), 111.5, 109.2 (d, J=19.5 Hz);
¹⁹F NMR (471 MHz, DMSO-d₆) δ (ppm) –134.5;
HRMS calcd for C₇H₄FO₃ [M–H]⁻ 155.0150, found 155.0151.

Preparative Example 39

5-formyl-2-hydroxy-3-methoxybenzonitrile

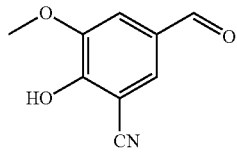

To 3-bromo-4-hydroxy-5-methoxybenzaldehyde (1.5 g, 6.5 mmol) and CuCN (1.16 g, 13 mmol) was added DMF (15 mL) and the mixture was heated to 150° C. for 16 h. The mixture was poured into water (50 mL) and filtered. The filtrate was extracted with EtOAc (2×20 mL). Organic fractions were combined and evaporated in vacuo. The residue was purified by column flash chromatography (hexane:EtOAc; 10:1 to 0:1). The product was obtained as an off-white solid (300 mg, 26%).

¹H NMR (500 MHz, DMSO-d₆) δ (ppm) 11.77 (s, 1H), 9.81 (s, 1H), 7.86 (d, J=1.7 Hz, 1H), 7.61 (d, J=1.7 Hz, 1H), 3.94 (s, 3H);

¹³C NMR (126 MHz, DMSO-d₆) δ (ppm) 190.1, 155.7, 148.5, 129.1, 128.6, 115.8, 113.2, 99.2, 56.3;
HRMS calcd for C₉H6NO₃ [M–H]⁻ 176.0353, found 176.0351.

Preparative Example 40

5-formyl-2,3-dihydroxybenzonitrile

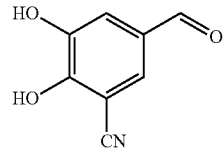

To a solution of 5-formyl-2-hydroxy-3-methoxybenzonitrile (300 mg, 1.69 mmol) in CH₂Cl₂ (5 mL) cooled to 0° C. was slowly added BBr₃ (1.26 g, 0.49 mL, 5.7 mol). The mixture was stirred at 25° C. for 60 min, then it was cooled to –78° C., iPrOH (3 mL) was slowly added, followed by water (15 mL). The mixture was extracted with CH₂Cl₂ (3×10 mL). The organic fractions were combined, washed with brine (20 mL), dried over MgSO₄, filtered, and the solvent was evaporated in vacuo. The product was obtained as a black solid (0.20 g, 73%).

¹H NMR (500 MHz, DMSO-d₆) δ (ppm) 11.39 (s, 1H), 10.81 (s, 1H), 9.74 (d, J=1.0 Hz, 1H), 7.71 (d, J=1.7 Hz, 1H), 7.46 (d, J=1.9 Hz, 1H);
¹³C NMR (126 MHz, DMSO-d₆) δ (ppm) 190.2, 155.0, 146.5, 128.8, 128.0, 116.3, 116.0, 99.4;
HRMS calcd for C₈H₄NO₃ [M–H]⁻ 162.0197, found 162.0195.

Preparative Example 41

1-(5-bromo-3-fluoropyridin-2-yl)ethan-1-one

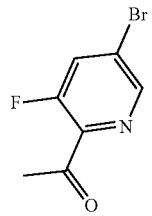

To a solution of 2,5-dibromo-3-fluoropyridine (2.077 g, 8.149 mmol) in toluene (35 mL) cooled to –78° C., was added BuLi (2.7 M, 3.169 mL, 8.556 mmol). The mixture was stirred 5 min at –78° C., then dimethylacetamide (1.035 g, 1.1 mL, 11.88 mmol) was added. The cooling bath was removed and the resulting mixture was stirred at 25° C. for 30 min. The mixture was quenched with saturated aqueous solution of NH₄Cl (30 mL) and the resulting mixture was extracted with CH₂Cl₂ (3×30 mL). The combined organic extracts were dried over MgSO₄, filtered, and the solvent was evaporated in vacuo. The residue was purified by flash column chromatography (hexane:EtOAc; 1:0 to 20:1 to 15:1 to 10:1). The product was obtained as a white solid (1.24 g, 70%).

¹H NMR (500 MHz, Chloroform-d) δ (ppm) 8.56 (dd, J=1.8, 1.1 Hz, 1H), 7.73 (dd, J=9.7, 1.8 Hz, 1H), 2.68 (d, J=1.0 Hz, 3H);

¹³C NMR (126 MHz, Chloroform-d) δ (ppm) 197.0 (d, J=4.5 Hz), 157.9 (d, J=280.5 Hz), 146.1 (d, J=4.7 Hz), 140.5 (d, J=5.4 Hz), 128.7 (d, J=22.5 Hz), 124.6 (d, J=3.6 Hz), 28.0;

¹⁹F NMR (471 MHz, Chloroform-d) δ (ppm) −116.90.

Preparative Example 42

5-bromo-3-fluoro-2-(2-methyl-1,3-dioxolan-2-yl)pyridine

To a solution of 1-(5-bromo-3-fluoropyridin-2-yl)ethan-1-one (1.93 g, 8.85 mmol) in benzene (15 mL) were added ethylene glycol (2.747 g, 2.47 mL, 44.26 mmol) and p-toluenesulfonic acid (84 mg, 0.443 mmol). The reaction mixture was refluxed for 6 hours with azeotropic removal of water (Dean-Stark apparatus). Saturated aqueous solution of NaHCO₃ (20 mL) was added and the mixture was extracted with EtOAc (2×50 mL). The combined organic extracts were dried over MgSO₄, filtered and the solvent was evaporated in vacuo. The product was obtained as a pale orange oil (2.31 g, 99%), which was used in the next step as such without further purification.

¹H NMR (500 MHz, Chloroform-d) δ (ppm) 8.61-8.28 (m, 1H), 7.59 (dd, J=9.7, 1.8 Hz, 1H), 4.16-4.05 (m, 2H), 3.98-3.87 (m, 2H), 1.76 (d, J=1.2 Hz, 3H).

¹³C NMR (126 MHz, Chloroform-d) δ (ppm) 156.8 (d, J=268.8 Hz), 147.3 (d, J=11.8 Hz), 145.4 (d, J=5.4 Hz), 127.6 (d, J=22.7 Hz), 120.0 (d, J=2.7 Hz), 107.7 (d, J=5.4 Hz), 65.3, 24.4, 24.4;

¹⁹F NMR (471 MHz, Chloroform-d) δ (ppm) −117.32;

HRMS calcd for $C_9H_{10}BrFNO_2$ [M+H]⁺ 261.9873, found 261.9873.

Preparative Example 43

4-(5-fluoro-6-(2-methyl-1,3-dioxolan-2-yl)pyridin-3-yl)morpholine

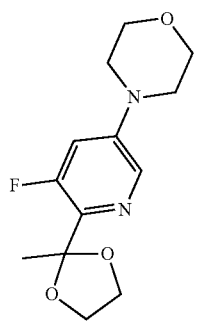 [SMILES: CC1(c2ncc(N3CCOCC3)cc2F)OCCO1]

To a solution of 5-bromo-3-fluoro-2-(2-methyl-1,3-dioxolan-2-yl)pyridine (502 mg, 1.92 mmol) in toluene (10 mL) were added morpholine (200 mg, 201 µL, 2.30 mmol), Pd₂(dba)₃ (53 mg, 0.058 mmol), Xantphos (99 mg, 0.172 mmol) and tBuONa (276 mg, 2.87 mmol). The reaction mixture was stirred at 80° C. for 90 min, then it was cooled to room temperature, and the solvent was removed in vacuo. The residue was purified by flash column chromatography (hexane:EtOAc; 2:1 to 1:1 to 1:2 to 1:3 to 1:4 to 1:10 to 0:1). The product was obtained as an off-white solid (0.355 g, 69%).

¹H NMR (500 MHz, Chloroform-d) δ (ppm) 8.17-7.98 (m, 1H), 6.86 (dd, J=13.4, 2.5 Hz, 1H), 4.12-4.07 (m, 2H), 3.98-3.92 (m, 2H), 3.89-3.81 (m, 4H), 3.27-3.15 (m, 4H), 1.76 (s, 3H).

¹³C NMR (126 MHz, Chloroform-d) δ (ppm) 157.9 (d, J=260.6 Hz), 148.6 (d, J=5.4 Hz), 138.1 (d, J=13.3 Hz), 131.4 (d, J=3.7 Hz), 110.2 (d, J=23.6 Hz), 107.8 (d, J=6.2 Hz), 66.5, 65.2, 48.1, 24.6 (d, J=2.7 Hz);

¹⁹F NMR (471 MHz, Chloroform-d) δ (ppm) −120.95.

HRMS calcd for $C_{13}H_{18}FN_2O_3$[M+H]⁺ 269.1296, found 269.1297.

Preparative Example 44

1-(3-fluoro-5-morpholinopyridin-2-yl)ethan-1-one

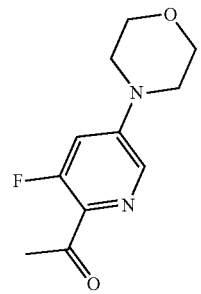 [SMILES: CC(=O)c1ncc(N2CCOCC2)cc1F]

To a solution of 4-(5-fluoro-6-(2-methyl-1,3-dioxolan-2-yl)pyridin-3-yl)morpholine (0.344 mg, 1.28 mmol) in THF (8 mL) was added aqueous HCl (2M, 3 mL). The mixture was stirred at room temperature for 2 h. Saturated aqueous solution of NaHCO₃ (16 mL) was added and the mixture was extracted with EtOAc (2×30 mL). The combined organic extracts were dried over MgSO₄, filtered, and the solvent was evaporated in vacuo. The product was obtained as a yellow wax (284 mg, 99%), which used without further purification.

¹H NMR (500 MHz, Chloroform-d) δ (ppm) 8.12 (s, 1H), 6.78 (dd, J=13.9, 2.4 Hz, 1H), 3.93-3.82 (m, 4H), 3.42-3.29 (m, 4H), 2.62 (d, J=1.3 Hz, 3H);

¹³C NMR (126 MHz, Chloroform-d) δ (ppm) 196.4 (d, J=4.6 Hz), 160.5 (d, J=272.3 Hz), 150.7, 131.2 (d, J=3.2 Hz), 107.7 (d, J=23.7 Hz), 66.3, 47.0, 27.9;

HRMS calcd for $C_{11}H_{14}FN_2O_2$[M+H]⁺ 225.1034, found 225.1035.

Preparative Example 45

4-phenylthiazol-2-amine

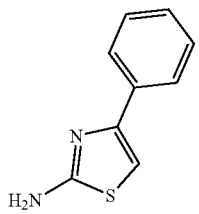

The compound was prepared according to General procedure B from 2-bromoacetophenone (3.21 g, 16.15 mmol) and thiourea (1.84 g, 24.22 mmol) in EtOH (20 mL). Work-up 2 of General procedure B.

The product was obtained as a white solid (2.82 g, 99%).

$^1$H NMR (500 MHz, DMSO-$d_6$) δ (ppm) 7.79 (d, J=7.3 Hz, 2H), 7.40-7.31 (m, 2H), 7.29-7.21 (m, 1H), 7.01 (s, 2H), 6.99 (s, 1H).

Preparative Example 46

4-(4-bromophenyl)thiazol-2-amine

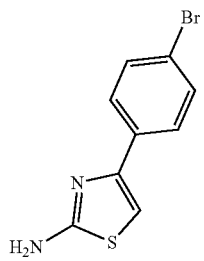 [SMILES: Nc1nc(-c2ccc(Br)cc2)cs1]

The compound was prepared according to General procedure B from 2,4'-dibromoacetophenone (2.07 g, 7.45 mmol) and thiourea (0.85 g, 11.17 mmol) in EtOH (20 mL). Work-up 1 of General procedure B. The product, obtained as a yellow solid (1.895 g, 100%), did not require any further purification.

$^1$H NMR (500 MHz, DMSO-$d_6$) δ (ppm) 7.78-7.70 (m, 2H), 7.58-7.50 (m, 2H), 7.07 (s, 1H), 7.06 (s, 1H);

$^{13}$C NMR (126 MHz, DMSO-$d_6$) δ (ppm) 168.3, 148.6, 134.1, 131.3, 127.5, 120.0, 102.4;

HRMS calcd for $C_9H_8BrN_2S$ [M+H]$^+$ 256.9565, found 256.9565.

Preparative Example 47

4-(4-methoxyphenyl)thiazol-2-amine

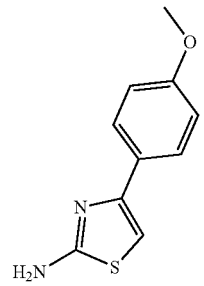

The compound was prepared according to General procedure B from 2-bromo-1-(4-methoxyphenyl)ethanone (0.521 g, 2.27 mmol) and thiourea (0.26 g, 3.41 mmol) in EtOH (5 mL). Work-up 1 of General procedure B. The product, obtained as a pale yellow solid (0.460 g, 98%), did not require any further purification.

$^1$H NMR (500 MHz, DMSO-$d_6$) δ (ppm) 7.76-7.67 (m, 2H), 6.96 (s, 2H), 6.95-6.88 (m, 2H), 6.81 (s, 1H), 3.76 (s, 3H);

$^{13}$C NMR (126 MHz, DMSO-$d_6$) δ (ppm) 168.0, 158.5, 149.7, 127.8, 126.8, 113.8, 99.3, 55.0;

HRMS calcd for $C_{10}H_{11}N_2OS$ [M+H]$^+$ 207.0587, found 207.0585.

Preparative Example 48

4-(naphthalen-2-yl)thiazol-2-amine

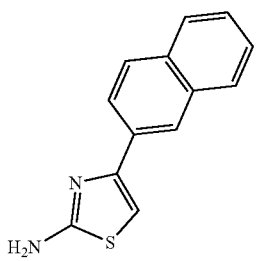 [SMILES: Nc1nc(-c2ccc3ccccc3c2)cs1]

The compound was prepared according to General procedure B from 2-bromo-2'-acetonaphthone (0.967 g, 3.88 mmol) and thiourea (0.443 g, 5.82 mmol) in EtOH (5 mL). Work-up 1 of General procedure B. The product, obtained as a pale pink solid (0.747 g, 85%), did not require any further purification.

$^1$H NMR (500 MHz, DMSO-$d_6$) δ (ppm) 8.32 (d, J=1.8 Hz, 1H), 7.99-7.84 (m, 4H), 7.55-7.43 (m, 2H), 7.16 (s, 1H), 7.09 (s, 2H);

$^{13}$C NMR (126 MHz, DMSO-$d_6$) δ (ppm) 168.2, 149.8, 133.2, 132.3, 132.2, 128.0, 127.8, 127.5, 126.3, 125.7, 124.0, 124.0, 102.4;

HRMS calcd for $C_{13}H_{11}N_2S$ [M+H]$^+$ 227.0637, found 227.0636.

Preparative Example 49

4-([1,1'-biphenyl]-4-yl)thiazol-2-amine

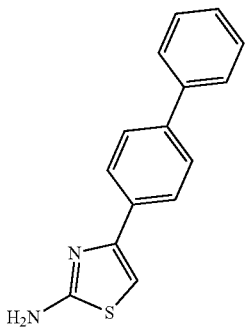 [SMILES: Nc1nc(-c2ccc(-c3ccccc3)cc2)cs1]

A mixture of dioxane and water (2.0+0.5 mL) was added to a mixture of 4-(4-bromophenyl)thiazol-2-amine (0.127 g, 0.5 mmol), phenylboronic acid (0.076 g, 0.62 mmol), $K_2CO_3$ (0.275 g, 1.99 mmol) and $PdCl_2(PPh_3)_2$ (0.035 g, 0.05 mmol). The reaction mixture was purged with $N_2$ for 5 min, then it was stirred at 80° C. for 16 h. The mixture was cooled to 25° C., diluted with EtOAc (5 mL), poured into a saturated aqueous solution of $NH_4Cl$ (20 mL), and extracted with EtOAc (3×25 mL). The combined organic extracts were washed with water (30 mL) and brine (30 mL), dried over $MgSO_4$, filtered, and the solvent was evaporated in vacuo. The residue was purified by column chromatography (hexane:EtOAc; 1:0 to 2:1). The product was obtained as a white solid (0.087 g, 55%).

$^1$H NMR (500 MHz, DMSO-$d_6$) δ (ppm) 7.9 (d, J=8.4 Hz, 2H), 7.7-7.6 (m, 4H), 7.5-7.4 (m, 2H), 7.4-7.3 (m, 1H), 7.1 (s, 1H), 7.0 (s, 2H);
$^{13}$C NMR (126 MHz, DMSO-$d_6$) δ (ppm) 168.2, 149.4, 139.7, 138.6, 128.9, 127.3, 126.6, 126.4, 126.0, 101.7;
HRMS calcd for $C_{15}H_{13}N_2S$ $[M+H]^+$ 253.0794, found 253.0796.

Preparative Example 50

4-(4-(trifluoromethoxy)phenylthiazol-2-amine

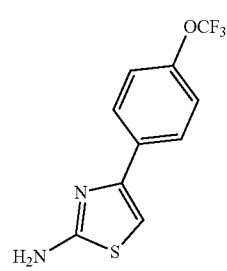 [SMILES: Nc1nc(-c2ccc(OC(F)(F)F)cc2)cs1]

The compound was prepared according to General procedure B from 2-bromo-4'-(trifluoromethoxy)acetophenone (0.260 g, 0.918 mmol) and thiourea (0.105 g, 1.38 mmol) in EtOH (6 mL). Work-up 1 of General procedure B. The product, obtained as a white solid (0.227 g, 95%), did not require any further purification.

$^1$H NMR (500 MHz, DMSO-$d_6$) δ (ppm) 7.95-7.85 (m, 2H), 7.38-7.30 (m, 2H), 7.12-7.03 (m, 3H);
$^{13}$C NMR (126 MHz, DMSO-$d_6$) δ (ppm) 168.4, 148.4, 147.2, 134.2, 127.2, 121.0, 120.1 (q, J=255.7 Hz), 102.5;
$^{19}$F NMR (471 MHz, DMSO-$d_6$) δ (ppm) −56.74;
HRMS calcd for $C_{10}H_8F_3N_2OS$ $[M+H]^+$ 261.0304, found 261.0303.

Preparative Example 51

4-(p-tolyl)thiazol-2-amine

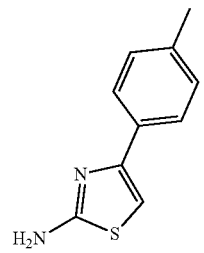

The compound was prepared according to General procedure B from 2-bromo-4'-methylacetophenone (0.598 g, 2.8 mmol) and thiourea (0.320 g, 4.21 mmol) in EtOH (6 mL). Work-up 1 of General procedure B. The product, obtained as a pale yellow solid (0.534 g, 100%), did not require any further purification.

$^1$H NMR (500 MHz, DMSO-$d_6$) δ (ppm) 7.68 (d, J=8.3 Hz, 2H), 7.16 (d, J=8.2 Hz, 2H), 6.98 (s, 2H), 6.90 (s, 1H), 2.30 (s, 3H);
$^{13}$C NMR (126 MHz, DMSO-$d_6$) δ (ppm) 168.0, 149.9, 136.3, 132.3, 129.0, 125.4, 101.0, 20.7;
HRMS calcd for $C_{10}H_{11}N_2S$ $[M+H]^+$ 191.0637, found 191.0636.

Preparative Example 52

5-(2-aminothiazol-4-yl)-2-methoxyphenol

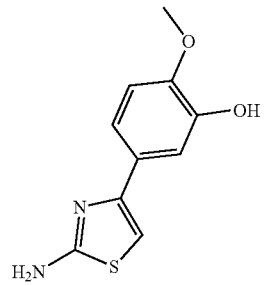

2-bromo-1-(3-hydroxy-4-methoxyphenyl)ethan-1-one was prepared according to General procedure A1 from 1-(3-hydroxy-4-methoxyphenyl)ethan-1-one (0.30 g, 1.8 mmol) and $Br_2$ (287.0 mg, 93 µL, 1.8 mmol) in $CH_2Cl_2$ (5 ml). The crude intermediate (2-bromo-1-(3-hydroxy-4-methoxyphenyl)ethan-1-one) was obtained as a white solid (0.44 g, 100%) and used as such in the next step:

5-(2-aminothiazol-4-yl)-2-methoxyphenol was prepared according to General procedure B from 2-bromo-1-(3-hydroxy-4-methoxyphenyl)ethan-1-one (200 mg, 0.8 mmol) and thiourea (90 mg, 1.2 mmol) in EtOH (3 mL). Work-up 2 of General procedure B. The product was obtained as a white solid (110 mg, 30%).

¹H NMR (500 MHz, DMSO-d₆) δ 8.88 (ppm) (s, 1H), 7.22 (d, J=2.1 Hz, 1H), 7.21-7.17 (m, 1H), 6.93 (s, 2H), 6.88 (d, J=8.4 Hz, 1H), 6.72 (s, 1H), 3.77 (s, 3H);
¹³C NMR (126 MHz, DMSO-d₆) δ (ppm) 167.8, 149.9, 147.1, 146.2, 128.3, 116.6, 113.1, 112.1, 99.2, 55.6;
HRMS calcd for $C_{10}H_{11}N_2O_2S$ [M+H]⁺ 223.0536, found 223.0535.

Preparative Example 53

2-(2-aminothiazol-4-yl)propan-2-ol

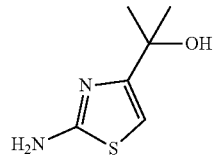

To a solution of ethyl-2-aminothiazole-4-carboxylate in anhydrous THF (5 mL) was slowly added MeMgCl (3M in THF, 2.9 mL, 8.7 mmol) at 0° C. The mixture was allowed to warm to 25° C. and stirred for 2 h. The reaction mixture was poured into a saturated aqueous solution of NH₄Cl (25 mL) and extracted with EtOAc (3×25 mL). The combined organic extracts were dried over MgSO₄, filtered, and the solvent was evaporated in vacuo. The residue was purified by column chromatography (EtOAc). The product was obtained as a white solid (160 mg, 60%).
¹H NMR (500 MHz, DMSO-d₆) δ (ppm) 6.76 (s, 2H), 6.21 (s, 1H), 4.72 (s, 1H), 1.34 (s, 6H);
¹³C NMR (126 MHz, DMSO-d₆) δ (ppm) 168.0, 160.5, 98.2, 70.1, 30.3;
HRMS calcd for $C_6H_{11}N_2OS$ [M+H]⁺ 159.0587, found 159.0588.

Preparative Example 54

4-(3-bromophenyl)thiazol-2-amine

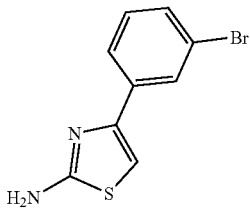 [SMILES: Nc1nc(-c2cccc(Br)c2)cs1]

2-bromo-1-(3-bromophenyl)ethan-1-one was prepared according to General procedure A1 from 1-(3-bromophenyl)ethan-1-one (1.50 g, 6.0 mmol) and Br₂ (960 mg, 310 μL, 6.0 mmol) in CH₂Cl₂ (5 ml). The crude intermediate (2-bromo-1-(3-bromophenyl)ethan-1-one) was obtained as a white solid (1.80 g, 90%) and used as such in the next step:

4-(3-bromophenyl)thiazol-2-amine was prepared according to General procedure B from 2-bromo-1-(3-bromophenyl)ethan-1-one (1.60 g, 6 mmol) and thiourea (690 mg, 9 mmol) in EtOH (10 mL). Work-up 2 of General procedure B. The product was obtained as a white solid (0.90 g, 60%).
¹H NMR (500 MHz, DMSO-d₆) δ (ppm) 7.99-7.97 (m, 1H), 7.82-7.76 (m, 1H), 7.47-7.40 (m, 1H), 7.34-7.30 (m, 1H), 7.15 (s, 1H), 7.09 (s, 2H);
¹³C NMR (126 MHz, DMSO-d₆) δ (ppm) 168.3, 148.0, 137.1, 130.6, 129.7, 128.1, 124.3, 121.9, 103.1;
HRMS calcd for $C_9H_8BrN_2S$ [M+H]⁺ 256.9586, found 256.9585.

Preparative Example 55

4-(2-bromophenyl)thiazol-2-amine

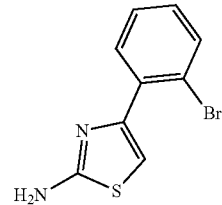

2-bromo-1-(2-bromophenyl)ethan-1-one was prepared according to General procedure A1 from 1-(2-bromophenyl)ethan-1-one (1.47 g, 7.41 mmol) and Br₂ (1.18 g, 380 μL, 7.41 mmol) in CH₂Cl₂ (10 mL). The crude intermediate (2-bromo-1-(2-bromophenyl)ethan-1-one) was obtained as a white solid (1.59 g, 80%) and used as such in the next step:
4-(2-bromophenyl)thiazol-2-amine was prepared according to General procedure B from 2-bromo-1-(2-bromophenyl)ethan-1-one (1.10 g, 4.1 mmol) and thiourea (850 mg, 11.11 mmol) in EtOH (10 mL). Work-up 2 of General procedure B. The product was obtained as a white solid (1.30 g, 70%).
¹H NMR (500 MHz, DMSO-d₆) δ (ppm) 7.70 (dd, J=7.8, 1.8 Hz, 1H), 7.66 (dd, J=8.0, 1.2 Hz, 1H), 7.40-7.37 (m, 1H), 7.24-7.20 (m, 1H), 7.02 (s, 2H), 6.94 (s, 1H);
¹³C NMR (126 MHz, DMSO-d₆) δ (ppm) 167.3, 148.0, 135.8, 133.4, 131.4, 129.0, 127.5, 120.6, 105.7;
HRMS calcd for $C_9H_8BrN_2S$ [M+H]⁺ 256.9565, found 256.9564.

Preparative Example 56

4-(3-(trifluoromethoxy)phenylthiazol-2-amine

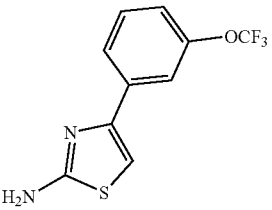 [SMILES: Nc1nc(-c2cccc(OC(F)(F)F)c2)cs1]

2-bromo-1-(3-(trifluoromethoxy)phenyl)ethan-1-one was prepared according to General procedure A1 from 1-(3-(trifluoromethoxy)phenyl)ethan-1-one (0.30 g, 1.46 mmol) and Br$_2$ (0.24 g, 75 µL, 1.46 mmol) in CH$_2$Cl$_2$ (5 mL). The crude intermediate (2-bromo-1-(3-(trifluoromethoxy)phenyl)ethan-1-one) was obtained as a white solid (370 mg, 90%) and used as such in the next step:

4-(3-(trifluoromethoxy)phenyl)thiazol-2-amine was prepared according to General procedure B from 2-bromo-1-(3-(trifluoromethoxy)phenyl)ethan-1-one (370 mg, 1.3 mmol) and thiourea (166 mg, 2.19 mmol) in EtOH (5 mL). Work-up 2 of General procedure B. The product was obtained as a white solid (170 mg, 45%).

$^1$H NMR (500 MHz, DMSO-d$_6$) δ (ppm) 7.85-7.79 (m, 1H), 7.75-7.69 (m, 1H), 7.51-7.48 (m, 1H), 7.27-7.20 (m, 1H), 7.19 (s, 1H), 7.12 (s, 2H);

$^{13}$C NMR (126 MHz, DMSO-d$_6$) δ (ppm) 168.4, 148.7, 148.0, 137.1, 130.4, 124.2, 120.1 (q, J=256.1 Hz), 119.3, 117.7, 103.4;

$^{19}$F NMR (471 MHz, DMSO-d$_6$) δ (ppm) −56.61;

HRMS calcd for C$_{10}$H$_8$F$_3$N$_2$OS [M+H]$^+$ 261.0304, found 261.0302.

Preparative Example 57

4-(4-phenoxyphenyl)thiazol-2-amine

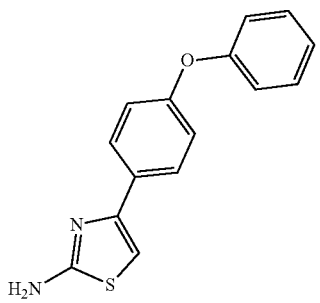 [SMILES: Nc1nc(-c2ccc(Oc3ccccc3)cc2)cs1]

2-bromo-1-(4-phenoxyphenyl)ethan-1-one was prepared according to General procedure A1 from 1-(4-phenoxyphenyl)ethan-1-one (0.90 g, 4.24 mmol) and Br$_2$ (0.67 g, 220 µL, 4.24 mmol) in CH$_2$Cl$_2$ (10 mL). The crude intermediate (2-bromo-1-(4-phenoxyphenyl)ethan-1-one) was obtained as a white solid (1.20 g, 100%) and used as such in the next step:

4-(4-phenoxyphenyl)thiazol-2-amine was prepared according to General procedure B from 2-bromo-1-(4-phenoxyphenyl)ethan-1-one (1.20 g, 4.24 mmol) and thiourea (480 mg, 6.36 mmol) in EtOH (10 ml). Work-up 2 of General procedure B. The product was obtained as a white solid (0.60 g, 55%).

$^1$H NMR (500 MHz, DMSO-d$_6$) δ (ppm) 7.86-7.74 (m, 2H), 7.45-7.36 (m, 2H), 7.18-7.12 (m, 1H), 7.07-6.97 (m, 4H), 6.94 (s, 1H), 6.92 (s, 2H);

$^{13}$C NMR (126 MHz, CDCl$_3$) δ (ppm) 168.2, 155.8, 155.2, 149.2, 132.8, 130.0, 127.2, 123.5, 120.7, 118.4, 100.6;

HRMS calcd for C$_{15}$H$_{13}$N$_2$OS [M+H]$^+$ 269.0743, found 269.0743.

Preparative Example 58

4-(benzofuran-2-yl)thiazol-2-amine

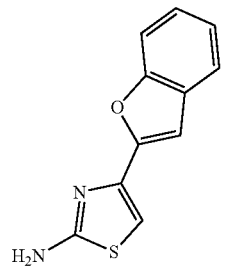 [SMILES: Nc1nc(-c2cc3ccccc3o2)cs1]

The compound was prepared according to General procedure B from 2-(bromoacetyl)benzofuran (0.30 g, 1.25 mmol), thiourea (0.143 g, 1.88 mmol) in EtOH (5 mL). Work-up 1 of General procedure B. The product (off-white solid, 0.271 g, 100%) did not require any additional purification.

$^1$H NMR (500 MHz, DMSO-d$_6$) δ (ppm) 7.65-7.60 (m, 1H), 7.60-7.52 (m, 1H), 7.33-7.26 (m, 1H), 7.26-7.17 (m, 3H), 7.04 (s, 1H), 6.96 (s, 1H);

$^{13}$C NMR (126 MHz, DMSO-d$_6$) δ (ppm) 168.8, 153.9, 152.2, 141.2, 128.5, 124.4, 123.1, 121.2, 110.8, 104.1, 101.9;

HRMS calcd for C$_{11}$H$_9$N$_2$OS [M+H]$^+$ 217.0430, found 217.0432.

Preparative Example 59

4-(adamantan-1-yl)thiazol-2-amine

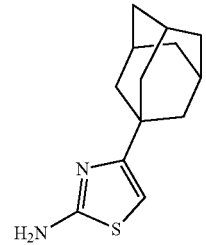 [SMILES: Nc1nc(C23CC4CC(CC(C4)C2)C3)cs1]

The compound was prepared according to General procedure B from 1-(adamantan-1-yl)-2-bromoethanone (0.30 g, 1.166 mmol) and thiourea (0.133 g, 1.75 mmol) in EtOH (3 mL). Work-up 2 of General procedure B. The product (off-white solid, 0.273 g, 100%) was used as such in the next step.

$^1$H NMR (500 MHz, DMSO-d$_6$) δ (ppm) 6.72 (s, 2H), 6.00 (s, 1H), 2.02-1.94 (m, 3H), 1.81 (d, J=3.1 Hz, 6H), 1.75-1.63 (m, 3H);

$^{13}$C NMR (126 MHz, DMSO-d$_6$) δ (ppm) 167.6, 161.8, 97.3, 41.5, 36.4, 35.9, 27.9;

HRMS calcd for C$_{13}$H$_{18}$N$_2$S [M+H]$^+$ 235.1263, found 235.1262.

Preparative Example 60

5-cyclohexyl-4-(4-(trifluoromethoxy)phenyl)thiazol-2-amine

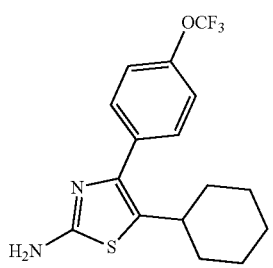 [SMILES: Nc1nc(-c2ccc(OC(F)(F)F)cc2)c(C2CCCCC2)s1]

2-bromo-2-cyclohexyl-1-(4-(trifluoromethoxy)phenyl)ethan-1-one was prepared according to General procedure A1 from 2-cyclohexyl-1-(4-(trifluoromethoxy)phenyl)ethan-1-one (0.20 g, 0.7 mmol) and Br$_2$ (0.11 g, 36 µL, 0.7 mmol) in CH$_2$Cl$_2$ (5 mL). The crude intermediate (2-bromo-1-(3-(trifluoromethoxy)phenyl)ethan-1-one) was obtained as a colorless oil (230 mg, 90%) and used as such in the next step:

5-cyclohexyl-4-(4-(trifluoromethoxy)phenyl)thiazol-2-amine was prepared according to General procedure B from 2-bromo-2-cyclohexyl-1-(4-(trifluoromethoxy)phenyl)ethan-1-one (230 mg, 0.63 mmol) and thiourea (72.0 mg, 0.95 mmol) in EtOH (5 mL). Work-up 2 of General procedure B. The product was obtained as a white solid (121 mg, 55%) and did not require any further purification.

$^1$H NMR (500 MHz, DMSO-d$_6$) δ (ppm) 7.60-7.55 (m, 2H), 7.45-7.34 (m, 2H), 6.79 (s, 2H), 2.91-2.78 (m, 1H), 1.92-1.88 (m, 2H), 1.78-1.69 (m, 2H), 1.68-1.61 (m, 1H), 1.37-1.13 (m, 5H);

$^{13}$C NMR (126 MHz, DMSO-d$_6$) δ (ppm) 164.7, 147.0, 142.1, 135.1, 129.8, 128.9, 120.7, 120.1 (q, J=256.2 Hz), 36.5, 35.9, 26.0, 25.2;

HRMS calcd for C$_{16}$H$_{18}$F$_3$N$_2$OS [M+H]$^+$ 343.1086, found 343.1080.

Preparative Example 61

5-bromo-4-phenylthiazol-2-amine

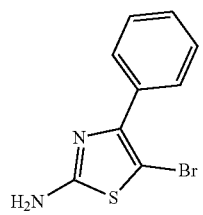 [SMILES: Nc1nc(-c2ccccc2)c(Br)s1]

A solution of NBS (1.062 g, 5.97 mmol) in CH$_2$Cl$_2$ (15 mL) was added to a solution of 4-phenylthiazol-2-amine (1.052 g, 5.97 mmol) in CH$_2$Cl$_2$ (50 mL) and the mixture was stirred at 25° C. for 2 h. A saturated aqueous solution of NH$_4$Cl (25 mL) was added to the mixture, the organic phase was separated, washed with water (25 mL), brine (25 mL), dried over MgSO$_4$, filtered, and the solvent was evaporated in vacuo. The residue was purified by column chromatography (hexane:EtOAc; 1:0 to 1:1). The product was obtained as a pale purple solid (1.211 g, 80%).

$^1$H NMR (500 MHz, DMSO-d$_6$) δ (ppm) 7.83-7.78 (m, 2H), 7.45-7.39 (m, 2H), 7.38-7.32 (m, 1H), 7.28 (s, 2H);

$^{13}$C NMR (126 MHz, DMSO-d$_6$) δ (ppm) 166.9, 147.2, 133.7, 128.1, 127.9, 87.0;

HRMS calcd for C$_9$H$_8$BrN$_2$S [M+H]$^+$ 256.9565, found 256.9565.

Preparative Example 62

4,5-diphenylthiazol-2-amine

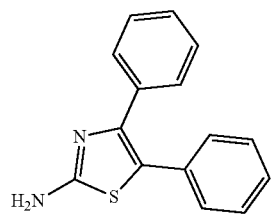 [SMILES: Nc1nc(-c2ccccc2)c(-c2ccccc2)s1]

A mixture of dioxane and water (2.0 mL+0.5 mL) was added to a mixture of 5-bromo-4-phenylthiazol-2-amine (0.116 g, 0.455 mmol), phenylboronic acid (0.069 g, 0.568 mmol), K$_2$CO$_3$ (0.251 g, 1.82 mmol) and Pd(PPh$_3$)$_4$ (0.026 g, 0.023 mmol). The reaction mixture mixture was degassed by bubbling N$_2$ for 5 min, then it was stirred at 55° C. for 5 h and then at 75° C. for 16 h. The mixture was cooled to 25° C., diluted with EtOAc (5 mL), poured into a saturated aqueous solution of NH$_4$Cl (20 mL) and extracted with EtOAc (3×25 mL). The combined organic extracts were washed with water (20 mL) and brine (20 mL), dried over MgSO$_4$, filtered, and the solvent was evaporated in vacuo. The residue was purified by column chromatography (hexane:EtOAc; 1:0 to 1:1). The product was obtained as a white solid (0.035 g, 30%).

$^1$H NMR (500 MHz, DMSO-d$_6$) δ (ppm) 7.39-7.35 (m, 2H), 7.31-7.18 (m, 8H), 7.09 (s, 2H);

$^{13}$C NMR (126 MHz, DMSO-d$_6$) δ (ppm) 166.0, 144.9, 135.4, 132.8, 128.9, 128.6, 128.4, 128.0, 127.2, 127.0, 119.0;

HRMS calcd for C$_{15}$H$_{13}$N$_2$S [M+H]$^+$ 253.0794, found 253.0793.

Preparative Example 63

4-(4-morpholinophenyl)thiazol-2-amine

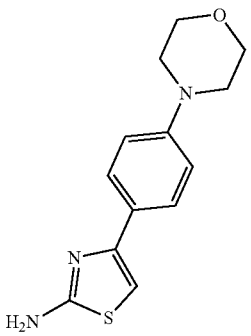 [SMILES: Nc1nc(-c2ccc(N3CCOCC3)cc2)cs1]

2-bromo-1-(4-morpholinophenyl)ethan-1-one was prepared according to General procedure A2 from 1-(4-morpholinophenyl)ethanone (0.29 g, 1.41 mmol), CuBr$_2$ (0.789 g, 3.53 mmol) in CHCl$_3$ (2 mL) and EtOAc (2 mL). The crude product was used as such in the next step.

4-(4-morpholinophenyl)thiazol-2-amine was prepared according to General procedure B from 2-bromo-1-(4-morpholinophenyl)ethan-1-one (400 mg, 1.41 mmol) and thiourea (215 mg, 2.826 mmol) in EtOH (10 mL). Work-up 1 of General procedure B. The product, purified by column chromatography (hexane:EtOAc; 1:0 to 1:4), was obtained as an orange-red solid (76 mg, 21%).

$^1$H NMR (300 MHz, CDCl$_3$) δ (ppm) 7.65 (d, J=8.9 Hz, 2H), 6.97-6.86 (m, 4H), 6.75 (s, 1H), 3.78-3.68 (m, 4H), 3.15-3.08 (m, 4H);

$^{13}$C NMR (126 MHz, CDCl$_3$) δ (ppm) 167.9, 150.1, 126.3, 114.7, 98.6, 66.0, 48.2;

HRMS calcd for C$_{13}$H$_{16}$N$_3$OS [M+H]$^+$ 262.1009, found 262.1008.

Preparative Example 64

4-(5-(trifluoromethylpyridin-2-yl)thiazol-2-amine

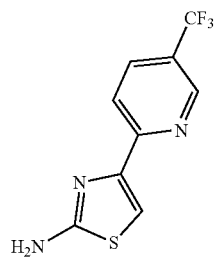 [SMILES: Nc1nc(-c2ccc(C(F)(F)F)cn2)cs1]

2-bromo-1-(5-(trifluoromethyl)pyridin-2-yl)ethan-1-one was prepared according to General procedure A4 from 1-(5-trifluoromethyl)pyridine-2-yl]ethanone (0.369 g, 1.95 mmol) and Br$_2$ (0.343 g, 100 µL, 2.146 mmol) in AcOH (5 mL). The crude intermediate was obtained as an off-white solid in a quantitative yield and used as such in the next step.

4-(5-(trifluoromethyl)pyridin-2-yl)thiazol-2-amine was prepared according to General procedure B from 2-bromo-1-(5-(trifluoromethyl)pyridin-2-yl)ethan-1-one (0.52 g, 1.94 mmol) and thiourea (223 mg, 2.93 mmol) in EtOH (5 mL). Work-up 1 of General procedure B. The product, purified by column chromatography (hexane:EtOAc; 2:1 to 0:1), was obtained as an off-white solid (359 mg, 75%).

$^1$H NMR (300 MHz, DMSO-d$_6$) δ (ppm) 8.91-8.87 (m, 1H), 8.21 (dd, J=8.4, 2.6 Hz, 1H), 7.99 (d, J=8.2 Hz, 1H), 7.46 (s, 1H), 7.23 (s, 2H);

$^{13}$C NMR (126 MHz, DMSO-d$_6$) δ (ppm) 168.8, 155.6, 148.6, 146.0 (q, J=4.1 Hz), 134.7 (q, J=3.7 Hz), 124.0 (q, J=271.8 Hz); 123.0 (q, J=32.2 Hz), 119.9, 108.5;

$^{19}$F NMR (471 MHz, DMSO-d$_6$) δ (ppm) −60.68;

HRMS calcd for C$_9$H$_7$F$_3$N$_3$S [M+H]$^+$ 246.0307, found 246.0309.

Preparative Example 65

3-(2-aminothiazol-4-yl)benzonitrile

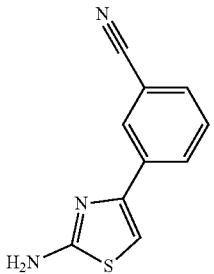 [SMILES: N#Cc1cccc(-c2csc(N)n2)c1]

3-(2-bromoacetyl)benzonitrile was prepared according to General procedure A1 from 3-acetylbenzonitrile (1.00 g, 7.08 mmol) and Br$_2$ (1.13 g, 360 µL, 7.08 mmol) in CH$_2$Cl$_2$ (10 mL). The crude intermediate (3-(2-bromoacetyl)benzonitrile) was obtained as a white solid in quantitative yield and was used as such in the next step:

3-(2-aminothiazol-4-yl)benzonitrile was prepared according to General procedure B from 3-(2-bromoacetyl)benzonitrile (1.6 g, 7.08 mmol) and thiourea (810 mg, 10.6 mmol) in EtOH (5 mL). Work-up 2 of General procedure B. The product was obtained as a white solid (950 mg, 70%).

$^1$H NMR (500 MHz, DMSO-d$_6$) δ (ppm) 8.21-8.18 (m, 1H), 8.14-8.09 (m, 1H), 7.72-7.69 (m, 1H), 7.61-7.55 (m, 1H), 7.25 (s, 1H), 7.13 (s, 2H);

$^{13}$C NMR (126 MHz, DMSO-d$_6$) δ (ppm) 168.5, 147.6, 135.9, 130.4, 129.9, 129.8, 128.8, 118.8, 111.6, 103.8;

HRMS calcd for C$_{10}$H$_8$N$_3$S [M+H]$^+$ 202.0433, found 202.0437.

Preparative Example 66

4-(2-aminothiazol-4-yl)-N,N-dimethylbenzamide

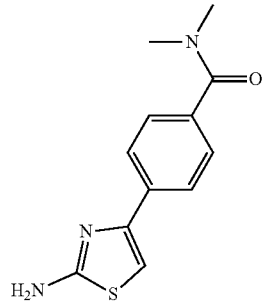

4-(2-bromoacetyl)-N,N-dimethylbenzamide was prepared according to General procedure A2 from 4-acetyl-N,N-dimethylbenzamide (0.335 g, 1.75 mmol) and CuBr$_2$ (0.78 g, 3.5 mmol) in CHCl$_3$ (3 mL) and EtOAc (3 mL). The crude intermediate was used as such in the next step.

4-(2-aminothiazol-4-yl)-N,N-dimethylbenzamide was prepared according to General procedure B from 4-(2-bromoacetyl)-N,N-dimethylbenzamide (473 mg, 1.75 mmol) and thiourea (200 mg, 2.6 mmol) in EtOH (3 mL). Work-up 1 of General procedure B. The product, purified by column chromatography (CH₂Cl₂:EtOAc; 7:3 to 0:1), was obtained as a white solid (220 mg, 50%).

¹H NMR (500 MHz, DMSO-d₆) δ (ppm) 7.86-7.81 (m, 2H), 7.43-7.36 (m, 2H), 7.05 (s, 1H), 6.91 (s, 2H), 2.97 (s, 6H);

¹³C NMR (126 MHz, DMSO-d₆) δ (ppm) 169.8, 168.0, 149.0, 135.5, 134.8, 126.9, 125.0, 102.4;

HRMS calcd for $C_{12}H_{14}N_3OS$ [M+H]⁺ 248.0852, found 248.0850.

Preparative Example 67

Methyl 4-(2-aminothiazol-4-yl)benzoate

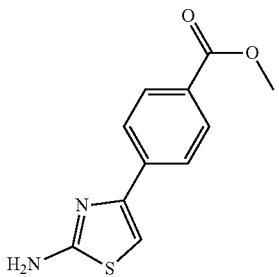 [SMILES: COC(=O)c1ccc(-c2csc(N)n2)cc1]

Methyl 4-(2-bromoacetyl)benzoate was prepared according to General procedure A1 from methyl 4-acetylbenzoate (1.00 g, 5.6 mmol) and Br₂ (0.90 g, 290 µL, 5.6 mmol) in CH₂Cl₂ (10 ml). The crude intermediate (methyl 4-(2-bromoacetyl)benzoate) was obtained as a white solid and used as such in the next step.

Methyl 4-(2-aminothiazol-4-yl)benzoate was prepared according to General procedure B from methyl 4-(2-bromoacetyl)benzoate (1.40 g, 5.6 mmol) and thiourea (640 mg, 8.4 mmol) in EtOH (10 mL). Work-up 2 of General procedure B. The product was obtained as a white solid (1.06 g, 82%).

¹H NMR (500 MHz, DMSO-d₆) δ (ppm) 7.99-7.89 (m, 4H), 7.23 (s, 1H), 7.12 (s, 2H), 3.85 (s, 3H);

¹³C NMR (126 MHz, DMSO-d₆) δ (ppm) 168.3, 166.0, 148.7, 139.1, 129.5, 127.8, 125.5, 104.4, 52.0;

HRMS calcd for $C_{11}H_{11}N_2O_2S$ [M+H]⁺ 235.0536, found 235.0533.

Preparative Example 68

2-(4-(2-aminothiazol-4-yl)phenyl)propan-2-ol

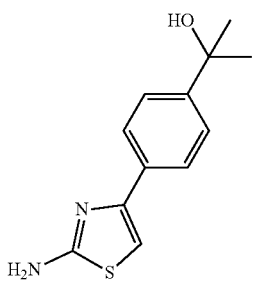 [SMILES: CC(C)(O)c1ccc(-c2csc(N)n2)cc1]

To a solution of methyl 4-(2-aminothiazol-4-yl)benzoate (300 mg, 1.28 mmol) in THF (5 mL) was added a solution of MeMgCl (3M in THF, 2.1 mL, 6.4 mmol) at −78° C. and the reaction mixture was stirred at 25° C. for 1 h. The mixture was poured into a saturated aqueous solution of NH₄Cl (20 mL) and extracted with EtOAc (3×10 mL). The combined organic extracts were washed with brine (20 mL), dried over MgSO₄, filtered, and the solvent was evaporated in vacuo. The residue was purified by column chromatography (hexane:EtOAc; 7:3). The product was obtained as a white solid (160 mg, 55%).

¹H NMR (500 MHz, DMSO-d₆) δ (ppm) 7.71 (d, J=8.4 Hz, 2H), 7.44 (d, J=8.3 Hz, 2H), 6.99 (s, 2H), 6.92 (s, 1H), 4.95 (s, 1H), 1.43 (s, 6H);

¹³C NMR (126 MHz, DMSO-d₆) δ (ppm) 168.0, 149.9, 149.4, 132.7, 124.9, 124.6, 100.7, 70.5, 31.8;

HRMS calcd for $C_{12}H_{15}N_2OS$ [M+H]⁺ 235.0900, found 235.0902.

Preparative Example 69

5-(2-aminothiazol-4-yl)thiophene-2-carbonitrile

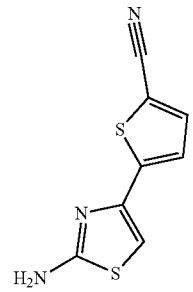

5-(2-bromoacetyl)thiophene-2-carbonitrile was prepared according to General procedure A2 from 5-acetylthiophene-2-carbonitrile (0.25 g, 1.65 mmol) and CuBr₂ (0.74 g, 3.3 mmol) in CHCl₃ (3 mL) and EtOAc (3 mL). The crude intermediate was used as such in the next step.

5-(2-aminothiazol-4-yl)thiophene-2-carbonitrile was prepared according to General procedure B from 5-(2-bromoacetyl)thiophene-2-carbonitrile (380 mg, 1.65 mmol) and thiourea (188 mg, 2.5 mmol) in EtOH (5 mL). Work-up 2 of General procedure B. The product was obtained as a white solid (243 mg, 71%).

¹H NMR (500 MHz, DMSO-d₆) δ (ppm) 7.87 (d, J=4.0 Hz, 1H), 7.54 (d, J=4.0 Hz, 1H), 7.32 (s, 2H), 7.25 (s, 1H);

¹³C NMR (126 MHz, DMSO-d₆) δ (ppm) 168.7, 146.6, 142.5, 139.7, 122.8, 114.9, 105.4, 104.3;

HRMS calcd for $C_8H_6N_3S_2$ [M+H]⁺ 207.9998, found 207.9995.

Preparative Example 70

4-(thiophen-2-yl)thiazol-2-amine

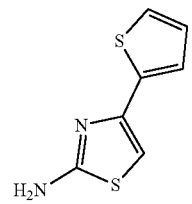 [SMILES: Nc1nc(-c2cccs2)cs1]

The compound was prepared according to General procedure B from 2-bromo-1-(2-thienyl)ethanone (0.506 g, 2.47 mmol) and thiourea (0.282 g, 3.70 mmol) in EtOH (7 mL). Work-up 1 of General procedure B. The product, obtained as a pale yellow solid (0.447 g, 99%), did not require any additional purification.

$^1$H NMR (500 MHz, DMSO-d$_6$) δ (ppm) 7.39 (dd, J=5.0, 1.4 Hz, 1H), 7.36 (dd, J=3.7, 1.4 Hz, 1H), 7.11 (s, 2H), 7.03 (dd, J=5.1, 3.6 Hz, 1H), 6.83 (s, 1H);

$^{13}$C NMR (126 MHz, DMSO-d$_6$) δ (ppm) 168.2, 144.5, 139.2, 127.7, 124.6, 122.7, 99.7;

HRMS calcd for C$_7$H$_7$N$_2$S$_2$[M+H]$^+$ 183.0045, found 183.0045.

Preparative Example 71

4-(3,5-difluorophenyl)thiazol-2-amine

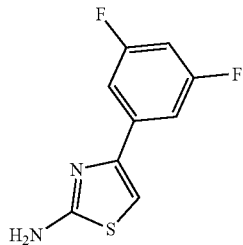 [SMILES: Nc1nc(-c2cc(F)cc(F)c2)cs1]

2-bromo-1-(3,5-difluorophenyl)ethan-1-one was prepared according to General procedure A1 from 3',5'-difluoroacetophenone (0.309 g, 1.98 mmol) and Br$_2$ (0.316 g, 101 μL, 1.98 mmol) in CH$_2$Cl$_2$ (16 mL). The crude intermediate (2-bromo-1-(3,5-difluorophenyl)ethan-1-one) was obtained as a pale yellow oil in quantitative yield and used as such in the next step.

4-(3,5-difluorophenyl)thiazol-2-amine was prepared according to General procedure B from 2-bromo-1-(3,5-difluorophenyl)ethan-1-one (449 mg, 1.91 mmol) and thiourea (226 mg, 2.97 mmol) in EtOH (6 mL). Work-up 1 of General procedure B. The product, purified by column chromatography (hexane:EtOAc; 1:0 to 2:1), was obtained as a white solid (334 mg, 79%).

$^1$H NMR (500 MHz, DMSO-d$_6$) δ (ppm) 7.52-7.44 (m, 2H), 7.27 (s, 1H), 7.14 (s, 2H), 7.09 (tt, J=9.1, 2.3 Hz, 1H);

$^{13}$C NMR (126 MHz, DMSO-d$_6$) δ (ppm) 168.8, 163.1 (dd, J=244.3, 13.6 Hz), 148.0, 138.9 (dd, J=10.0 Hz), 108.8 (d, J=26.3 Hz), 105.0, 102.7 (dd, J=25.9 Hz);

$^{19}$F NMR (471 MHz, DMSO-d$_6$) δ (ppm) −110.03;

HRMS calcd for C$_9$H$_7$F$_2$N$_2$S [M+H]$^+$ 213.0293, found 213.0294.

Preparative Example 72

4-(pyridazin-3-yl)thiazol-2-amine

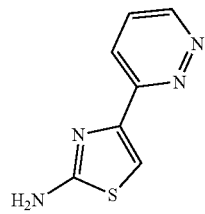 [SMILES: Nc1nc(-c2cccnn2)cs1]

2-bromo-1-(pyridazin-3-yl)ethan-1-one was prepared according to General procedure A4 from 1-(pyridazine-3-yl)ethanone (0.244 g, 2.0 mmol) and Br$_2$ (0.319 g, 100 μL, 2.0 mmol) in AcOH (5 mL) and HBr (47% in H$_2$O, 0.69 mL, 6.0 mmol). The crude 2-bromo-1-(pyridazin-3-yl)ethan-1-one was obtained as an orange solid and used as such in the next step.

4-(pyridazin-3-yl)thiazol-2-amine was prepared according to General procedure B from 2-bromo-1-(pyridazin-3-yl)ethan-1-one (0.155 g, 0.771 mmol) and thiourea (230 mg, 3.0 mmol) in EtOH (8 mL).

Work-up 1 of General procedure B. The product, purified by column chromatography (EtOAc:MeOH; 1:0 to 5:1), was obtained as an orange-red solid (66 mg, 19%).

$^1$H NMR (500 MHz, DMSO-d$_6$) δ (ppm) 9.11 (dd, J=4.8, 1.9 Hz, 1H), 7.98 (dd, J=8.5, 2.1 Hz, 1H), 7.71 (dd, J=8.5, 5.0 Hz, 1H), 7.53 (s, 1H), 7.25 (s, 2H);

$^{13}$C NMR (126 MHz, DMSO-d$_6$) δ (ppm) 149.8, 127.2, 123.3, 106.5;

HRMS calcd for C$_9$H$_7$N$_4$S [M+H]$^+$ 179.0386, found 179.0388.

Preparative Example 73

4-(4-fluorophenyl)thiazol-2-amine

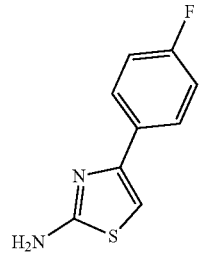 [SMILES: Nc1nc(-c2ccc(F)cc2)cs1]

4-(4-fluorophenyl)thiazol-2-amine was prepared according to General procedure B from 2-bromo-4'-fluoroacetophenone (586 mg, 2.70 mmol) and thiourea (308 mg, 4.05 mmol) in EtOH (8 mL). Work-up 1 of General procedure B. The product, purified by column chromatography (hexane:EtOAc; 1:0 to 1:1), was obtained as a white solid (502 mg, 96%).

$^1$H NMR (500 MHz, DMSO-d$_6$) δ (ppm) 7.86-7.78 (m, 2H), 7.23-7.13 (m, 2H), 7.03 (s, 2H), 6.96 (s, 1H);

$^{13}$C NMR (126 MHz, DMSO-d$_6$) δ (ppm) 168.3, 161.3 (d, J=244.3 Hz), 148.8, 131.5, 127.4 (d, J=8.2 Hz), 115.2 (d, J=20.9 Hz), 101.2;

$^{19}$F NMR (471 MHz, DMSO-d$_6$) δ (ppm) −115.16;

HRMS calcd for C$_9$H$_8$FN$_2$S [M+H]$^+$ 195.0387, found 195.0388.

Preparative Example 74

4-(pyridin-4-yl)thiazol-2-amine

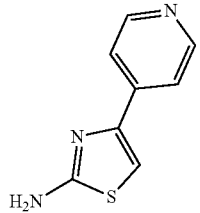 [SMILES: Nc1nc(-c2ccncc2)cs1]

4-acetylpyridine (1.00 mL, 9.04 mmol) was added to a solution of HBr (47% in H$_2$O, 4.56 mL, 27.12 mmol) in AcOH (20 mL) at 25° C. Bromine (1.59 g, 0.51 mL, 9.94 mmol) was added dropwise to the solution, then a white precipitate appeared slowly. The mixture was stirred for 20 h. Diethyl ether (20 mL) was added, the solid was filtered and washed with diethyl ether (2×5 mL). After drying under vacuum, 4-(2-bromoacetyl)pyridin-1-ium bromide was obtained as an off-white solid (2.529 g) which was used without further purification.

4-(pyridin-4-yl)thiazol-2-amine was prepared according to general procedure B from 4-(2-bromoacetyl)pyridin-1-ium bromide (1.483 g, 5.28 mmol) and thiourea (0.603 g, 7.92 mmol) in EtOH (15 mL). The solvent was evaporated in vacuo. The residue was sonicated in diethyl ether (10 mL) and the orange solid was collected by filtration. The solid was mixed with NaOH (2M in H$_2$O, 20 mL) and EtOAc (50 mL). The organic extract was washed with water (20 mL), brine (20 mL), dried over MgSO$_4$, filtered, and the solvent was evaporated in vacuo. The product was obtained as an orange solid (0.889 g, 95%).

$^1$H NMR (500 MHz, DMSO-d$_6$) δ (ppm) 8.57-8.50 (m, 2H), 7.77-7.67 (m, 2H), 7.37 (s, 1H), 7.17 (s, 2H);

$^{13}$C NMR (126 MHz, DMSO-d$_6$) δ (ppm) 168.6, 150.0, 147.5, 141.4, 119.8, 106.1;

HRMS calcd for C$_8$H$_8$N$_3$S [M+H]$^+$ 178.0433, found 178.0432.

Preparative Example 75

Methyl 4-(2-aminothiazol-4-yl)benzoate

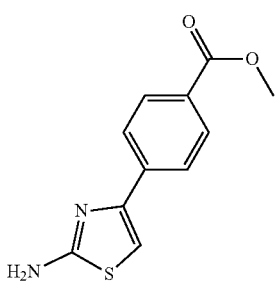 [SMILES: COC(=O)c1ccc(-c2csc(N)n2)cc1]

Methyl 4-(2-bromoacetyl)benzoate was prepared according to General procedure A1 from methyl 4-acetylbenzoate (1.00 g, 5.6 mmol) and Br$_2$ (0.90 g, 290 µL, 5.6 mmol) in CH$_2$Cl$_2$ (10 mL). The crude intermediate (methyl 4-(2-bromoacetyl)benzoate) was obtained as a white solid and used as such in the next step.

Methyl 4-(2-aminothiazol-4-yl)benzoate was prepared according to General procedure B from methyl 4-(2-bromoacetyl)benzoate (1.40 g, 5.6 mmol) and thiourea (640 mg, 8.4 mmol) in EtOH (10 mL). Work-up 2 of General procedure B. The product was obtained as a white solid (1.06 g, 82%).

$^1$H NMR (500 MHz, DMSO-d$_6$) δ (ppm) 7.99-7.89 (m, 4H), 7.23 (s, 1H), 7.12 (s, 2H), 3.85 (s, 3H);

$^{13}$C NMR (126 MHz, DMSO-d$_6$) δ (ppm) 168.3, 166.0, 148.7, 139.1, 129.5, 127.8, 125.5, 104.4, 52.0;

HRMS calcd for C$_{11}$H$_{11}$N$_2$O$_2$S [M+H]$^+$ 235.0536, found 235.0533.

Preparative Example 76

4,5,6,7-tetrahydrobenzo[d]thiazol-2-amine

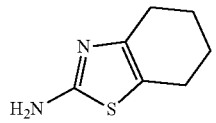

To cyclohexanone (4.70 g, 5.0 mL, 48.0 mmol) in CH$_2$Cl$_2$ (10 mL) at 0° C. was added a solution of NBS (10.23 g, 57 mmol) and TsOH (0.90 g, 4.8 mmol) in CH$_2$Cl$_2$ (40 ml). The mixture was stirred at 25° C. for 3 h. Water (30 mL) was added to the mixture, the organic phase was separated, dried over MgSO$_4$, filtered, and the solvent was evaporated in vacuo. 2-bromocyclohexan-1-one, obtained as a white solid (7.16 g, 85%), was used in the next step without further purification.

4,5,6,7-tetrahydrobenzo[d]thiazol-2-amine was prepared according to general procedure B with 2-bromocyclohexan-1-one (0.51 g, 2.9 mmol) and thiourea (330 mg, 4.35 mmol) in EtOH (5 mL). Workup 2 of General procedure B. The product was obtained as a white solid (350 mg, 80%).

$^1$H NMR (300 MHz, DMSO-d$_6$) δ (ppm) 6.54 (s, 2H), 2.48-2.31 (m, 4H), 1.75-1.63 (m, 4H);

$^{13}$C NMR (75 MHz, DMSO-d$_6$) δ (ppm) 165.3, 144.7, 114.5, 26.2, 23.2, 22.6, 22.5;

HRMS calcd for C$_7$H$_{11}$N$_2$S [M+H]$^+$ 155.0598, found 155.0596.

Preparative Example 77

5-methyl-4-phenylthiazol-2-amine

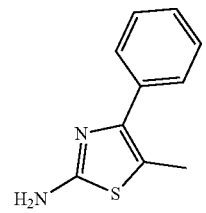

The compound was prepared according to General procedure B from 2-bromo-1-phenylpropan-1-one (1.555 g, 7.3 mmol) and thiourea (0.839 g, 11.02 mmol) in EtOH (15 mL). Work-up 1 of General procedure B. The product was obtained as a yellow solid (1.361 g, 98%).

$^1$H NMR (500 MHz, DMSO-d$_6$) δ (ppm) 7.55 (d, J=7.0 Hz, 2H), 7.38 (dd, J=7.7 Hz, 2H), 7.31-7.23 (m, 1H), 6.74 (s, 2H), 2.32 (s, 3H);

$^{13}$C NMR (126 MHz, DMSO-d$_6$) δ (ppm) 164.2, 144.9, 135.4, 128.0, 127.9, 126.6, 114.6, 12.1;

HRMS calcd for C$_{10}$H$_{11}$N$_2$S [M+H]$^+$ 191.0637, found 191.0637.

Preparative Example 78

5-chloro-4-phenylthiazol-2-amine

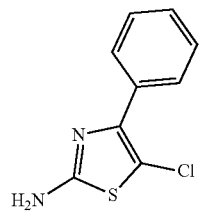

To a solution of 4-phenylthiazol-2-amine (150 mg, 0.84 mmol) in CH$_2$Cl$_2$ (5 mL) was slowly added a solution of NCS (124 mg, 0.93 mmol) in CH$_2$Cl$_2$ (5 mL) at 0° C. The reaction mixture was stirred at 25° C. for 4 h. Water (20 mL) was added and the mixture was extracted with EtOAc (3×20 mL). The combined organic extracts were dried over MgSO$_4$, filtered, and the solvent was evaporated in vacuo. The product, purified by column chromatography on silica gel (hexane:EtOAc; 1:1), was obtained as a white solid (160 mg, 91%).

$^1$H NMR (500 MHz, CDCl$_3$) δ (ppm) 7.86 (dd, J=8.4, 1.3 Hz, 2H), 7.42 (d, J=7.8 Hz, 2H), 7.35 (t, J=7.4 Hz, 1H), 5.08 (s, 2H);

$^{13}$C NMR (126 MHz, CDCl$_3$) δ (ppm) 163.2, 145.6, 133.1, 128.5, 128.4, 128.3, 108.7;

HRMS calcd for C$_9$H$_8$ClN$_2$S [M+H]$^+$ 211.0091, found 211.0090.

Preparative Example 79

5-bromo-4-phenylthiazol-2-amine

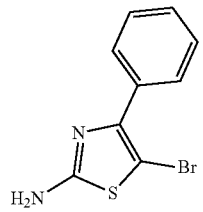 [SMILES: Nc1nc(-c2ccccc2)c(Br)s1]

A solution of NBS (1.062 g, 5.97 mmol) in CH$_2$Cl$_2$ (15 mL) was added to a solution of 2-amino-4-phenylthiazole (1.052 g, 5.97 mmol) in CH$_2$Cl$_2$ (50 mL) and the mixture was stirred at 25° C. for 2 h. A saturated aqueous solution of NH$_4$Cl (25 mL) was added to the mixture. The organic part was separated, washed with water (25 mL), brine (25 mL), dried over MgSO$_4$, filtered, and the solvent was evaporated in vacuo. The product, purified by column chromatography on silica gel (hexane:EtOAc; 1:0 to 1:1), was obtained as a pale purple solid (1.211 mg, 80%).

$^1$H NMR (500 MHz, DMSO-d$_6$) δ (ppm) 7.83-7.78 (m, 2H), 7.45-7.39 (m, 2H), 7.38-7.32 (m, 1H), 7.28 (s, 2H);

$^{13}$C NMR (126 MHz, DMSO-d$_6$) δ (ppm) 166.9, 147.2, 133.7, 128.1, 127.9, 87.0;

HRMS calcd for C$_9$H$_8$BrN$_2$S [M+H]$^+$ 256.9565, found 256.9565.

Preparative Example 80

4-(4-((trimethylsilyl)ethynyl)phenyl)thiazol-2-amine

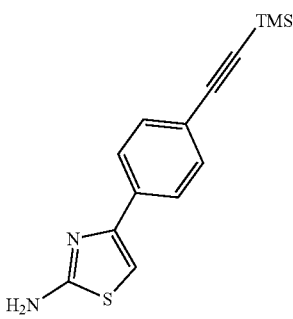 [SMILES: C[Si](C)(C)C#Cc1ccc(-c2csc(N)n2)cc1]

2-bromo-1-(4-((trimethylsilyl)ethynyl)phenyl)ethan-1-one was prepared according to General procedure A2 from 1-(4-((trimethylsilyl)ethynyl)phenyl)ethan-1-one (0.25 g, 1.15 mmol) and CuBr$_2$ (0.52 g, 2.3 mmol) in CHCl$_3$ (4 mL) and EtOAc (4 mL). The crude intermediate was used as such in the next step. 4-(4-((trimethylsilyl)ethynyl)phenyl)thiazol-2-amine was prepared according to General procedure B from 2-bromo-1-(4-((trimethylsilyl)ethynyl)phenyl)ethan-1-one (340 mg, 1.15 mmol) and thiourea (133 mg, 1.73 mmol) in EtOH (5 mL). Work-up 2 of General procedure B. The product was obtained as a white solid (100 mg, 30%) and did not require any further purification.

$^1$H NMR (500 MHz, CDCl$_3$) δ (ppm) 7.75-7.70 (m, 2H), 7.50-7.45 (m, 2H), 6.77 (s, 1H), 5.04 (s, 2H), 0.27 (s, 9H);

$^{13}$C NMR (126 MHz, CDCl$_3$) δ (ppm) 167.3, 150.9, 134.8, 132.5, 125.9, 122.5, 105.4, 104.1, 95.1, 0.2;

HRMS calcd for C$_{14}$H$_{17}$N$_2$SSi [M+H]$^+$ 273.0876, found 273.0873.

Preparative Example 81

4-(3-cyclopropyl-4-methoxyphenyl)thiazol-2-amine

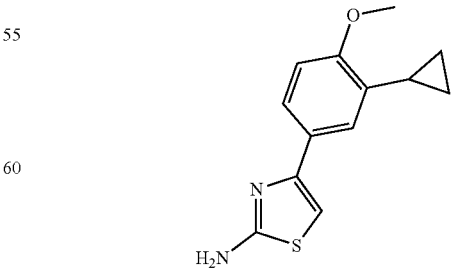

2-bromo-1-(3-cyclopropyl-4-methoxyphenyl)ethan-1-one was prepared according to General procedure A2 from 1-(3-cyclopropyl-4-methoxyphenyl)ethan-1-one (0.12 g, 0.7 mmol) and CuBr$_2$ (0.31 g, 1.4 mmol) in CHCl$_3$ (2 mL) and EtOAc (2 mL). The crude intermediate was used as such in the next step.

4-(3-cyclopropyl-4-methoxyphenyl)thiazol-2-amine was prepared according to General procedure B from 2-bromo-1-(3-cyclopropyl-4-methoxyphenyl)ethan-1-one (188 mg, 0.7 mmol) and thiourea (75 mg, 0.95 mmol) in EtOH (3 mL). Work-up 1 of General procedure B. The product, purified by column chromatography (hexane:EtOAc; 7:3), was obtained as a white solid (100 mg, 60%).

$^1$H NMR (500 MHz, CDCl$_3$) δ (ppm) 7.55 (dd, J=8.5, 2.3 Hz, 1H), 7.28 (d, J=2.3 Hz, 1H), 6.85 (d, J=8.4 Hz, 1H), 6.56 (s, 1H), 5.12 (s, 2H), 3.90 (s, 3H), 2.18 (tt, J=8.5, 5.4 Hz, 1H), 0.99-0.90 (m, 2H), 0.79-0.70 (m, 2H);

$^{13}$C NMR (126 MHz, CDCl$_3$) δ (ppm) 167.3, 158.4, 151.6, 132.3, 127.6, 124.3, 123.2, 110.5, 101.1, 55.9, 9.8, 7.8;

HRMS calcd for C$_{13}$H$_{17}$N$_2$OS [M+2H+H]$^+$ 249.1056, found 249.1060.

Preparative Example 82

4-(5-bromothiophen-2-yl)thiazol-2-amine

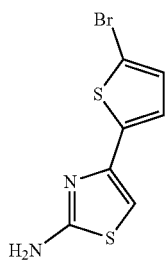 [SMILES: Nc1nc(-c2ccc(Br)s2)cs1]

2-bromo-1-(5-bromothiophen-2-yl)ethan-1-one was prepared according to General procedure A2 from 2-acetyl-5-bromothiophene (0.53 g, 2.58 mmol) and CuBr$_2$ (1.15 g, 5.16 mmol) in chloroform (10 mL) and ethyl acetate (10 mL); the reaction time was 2 h. The crude intermediate (2-bromo-1-(5-bromothiophen-2-yl)ethan-1-one) was obtained as a yellow solid (630 mg) which was used as such in the next step. 4-(5-bromothiophen-2-yl)thiazol-2-amine was prepared according to General procedure B from 2-bromo-1-(5-bromothiophen-2-yl)ethan-1-one (630 mg, 2.21 mmol) and thiourea (253 mg, 3.32 mmol) in EtOH (15 mL). Work-up 1 of General procedure B. The product, purified by column chromatography on silica gel (hexane:EtOAc; 1:0 to 1:1), was obtained as a pale yellow solid (250 mg, 38%).

$^1$H NMR (500 MHz, CDCl$_3$) δ (ppm) 7.07 (d, J=3.91 Hz, 1H), 6.97 (d, J=3.90 Hz, 1H), 6.56 (s, 1H), 5.17 (brs, 2H);

$^{13}$C NMR (126 MHz, CDCl$_3$) δ (ppm) 167.5, 144.7, 140.0, 130.6, 123.6, 111.8, 101.9;

HRMS calcd for C$_7$H$_6$BrN$_2$S$_2$ [M+H]$^+$ 262.9128, found 262.9131.

Preparative Example 83

4-(4-(tert-butyl)phenyl)thiazol-2-amine

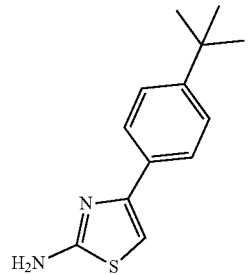 [SMILES: CC(C)(C)c1ccc(-c2csc(N)n2)cc1]

4-(4-(tert-butyl)phenyl)thiazol-2-amine was prepared according to General procedure B from 1-(4-(tert-butyl)phenyl)-2-chloroethanone (570 mg, 2.705 mmol) and thiourea (309 mg, 4.058 mmol) in EtOH (15 mL). The reaction mixture was stirred at 90° C. for 3 h. Work-up 1 of General procedure B. The product, purified by column chromatography (hexane:EtOAc, 10:1 to 1:1), was obtained as a white solid (616 mg, 98%).

$^1$H NMR (500 MHz, DMSO-d$_6$) δ (ppm) 7.73-7.68 (m, 2H), 7.40-7.34 (m, 2H), 6.99 (s, 2H), 6.90 (s, 1H), 1.29 (s, 9H);

$^{13}$C NMR (126 MHz, DMSO-d$_6$) δ (ppm) 168.1, 149.9, 149.5, 132.3, 125.2, 125.1, 100.6, 34.2, 31.1;

HRMS calcd for C$_{13}$H$_{17}$N$_2$S [M+H]$^+$ 233.1107, found 233.1107.

Preparative Example 84

4-(5-methylthiophen-2-yl)thiazol-2-amine

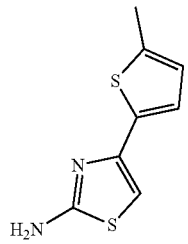

2-bromo-1-(5-methylthiophen-2-yl)ethan-1-one was prepared according to General procedure A2 from 1-(5-methylthiophen-2-yl)ethan-1-one (0.37 g, 2.66 mmol) and CuBr$_2$ (1.20 g, 5.3 mmol) in CHCl$_3$ (2 mL) and EtOAc (2 mL). The crude intermediate was used as such in the next step.

4-(5-methylthiophen-2-yl)thiazol-2-amine was prepared according to General procedure B from 2-bromo-1-(5-methylthiophen-2-yl)ethan-1-one (580 mg, 2.66 mmol) and thiourea (300 mg, 4 mmol) in EtOH (5 mL). Work-up 2 of General procedure B. The product was obtained as a white solid (450 mg, 85%).

$^1$H NMR (500 MHz, DMSO-d$_6$) δ (ppm) 7.13 (d, J=3.5 Hz, 1H), 7.06 (s, 2H), 6.71 (dd, J=3.6, 1.2 Hz, 1H), 6.70 (s, 1H), 2.41 (d, J=1.1 Hz, 3H);

$^{13}$C NMR (126 MHz, DMSO-d$_6$) δ (ppm) 168.6, 145.2, 138.4, 137.4, 126.4, 123.1, 99.3, 15.4;

HRMS calcd for $C_8H_8N_2S_2[M+H]^+$ 197.0202, found 197.0199.

Preparative Example 85

N-(4-phenylthiazol-2-yl) formamide

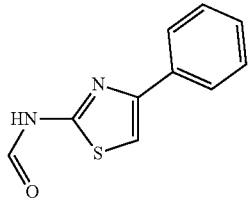 [SMILES: O=CNc1nc(-c2ccccc2)cs1]

The compound was prepared according to General procedure C1 from 4-phenylthiazol-2-amine (1.23 g, 6.9 mmol), methyl formate (0.70 g, 0.85 mL, 10 mmol) (instead of ethyl cyanoacetate), and NaOEt (21% in EtOH, 2.60 mL, 6.9 mmol) in EtOH (2 mL). The mixture was stirred at 50° C. for 21 h. The product, purified by column chromatography (toluene:EtOAc; 1:1), was obtained as a white solid (1.26 g, 90%).

$^1$H NMR (500 MHz, DMSO-$d_6$) δ (ppm) 12.37 (s, 1H), 8.52 (s, 1H), 7.93-7.87 (m, 2H), 7.66 (d, J=1.0 Hz, 1H), 7.43 (dd, J=8.4, 7.0 Hz, 2H), 7.37-7.29 (m, 1H);

$^{13}$C NMR (126 MHz, DMSO-$d_6$) δ (ppm) 159.7, 156.2, 148.9, 134.1, 128.7, 127.8, 125.7, 108.4;

HRMS calcd for $C_{10}H_9N_2OS$ $[M+H]^+$ 205.0430, found 205.0433.

Preparative Example 86

N-methyl-4-phenylthiazol-2-amine

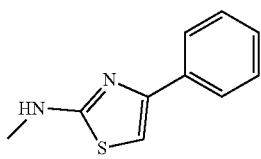

A solution of LiAlH$_4$ (1M in THF, 9.80 mL, 9.8 mmol) was slowly added to a solution of N-(4-phenylthiazol-2-yl) formamide (1.00 g, 4.9 mmol) in THF (5 mL) at 0° C. The mixture was allowed to warm up to 25° C. and stirred for 16 h. A saturated aqueous solution of NH$_4$Cl (15 mL) was added at 0° C., and the mixture was extracted with EtOAc (3×10 mL). The combined organic extracts were dried over MgSO$_4$, filtered, and the solvent was evaporated in vacuo. The residue was purified by column chromatography (hexane:EtOAc; 1:1). The product was obtained as a white solid (650 mg, 70%).

$^1$H NMR (500 MHz, CDCl$_3$) δ (ppm) 7.82-7.77 (m, 2H), 7.42-7.38 (m, 2H), 7.34-7.30 (m, 1H), 6.71 (s, 1H), 6.08 (s, 1H), 3.05 (d, J=3.6 Hz, 3H);

$^{13}$C NMR (126 MHz, CDCl$_3$) δ (ppm) 171.0, 150.1, 133.8, 129.0, 128.4, 126.2, 100.5, 32.6;

HRMS calcd for $C_{10}H_{11}N_2S$ $[M+H]^+$ 191.0637, found 191.0639.

Preparative Example 87

4-(6-methylpyridin-3-yl)thiazol-2-amine

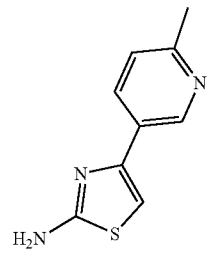

2-bromo-1-(6-methylpyridin-3-yl)ethan-1-one was prepared from 1-(6-methylpyridin-3-yl)ethan-1-one (0.5 g, 3.7 mmol), which was dissolved in HBr (47% in H$_2$O, 0.67 ml, 11.1 mmol) and CH$_3$COOH (3 mL), MeOH (3 mL). Br$_2$ (448 mg, 0.14 mL, 3.7 mmol) was added and the mixture was stirred at 25° C. for 16 h. The solvent was evaporated in vacuo, the residue was poured into a saturated aqueous solution of NaHCO$_3$ (50 mL) and the mixture was extracted with EtOAc (3×10 mL). Combined organic fractions were washed with brine (10 mL), dried over MgSO$_4$ and the solvent was evaporated in vacuo. The crude intermediate (2-bromo-1-(6-methylpyridin-3-yl)ethan-1-one) was used as such in the next step:

4-(6-methylpyridin-3-yl)thiazol-2-amine was prepared according to General procedure B from 2-bromo-1-(6-methylpyridin-3-yl)ethan-1-one (790 mg, 3.7 mmol) and thiourea (420 mg, 5.5 mmol) in EtOH (5 mL). Work-up 2 of General procedure B. The product was obtained as a white solid (350 mg, 65%).

$^1$H NMR (500 MHz, DMSO-$d_6$) δ (ppm) 8.87 (d, J=2.2 Hz, 1H), 8.00 (dd, J=8.0, 2.3 Hz, 1H), 7.23 (d, J=8.1 Hz, 1H), 7.10 (s, 2H), 7.08 (s, 1H), 2.46 (s, 3H);

$^{13}$C NMR (126 MHz, DMSO-$d_6$) δ (ppm) 168.5, 156.3, 147.1, 146.1, 132.9, 127.8, 122.8, 102.0, 23.7;

HRMS calcd for $C_9H_{10}N_3S$ $[M+H]^+$ 192.0590, found 192.0588.

Preparative Example 88

4-phenyl-5-(tetrahydro-2H-pyran-4-yl)thiazol-2-amine

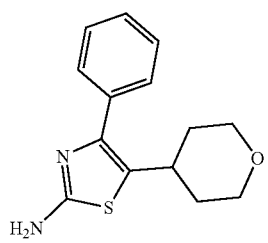

2-bromo-1-phenyl-2-(tetrahydro-2H-pyran-4-yl)ethan-1-one was prepared according to General procedure A2 from 1-phenyl-2-(tetrahydro-2H-pyran-4-yl)ethan-1-one (235 mg, 1.15 mmol) and CuBr$_2$ (0.51 g, 2.3 mmol, 36 μL) in CHCl$_3$ (2 mL) and EtOAc (2 mL). The crude intermediate was used as such in the next step.

4-(4-methylthiophen-2-yl)thiazol-2-amine was prepared according to General procedure B from 2-bromo-1-(4-methylthiophen-2-yl)ethan-1-one (650 mg, 2.3 mmol) and thiourea (260 mg, 3.45 mmol) in EtOH (5 mL). Work-up 2 of General procedure B. The product was obtained as a white solid (66 mg, 45%).

$^1$H NMR (500 MHz, CDCl$_3$) δ (ppm) 7.51-7.46 (m, 2H), 7.45-7.40 (m, 2H), 7.38-7.32 (m, 1H), 5.10 (s, 2H), 4.01 (dd, J=11.8, 4.6, 1.1 Hz, 2H), 3.43 (td, J=11.8, 2.1 Hz, 2H), 3.19 (tt, J=11.7, 4.0 Hz, 1H), 1.89-1.81 (m, 2H), 1.81-1.70 (m, 2H);

$^{13}$C NMR (126 MHz, CDCl$_3$) δ (ppm) 164.5, 145.3, 135.4, 129.4, 128.7, 128.7, 128.0, 68.2, 36.1, 34.5;

HRMS calcd for C$_{14}$H$_{17}$N$_2$O [M+H]$^+$ 261.1056, found 261.1053.

Preparative Example 89

4-(3-fluorophenyl)thiazol-2-amine

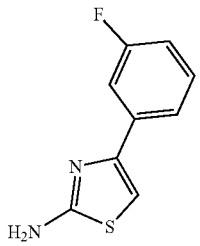 [SMILES: Nc1nc(-c2cccc(F)c2)cs1]

4-(4-methylthiophen-2-yl)thiazol-2-amine was prepared according to General procedure B from 2-bromo-1-(3-fluorophenyl)ethanone (300 mg, 1.382 mmol) and thiourea (158 mg, 2.073 mmol) in EtOH (5 mL). Work-up 2 of General procedure B. The product was obtained as an off-white solid (242 mg, 90%).

$^1$H NMR (500 MHz, DMSO-d$_6$) δ (ppm) 7.64 (d, J=7.9 Hz, 1H), 7.57 (ddd, J=10.8, 2.7, 1.5 Hz, 1H), 7.43-7.36 (m, 1H), 7.13 (s, 1H), 7.11-7.02 (m, 3H);

$^{13}$C NMR (126 MHz, DMSO-d$_6$) δ (ppm) 168.2, 162.4 (d, J=242.5 Hz), 148.5, 137.3 (d, J=8.2 Hz), 130.4 (d, J=9.1 Hz), 121.5, 113.7 (d, J=20.9 Hz), 112.0 (d, J=22.7 Hz), 103.0;

$^{19}$F NMR (471 MHz, DMSO-d$_6$) δ (ppm) −113.4;

HRMS calcd for C$_9$H$_8$FN$_2$S [M+H]$^+$ 195.0387, found 195.0385.

Preparative Example 90

4-phenyl-5-(pyrazin-2-yl)thiazol-2-amine

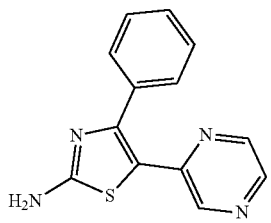 [SMILES: Nc1nc(-c2ccccc2)c(-c2cnccn2)s1]

2-bromo-1-phenyl-2-(pyrazin-2-yl)ethan-1-one was prepared according to General procedure A3 from 1-phenyl-2-(pyrazin-2-yl)ethan-1-one (0.2 g, 1 mmol), Et$_3$N (0.12 g, 0.17 mL, 1.2 mmol), TMSOTf (0.245 g, 0.2 mL, 1.1 mmol) and NBS (0.2 g, 1.1 mmol) in CH$_2$Cl$_2$ (3 mL). The crude intermediate was used as such in the next step.

4-phenyl-5-(pyrazin-2-yl)thiazol-2-amine was prepared according to General procedure B from 2-bromo-1-phenyl-2-(pyrazin-2-yl)ethan-1-one (277 mg, 1 mmol) and thiourea (115 mg, 1.5 mmol) in EtOH (3 mL). Work-up 2 of General procedure B. The product was obtained as a yellow solid (150 mg, 60%).

$^1$H NMR (500 MHz, DMSO-d$_6$) δ (ppm) 8.50-8.47 (m, 1H), 8.25 (d, J=2.6 Hz, 1H), 8.10 (d, J=1.6 Hz, 1H), 7.52 (s, 2H), 7.50-7.46 (m, 2H), 7.43 (dt, J=4.5, 2.7 Hz, 3H);

$^{13}$C NMR (126 MHz, DMSO-d$_6$) δ (ppm) 168.8, 150.5, 148.4, 143.9, 141.2, 140.3, 135.7, 128.7, 128.6, 128.6, 117.8;

HRMS calcd for C$_{13}$H$_{11}$N$_4$S [M+H]$^+$ 255.0699, found 255.0695.

Preparative Example 91

4-(3-methylpyridin-2-yl)thiazol-2-amine

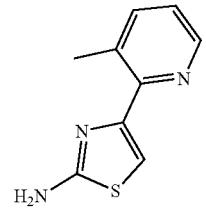

2-bromo-1-(3-methylpyridin-2-yl)ethan-1-one was prepared according to General procedure A3 from 1-(3-methylpyridin-2-yl)ethan-1-one (0.34 g, 2.5 mmol), Et$_3$N (0.28 g, 0.39 mL, 2.76 mmol), TMSOTf (0.61 g, 0.5 mL, 2.76 mmol) and NBS (0.49 g, 2.76 mmol) in CH$_2$Cl$_2$ (3 mL). The crude product was used as such in the next step.

4-(3-methylpyridin-2-yl)thiazol-2-amine was prepared according to General procedure B from 2-bromo-1-(3-methylpyridin-2-yl)ethan-1-one (0.54 g, 2.5 mmol) and thiourea (285 mg, 3.75 mmol) in EtOH (3 mL). Work-up 2 of General procedure B. The product was obtained as a white solid (340 mg, 70%).

$^1$H NMR (500 MHz, DMSO-d$_6$) δ (ppm) 8.37 (dd, J=4.8, 1.6 Hz, 1H), 7.62-7.57 (m, 1H), 7.22-7.17 (m, 1H), 6.99 (s, 1H), 6.95 (s, 2H), 2.52 (s, 3H);

$^{13}$C NMR (126 MHz, DMSO-d$_6$) δ (ppm) 167.4, 151.8, 151.3, 146.2, 139.0, 130.7, 122.1, 107.1, 20.2;

HRMS calcd for C$_9$H$_{10}$N$_3$S [M+H]$^+$ 192.0590, found 192.0592.

Preparative Example 92

4-(6-methoxypyridin-3-yl)thiazol-2-amine

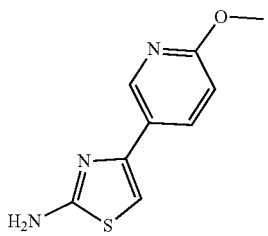

2-bromo-1-(6-methoxypyridin-3-yl)ethan-1-one was prepared according to General procedure A3 from 1-(6-methoxypyridin-3-yl)ethan-1-one (0.3 g, 2 mmol), Et$_3$N (0.25 g, 0.35 mL, 2.51 mmol), TMSOTf (0.51 g, 0.42 mL, 2.31 mmol) and NBS (0.45 g, 2.51 mmol) in CH$_2$Cl$_2$ (3 mL). The crude intermediate was used as such in the next step.

4-(6-methoxypyridin-3-yl)thiazol-2-amine was prepared according to General procedure B from 2-bromo-1-(6-methoxypyridin-3-yl)ethan-1-one (460 mg, 2 mmol) and thiourea (270 mg, 3.43 mmol) in EtOH (3 mL). Work-up 2 of General procedure B. The product was obtained as a pale yellow solid (320 mg, 80%).

$^1$H NMR (500 MHz, CDCl$_3$) δ (ppm) 8.60-8.56 (m, 1H), 7.94 (dd, J=8.6, 2.5 Hz, 1H), 6.76 (dd, J=8.7, 0.7 Hz, 1H), 6.62 (s, 1H), 5.25 (s, 2H), 3.97 (s, 3H);

$^{13}$C NMR (126 MHz, CDCl$_3$) δ (ppm) 167.9, 163.9, 148.7, 144.8, 136.7, 124.6, 110.8, 102.0, 53.8;

HRMS calcd for C$_9$H$_{10}$N$_3$OS [M+H]$^+$ 208.0539, found 208.0536.

Preparative Example 93

4-(3-methoxypyridin-2-yl)thiazol-2-amine

2-bromo-1-(3-methoxypyridin-2-yl)ethan-1-one was prepared according to General procedure A3 from 1-(3-methoxypyridin-2-yl)ethan-1-one (0.4 g, 2.6 mmol), Et$_3$N (0.32 g, 440 µL, 3.13 mmol), TMSOTf (0.7 g, 0.57 mL, 3.13 mmol) and NBS (0.55 g, 3.1 mmol) in CH$_2$Cl$_2$ (3 mL). The crude intermediate was used as such in the next step.

4-(3-methoxypyridin-2-yl)thiazol-2-amine was prepared according to General procedure B from 2-bromo-1-(3-methoxypyridin-2-yl)ethan-1-one (0.6 g, 2.6 mmol) and thiourea (300 mg, 3.9 mmol) in EtOH (3 mL). Work-up 2 of General procedure B. The product was obtained as a white solid (265 mg, 50%).

$^1$H NMR (500 MHz, DMSO-d$_6$) δ (ppm) 8.15 (dd, J=4.5, 1.4 Hz, 1H), 7.47 (dd, J=8.3, 1.3 Hz, 1H), 7.27 (dd, J=8.3, 4.5 Hz, 1H), 7.15 (s, 1H), 6.97 (s, 2H), 3.86 (s, 3H);

$^{13}$C NMR (126 MHz, DMSO-d$_6$) δ (ppm) 166.5, 153.2, 147.5, 142.1, 140.3, 122.8, 118.8, 108.6, 55.5;

HRMS calcd for C$_9$H$_{10}$N$_3$OS [M+H]$^+$ 208.0539, found 208.0536.

Preparative Example 94

4-(pyridin-2-yl)thiazol-2-amine

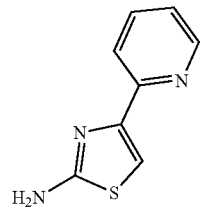 [SMILES: Nc1nc(-c2ccccn2)cs1]

To a solution of 1-(pyridin-2-yl)ethan-1-one (1.21 g, 10 mmol) in anhydrous THF (2 mL) at −78° C. was added NaHMDS (1M in THF, 11 mL, 11 mmol). The mixture was allowed to warm to 25° C. and stirred for 1 h. The mixture was then cooled to −78° C., TMSCl (1.30 g, 1.50 mL, 12 mmol) was added and the mixture was stirred at 25° C. for 16 h. The mixture was cooled to 0° C., NBS (1.96 g, 11 mmol) was added and the mixture was stirred at 0° C. for 30 min. The crude mixture was pre-adsorbed on a plug of silica gel and the product was quickly eluted with hexane:EtOAc (1:1). The crude intermediate (2-bromo-1-(pyridin-2-yl)ethan-1-one) was obtained as a pale yellow solid, which was used as such in the next step.

4-(pyridin-2-yl)thiazol-2-amine was prepared according to General procedure B from 2-bromo-1-(pyridin-2-yl)ethan-1-one (1.47 g, 7.4 mmol) and thiourea (840 mg, 11 mmol) in EtOH (5 mL). Work-up 2 of General procedure B. The product was obtained as a white solid (1.2 g, 68%).

$^1$H NMR (500 MHz, DMSO-d$_6$) δ (ppm) 8.53 (dt, J=4.7, 1.4 Hz, 1H), 7.84-7.77 (m, 2H), 7.27-7.22 (m, 2H), 7.07 (s, 2H);

$^{13}$C NMR (126 MHz, DMSO-d$_6$) δ (ppm) 168.4, 152.4, 150.1, 149.2, 136.9, 122.2, 120.1, 105.3;

HRMS calcd for C$_8$H$_8$N$_3$S [M+H]$^+$ 178.0433, found 178.0435.

Preparative Example 95

4-(4-methylsulfonyl)phenyl)thiazol-2-amine

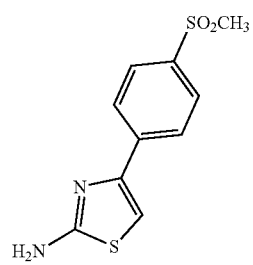 [SMILES: CS(=O)(=O)c1ccc(-c2csc(N)n2)cc1]

2-bromo-1-(4-(methylsulfonyl)phenyl)ethan-1-one was prepared according to General procedure A2 from 1-(4-(methylsulfonyl)phenyl)ethan-1-one (0.4 g, 2 mmol) and CuBr$_2$ (0.89 g, 4 mmol) in CHCl$_3$:EtOAc (1:1, 6 mL). The crude intermediate (2-bromo-1-(4-(methylsulfonyl)phenyl)ethan-1-one) was obtained as a white solid, which was used as such in the next step.

4-(4-(methylsulfonyl)phenyl)thiazol-2-amine was prepared according to General procedure B from 2-bromo-1-(4-(methylsulfonyl)phenyl)ethan-1-one (0.55 g, 2 mmol) and thiourea (230 mg, 3 mmol) in EtOH (3 mL). Work-up 2 of General procedure B. The product was obtained as a white solid (390 mg, 75%).

$^1$H NMR (500 MHz, DMSO-d$_6$) δ (ppm) 8.05-8.02 (m, 2H), 7.93-7.88 (m, 2H), 7.29 (s, 1H), 7.15 (s, 2H), 3.21 (s, 3H);

$^{13}$C NMR (126 MHz, DMSO-d$_6$) δ (ppm) 168.5, 148.2, 139.4, 138.8, 127.3, 126.0, 105.2, 43.6;

HRMS calcd for C$_{10}$H$_{11}$N$_2$O$_2$S$_2$ [M+H]$^+$ 255.0256, found 255.0259.

Preparative Example 96

4-(4-(tert-butyl)-2,6-dimethylphenyl)thiazol-2-amine

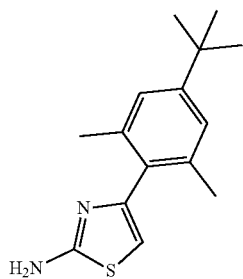 [SMILES: Cc1cc(C(C)(C)C)cc(C)c1-c1csc(N)n1]

2-bromo-1-(4-(tert-butyl)-2,6-dimethylphenyl)ethanone was prepared according to General procedure A2 from 1-(4-(tert-butyl)-2,6-dimethylphenyl)ethanone (0.110 g, 5.38 mmol) and CuBr$_2$ (0.240 g, 10.08 mmol) in CHCl$_3$ (2 mL) and EtOAc (2 mL). The crude intermediate was used as such in the next step.

4-(4-(tert-butyl)-2,6-dimethylphenyl)thiazol-2-amine was prepared according to General procedure B from 2-bromo-1-(4-(tert-butyl)-2,6-dimethylphenyl)ethanone (133 mg, 5.38 mmol) and thiourea (62 mg, 8.07 mmol) in EtOH (2 mL). Work-up 2 of General procedure B. The product was obtained as a white solid (85 mg, 71%).

$^1$H NMR (500 MHz, CDCl$_3$) δ (ppm) 7.07 (s, 2H), 6.29 (s, 1H), 2.18 (s, 6H), 1.31 (s, 9H);

$^{13}$C NMR (126 MHz, CDCl$_3$) δ (ppm) 166.9, 151.0, 149.8, 137.1, 132.2, 124.5, 105.9, 34.5, 31.5, 20.8;

HRMS calcd for C$_{15}$H$_{21}$N$_2$S [M+H]$^+$ 261.1420, found 261.1423.

Preparative Example 97

3-(tert-butyl)phenyl)thiazol-2-amine

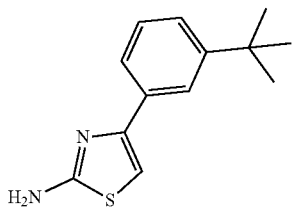 [SMILES: CC(C)(C)c1cccc(-c2csc(N)n2)c1]

2-bromo-1-(3-(tert-butyl)phenyl)ethanone was prepared according to General procedure A2 from 1-(3-(tert-butyl)phenyl)ethanone (0.250 g, 1.41 mmol) and CuBr$_2$ (0.633 g, 2.83 mmol) in CHCl$_3$ (4 mL) and EtOAc (4 mL). The crude intermediate was used as such in the next step.

4-(3-(tert-butyl)phenyl)thiazol-2-amine was prepared according to General procedure B from 2-bromo-1-(3-(tert-butyl)phenyl)ethanone (359 mg, 1.41 mmol) and thiourea (160 mg, 2.11 mmol) in EtOH (4 mL). Work-up 2 of General procedure B. The product was obtained as a white solid (85 mg, 71%).

$^1$H NMR (500 MHz, CDCl$_3$) δ (ppm) 7.83 (m, 1H), 7.57 (dt, J=6.5, 1.9 Hz, 1H), 7.38-7.28 (m, 2H), 6.71 (s, 1H), 5.06 (br s, 2H), 1.36 (s, 9H).

Preparative Example 98

(2-aminothiazol-4-yl)(phenyl)methanone

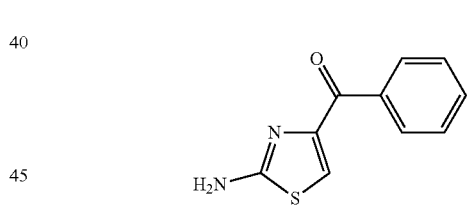

3-bromo-1-phenylpropane-1,2-dione was prepared according to General procedure A1 from 1-phenylpropane-1,2-dione (0.55 g, 3.7 mmol) and Br$_2$ (0.6 g, 200 μL, 3.7 mmol) in CH$_2$Cl$_2$ (5 mL). The crude intermediate (3-bromo-1-phenylpropane-1,2-dione) was obtained as a brown solid, which was used as such in the next step.

(2-aminothiazol-4-yl)(phenyl)methanone was prepared according to General procedure B from methyl 4-(2-bromoacetyl)benzoate (0.84 g, 3.7 mmol) and thiourea (0.56 g, 7.4 mmol) in EtOH (10 mL). Work-up 2 of General procedure B. The product was obtained as a white solid (0.7 g, 95%).

$^1$H NMR (300 MHz, DMSO-d$_6$) δ (ppm) 8.05-7.94 (m, 2H), 7.65-7.56 (m, 1H), 7.55-7.49 (m, 2H), 7.48 (s, 1H), 7.26 (s, 2H);

$^{13}$C NMR (75 MHz, DMSO-d$_6$) δ (ppm) 186.5, 168.1, 149.8, 137.7, 132.2, 129.6, 128.1, 118.7;

HRMS calcd for C$_{10}$H$_9$N$_2$OS [M+H]$^+$ 205.0430, found 205.0427.

Preparative Example 99

5-(pyrazin-2-yl)-4-(pyridin-2-yl)thiazol-2-amine

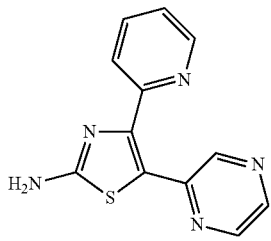 [SMILES: Nc1nc(-c2ccccn2)c(-c2cnccn2)s1]

2-bromo-2-(pyrazin-2-yl)-1-(pyridin-2-yl)ethan-1-one was prepared according to General procedure A3 from 12-(pyrazin-2-yl)-1-(pyridin-2-yl)ethan-1-one (0.5 g, 2.5 mmol), Et$_3$N (0.33 g, 0.45 mL, 3.25 mmol), TMSOTf (0.61 g, 0.5 mL, 2.75 mmol) and NBS (0.49 g, 2.75 mmol) in CH$_2$Cl$_2$ (5 mL). The crude intermediate was used as such in the next step.

5-(pyrazin-2-yl)$_4$-(pyridin-2-yl)thiazol-2-amine was prepared according to General procedure B from 2-bromo-2-(pyrazin-2-yl)-1-(pyridin-2-yl)ethan-1-one (695 mg, 2.5 mmol) and thiourea (285 mg, 3.75 mmol) in EtOH (5 mL). Work-up 2 of General procedure B. The product was obtained as a white solid (260 mg, 40%).

$^1$H NMR (500 MHz, DMSO-d$_6$) δ (ppm) 8.54 (d, J=1.7 Hz, 1H), 8.51-8.46 (m, 2H), 8.31 (d, J=2.7 Hz, 1H), 7.96-7.88 (m, 1H), 7.84-7.77 (m, 1H), 7.50 (s, 2H), 7.40 (ddd, J=1.2, 4.7, 7.5 Hz, 1H);

$^{13}$C NMR (126 MHz, DMSO-d$_6$) δ (ppm) 168.6, 153.6, 148.6, 148.3, 147.9, 143.3, 143.2, 140.6, 137.1, 123.7, 123.6, 120.7;

HRMS calcd for C$_{12}$H$_{10}$N$_5$S [M+H]$^+$ 256.0651, found 256.0650.

Preparative Example 100

4-(6-morpholinopyridin-2-yl)thiazol-2-amine

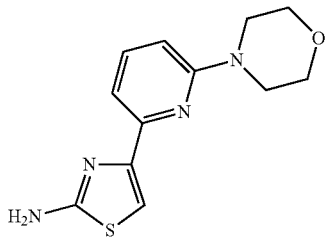

The compound was prepared according to General procedure E from tert-butyl (4-methoxybenzyl)(4-(6-morpholinopyridin-2-yl)thiazol-2-yl)carbamate (0.109 g, 0.226 mmol) and trifluoroacetic acid (1 mL); the reaction time was 3 hours at 70° C. The product, purified by flash column chromatography (hexane:EtOAc; 2:1 to 1:3), was obtained as a white solid (48 mg, 0.183 mmol, 81%).

$^1$H NMR (500 MHz, Chloroform-d) δ (ppm) 7.55 (dd, J=8.5, 7.3 Hz, 1H), 7.29 (d, J=7.5 Hz, 1H), 7.26 (s, 1H), 6.57 (d, J=8.4 Hz, 1H), 3.82-3.87 (m, 4H), 3.53-3.59 (m, 4H);

$^{13}$C NMR (126 MHz, Chloroform-d) δ (ppm) 167.3, 159.1, 151.9, 150.7, 138.5, 111.1, 107.1, 106.2, 67.0, 45.8;

HRMS calcd for C$_{12}$H$_{15}$N$_4$OS [M+H]$^+$ 263.0961, found 263.0961.

Preparative Example 101

4-(6-morpholinopyridin-3-yl)thiazol-2-amine

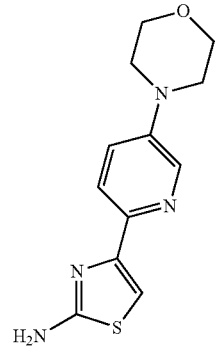 [SMILES: Nc1nc(-c2ccc(N3CCOCC3)cn2)cs1]

The compound was prepared according to General procedure E from tert-butyl (4-methoxybenzyl)(4-(6-morpholinopyridin-3-yl)thiazol-2-yl)carbamate (0.32 g, 0.66 mmol) and trifluoroacetic acid (3 mL); the reaction time was 2 hours at 70° C. The product, purified by column chromatography (CH$_2$Cl$_2$:MeOH; 10:1), was obtained as a white solid (150 mg, 86%).

$^1$H NMR (500 MHz, DMSO-d$_6$) δ (ppm) 8.56 (d, J=2.4 Hz, 1H), 7.91 (dd, J=2.4, 8.8 Hz, 1H), 7.01 (s, 2H), 6.86-6.81 (m, 2H), 3.76-3.66 (m, 4H), 3.52-3.40 (m, 4H);

$^{13}$C NMR (126 MHz DMSO-d$_6$) δ (ppm) 168.3, 158.1, 147.6, 144.9, 134.7, 121.1, 106.5, 98.9, 65.9, 45.1;

HRMS calcd for C$_{12}$H$_{15}$N$_4$OS [M+H]$^+$ 263.0961, found 263.0963.

Preparative Example 102

4-(3-fluoro-5-morpholinopyridin-2-yl)thiazol-2-amine

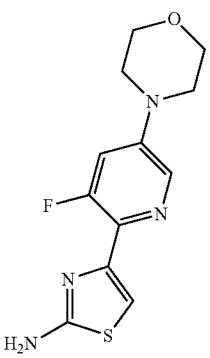 [SMILES: Nc1nc(-c2ncc(N3CCOCC3)cc2F)cs1]

2-bromo-1-(3-fluoro-5-morpholinopyridin-2-yl)ethan-1-one was prepared according to General procedure A3 from 1-(3-fluoro-5-morpholinopyridin-2-yl)ethan-1-one (273 mg, 1.22 mmol), Et$_3$N (147 mg, 0.2 mL, 1.46 mmol), TMSOTf (0.3 g, 0.24 mL, 1.34 mmol) and NBS (0.26 g, 1.46 mmol) in CH$_2$Cl$_2$ (3 mL). The crude intermediate was used as such in the next step.

4-(3-fluoro-5-morpholinopyridin-2-yl)thiazol-2-amine was prepared according to General procedure B from 2-bromo-1-(3-fluoro-5-morpholinopyridin-2-yl)ethan-1-one (368 mg, 1.22 mmol) and thiourea (140 mg, 1.83 mmol) in EtOH (5 mL). Work-up 2 of General procedure B. The product was obtained as a white solid (250 mg, 73%).

$^1$H NMR (500 MHz, DMSO-d$_6$) δ (ppm) 8.20-8.13 (m, 1H), 7.23 (dd, J=14.5, 2.5 Hz, 1H), 7.00 (s, 2H), 6.92 (d, J=1.1 Hz, 1H), 3.78-3.72 (m, 4H), 3.27-3.21 (m, 4H);

$^{13}$C NMR (126 MHz, DMSO-d$_6$) δ (ppm) 167.7, 156.6 (d, J=260.6 Hz), 147.2 (d, J=5.4 Hz), 146.4 (d, J=7.9 Hz), 132.2 (d, J=3.6 Hz), 130.8 (d, J=10.1 Hz), 108.8 (d, J=23.6 Hz), 105.3 (d, J=7.1 Hz), 65.7, 47.2;

$^{19}$F NMR (471 MHz, DMSO-d$_6$) δ (ppm) −120.88;

HRMS calcd for C$_{12}$H$_{14}$FN$_4$OS [M+H]$^+$ 281.0867, found 281.0864.

Preparative Example 103

2-cyano-N-(4-phenylthiazol-2-yl)acetamide

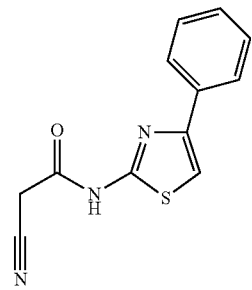 [SMILES: N#CCC(=O)Nc1nc(-c2ccccc2)cs1]

The compound was prepared according to General procedure C1 from 2-amino-4-phenylthiazole (0.5 g, 2.837 mmol), ethyl cyanoacetate (0.453 mL, 4.255 mmol) and NaOEt (21% in EtOH, 1.59 mL, 4.255 mmol) in EtOH (10 mL); the reaction time was 3 h at reflux. The product, purified by column chromatography (toluene:EtOAc; 5:1 to 1:1), was obtained as an off-white solid (0.586 g, 85%).

IR (cm$^{-1}$) 3207, 3081, 2944, 2913, 2211, 1660, 1554, 1480, 1445, 1389, 1265, 1180, 945, 781, 733;

$^1$H NMR (500 MHz, DMSO-d$_6$) δ (ppm) 12.59 (s, 1H), 7.93-7.85 (m, 2H), 7.69 (s, 1H), 7.43 (dd, J=8.3, 7.0 Hz, 2H), 7.36-7.29 (m, 1H), 4.06 (s, 2H);

$^{13}$C NMR (126 MHz, DMSO-d$_6$) δ (ppm) 161.8, 157.3, 149.0, 134.0, 128.7, 127.9, 125.6, 115.1, 108.6, 25.9;

HRMS calcd for C$_{12}$H$_{10}$N$_3$OS [M+H]$^+$ 244.0539, found 244.0538.

Preparative Example 104

2-cyano-N-(4-(4-methoxyphenyl)thiazol-2-yl)acetamide

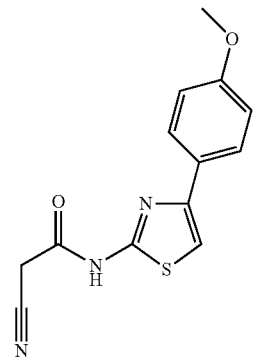 [SMILES: COc1ccc(-c2csc(NC(=O)CC#N)n2)cc1]

The compound was prepared according to General procedure C1 from 4-(4-methoxyphenyl)thiazol-2-amine (0.46 g, 2.23 mmol), ethyl cyanoacetate (356 µL, 3.345 mmol) and NaOEt (21% in EtOH, 1.25 mL, 3.345 mmol) in MeOH (15 mL); refluxed for 3 h. The product was purified by column chromatography (toluene:EtOAc; 1:0 to 1:1) and then by preparative TLC (toluene:EtOAc; 1:1). The product was obtained as a pale yellow solid (0.312 g, 51%).

$^1$H NMR (500 MHz, DMSO-d$_6$) δ (ppm) 12.54 (s, 1H), 7.82 (d, J=8.9 Hz, 2H), 7.51 (s, 1H), 6.99 (d, J=8.9 Hz, 2H), 4.05 (s, 2H), 3.79 (s, 3H);

$^{13}$C NMR (126 MHz, DMSO-d$_6$) δ (ppm) 161.7, 159.0, 157.1, 148.9, 127.0, 115.2, 114.1, 106.5, 55.1, 25.9;

HRMS calcd for C$_{13}$H$_{12}$N$_3$O$_2$S [M+H]$^+$ 274.0645, found 274.0646.

Preparative Example 105

2-cyano-N-(4-(naphthalen-2-yl)thiazol-2-yl)acetamide

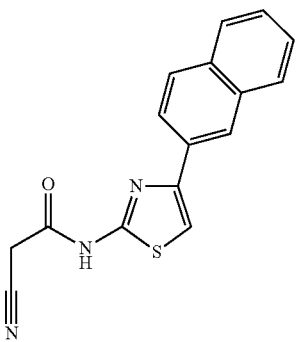 [SMILES: N#CCC(=O)Nc1nc(-c2ccc3ccccc3c2)cs1]

The compound was prepared according to General procedure C1 from 4-(naphthalen-2-yl)thiazol-2-amine (0.207 g, 0.915 mmol), ethyl cyanoacetate (146 µL, 1.37 mmol) and NaOEt (21% in EtOH, 512 μL, 1.37 mmol) in EtOH (2 mL). The mixture was stirred at 50° C. for 21 h. The solvent was evaporated in vacuo, the solid residue was mixed with a saturated aqueous solution of NH₄Cl (20 mL), and the mixture was extracted with EtOAc (3×25 mL). The combined organic extracts were washed with brine (20 mL), dried over MgSO₄, filtered, and the solvent was evaporated in vacuo. The product, obtained as a pale pink solid (0.161 g, 60%), did not require any other purification.

$^1$H NMR (500 MHz, DMSO-$d_6$) δ (ppm) 12.68 (s, 1H), 8.42 (s, 1H), 8.05 (d, J=8.5, 1.7 Hz, 1H), 8.00-7.90 (m, 3H), 7.83 (d, J=1.5 Hz, 1H), 7.59-7.47 (m, 2H), 4.08 (s, 2H);

$^{13}$C NMR (126 MHz, DMSO-$d_6$) δ (ppm) 161.9, 157.4, 148.9, 133.1, 132.5, 131.5, 128.3, 128.1, 127.6, 126.5, 126.2, 124.3, 123.9, 115.1, 109.2, 25.9;

HRMS calcd for $C_{16}H_{12}N_3OS$ [M+H]$^+$ 294.0696, found 294.0695.

Preparative Example 106

2-cyano-N-(4-(4-(trifluoromethoxy)phenyl)thiazol-2-yl)acetamide

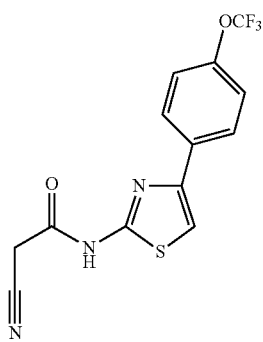 [SMILES: N#CCC(=O)Nc1nc(-c2ccc(OC(F)(F)F)cc2)cs1]

The compound was prepared according to General procedure C1 from 4-(4-(trifluoromethoxy)phenyl)thiazol-2-amine (0.20 g, 0.77 mmol), ethyl cyanoacetate (123 μL, 1.15 mmol) and NaOEt (21% in EtOH, 430 μL, 1.15 mmol) in EtOH (2 mL). The mixture was heated at 55° C. for 6 h. The product, purified by column chromatography (hexane:EtOAc; 1:0 to 1:1), was obtained as an off-white solid (0.216 g, 85%).

$^1$H NMR (500 MHz, DMSO-$d_6$) δ (ppm) 12.62 (s, 1H), 8.00 (d, J=8.7 Hz, 2H), 7.77 (s, 1H), 7.43 (d, J=8.7 Hz, 2H), 4.06 (s, 2H);

$^{13}$C NMR (126 MHz, DMSO-$d_6$) δ (ppm) 162.5, 158.1, 148.3, 148.0, 133.8, 128.0, 121.8, 120.6 (q, J=256.2 Hz), 115.6, 110.1, 26.4;

$^{19}$F NMR (471 MHz, DMSO-$d_6$) δ (ppm) −56.73;

HRMS calcd for $C_{13}H_9F_3N_3O_2S$ [M+H]$^+$ 328.0362, found 328.0360.

Preparative Example 107

2-cyano-N-(4-(p-tolyl)thiazol-2-yl)acetamide

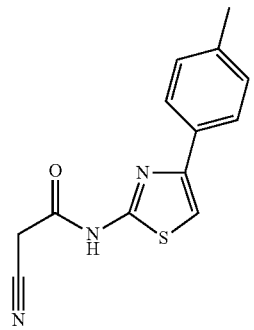 [SMILES: Cc1ccc(-c2csc(NC(=O)CC#N)n2)cc1]

The compound was prepared according to General procedure C1 from 4-(p-tolyl)thiazol-2-amine (0.259 g, 1.36 mmol), ethyl cyanoacetate (217 μL, 2.04 mmol) and NaOEt (21% in EtOH, 763 μL, 2.04 mmol) in EtOH (2 mL). The mixture was stirred at 55° C. for 6 h. The product, purified by column chromatography (hexane:EtOAc; 1:0 to 1:1), was obtained as a pale yellow solid (0.284 g, 81%).

$^1$H NMR (500 MHz, DMSO-$d_6$) δ (ppm) 12.56 (s, 1H), 7.78 (d, J=8.4 Hz, 2H), 7.60 (s, 1H), 7.24 (d, J=8.1 Hz, 2H), 4.05 (s, 2H), 2.32 (s, 3H);

$^{13}$C NMR (126 MHz, DMSO-$d_6$) δ (ppm) 161.8, 157.2, 149.1, 137.2, 131.4, 129.3, 125.6, 115.1, 107.7, 25.9, 20.8;

HRMS calcd for $C_{13}H_{12}N_3OS$ [M+H]$^+$ 258.0696 found 258.0696.

Preparative Example 108

N-(4-([1,1'-biphenyl]-4-yl)thiazol-2-yl)-2-cyanoacetamide

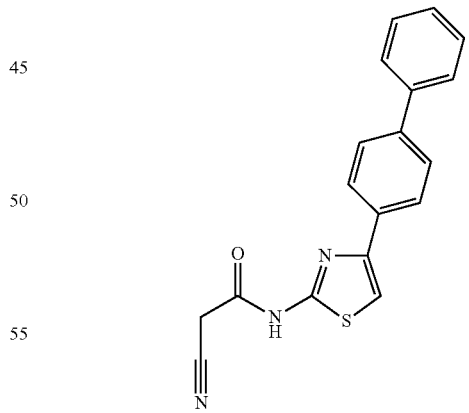

The compound was prepared according to General procedure C1 from 4-([1,1'-biphenyl]-4-yl)thiazol-2-amine (197 mg, 0.78 mmol), ethyl cyanoacetate (125 μL, 1.17 mmol) and NaOEt (21% in EtOH, 0.437 mL, 1.17 mmol) in EtOH (2 mL). The mixture was stirred at 55° C. for 6 h. The product, purified by column chromatography (hexane:EtOAc; 1:0 to 1:1), was obtained as a white solid (210 mg, 84%).

¹H NMR (500 MHz, DMSO-d₆) δ (ppm) 12.41 (s, 1H), 6.74 (s, 1H), 3.97 (s, 2H), 2.02 (s, 3H), 1.87 (d, J=3.1 Hz, 6H), 1.77-1.66 (m, 6H);
¹³C NMR (126 MHz, DMSO-d₆) δ (ppm) 161.3, 160.7, 156.5, 115.2, 105.1, 41.6, 36.3, 35.8, 27.9, 25.7;
HRMS calcd for C₁₈H₁₂N₃OS [M−H]⁻ 318.0707, found 3180704.

Preparative Example 109

N-(4-(4-bromophenyl)thiazol-2-yl)-2-cyanoacetamide

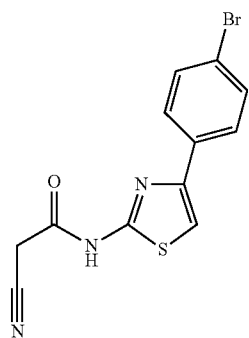 [SMILES: N#CCC(=O)Nc1nc(-c2ccc(Br)cc2)cs1]

The compound was prepared according to General procedure C1 from 4-(4-bromophenyl)thiazol-2-amine (540 mg, 2.12 mmol), ethyl cyanoacetate (250 μL, 2.33 mmol) and NaOEt (21% in EtOH, 0.80 mL, 2.12 mmol). The product, purified by column chromatography (toluene:EtOAc; 1:1), was obtained as a white solid (425 mg, 65%).
¹H NMR (500 MHz, DMSO-d₆) δ (ppm) 12.60 (s, 1H), 7.87-7.81 (m, 2H), 7.76 (s, 1H), 7.66-7.60 (m, 2H), 4.06 (s, 2H);
¹³C NMR (126 MHz, DMSO-d₆) δ (ppm) 161.9, 157.5, 147.8, 133.2, 131.7, 127.6, 120.9, 115.1, 109.4, 25.9;
HRMS calcd for C₁₂H₇BrN₃OS [M−H]⁻ 321.9478, found 321.9479.

Preparative Example 110

2-cyano-N-(4-(3-hydroxy-4-methoxyphenyl)thiazol-2-yl)acetamide

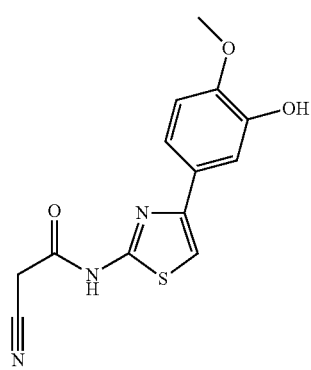 [SMILES: COc1ccc(-c2csc(NC(=O)CC#N)n2)cc1O]

The compound was prepared according to General procedure C1 from 5-(2-aminothiazol-4-yl)-2-methoxyphenol (90 mg, 0.4 mmol), ethyl cyanoacetate (65 μL, 0.6 mmol) and NaOEt (21% in EtOH, 225 μL, 0.6 mmol). The product, purified by column chromatography (EtOAc:toluene; 1:1), was obtained as a white solid (43 mg, 40%).
¹H NMR (500 MHz, DMSO-d₆) δ (ppm) 12.51 (s, 1H), 9.03 (s, 1H), 7.42 (s, 1H), 7.31-7.28 (m, 2H), 6.95 (d, 1H), 4.04 (s, 2H), 3.79 (s, 3H);
¹³C NMR (126 MHz, DMSO-d₆) δ (ppm) 161.7, 156.9, 149.1, 147.7, 146.5, 127.3, 116.9, 115.1, 113.1, 112.3, 106.4, 55.6, 25.8;
HRMS calcd for C₁₃H₁₀N₃O₃S [M−H]⁻ 288.0448, found 288.0447.

Preparative Example 111

2-cyano-N-(4-(2-hydroxypropan-2-yl)thiazol-2-yl)acetamide

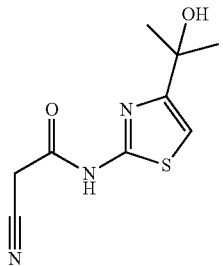

The compound was prepared according to General procedure C1 from 2-(2-aminothiazol-4-yl)propan-2-ol (126 mg, 0.8 mmol), ethyl cyanoacetate (125 μL, 1.2 mmol) and NaOEt (21% in EtOH, 300 μL, 0.8 mmol). The precipitate was collected by filtration and washed with EtOAc (2 mL). The solid was mixed with aqueous saturated solution of NH₄Cl and EtOAc (25 mL+25 mL) and the phases were separated. The aqueous phase was extracted with EtOAc (2×25 mL). The combined organic extracts were dried over MgSO₄ and the solvent was evaporated in vacuo. The product was obtained as a white solid (115 mg, 65%).
¹H NMR (500 MHz, DMSO-d₆) δ (ppm) 12.41 (s, 1H), 6.93 (s, 1H), 5.04 (s, 1H), 3.98 (s, 2H), 1.41 (s, 6H);
¹³C NMR (126 MHz, DMSO-d₆) δ (ppm) 161.9, 160.3, 157.1, 115.7, 106.7, 70.6, 30.9, 26.2;
HRMS calcd for C₉H₁₂N₃O₂S [M+H]⁺ 226.0645, found 226.0646.

Preparative Example 112

N-(4-(3-bromophenyl)thiazol-2-yl)-2-cyanoacetamide

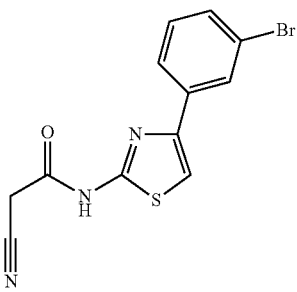 [SMILES: N#CCC(=O)Nc1nc(-c2cccc(Br)c2)cs1]

The compound was prepared according to General procedure C1 from 4-(3-bromophenyl)thiazol-2-amine (0.50 g, 1.98 mmol) in EtOH (5 mL), ethyl cyanoacetate (320 μL, 3.0 mmol) and NaOEt (21% in EtOH, 750 μL, 1.98 mmol). The product, purified by column chromatography (hexane:EtOAc; 1:1), was obtained as a yellow solid (455 mg, 70%).

$^1$H NMR (500 MHz, DMSO-d$_6$) δ (ppm) 12.61 (s, 1H), 8.11-8.08 (m, 1H), 7.93-7.87 (m, 1H), 7.83 (d, J=1.2 Hz, 1H), 7.56-7.50 (m, 1H), 7.40 (t, J=7.9 Hz, 1H), 4.06 (s, 2H); $^{13}$C NMR (126 MHz, DMSO-d$_6$) δ (ppm) 162.5, 158.0, 147.7, 136.8, 131.5, 131.0, 128.8, 125.0, 122.7, 115.6, 110.6, 26.4;

HRMS calcd for C$_{12}$H$_7$BrN$_3$OS [M−H]$^-$ 321.9478, found 321.9478.

Preparative Example 113

N-(4-(2-bromophenyl)thiazol-2-yl)-2-cyanoacetamide

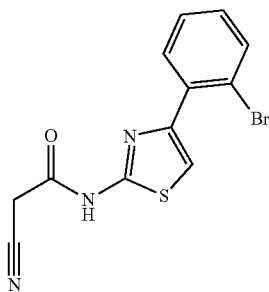 [SMILES: N#CCC(=O)Nc1nc(-c2ccccc2Br)cs1]

The compound was prepared according to General procedure C1 from 4-(2-bromophenyl)thiazol-2-amine (0.30 g, 1.18 mmol) in EtOH (5 mL), ethyl cyanoacetate (190 μL, 1.78 mmol) and NaOEt (21% in EtOH, 440 μL, 1.18 mmol). The product, purified by column chromatography (hexane:EtOAc; 1:1), was obtained as a white solid (100 mg, 30%).

$^1$H NMR (500 MHz, DMSO-d$_6$) δ (ppm) 12.60 (s, 1H), 7.73 (dd, J=8.0, 1.2 Hz, 1H), 7.68 (dd, J=7.8, 1.7 Hz, 1H), 7.58 (s, 1H), 7.48-7.45 (m, 1H), 7.32-7.30 (m, 1H), 4.06 (s, 2H); $^{13}$C NMR (126 MHz, DMSO-d$_6$) δ (ppm) 161.9, 156.5, 147.4, 135.2, 133.5, 131.4, 129.7, 127.7, 121.1, 115.1, 113.0, 25.9;

HRMS calcd for C$_{12}$H$_7$BrN$_3$OS [M−H]$^-$ 321.9478, found 321.9478.

Preparative Example 114

2-cyano-N-(4-(3-(trifluoromethoxy)phenyl)thiazol-2-yl)acetamide

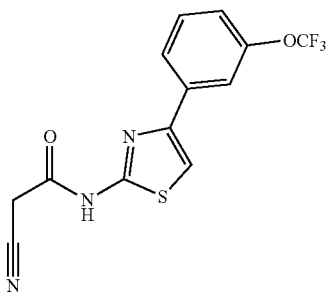 [SMILES: N#CCC(=O)Nc1nc(-c2cccc(OC(F)(F)F)c2)cs1]

The compound was prepared according to General procedure C1 from 4-(3-(trifluoromethoxy)phenyl)thiazol-2-amine (0.10 g, 0.38 mmol), ethyl cyanoacetate (62 μL, 0.6 mmol) and NaOEt (21% in EtOH, 140 μL, 0.38 mmol) in EtOH (3 mL). The product, purified by column chromatography (hexane:EtOAc; 3:2), was obtained as a white solid (75 mg, 60%).

$^1$H NMR (500 MHz, DMSO-d$_6$) δ (ppm) 12.64 (s, 1H), 7.96-7.91 (m, 1H), 7.88 (s, 1H), 7.86-7.84 (m, 1H), 7.59-7.56 (m, 1H), 7.35-7.30 (m, 1H), 4.07 (s, 2H); $^{13}$C NMR (126 MHz, DMSO-d$_6$) δ (ppm) 162.0, 157.6, 148.9, 147.2, 136.3, 130.8, 124.5, 120.2, 120.1 (q, J=256.4 Hz), 117.8, 115.1, 110.4, 25.9;

$^{19}$F NMR (471 MHz, DMSO-d$_6$) δ (ppm) −56.63;

HRMS calcd for C$_{13}$H$_7$F$_3$N$_3$O$_2$S [M−H]$^-$ 326.0217, found 326.0217.

Preparative Example 115

2-cyano-N-(4-(4-phenoxyphenyl)thiazol-2-yl)acetamide

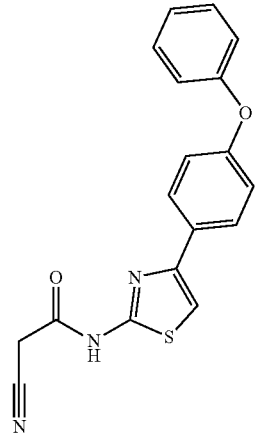 [SMILES: N#CCC(=O)Nc1nc(-c2ccc(Oc3ccccc3)cc2)cs1]

The compound was prepared according to General procedure C1 from 4-(4-phenoxyphenyl)thiazol-2-amine (270 mg, 1.0 mmol) in EtOH (3 mL), ethyl cyanoacetate (130 μL, 1.5 mmol) and NaOEt (21% in EtOH, 370 μL, 1.0 mmol). The product, purified by column chromatography (toluene:EtOAc; 3:2), was obtained as a white solid (75 mg, 25%).

$^1$H NMR (500 MHz, DMSO-d$_6$) δ (ppm) 12.59 (s, 1H), 7.96-7.87 (m, 2H), 7.65-7.56 (m, 1H), 7.45-7.38 (m, 2H), 7.20-7.15 (m, 1H), 7.11-6.99 (m, 4H), 4.05 (s, 2H);

$^{13}$C NMR (126 MHz, DMSO-d$_6$) δ (ppm) 161.8, 157.3, 156.6, 156.3, 148.4, 132.8, 130.1, 127.4, 123.7, 120.9, 118.9, 118.6, 107.7, 25.9;

HRMS calcd for C$_{18}$H$_{14}$N$_3$O$_2$S [M+H]$^+$ 336.0801, found 336.0801.

Preparative Example 116

N-(4-(benzofuran-2-yl)thiazol-2-yl)-2-cyanoacetamide

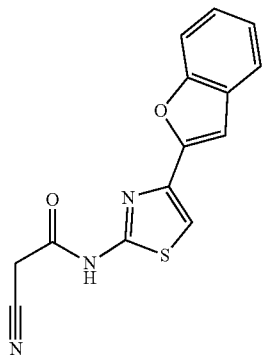 [SMILES: N#CCC(=O)Nc1nc(-c2cc3ccccc3o2)cs1]

The compound was prepared according to General procedure C1 from 4-(benzofuran-2-yl)thiazol-2-amine (0.148 g, 0.684 mmol), ethyl cyanoacetate (109 μL, 1.026 mmol) and NaOEt (21% in EtOH, 383 μL, 0.47 mmol) in EtOH (3 mL). The mixture was heated at 55° C. for 3 h, then it was cooled to 25° C., the precipitate was collected by filtration and washed with cold EtOH (1 mL). The product was obtained as a white solid (0.129 g, 67%).

$^1$H NMR (500 MHz, DMSO-$d_6$) δ (ppm) 12.77 (s, 1H), 7.70 (s, 1H), 7.70-7.66 (m, 1H), 7.61 (dd, J=8.2, 1.0 Hz, 1H), 7.34 (ddd, J=8.4, 7.2, 1.4 Hz, 1H), 7.27 (ddd, J=7.6, 7.6, 1.2 Hz, 1H), 7.14 (d, J=1.1 Hz, 1H), 4.07 (s, 2H);

$^{13}$C NMR (126 MHz, DMSO-$d_6$) δ (ppm) 162.1, 158.3, 154.1, 151.5, 140.4, 128.3, 124.8, 123.3, 121.5, 115.1, 111.0, 110.8, 102.6, 25.9;

HRMS calcd for $C_{14}H_8N_3O_2S$ [M−H]$^-$ 282.0343, found 282.0342.

Preparative Example 117

N-(4-adamantan-1-yl)thiazol-2-yl)-2-cyanoacetamide

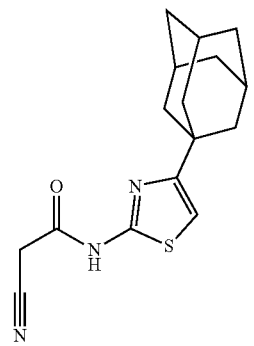 [SMILES: N#CCC(=O)Nc1nc(C23CC4CC(CC(C4)C2)C3)cs1]

The compound was prepared according to General procedure C1 from 4-(adamantan-1-yl)thiazol-2-amine (0.253 g, 1.079 mmol), ethyl cyanoacetate (172 μL, 1.62 mmol) and NaOEt (21% in EtOH, 0.403 mL, 1.079 mmol) in EtOH (2 mL). The mixture was heated at 55° C. for 3 h. The solvent was evaporated in vacuo. The product, purified by column chromatography (hexane:EtOAc; 1:0 to 1:1), was obtained as an off-white solid (0.223 g, 69%).

$^1$H NMR (500 MHz, DMSO-$d_6$) δ (ppm) 12.41 (s, 1H), 6.74 (s, 1H), 3.97 (s, 2H), 2.02 (s, 3H), 1.87 (d, J=3.1 Hz, 6H), 1.77-1.66 (m, 6H);

$^{13}$C NMR (126 MHz, DMSO-$d_6$) δ (ppm) 161.3, 160.7, 156.5, 115.2, 105.1, 41.6, 36.3, 35.8, 27.9, 25.7;

HRMS calcd for $C_{16}H_{20}N_3OS$ [M+H]$^+$ 302.1322, found 302.1321.

Preparative Example 118

2-cyano-N-(5-cyclohexyl-4-(4-(trifluoromethoxy)phenyl)thiazol-2-yl)acetamide

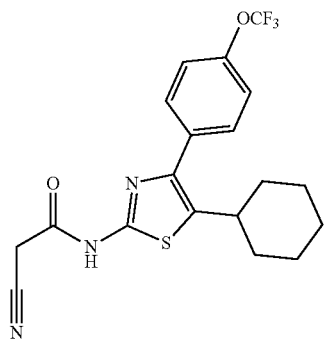 [SMILES: N#CCC(=O)Nc1nc(-c2ccc(OC(F)(F)F)cc2)c(C2CCCCC2)s1]

The compound was prepared according to General procedure C1 from 5-cyclohexyl-4-(4-(trifluoromethoxy)phenyl)thiazol-2-amine (0.1 g, 0.3 mmol), ethyl cyanoacetate (50 μL, 0.45 mmol) and NaOEt (21% in EtOH, 110 μL, 0.3 mmol) in EtOH (2 mL). The mixture was stirred at 50° C. for 5 h. The solvent was evaporated in vacuo, the residue was mixed with a saturated aqueous solution of NH$_4$Cl (10 mL), and the mixture was extracted with EtOAc (3×10 mL). The combined organic extracts were washed with brine (10 mL), dried over MgSO$_4$, filtered, and the solvent was evaporated in vacuo. The product, purified by column chromatography (hexane:EtOAc; 1:1), was obtained as a colorless semi-solid (0.110 g, 90%).

$^1$H NMR (500 MHz, CDCl$_3$) δ 11.39 (s, 1H), 7.59-7.54 (m, 2H), 7.38-7.31 (m, 2H), 3.02-2.97 (m, 1H), 2.94 (s, 2H), 2.05-1.98 (m, 2H), 1.89-1.82 (m, 2H), 1.80-1.72 (m, 1H), 1.50 (qd, J=12.2, 3.1 Hz, 2H), 1.41-1.24 (m, 3H);

$^{13}$C NMR (126 MHz, CDCl$_3$) δ 159.7, 155.7, 149.3, 141.8, 137.6, 133.7, 130.4, 121.5, 120.3 (q, J=258.0 Hz), 112.8, 37.2, 36.6, 26.7, 25.8, 25.4;

$^{19}$F NMR (471 MHz, CDCl$_3$) δ −57.72;

HRMS calcd for $C_{19}H_{19}F_3N_3O_2S$ [M+H]$^+$ 410.1145, found 410.1149.

Preparative Example 119

2-cyano-N-(4,5-diphenylthiazol-2-yl)acetamide

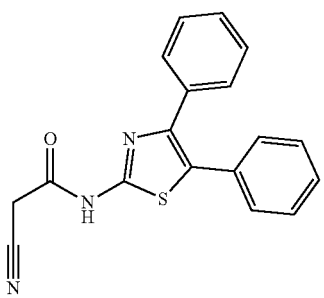 [SMILES: N#CCC(=O)Nc1nc(-c2ccccc2)c(-c2ccccc2)s1]

The compound was prepared according to General procedure C1 from 4,5-diphenylthiazol-2-amine (0.079 g, 0.313 mmol), ethyl cyanoacetate (50 µL, 0.47 mmol) and NaOEt (21% in EtOH, 175 µL, 0.47 mmol) in EtOH (2 mL). The reaction mixture was stirred at 55° C. for 3 h. The crude product was triturated with $CH_2Cl_2$:EtOAc (1:1, 2 mL), and the solid was collected by filtration. The product was obtained as a white solid (0.059 g, 59%).

$^1$H NMR (500 MHz, DMSO-$d_6$) δ (ppm) 12.66 (s, 1H), 7.47-7.36 (m, 5H), 7.36-7.27 (m, 5H), 4.08 (s, 2H);

$^{13}$C NMR (126 MHz, DMSO-$d_6$) δ (ppm) 162.0, 155.3, 143.9, 134.4, 131.6, 129.3, 128.9, 128.4, 128.3, 128.1, 127.8, 125.9, 115.1, 25.9;

HRMS calcd for $C_{18}H_{12}N_3OS$ [M−H]$^-$ 318.0707, found 318.0709.

Preparative Example 120

2-cyano-N-(4-(4-morpholinophenyl)thiazol-2-yl)acetamide

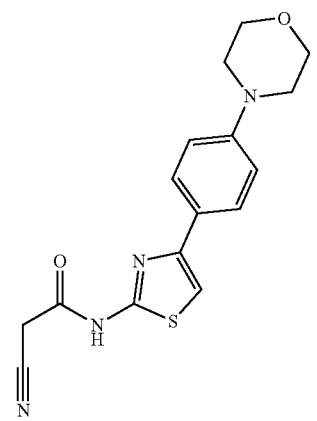 [SMILES: N#CCC(=O)Nc1nc(-c2ccc(N3CCOCC3)cc2)cs1]

The compound was prepared according to General procedure C2:

Step 1: from 4-(4-morpholinophenyl)thiazol-2-amine (72 mg, 0.276 mmol), Et$_3$N (28 mg, 38 µL, 0.276 mmol), and chloroacetyl chloride (47 mg, 33 µL, 0.413 mmol) in anhydrous CH$_3$CN (3 mL). After the work-up, the residue was quickly filtered through a pad of silica gel (hexane:EtOAc; 1:1) to provide the corresponding chloroacetamide as an off-white solid (62 mg, 0.184 mmol), which was used in Step 2.

Step 2: from KCN (13 mg, 0.193 mmol) in DMF (1 mL). The product, purified by column chromatography (hexane:EtOAc; 1:0 to 1:2), was obtained as an off-white solid (27 mg, 30%).

$^1$H NMR (500 MHz, DMSO-$d_6$) δ (ppm) 12.52 (s, 1H), 7.75 (d, J=9.0 Hz, 2H), 7.45 (s, 1H), 6.98 (d, J=8.9 Hz, 2H), 4.04 (s, 2H), 3.79-3.68 (m, 4H), 3.15 (dd, J=6.0, 3.9 Hz, 4H);

$^{13}$C NMR (126 MHz, DMSO-$d_6$) δ (ppm) 161.7, 157.0, 150.6, 149.2, 126.5, 125.1, 115.2, 114.8, 105.7, 66.0, 48.0, 25.8;

HRMS calcd for $C_{16}H_{17}N_4O_2S$ [M+H]$^+$ 329.1067, found 329.1070.

Preparative Example 121

2-cyano-N-(4-(3-cyanophenyl)thiazol-2-yl)acetamide

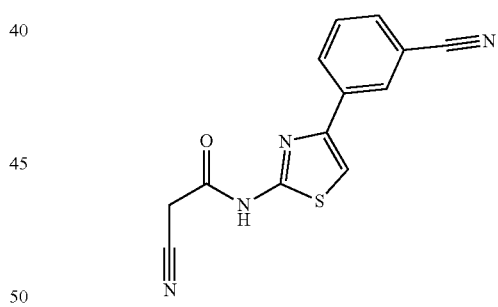

The compound was prepared according to General procedure C1 from 3-(2-aminothiazol-4-yl)benzonitrile (300 mg, 1.5 mmol), ethyl cyanoacetate (250 mg, 250 µL, 2.25 mmol) and Na (35 mg, 1.5 mmol) in EtOH (3.5 mL). The product, purified by column chromatography (hexane:EtOAc; 1:1), was obtained as a white solid (125 mg, 30%).

$^1$H NMR (500 MHz, DMSO-$d_6$) δ (ppm) 12.64 (s, 1H), 8.31 (s, 1H), 8.23-8.19 (m, 1H), 7.92 (s, 1H), 7.81-7.77 (m, 1H), 7.71-7.63 (m, 1H), 4.07 (s, 2H);

$^{13}$C NMR (126 MHz, DMSO-$d_6$) δ (ppm) 162.1, 157.7, 146.8, 135.1, 131.2, 130.1, 129.0, 118.6, 115.1, 111.9, 110.7, 25.9;

HRMS calcd for $C_{13}H_9N_4OS$ [M+H]$^+$ 269.0492, found 269.0495.

Preparative Example 122

4-(2-(2-cyanoacetamido)thiazol-4-yl)-N,N-dimethylbenzamide

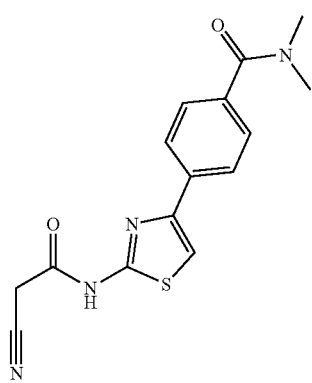 [SMILES: CN(C)C(=O)c1ccc(-c2csc(NC(=O)CC#N)n2)cc1]

The compound was prepared according to General procedure C3 from 4-(2-aminothiazol-4-yl)-N,N-dimethylbenzamide (85 mg, 0.34 mmol), ethyl cyanoacetate (58 mg, 55 μL, 0.51 mmol) and NaH (60% in mineral oil, 14 mg, 0.34 mmol) in THF (2 mL) and MeOH (0.1 mL). The product, purified by column chromatography (hexane:EtOAc; 1:1), was obtained as a white solid (80 mg, 75%).

$^1$H NMR (500 MHz, DMSO-$d_6$) δ (ppm) 12.61 (s, 1H), 7.97-7.91 (m, 2H), 7.79 (s, 1H), 7.50-7.45 (m, 2H), 4.07 (s, 2H), 2.96 (s, 6H);

$^{13}$C NMR (126 MHz, DMSO-$d_6$) δ (ppm) 169.7, 161.9, 157.4, 148.2, 135.7, 134.8, 127.6, 125.4, 115.1, 109.6, 34.8, 25.9;

HRMS calcd for $C_{15}H_{13}N_4O_2S$ [M−H]$^-$ 313.0765, found 313.0766.

Preparative Example 123

2-cyano-N-(4-(4-(2-hydroxypropan-2-yl)phenyl)thiazol-2-yl)acetamide

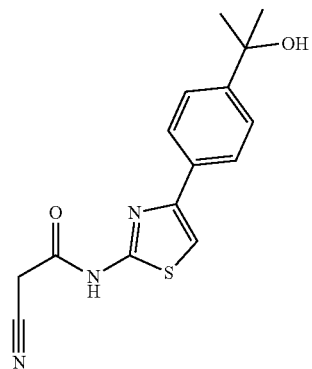 [SMILES: CC(C)(O)c1ccc(-c2csc(NC(=O)CC#N)n2)cc1]

The compound was prepared according to General procedure C1 from 2-(4-(2-aminothiazol-4-yl)phenyl)propan-2-ol (150 mg, 0.64 mmol), ethyl cyanoacetate (110 mg, 100 μL, 0.96 mmol) and Na (15 mg, 0.64 mmol) in EtOH (2 mL). The product, purified by column chromatography (hexane:EtOAc; 7:3), was obtained as a white solid (55 mg, 30%).

$^1$H NMR (500 MHz, DMSO-$d_6$) δ (ppm) 12.58 (s, 1H), 7.85-7.79 (m, 2H), 7.61 (s, 1H), 7.54-7.49 (m, 2H), 5.00 (s, 1H), 4.05 (s, 2H), 1.44 (s, 6H);

$^{13}$C NMR (126 MHz, DMSO-$d_6$) δ (ppm) 161.8, 157.2, 150.26, 149.04, 131.82, 125.10, 124.89, 115.13, 107.82, 70.52, 31.79, 25.85;

HRMS calcd for $C_{15}H_{16}N_3O_2S$ [M+H]$^+$ 302.0958, found 302.0960.

Preparative Example 124

2-cyano-N-(4-(5-cyanothiophen-2-yl)thiazol-2-yl)acetamide

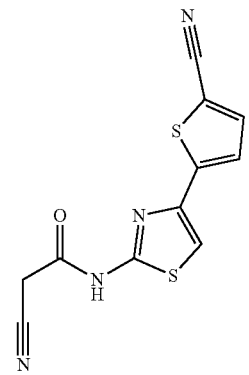 [SMILES: N#CCC(=O)Nc1nc(-c2ccc(C#N)s2)cs1]

The compound was prepared according to General procedure C2:

Step 1: from 5-(2-aminothiazol-4-yl)thiophene-2-carbonitrile (230 mg, 1.11 mmol), chloroacetyl chloride (188 mg, 133 μL, 1.67 mmol) and Et$_3$N (168 mg, 230 μL, 1.67 mmol) in CH$_3$CN (2 mL). After the work-up, the crude mixture was purified by column chromatography (hexane:EtOAc; 7:3), the corresponding 2-chloroacetamide was obtained as a white solid (314 mg, 1.11 mmol), which was used in Step 2.

Step 2: from KCN (150 mg, 2.22 mmol) in DMF (2 mL). The product, purified by column chromatography (hexane:EtOAc; 7:3), was obtained as an off-white solid (70 mg, 23%).

$^1$H NMR (500 MHz, DMSO-$d_6$) δ (ppm) 12.81 (s, 1H), 7.95 (d, J=4.0 Hz, 1H), 7.91 (s, 1H), 7.71 (d, J=4.0 Hz, 1H), 4.05 (s, 2H);

$^{13}$C NMR (126 MHz, DMSO-$d_6$) δ (ppm) 162.2, 158.1, 145.5, 141.8, 140.1, 124.2, 115.0, 114.6, 111.1, 106.5, 25.9;

HRMS calcd for $C_{11}H_5N_4OS_2$ [M−H]$^-$ 272.991, found 272.9906.

Preparative Example 125

2-cyano-N-(4-(thiophen-2-yl)thiazol-2-yl)acetamide

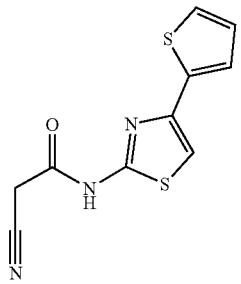 [SMILES: N#CCC(=O)Nc1nc(-c2cccs2)cs1]

The compound was prepared according to General procedure C1 from 4-(thiophen-2-yl)thiazol-2-amine (0.173 g, 0.949 mmol), ethyl cyanoacetate (151 µL, 1.42 mmol) and NaOEt (21% in EtOH, 532 µL, 1.42 mmol) in MeOH (5 mL); reaction time 3 h at reflux. The product, purified by column chromatography (hexane:EtOAc; 1:0 to 1:1), was obtained as a yellow solid (0.081 g, 34%).

$^1$H NMR (500 MHz, DMSO-$d_6$) δ (ppm) 12.68 (s, 1H), 7.55-7.51 (m, 2H), 7.50 (dd, J=5.0, 1.2 Hz, 1H), 7.11 (dd, J=5.0, 3.7 Hz, 1H), 4.04 (s, 2H);

$^{13}$C NMR (126 MHz, DMSO-$d_6$) δ (ppm) 161.9, 157.4, 143.8, 138.1, 128.1, 125.6, 123.9, 115.1, 106.9, 25.8;

HRMS calcd for $C_{10}H_8N_3OS_2$ [M+H]$^+$ 250.0103, found 250.0103.

Preparative Example 126

2-cyano-N-(4-(3,5-difluorophenyl)thiazol-2-yl)acetamide

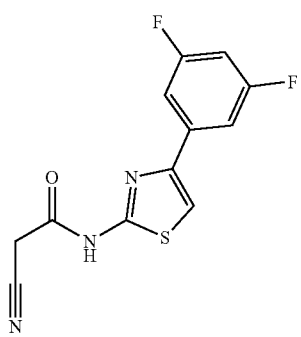 [SMILES: N#CCC(=O)Nc1nc(-c2cc(F)cc(F)c2)cs1]

The compound was prepared according to General procedure C3 from 4-(3,5-difluorophenyl)thiazol-2-amine (297 mg, 1.40 mmol), ethyl cyanoacetate (237 mg, 0.223 mL, 2.10 mmol) and NaH (60% in mineral oil, 62 mg, 1.54 mmol) in THF (5 mL) and MeOH (1 mL). After the reaction was completed, the precipitate was collected by filtration, washed with hexane (5 mL), and mixed with a saturated aqueous solution of NaHCO$_3$ (15 mL) and EtOAc (25 mL). The phases were separated, the organic phase was washed with brine (15 mL), dried over MgSO$_4$, filtered, and the solvent was evaporated in vacuo. The product was obtained as a pale pink solid (312 mg, 80%).

$^1$H NMR (500 MHz, DMSO-$d_6$) δ (ppm) 12.64 (s, 1H), 7.93 (s, 1H), 7.62-7.54 (m, 2H), 7.24-7.16 (m, 1H), 4.07 (s, 2H);

$^{13}$C NMR (126 MHz, DMSO-$d_6$) δ (ppm) 162.8 (dd, J=245.2, 13.6 Hz), 162.1, 157.7, 146.6, 137.5 (d, J=10.2 Hz), 115.1, 111.3, 109.2-107.9 (m), 103.1 (dd, J=26.3 Hz), 25.9;

$^{19}$F NMR (471 MHz, DMSO-$d_6$) δ (ppm) −109.41;

HRMS calcd for $C_{12}H_8F_2N_3OS$ [M+H]$^+$ 280.0351, found 280.0349.

Preparative Example 127

2-cyano-N-(4-(pyridazin-3-yl)thiazol-2-yl)acetamide

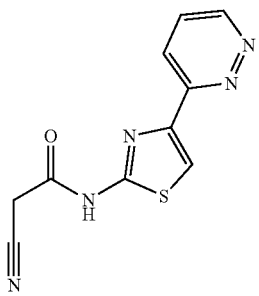 [SMILES: N#CCC(=O)Nc1nc(-c2cccnn2)cs1]

The compound was prepared according to General procedure C2:

Step 1: from 4-(pyridazin-3-yl)thiazol-2-amine (64 mg, 0.363 mmol), Et$_3$N (37 mg, 51 µL, 0.363 mmol), and chloroacetyl chloride (43 µL, 62 mg, 0.545 mmol) in CH$_3$CN (3 mL). After the work-up, the residue was quickly loaded onto a pad of silica gel and eluted with EtOAc to provide the corresponding chloroacetamide as an orange solid (50 mg, 0.196 mmol), which was used in Step 2.

Step 2: from KCN (13 mg, 0.206 mmol) in anhydrous DMF (1 mL). The product, purified by column chromatography (hexane:EtOAc; 1:1 to 0:1), was obtained as a pale pink-orange solid (8 mg, 50%).

$^1$H NMR (500 MHz, DMSO-$d_6$) δ (ppm) 12.72 (s, 1H), 9.20 (dd, J=5.0, 1.6 Hz, 1H), 8.17 (s, 1H), 8.09 (dd, J=8.5, 1.7 Hz, 1H), 7.80 (dd, J=8.5, 5.0 Hz, 1H), 4.08 (s, 2H);

$^{13}$C NMR (126 MHz, DMSO-$d_6$) δ (ppm) 162.2, 158.1, 154.6, 150.6, 146.2, 127.8, 123.6, 115.1, 113.7, 26.0;

HRMS calcd for $C_{10}H_8N_5OS$ [M+H]$^+$ 246.0444, found 246.0447.

Preparative Example 128

2-cyano-N-(4-(4-fluorophenyl)thiazol-2-yl)acetamide

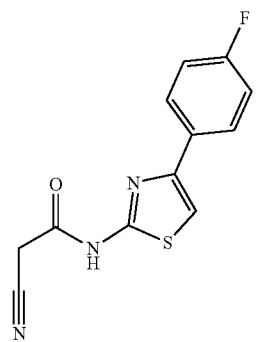 [SMILES: N#CCC(=O)Nc1nc(-c2ccc(F)cc2)cs1]

The compound was prepared according to General procedure C3 from 4-(4-fluorophenyl)thiazol-2-amine (438 mg, 2.25 mmol), ethyl cyanoacetate (383 mg, 0.360 mL, 3.38 mmol) and NaH (60% in mineral oil, 99 mg, 2.48 mmol) in THF (5 mL) and MeOH (1 mL). After the reaction was completed, the precipitate was collected by filtration and washed with hexane (5 mL). The solid was mixed with a saturated aqueous solution of NaHCO$_3$ (15 mL) and EtOAc (25 mL). The phases were separated, the organic phase was washed with brine (15 mL), dried over MgSO$_4$, filtered, and the solvent was evaporated in vacuo. The product was obtained as a pale pink solid (499 mg, 85%).

$^1$H NMR (500 MHz, DMSO-d$_6$) δ (ppm) 12.58 (s, 1H), 8.01-7.83 (m, 2H), 7.66 (s, 1H), 7.31-7.18 (m, 2H), 4.06 (s, 2H);

$^{13}$C NMR (126 MHz, DMSO-d$_6$) δ (ppm) 161.9, 161.8 (d, J=244.3 Hz), 157.4, 148.0, 130.7, 127.7 (d, J=8.2 Hz), 115.6 (d, J=20.9 Hz), 115.1, 108.3, 25.9;

$^{19}$F NMR (471 MHz, DMSO-d$_6$) δ (ppm) −114.14;

HRMS calcd for C$_{12}$H$_9$FN$_3$OS [M+H]$^+$ 262.0445, found 262.0447.

Preparative Example 129

2-cyano-N-(4-(pyridin-4-yl)thiazol-2-yl)acetamide

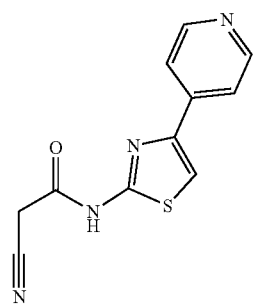 [SMILES: N#CCC(=O)Nc1nc(-c2ccncc2)cs1]

The compound was prepared according to General procedure C1 from 4-(pyridin-4-yl)thiazol-2-amine (0.05 g, 0.282 mmol), ethyl cyanoacetate (45 µL, 0.423 mmol) and NaOEt (21% in EtOH, 158 µL, 0.423 mmol) in MeOH (2 mL); the reaction time was 3 h at reflux. The product, purified by column chromatography (toluene:EtOAc; 5:1 to 1:1), was obtained as an off-white solid (0.033 g, 48%).

$^1$H NMR (500 MHz, DMSO-d$_6$) δ (ppm) 12.69 (s, 1H), 8.66-8.59 (m, 2H), 8.05 (s, 1H), 7.87-7.78 (m, 2H), 4.07 (s, 2H);

$^{13}$C NMR (126 MHz, DMSO-d$_6$) δ (ppm) 162.2, 157.9, 150.3, 146.5, 140.7, 119.9, 115.1, 112.8, 25.9;

HRMS calcd for C$_{11}$H$_9$N$_4$OS [M+H]$^+$ 245.0492, found 245.0491.

Preparative Example 130

Methyl 4-(2-(2-cyanoacetamido)thiazol-4-yl)benzoate

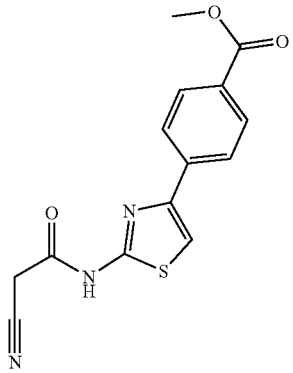 [SMILES: COC(=O)c1ccc(-c2csc(NC(=O)CC#N)n2)cc1]

The compound was prepared according to General procedure C2:

Step 1: from methyl 4-(2-aminothiazol-4-yl)benzoate (200 mg, 0.854 mmol), chloroacetyl chloride (130 mg, 95 µL, 0.1.18 mmol) and Et$_3$N (85 mg, 120 µL, 0.85 mmol) in CH$_3$CN (2+0.5 mL). After the work-up, the crude mixture was purified by column chromatography (hexane:EtOAc; 7:3) to afford the corresponding chloroacetamide as a white solid (263 mg, 0.85 mmol), which was used in Step 2.

Step 2: from KCN (55 mg, 0.85 mmol) in DMF (1 mL). The product, purified by column chromatography (hexane:EtOAc; 7:3), was obtained as an off-white solid (30 mg, 12%).

$^1$H NMR (500 MHz, DMSO-d$_6$) δ (ppm) 12.69 (s, 1H), 8.09-8.00 (m, 4H), 7.90 (s, 1H), 4.42 (s, 2H), 3.87 (s, 3H);

$^{13}$C NMR (126 MHz, DMSO-d$_6$) δ (ppm) 165.9, 162.0, 157.6, 147.8, 138.3, 129.7, 128.6, 125.8, 115.1, 111.2, 52.1, 25.9;

HRMS calcd for C$_{14}$H$_{10}$N$_3$O$_3$S [M−H]$^−$ 300.0448, found 300.0443.

Preparative Example 131

2-cyano-N-(4,5,6,7-tetrahydrobenzo[d]thiazol-2-yl)acetamide

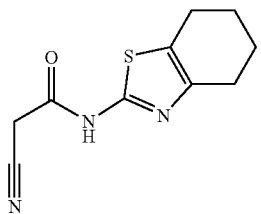 [SMILES: N#CCC(=O)Nc1nc2c(s1)CCCC2]

The compound was prepared according to General procedure C1 from 4,5,6,7-tetrahydrobenzo[d]thiazol-2-amine (200 mg, 1.3 mmol), ethyl cyanoacetate (240 µL, 2.25 mmol) and NaOEt (21% in EtOH, 510 µL, 1.3 mmol). The product, purified by column chromatography (hexane:EtOAc; 1:1), was obtained as a white solid (55 mg, 0.24 mmol, 20%).

$^1$H NMR (500 MHz, DMSO-$d_6$) δ (ppm) 12.18 (s, 1H), 3.98 (s, 2H), 2.67-2.52 (m, 4H), 1.77 (q, J=3.6 Hz, 4H);

$^{13}$C NMR (126 MHz, DMSO-$d_6$) δ (ppm) 161.2, 144.3, 121.9, 115.3, 25.8, 22.8, 22.2;

HRMS calcd for $C_{10}H_{10}N_3OS$ [M−H]$^-$ 220.0623, found 220.0624.

Preparative Example 132

2-cyano-N-(5-methyl-4-phenylthiazol-2-yl)acetamide

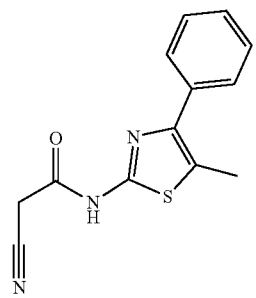 [SMILES: Cc1sc(NC(=O)CC#N)nc1-c1ccccc1]

The compound was prepared according to General procedure C1 with 5-methyl-4-phenylthiazol-2-amine (0.686 g, 3.60 mmol), ethyl cyanoacetate (575 µL, 5.41 mmol) and NaOEt (21% in EtOH, 1.35 mL, 3.60 mmol) in EtOH (3 mL). The mixture was heated at 55° C. for 3 h, then it was cooled to 25° C., the precipitate was collected by filtration and washed with cold EtOH (1 mL). The product was obtained as a pale brown solid (0.736 g, 79%).

$^1$H NMR (500 MHz, DMSO-$d_6$) δ (ppm) 12.42 (s, 1H), 7.67-7.60 (m, 2H), 7.45 (dd, J=7.7 Hz, 2H), 7.38-7.32 (m, 1H), 4.02 (s, 2H), 2.48 (s, 3H);

$^{13}$C NMR (126 MHz, DMSO-$d_6$) δ (ppm) 161.5, 153.3, 144.3, 134.6, 128.4, 127.9, 127.3, 121.7, 115.2, 25.8, 11.8;

HRMS calcd for $C_{13}H_{10}N_3OS$ [M−H]$^-$ 256.0550, found 256.0552.

Preparative Example 133

N-(5-chloro-4-phenylthiazol-2-yl)-2-cyanoacetamide

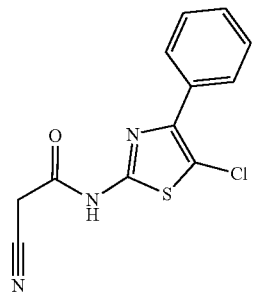 [SMILES: N#CCC(=O)Nc1nc(-c2ccccc2)c(Cl)s1]

The compound was prepared according to General procedure C1 from 5-chloro-4-phenylthiazol-2-amine (100 mg, 0.48 mmol), ethyl cyanoacetate (77 µL, 0.73 mmol) and NaOEt (21% in EtOH, 180 µL, 0.48 mmol). The product, purified by column chromatography (hexane:EtOAc; 1:1), was obtained as a white solid (50 mg, 40%).

$^1$H NMR (500 MHz, DMSO-$d_6$) δ (ppm) 12.86 (s, 1H), 7.91-7.84 (m, 2H), 7.55-7.47 (m, 2H), 7.46-7.39 (m, 1H), 4.08 (s, 2H);

$^{13}$C NMR (126 MHz, DMSO-$d_6$) δ (ppm) 162.6, 153.5, 143.5, 132.3, 128.5, 128.5, 127.6, 114.9, 113.2, 25.8;

HRMS calcd for $C_{12}H_7ClN_3O_3S$ [M−H]$^-$ 276.0004, found 276.0005.

Preparative Example 134

N-(5-bromo-4-phenylthiazol-2-yl)-2-cyanoacetamide

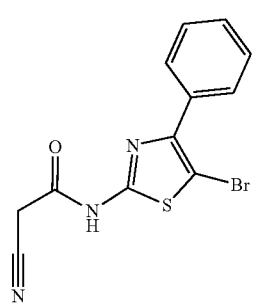 [SMILES: N#CCC(=O)Nc1nc(-c2ccccc2)c(Br)s1]

The compound was prepared according to General procedure C1 from 5-bromo-4-phenylthiazol-2-amine (0.253 g, 0.99 mmol), ethyl cyanoacetate (158 µL, 1.49 mmol) and NaOEt (21% in EtOH, 555 µL, 1.49 mmol) in EtOH (2 mL). The mixture was heated at 55° C. for 6 h. After two purifications by column chromatography (hexane:EtOAc; 1:0 to 1:1), the product was obtained as a brown-yellow solid (0.059 g, 18%).

$^1$H NMR (500 MHz, DMSO-$d_6$) δ (ppm) 7.84-7.79 (m, 2H), 7.54-7.46 (m, 3H), 2.80 (s, 2H);

$^{13}$C NMR (126 MHz, DMSO-$d_6$) δ (ppm) 160.2, 158.0, 146.7, 133.0, 129.6, 129.1, 128.9, 126.7, 112.6, 25.0;

HRMS calcd for $C_2H_9BrN_3OS$ [M+H]$^+$ 321.9644, found 321.9645.

Preparative Example 135

2-cyano-N-(4-(4-((trimethylsilyl)ethynyl)phenyl)thiazol-2-yl)acetamide

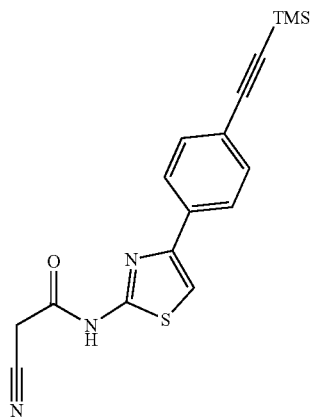 [SMILES: C[Si](C)(C)C#Cc1ccc(-c2csc(NC(=O)CC#N)n2)cc1]

The compound was prepared according to General procedure C2:

Step 1: from 4-(4-((trimethylsilyl)ethynyl)phenyl)thiazol-2-amine (87 mg, 0.32 mmol), chloroacetyl chloride (54 mg, 38 μL, 0.48 mmol), and Et$_3$N (50 mg, 68 μL, 0.48 mmol) in CH$_3$CN (1.5 mL). After the work-up, the crude mixture was purified by column chromatography (hexane:EtOAc; 7:3), the corresponding chloroacetamide was obtained as a white solid, which was used in Step 2.

Step 2: from KCN (33 mg, 0.48 mmol) in anhydrous DMF (1 mL). The product, purified by column chromatography (hexane:EtOAc; 7:3), was obtained as an off-white solid (40 mg, 40%).

$^1$H NMR (500 MHz, CDCl$_3$) δ (ppm) 11.04 (s, 1H), 7.77-7.73 (m, 2H), 7.57-7.53 (m, 2H), 7.25 (s, 1H), 3.30 (s, 2H), 0.28 (s, 9H);

$^{13}$C NMR (126 MHz, CDCl$_3$) δ (ppm) 159.6, 158.2, 149.5, 133.9, 132.9, 126.2, 123.7, 112.9, 109.9, 104.6, 96.3, 26.0, 0.1;

HRMS calcd for C$_{17}$H$_{18}$N$_3$OSSi [M+H]$^+$ 340.0934, found 340.0928.

Preparative Example 136

2-cyano-N-(4-(4-ethynyl)phenyl)thiazol-2-yl)acetamide

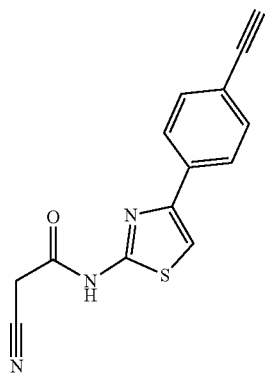 [SMILES: C#Cc1ccc(-c2csc(NC(=O)CC#N)n2)cc1]

To a solution of 2-cyano-N-(4-(4-((trimethylsilyl)ethynyl)phenyl)thiazol-2-yl)acetamide (40 mg, 0.11 mmol) dissolved in MeOH (1 mL) was added K$_2$CO$_3$ (65 mg, 0.44 mmol) and the mixture was stirred at 25° C. for 48 h. The mixture was pre-adsorbed on silica gel and purified by column chromatography (hexane:EtOAc; 2:1). The product was isolated as a white solid (25 mg, 85%).

$^1$H NMR (500 MHz, DMSO-d$_6$) δ (ppm) 12.61 (s, 1H), 7.93-7.88 (m, 2H), 7.79 (s, 1H), 7.56-7.52 (m, 2H), 4.24 (s, 1H), 4.06 (s, 2H);

$^{13}$C NMR (126 MHz, DMSO-d$_6$) δ (ppm) 161.9, 157.5, 148.0, 134.3, 132.1, 125.8, 120.9, 115.1, 109.9, 83.3, 81.5, 25.9;

HRMS calcd for C$_{14}$H$_{10}$N$_3$OS [M+H]$^+$ 268.0539, found 268.0537.

Preparative Example 137

2-cyano-N-(4-(3-cyclopropyl-4-methoxyphenyl)thiazol-2-yl)acetamide

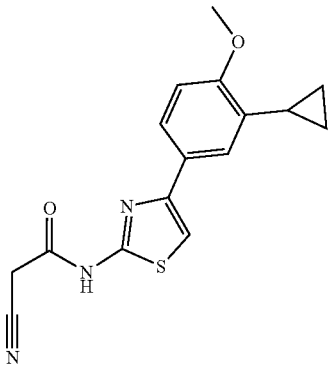 [SMILES: COc1ccc(-c2csc(NC(=O)CC#N)n2)cc1C1CC1]

The compound was prepared according to General procedure C1 from 4-(3-cyclopropyl-4-methoxyphenyl)thiazol-2-amine (100 mg, 0.4 mmol), ethyl cyanoacetate (68 mg, 65 μL, 0.6 mmol) and Na (9 mg, 0.4 mmol) in EtOH (2 mL). The product, purified by column chromatography (hexane:EtOAc; 7:3), was obtained as a white solid (70 mg, 55%).

$^1$H NMR (500 MHz, DMSO-d$_6$) δ (ppm) 12.53 (s, 1H), 7.65 (dd, J=8.5, 2.2 Hz, 1H), 7.53 (s, 1H), 7.33 (d, J=2.2 Hz, 1H), 6.99 (d, J=8.5 Hz, 1H), 4.04 (s, 2H), 3.84 (s, 3H), 2.19-2.07 (m, 1H), 0.98-0.86 (m, 2H), 0.72-0.60 (m, 2H);

$^{13}$C NMR (126 MHz, DMSO-d$_6$) δ (ppm) 161.7, 157.6, 157.0, 149.1, 131.3, 126.7, 123.8, 121.8, 115.1, 110.6, 106.4, 55.5, 25.8, 9.2, 7.8;

HRMS calcd for C$_{16}$H$_{16}$N$_3$O$_3$S [M+H]$^+$ 314.0958, found 314.0955.

Preparative Example 138

N-(4-(tert-butyl)thiazol-2-yl)-2-cyanoacetamide

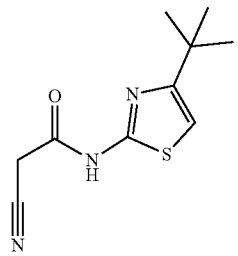

The compound was prepared according to General procedure C1 from 4-tert-butylthiazol-2-ylamine (0.228 g, 1.46 mmol), ethyl cyanoacetate (233 µL, 2.19 mmol) and NaOEt (21% in EtOH, 817 µL, 2.19 mmol) in EtOH (2 mL). The mixture was heated at 50° C. for 21 h. The product, purified by column chromatography (hexane:EtOAc; 1:0 to 2:1), was obtained as a pale pink solid (0.242 g, 74%).

$^1$H NMR (500 MHz, DMSO-$d_6$) δ (ppm) 12.39 (s, 1H), 6.81 (s, 1H), 3.98 (s, 2H), 1.26 (s, 9H);

$^{13}$C NMR (126 MHz, DMSO-$d_6$) δ (ppm) 161.4, 160.3, 156.5, 115.2, 105.2, 34.1, 29.7, 25.7;

HRMS calcd for $C_{10}H_{14}N_3OS$ [M+H]$^+$ 224.0852, found 224.0852.

Preparative Example 139

N-(4-(5-bromothiophen-2-yl)thiazol-2-yl)-2-cyanoacetamide

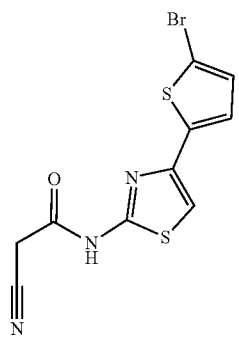 [SMILES: N#CCC(=O)Nc1nc(-c2ccc(Br)s2)cs1]

The compound was prepared according to General procedure C3 from 4-(5-bromothiophen-2-yl)thiazol-2-amine (240 mg, 0.919 mmol) in MeOH (6 mL), ethyl cyanoacetate (0.147 mL, 1.37 mmol) and NaH (60% in mineral oil, 0.040 mg, 1.01 mmol); reaction time 14 h at 60° C. The product, purified by column chromatography (hexane:EtOAc; 1:1 to 0:1), was obtained as a yellow solid (300 mg, 0.914 mmol, 99%).

$^1$H NMR (300 MHz, DMSO-$d_6$) δ (ppm) 12.7 (s, 1H), 7.6 (s, 1H), 7.4 (d, J=3.9 Hz, 1H), 7.2 (d, J=3.9 Hz, 1H), 4.0 (s, 2H);

HRMS calcd for $C_{10}H_7BrN_3OS_2$ [M+H]$^+$: 329.9187, found 329.9191.

Preparative Example 140

N-(4-(4-(tert-butyl)phenylthiazol-2-yl)-2-cyanoacetamide

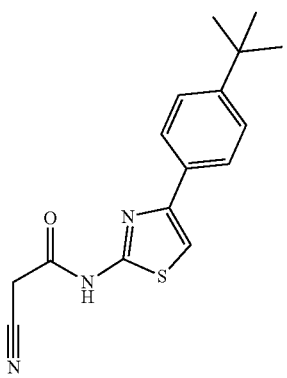 [SMILES: CC(C)(C)c1ccc(-c2csc(NC(=O)CC#N)n2)cc1]

The compound was prepared according to General procedure C1 from 4-(4-(tert-butyl)phenyl)thiazol-2-amine (626 mg, 2.694 mmol), ethyl cyanoacetate (0.430 mL, 4.041 mmol) and NaOEt (21% in EtOH, 1.509 mL, 4.041 mmol) in EtOH (6 mL). The product, purified by column chromatography (toluene:EtOAc; 10:1 to 4:1), was obtained as a white solid (575 mg, 71%).

$^1$H NMR (500 MHz, DMSO-$d_6$) δ (ppm) 12.58 (s, 1H), 7.82 (d, J=8.5 Hz, 2H), 7.60 (s, 1H), 7.45 (d, J=8.6 Hz, 2H), 4.05 (s, 2H), 1.30 (s, 9H);

$^{13}$C NMR (126 MHz, DMSO-$d_6$) δ (ppm) 161.8, 157.2, 150.4, 149.0, 131.4, 125.5, 125.4, 115.1, 107.8, 34.3, 31.0, 25.9;

HRMS calcd for $C_{16}H_{18}N_3OS$ [M+H]$^+$ 300.1165, found 300.1168.

Preparative Example 141

2-cyano-N-(4-(5-methylthiophen-2-yl)thiazol-2-yl)acetamide

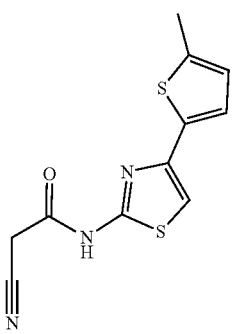 [SMILES: Cc1ccc(-c2csc(NC(=O)CC#N)n2)s1]

The compound was prepared according to General procedure C2:

Step 1: from 4-(5-methylthiophen-2-yl)thiazol-2-amine (240 mg, 1.22 mmol), chloroacetyl chloride (205 mg, 145

µL, 1.84 mmol) and Et₃N (186 mg, 255 µL, 1.84 mmol) in CH₃CN (2.5 mL). After the work-up, the crude mixture was purified by column chromatography (hexane:EtOAc; 7:3), the corresponding chloroacetamide was obtained as a white solid (331 mg), which was used in Step 2.

Step 2: from KCN (165 mg, 2.44 mmol) in DMF (2 mL). The product, purified by column chromatography (hexane:EtOAc; 7:3), was obtained as an off-white solid (150 mg, 50%).

$^1$H NMR (500 MHz, DMSO-d₆) δ (ppm) 12.64 (s, 1H), 7.41 (s, 1H), 7.29 (d, J=3.5 Hz, 1H), 6.79 (dd, J=3.5, 1.3 Hz, 1H), 4.03 (s, 2H), 2.45 (d, J=1.1 Hz, 3H);

$^{13}$C NMR (126 MHz, DMSO-d₆) δ (ppm) 162.3, 157.7, 144.5, 139.6, 136.2, 126.8, 124.3, 115.6, 106.5, 26.3, 15.5;

HRMS calcd for $C_{11}H_{10}N_3OS_2$ [M+H]⁺ 264.0260, found 264.0256.

Preparative Example 142

2-cyano-N-methyl-N-(4-phenylthiazol-2-yl)acetamide

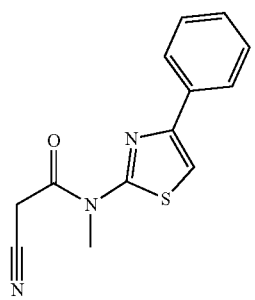 [SMILES: CN(C(=O)CC#N)c1nc(-c2ccccc2)cs1]

The compound was prepared according to General procedure C2:

Step 1: from N-methyl-4-phenylthiazol-2-amine (130 mg, 0.70 mmol), Et₃N (70 mg, 0.1 mL, 0.70 mmol), and chloroacetyl chloride (120 mg, 85 µL, 1.05 mmol) in CH₃CN (1.5 mL). After the work-up, the crude mixture was purified by column chromatography (hexane:EtOAc; 7:3), the corresponding chloroacetamide was obtained as a white solid (187 mg, 0.70 mmol), which was used in step 2.

Step 2: from KCN (90 mg, 1.4 mmol) in anhydrous DMF (1 mL). The product, purified by column chromatography (hexane:EtOAc; 7:3), was obtained as a white solid (90 mg, 50%).

$^1$H NMR (500 MHz, DMSO-d₆) δ (ppm) 7.98-7.92 (m, 2H), 7.75 (s, 1H), 7.48-7.39 (m, 2H), 7.37-7.30 (m, 1H), 4.49 (s, 2H), 3.70 (s, 3H);

$^{13}$C NMR (126 MHz, DMSO-d₆) δ (ppm) 164.2, 158.9, 148.0, 134.0, 128.7, 127.8, 125.7, 115.1, 110.1, 34.7, 26.7;

HRMS calcd for $C_{13}H_{12}N_3OS$ [M+H]⁺ 258.0696, found 258.0700.

Preparative Example 143

2-cyano-N-(4-(6-methylpyridin-3-yl)thiazol-2-yl)acetamide

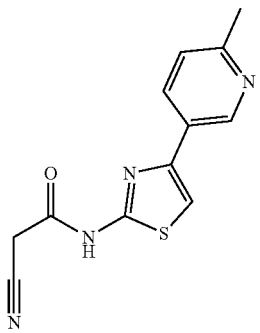 [SMILES: Cc1ccc(-c2csc(NC(=O)CC#N)n2)cn1]

The compound was prepared according to General procedure C3 from 4-(6-methylpyridin-3-yl)thiazol-2-amine (320 mg, 1.67 mmol), ethyl cyanoacetate (280 mg, 270 µL, 2.5 mmol), and NaH (60% in mineral oil, 40 mg, 1.67 mmol) in THF (3 mL) and MeOH (0.1 mL). The product, purified by column chromatography (hexane:EtOAc; 7:3 to 0:1), was obtained as a white solid (320 mg, 75%).

$^1$H NMR (500 MHz, DMSO-d₆) δ (ppm) 12.64 (s, 1H), 8.97 (d, J=2.3 Hz, 1H), 8.11 (dd, J=8.1, 2.3 Hz, 1H), 7.77 (s, 1H), 7.32 (d, J=8.2 Hz, 1H), 4.06 (s, 2H), 2.49 (s, 3H);

$^{13}$C NMR (126 MHz, DMSO-d₆) δ (ppm) 162.5, 158.3, 157.7, 146.9, 146.7, 133.7, 127.6, 123.6, 115.6, 109.7, 26.4, 24.3;

HRMS calcd for $C_{12}H_{11}N_4OS$ [M+H]⁺ 259.0648, found 259.0644.

Preparative Example 144

2-cyano-N-(4-phenyl-5-(tetrahydro-2H-pyran-4-yl)thiazol-2-yl)acetamide

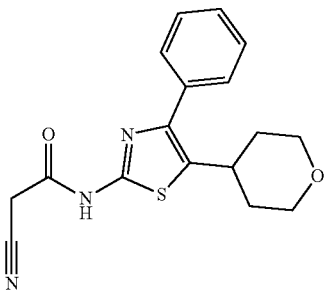 [SMILES: N#CCC(=O)Nc1nc(-c2ccccc2)c(C2CCOCC2)s1]

The compound was prepared according to General procedure C2:

Step 1: 4-(4-methylthiophen-2-yl)thiazol-2-amine (65 mg, 0.24 mmol), chloroacetyl chloride (40 mg, 30 µL, 0.5 mmol) and Et₃N (24 mg, 34 µL, 0.24 mmol) in CH₃CN (2.5 mL). After the work-up, the crude mixture was purified by column chromatography (hexane:EtOAc; 7:3), the corresponding chloroacetamide was obtained as a white solid (80 mg), which was used in Step 2.

Step 2: from KCN (31 mg, 0.48 mmol) in DMF (2 mL). The product, purified by column chromatography (hexane:EtOAc; 2:3), was obtained as an off-white solid (43 mg, 55%).

$^1$H NMR (500 MHz, DMSO-$d_6$) δ (ppm) 12.46 (s, 1H), 7.57-7.53 (m, 2H), 7.49-7.44 (m, 2H), 7.41-7.36 (m, 1H), 4.02 (s, 2H), 3.96-3.85 (m, 2H), 3.37 (td, J=11.8, 1.9 Hz, 2H), 3.33-3.21 (m, 1H), 1.90-1.83 (m, 2H), 1.74-1.57 (m, 2H);

$^{13}$C NMR (126 MHz, DMSO-$d_6$) δ (ppm) 161.5, 153.9, 143.9, 134.9, 132.7, 128.5, 128.3, 127.7, 115.1, 67.0, 35.4, 33.7, 25.8;

HRMS calcd for $C_{17}H_{18}N_3O_2S$ [M+H]$^+$ 328.1114, found 328.1109.

Preparative Example 145

2-cyano-N-(4-(3-fluorophenyl)thiazol-2-yl)acetamide

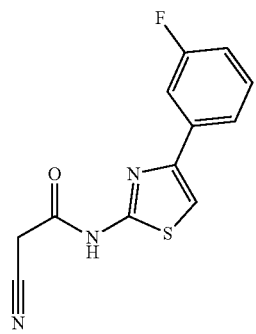 [SMILES: N#CCC(=O)Nc1nc(-c2cccc(F)c2)cs1]

The compound was prepared according to General procedure C1 from 4-(3-fluorophenyl)thiazol-2-amine (150 mg, 0.772 mmol), ethyl cyanoacetate (174 μL, 1.544 mmol) and NaH (60% in mineral oil, 34 mg, 0.849 mmol) in MeOH (1 mL) and THF (3 mL). The mixture was stirred at 50° C. for 24 h. The product, purified by column chromatography (hexane:EtOAc; 10:1 to 2:1), was obtained as a white solid (126 mg, 63%).

$^1$H NMR (500 MHz, DMSO-$d_6$) δ (ppm) 12.61 (s, 1H), 7.82 (s, 1H), 7.74 (d, J=7.9 Hz, 1H), 7.68 (ddd, J=10.7, 2.7, 1.5 Hz, 1H), 7.53-7.42 (m, 1H), 7.22-7.07 (m, 1H), 4.06 (s, 2H);

$^{13}$C NMR (126 MHz, DMSO-$d_6$) δ (ppm) 162.5 (d, J=243.0), 162.0, 157.4, 147.7, 136.4 (d, J=8.2 Hz), 130.8 (d, J=8.8 Hz), 121.7, 115.1, 114.6 (d, J=21.2 Hz), 112.2 (d, J=23.4 Hz), 110.0, 25.9;

$^{19}$F NMR (471 MHz, DMSO-$d_6$) δ (ppm) −112.94;

HRMS calcd for $C_{12}H_9FN_3OS$ [M+H]$^+$ 262.0445, found 262.0444.

Preparative Example 146

2-cyano-N-(4-phenyl-5-(pyrazin-2-yl)thiazol-2-yl)acetamide

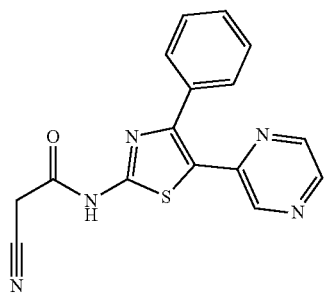

The compound was prepared according to General procedure C3 from 4-phenyl-5-(pyrazin-2-yl)thiazol-2-amine (140 mg, 0.55 mmol), ethyl cyanoacetate (95 mg, 90 μL, 0.83 mmol) and NaH (60% in mineral oil, 22 mg, 0.55 mmol) in THF (1 mL) and MeOH (0.1 mL). The product, purified by column chromatography (CH$_2$Cl$_2$:EtOAc; 2:1), was obtained as a yellow solid (77 mg, 45%).

$^1$H NMR (500 MHz, DMSO-$d_6$) δ (ppm) 12.78 (s, 1H), 8.68-8.61 (m, 1H), 8.46 (d, J=2.5 Hz, 1H), 8.29 (d, J=1.6 Hz, 1H), 7.55-7.50 (m, 2H), 7.47 (q, J=3.2, 2.8 Hz, 3H), 4.10 (s, 2H);

$^{13}$C NMR (126 MHz, DMSO-$d_6$) δ (ppm) 162.9, 158.4, 148.6, 148.0, 144.9, 142.9, 142.8, 135.1, 129.5, 129.4, 129.3, 124.8, 115.6, 26.5;

HRMS calcd for $C_{16}H_{12}N_5OS$ [M+H]$^+$ 322.0757, found 322.0759.

Preparative Example 147

2-cyano-N-(4-(3-methylpyridin-2-yl)thiazol-2-yl)acetamide

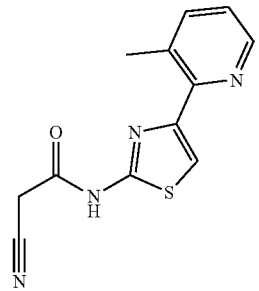 [SMILES: Cc1cccnc1-c1csc(NC(=O)CC#N)n1]

The compound was prepared according to General procedure C3 from 4-(3-methylpyridin-2-yl)thiazol-2-amine (290 mg, 1.52 mmol), ethyl cyanoacetate (270 mg, 250 μL, 2.3 mmol) and NaH (60% in mineral oil, 61 mg, 1.52 mmol) in THF (3 mL) and MeOH (0.1 mL). The product, purified by column chromatography (CH$_2$Cl$_2$:MeOH; 10:1), was obtained as an orange solid (275 mg, 70%).

$^1$H NMR (500 MHz, DMSO-$d_6$) δ (ppm) 12.48 (s, 1H), 8.44 (dd, J=4.7, 1.6 Hz, 1H), 7.69-7.68 (m, 1H), 7.67 (s, 1H), 7.27 (dd, J=7.7, 4.7 Hz, 1H), 4.07 (s, 2H), 2.55 (s, 3H);

¹³C NMR (126 MHz, DMSO-d₆) δ (ppm) 161.9, 156.3, 150.9, 150.2, 146.6, 139.3, 130.9, 122.7, 115.2, 114.1, 25.9, 20.1;

HRMS calcd for $C_{12}H_{11}N_4OS$ [M+H]⁺ 259.0648, found 259.0651.

Preparative Example 148

2-cyano-N-(4-(6-methoxypyridin-3-yl)thiazol-2-yl)acetamide

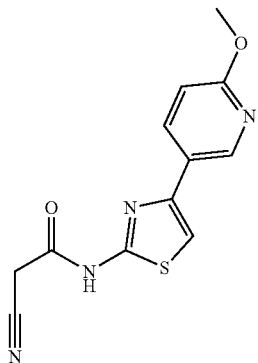 [SMILES: COc1ccc(-c2csc(NC(=O)CC#N)n2)cn1]

The compound was prepared according to General procedure C3 from 4-(6-methoxypyridin-3-yl)thiazol-2-amine (270 mg, 1.3 mmol), ethyl cyanoacetate (220 mg, 200 μL, 1.95 mmol) and NaH (60% in mineral oil, 60 mg, 1.43 mmol) in THF (2 mL) and MeOH (0.1 mL). The reaction mixture was poured into a saturated aqueous solution of NH₄Cl (10 mL). The precipitate was collected by filtration, washed with water (10 mL) and Et₂O (5 mL). The product, dried under vacuum, was obtained as a white solid (270 mg, 75%).

¹H NMR (500 MHz, DMSO-d₆) δ (ppm) 12.61 (s, 1H), 8.69 (d, J=2.5 Hz, 1H), 8.16 (dd, J=8.6, 2.5 Hz, 1H), 7.66 (s, 1H), 6.90 (d, J=8.6 Hz, 1H), 4.06 (s, 2H), 3.89 (s, 3H);

¹³C NMR (126 MHz, DMSO-d₆) δ (ppm) 163.1, 161.9, 157.6, 146.2, 144.1, 136.5, 123.9, 115.1, 110.6, 107.8, 53.3, 25.9;

HRMS calcd for $C_{12}H_{11}N_4O_2S$ [M+H]⁺ 275.0597, found 275.0594.

Preparative Example 149

2-cyano-N-(4-(3-methoxypyridin-2-yl)thiazol-2-yl)acetamide

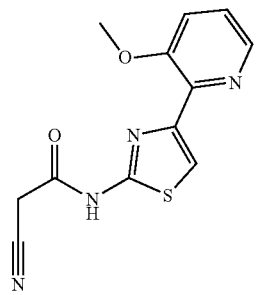 [SMILES: COc1cccnc1-c1csc(NC(=O)CC#N)n1]

The compound was prepared according to General procedure C3 from 4-(3-methoxypyridin-2-yl)thiazol-2-amine (235 mg, 1.13 mmol), ethyl cyanoacetate (190 mg, 180 μL, 1.7 mmol) and NaH (60% in mineral oil, 45 mg, 1.13 mmol) in THF (3 mL) and MeOH (0.1 mL). The mixture was poured into a saturated aqueous solution of NH₄Cl (10 mL). The precipitate was collected by filtration, washed with water (10 mL) and Et₂O (5 mL). The product was dried under vacuum and obtained as a white solid (190 mg, 60%).

¹H NMR (500 MHz, DMSO-d₆) δ (ppm) 12.72 (s, 1H), 8.21 (dd, J=4.5, 1.3 Hz, 1H), 7.78 (s, 1H), 7.56 (dd, J=8.4, 1.3 Hz, 1H), 7.36 (dd, J=8.4, 4.5 Hz, 1H), 4.03 (s, 2H), 3.91 (s, 3H);

¹³C NMR (126 MHz, DMSO-d₆) δ (ppm) 162.4, 156.5, 154.0, 150.0, 146.9, 141.1, 128.1, 124.1, 119.8, 115.5, 56.1, 26.4;

HRMS calcd for $C_{12}H_{11}N_4O_2S$ [M+H]⁺ 275.0597, found 275.0594.

Preparative Example 150

2-cyano-N-(4-(pyridin-2-yl)thiazol-2-yl)acetamide

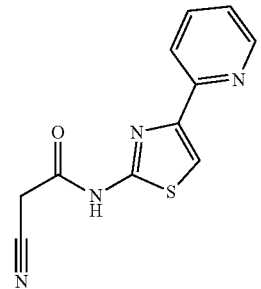 [SMILES: N#CCC(=O)Nc1nc(-c2ccccn2)cs1]

The compound was prepared according to General procedure C3 from 4-(pyridin-2-yl)thiazol-2-amine (440 mg, 2.2 mmol), ethyl cyanoacetate (370 mg, 350 μL, 3.3 mmol) and NaH (60% in mineral oil, 90 mg, 2.2 mmol) in THF (3 mL) and MeOH (0.1 mL). The product, purified by column chromatography (hexane:EtOAc; 1:1), was obtained as a white solid (385 mg, 70%).

¹H NMR (500 MHz, DMSO-d₆) δ (ppm) 12.63 (s, 1H), 8.61 (dt, J=4.66, 1.47 Hz, 1H), 7.95-7.86 (m, 3H), 7.36-7.32 (m, 1H), 4.07 (s, 2H);

¹³C NMR (126 MHz, DMSO-d₆) δ (ppm) 161.9, 157.5, 151.8, 149.5, 149.1, 137.3, 122.9, 119.9, 115.1, 112.1, 25.9;

HRMS calcd for $C_{11}H_9N_4OS$ [M+H]⁺ 245.0492, found 245.0497.

Preparative Example 151

2-cyano-N-(4-(2-fluoro-4-methoxyphenyl)thiazol-2-yl)acetamide

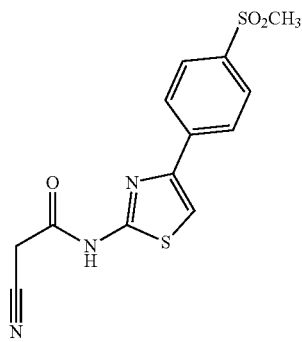 [SMILES: CS(=O)(=O)c1ccc(-c2csc(NC(=O)CC#N)n2)cc1]

The compound was prepared according to General procedure C3 from 4-(4-(methylsulfonyl)phenyl)thiazol-2-amine (300 mg, 1.18 mmol), ethyl cyanoacetate (200 mg, 200 μL, 1.77 mmol) and NaH (60% in mineral oil, 52 mg, 1.3 mmol) in THF (3 mL) and MeOH (0.1 mL). The reaction mixture was poured into a saturated aqueous solution of NH$_4$Cl (10 mL). The precipitate was collected by filtration and washed with water (10 mL) and Et$_2$O (5 mL) and dried under vacuum. The product was obtained as a white solid (320 mg, 85%).

$^1$H NMR (500 MHz, DMSO-d$_6$) δ (ppm) 2.61 (s, 1H), 8.16-8.13 (m, 2H), 8.00-7.97 (m, 2H), 7.97 (s, 1H), 4.08 (s, 2H), 3.24 (s, 3H);

$^{13}$C NMR (126 MHz, DMSO-d$_6$) δ (ppm) 162.1, 157.8, 147.2, 139.6, 138.5, 127.6, 126.2, 115.1, 111.8, 43.5, 25.9;

HRMS calcd for C$_{13}$H$_{12}$N$_3$O$_3$S$_2$ [M+H]$^+$ 322.0315, found 322.0318.

Preparative Example 152

2-cyano-N-(5-phenylthiazol-2-yl)acetamide

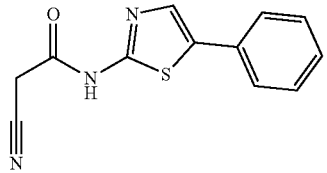 [SMILES: N#CCC(=O)Nc1ncc(-c2ccccc2)s1]

The compound was prepared according to General procedure C3 from 5-phenylthiazol-2-amine (250 mg, 1.41 mmol), ethyl cyanoacetate (191 mg, 0.18 mL, 1.69 mmol) and NaH (60% in mineral oil, 56 mg, 1.74 mmol) in THF (3 mL) and MeOH (7 mL). The reaction mixture was poured into a saturated aqueous solution of NH$_4$Cl (20 mL), the precipitate was collected by filtration, washed with water (15 mL) and EtOAc (25 mL), and dried under vacuum. The product was obtained as a white solid (205 mg, 60%).

$^1$H NMR (500 MHz, DMSO-d$_6$) δ (ppm) 7.89 (s, 1H), 7.72-7.53 (m, 2H), 7.48-7.35 (m, 2H), 7.38-7.26 (m, 1H), 4.05 (s, 2H);

HRMS calcd for C$_{12}$H$_8$N$_3$OS [M−H]$^−$ 242.0394, found [M+H]$^+$: 242.0395.

Preparative Example 153

N-(4-(4-(tert-butyl)-2,6-dimethylphenyl)thiazol-2-yl)-2-cyanoacetamide

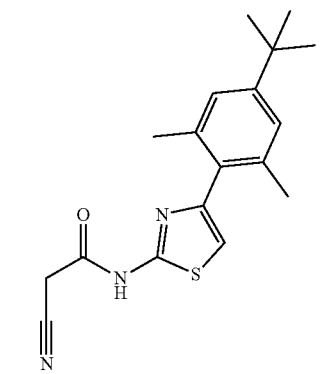 [SMILES: Cc1cc(C(C)(C)C)cc(C)c1-c1csc(NC(=O)CC#N)n1]

The compound was prepared according to General procedure C3 from 4-(4-(tert-butyl)-2,6-dimethylphenyl)thiazol-2-amine (88 mg, 0.34 mmol), ethyl cyanoacetate (38 mg, 0.04 mL, 0.34 mmol,) and NaH (13 mg, 0.34 mmol) in THF (1.5 mL) and MeOH (0.1 mL). The reaction mixture was poured into a saturated aqueous solution of NH$_4$Cl (10 mL), the precipitate was collected by filtration, washed with water (3 mL) and EtOAc (5 mL), and dried under vacuum. The product was obtained as a white solid (82 mg, 75%).

$^1$H NMR (500 MHz, DMSO-d$_6$) δ (ppm) 7.22 (s, 2H), 6.86 (s, 1H), 2.44 (s, 2H), 2.13 (s, 6H), 1.36 (s, 9H);

$^{13}$C NMR (126 MHz, CDCl$_3$) δ (ppm) 160.6, 159.2, 153.0, 147.5, 137.6, 131.2, 125.4, 112.8, 112.4, 34.8, 31.4, 24.3, 20.9, 20.8;

HRMS calcd for C$_{18}$H$_{22}$N$_3$SO [M+H]$^+$ 328.1478, found 328.1481.

Preparative Example 154

N-(4-(3-(tert-butyl)phenyl)thiazol-2-yl)-2-cyanoacetamide

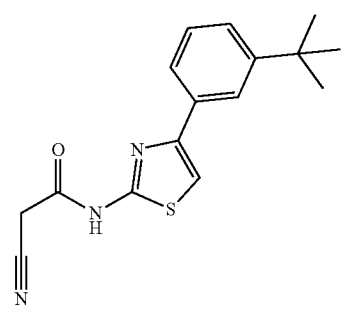 [SMILES: CC(C)(C)c1cccc(-c2csc(NC(=O)CC#N)n2)c1]

The compound was prepared according to General procedure C3 from 4-(3-(tert-butyl)phenyl)thiazol-2-amine (265 mg, 1.13 mmol, ethyl cyanoacetate (128 mg, 0.12 mL, 1.13 mmol) and NaH (60% in mineral oil, 45 mg, 1.13 mmol) in THF (3 mL) and MeOH (3 mL). The reaction mixture was poured into a saturated aqueous solution of NH$_4$Cl (20 mL), the precipitate was collected by filtration, washed with water (5 mL) and EtOAc (10 mL), and dried under vacuum. The product was obtained as a white solid (277 mg, 82%).

$^1$H NMR (500 MHz, CDCl$_3$) δ (ppm) 7.81 (t, J=1.9 Hz, 1H), 7.58 (dt, J=7.2, 1.6 Hz, 1H), 7.49-7.36 (m, 2H), 7.19 (s, 1H), 3.10 (s, 2H), 1.37 (s, 9H);

Preparative Example 155

N-(4-benzoylthiazol-2-yl)-2-cyanoacetamide

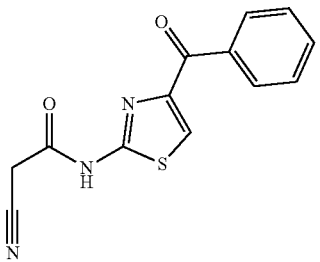 [SMILES: N#CCC(=O)Nc1nc(C(=O)c2ccccc2)cs1]

The compound was prepared according to General procedure C3 from (2-aminothiazol-4-yl)(phenyl)methanone (300 mg, 1.47 mmol), ethyl cyanoacetate (250 mg, 0.245 mL, 2.2 mmol) and NaH (60% in mineral oil, 71 mg, 1.76 mmol) in THF (5 mL) and MeOH (1 mL). After the reaction was completed, the precipitate was collected by filtration and washed with hexane (5 mL). The solid was dissolved in a mixture of EtOAc (25 mL) and a saturated aqueous solution of NH$_4$Cl (15 mL). The phases were separated and the organic phase was washed with brine (15 mL), dried over MgSO$_4$, filtered, and the solvent was evaporated in vacuo. The product was obtained as a pale pink solid (30 mg, 8%).

$^1$H NMR (500 MHz, DMSO-d$_6$) δ (ppm) 12.78 (s, 1H), 8.14 (s, 1H), 8.05-7.99 (m, 2H), 7.71-7.63 (m, 1H), 7.58-7.52 (m, 2H), 4.07 (s, 2H);

$^{13}$C NMR (126 MHz, DMSO-d$_6$) δ (ppm) 186.7, 162.5, 157.3, 148.1, 137.1, 132.7, 129.7, 128.3, 124.3, 115.0, 25.9;

HRMS calcd for C$_{13}$H$_{10}$N$_3$O$_2$S [M+H]$^+$ 272.0488, found 272.0491.

Preparative Example 156

2-cyano-N-(5-pyrazin-2-yl)thiazol-2-ylacetamide

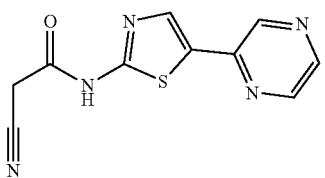 [SMILES: N#CCC(=O)Nc1ncc(-c2cnccn2)s1]

5-(pyrazin-2-yl)thiazol-2-amine was prepared according to General procedure E from tert-butyl (4-methoxybenzyl) (5-(pyrazin-2-yl)thiazol-2-yl)carbamate (0.9 g, 2.25 mmol) and trifluoroacetic acid (6 mL)); the reaction time was 2 hours at 70° C. The product, purified by column chromatography (CH$_2$Cl$_2$:MeOH; 10:1), was obtained as a brown solid (80 mg, 20%).

2-cyano-N-(5-(pyrazin-2-yl)thiazol-2-yl)acetamide was prepared according to General procedure C3 from 5-(pyrazin-2-yl)thiazol-2-amine (80 mg, 0.45 mmol), ethyl cyanoacetate (85 mg, 0.084 mL, 0.75 mmol) and NaH (60% in mineral oil, 18 mg, 0.46 mmol) in THF (2 mL) and MeOH (0.1 mL). The mixture was stirred for 10 h at 50° C. and 16 h at room temperature. The mixture was poured into saturated solution of NH$_4$Cl (10 mL), CH$_2$Cl$_2$ (10 mL) and EtOAc (10 mL). The precipitate was collected by filtration, washed with water (2 mL), then with EtOAc (2 mL) and dried under vacuum. The product was obtained as a white solid (80 mg, 73%).

$^1$H NMR (500 MHz, DMSO-d$_6$) δ (ppm) 12.68 (s, 1H), 9.24 (d, J=1.6 Hz, 1H), 8.59 (dd, J=1.6, 2.6 Hz, 1H), 8.49 (d, J=2.6 Hz, 1H), 8.37 (s, 1H), 4.09 (s, 2H);

$^{13}$C NMR (126 MHz, DMSO-d$_6$) δ (ppm) 162.1, 159.4, 146.9, 144.2, 142.5, 141.0, 137.6, 130.0, 115.1, 26.0;

HRMS calcd for C$_{10}$H$_8$N$_5$OS [M+H]$^+$ 246.0444, found 246.0442.

Preparative Example 157

2-cyano-N-(5-(pyrazin-2-yl)-(pyridin-2-yl)thiazol-2-yl)acetamide

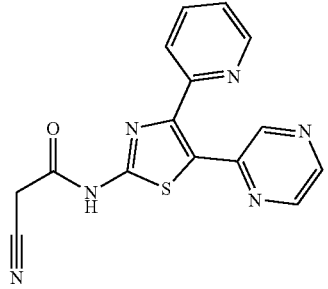

5-(pyrazin-2-yl)$_4$-(pyridin-2-yl)thiazol-2-amine (100 mg, 0.4 mmol) and ethyl cyanoacetate (93 mg, 0.091 mL, 0.4 mmol) were heated at 90° C. in acetic anhydride (1 mL) for 30 min. The mixture was poured into water (10 mL) and extracted with EtOAc (3×10 mL). Organic fractions were combined, washed with brine (30 mL), dried over MgSO$_4$, filtered, and the solvent was evaporated in vacuo. The residue was purified by column flash chromatography (CH$_2$Cl$_2$:MeOH; 10:1 to 5:1). The product was obtained as an off-white solid (80 mg, 63%).

$^1$H NMR (500 MHz, DMSO-d$_6$) δ (ppm) 12.81 (s, 1H), 8.72 (d, J=1.6 Hz, 1H), 8.63 (dd, J=1.6, 2.6 Hz, 1H), 8.52-8.48 (m, 2H), 8.01-7.94 (m, 1H), 7.92-7.90 (m, 1H), 7.47-7.40 (m, 1H), 4.11 (s, 2H);

$^{13}$C NMR (126 MHz, DMSO-d$_6$) δ (ppm) 169.6, 163.0, 158.2, 153.3, 149.4, 148.0, 146.3, 144.8, 144.1, 142.9, 137.9, 124.4, 123.9, 115.5, 26.5;

HRMS calcd for C$_{15}$H$_{11}$N$_6$OS [M+H]$^+$ 323.0710, found 323.0707.

Preparative Example 158

2-cyano-N-(4-(6-morpholinopyridin-2-yl)thiazol-2-yl)acetamide

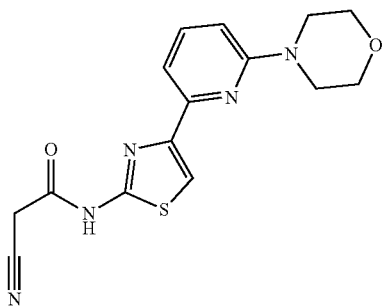 [SMILES: N#CCC(=O)Nc1nc(-c2cccc(N3CCOCC3)n2)cs1]

The compound was prepared according to General procedure C3 from 4-(6-morpholinopyridin-2-yl)thiazol-2-amine (126 mg, 0.48 mmol), ethyl cyanoacetate (82 mg, 77 µL, 2.41 mmol) and NaH (60% in mineral oil, 34 mg, 1.38 mmol) in THF (2 mL) and MeOH (0.4 mL). The product, purified by column chromatography (hexane:EtOAc; 5:1 to 2:1 to 1:1 to 1:2), was obtained as a yellow solid (141 mg, 89%).

$^1$H NMR (500 MHz, DMSO-d$_6$) δ (ppm) 12.57 (s, 1H), 7.79 (s, 1H), 7.64 (dd, J=8.5, 7.4 Hz, 1H), 7.26 (d, J=7.3 Hz, 1H), 6.79 (d, J=8.5 Hz, 1H), 4.05 (s, 2H), 3.77-3.70 (m, 4H), 3.56-3.50 (m, 4H);

$^{13}$C NMR (176 MHz, DMSO-d$_6$) δ (ppm) 161.9, 158.6, 157.2, 149.9, 149.7, 138.5, 115.1, 111.6, 109.7, 106.5, 66.0, 45.0, 25.9;

HRMS calcd for C$_{15}$H$_{16}$N$_5$O$_2$S [M+H]$^+$ 330.1019, found 330.1022.

Preparative Example 159

2-cyano-N-(4-(6-morpholinopyridin-3-yl)thiazol-2-yl)acetamide

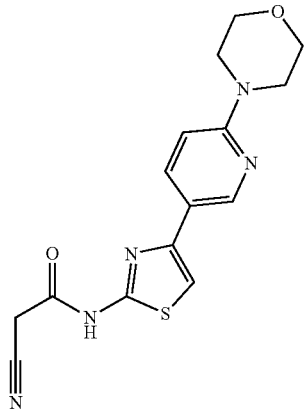 [SMILES: N#CCC(=O)Nc1nc(-c2ccc(N3CCOCC3)nc2)cs1]

The compound was prepared according to General procedure C3 from 4-(6-morpholinopyridin-3-yl)thiazol-2-amine (190 mg, 0.5 mmol), ethyl cyanoacetate (85 mg, 0.82 mL, 0.75 mmol) and NaH (60% in mineral oil, 60 mg, 1.5 mmol) in THF (2 mL) and MeOH (0.4 mL). After the reaction was completed, the solution was poured into saturated aqueous solution of NH$_4$Cl (10 mL) and the mixture was extracted with EtOAc (3×10 mL). Organic fractions were combined, washed with brine (30 mL), dried under MgSO$_4$, filtered, and the solvent was evaporated in vacuo. The residue was purified by column flash chromatography (hexane:EtOAc; 10:1 to 0:1). The product was obtained as a white solid (50 mg, 30%).

$^1$H NMR (500 MHz, DMSO-d$_6$) δ (ppm) 12.56 (s, 1H), 8.66 (d, J=2.4 Hz, 1H), 8.01 (dd, J=2.4, 8.9 Hz, 1H), 7.52 (s, 1H), 6.90 (d, J=8.9 Hz, 1H), 4.05 (s, 2H), 3.75-3.67 (m, 4H), 3.55-3.45 (m, 4H);

$^{13}$C NMR (126 MHz, DMSO-d$_6$) δ (ppm) 162.2, 158.9, 157.9, 147.5, 145.6, 135.4, 120.6, 115.6, 107.2, 106.6, 66.4, 45.5, 26.4;

HRMS calcd for C$_{15}$H$_{16}$N$_5$O$_2$S [M+H]$^+$ 330.1019, found 330.1017.

Preparative Example 160

2-cyano-N-(4-(3-fluoro-5-morpholinopyridin-2-yl)thiazol-2-yl)acetamide

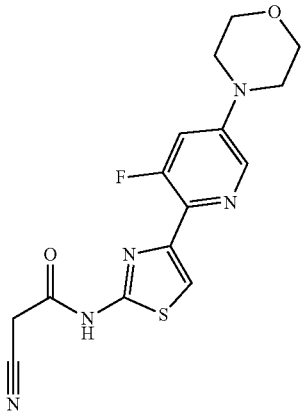 [SMILES: N#CCC(=O)Nc1nc(-c2ncc(N3CCOCC3)cc2F)cs1]

The compound was prepared according to General procedure C3 from 4-(3-fluoro-5-morpholinopyridin-2-yl)thiazol-2-amine (167 mg, 0.60 mmol), ethyl cyanoacetate (101 mg, 95 µL, 0.90 mmol) and NaH (60% in mineral oil, 57 mg, 1.43 mmol) in THF (2.5 mL) and MeOH (0.25 mL). The product, purified by column chromatography (CH$_2$Cl$_2$:MeOH; 100:1 to 75:1 to 50:1 to 25:1 to 20:1 to 10:1), was obtained as an orange solid (181 mg, 87%).

$^1$H NMR (500 MHz, DMSO-d$_6$) δ (ppm) 12.68 (s, 1H), 8.23 (t, J=2.1 Hz, 1H), 7.58 (d, J=1.1 Hz, 1H), 7.30 (dd, J=14.5, 2.4 Hz, 1H), 4.04 (s, 2H), 3.81-3.71 (m, 4H), 3.30-3.26 (m, 4H);

$^{13}$C NMR (126 MHz, DMSO-d$_6$) δ (ppm) 161.8, 156.9 (d, J=260.6 Hz), 156.8, 147.8 (d, J=5.4 Hz), 145.7, 132.5 (d, J=3.9 Hz), 129.8 (d, J=10.7 Hz), 115.1, 112.1 (d, J=6.4 Hz), 108.7 (d, J=23.5 Hz), 65.6, 47.1, 25.8;

$^{19}$F NMR (471 MHz, DMSO-d$_6$) δ (ppm) −121.44;

HRMS calcd for C$_{15}$H$_{15}$FN$_5$O$_2$S [M+H]$^+$ 348.0925, found 348.0926.

Preparative Example 161

N-(4-benzylthiazol-2-yl)-2-cyanoacetamide

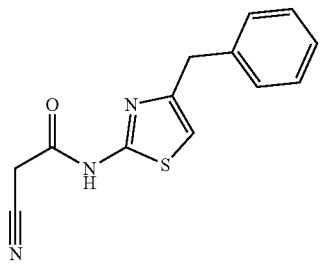 [SMILES: N#CCC(=O)Nc1nc(Cc2ccccc2)cs1]

The compound was prepared according to General procedure C3 from 4-benzyl-1,3-thiazol-2-amine (306 mg, 1.61 mmol), ethyl cyanoacetate (273 mg, 260 µL, 2.41 mmol) and NaH (60% in mineral oil, 71 mg, 1.77 mmol) in THF (4 mL) and MeOH (1 mL). The product, purified by column chromatography (hexane:EtOAc; 4:1 to 2:1 to 1:1), was obtained as a yellow solid (370 mg, 89%).

$^1$H NMR (300 MHz, DMSO-d$_6$) δ (ppm) 12.39 (s, 1H), 7.34-7.15 (m, 5H), 6.89 (s, 1H), 3.97 (d, J=1.4 Hz, 2H), 3.94 (s, 2H);
$^{13}$C NMR (75 MHz, DMSO-d$_6$) δ (ppm) 161.4, 157.0, 150.4, 139.4, 128.7, 128.2, 126.1, 115.1, 109.0, 37.0, 25.7;
HRMS calcd for C$_{13}$H$_{12}$N$_3$OS [M+H]$^+$ 258.0696, found 258.0696.

Preparative Example 162

(E)-2-cyano-3-(3,4-dihydroxyphenyl)-N-(4-(4-methoxyphenyl)thiazol-2-yl)acrylamide

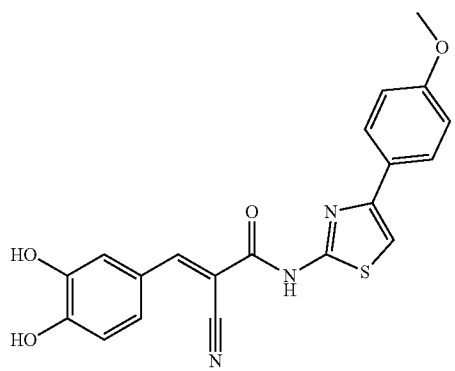 [SMILES: COc1ccc(-c2csc(NC(=O)/C(C#N)=C/c3ccc(O)c(O)c3)n2)cc1]

The compound was prepared according to General procedure D1 from 2-cyano-N-(4-(4-methoxyphenyl)thiazol-2-yl)acetamide (41 mg, 0.15 mmol), 3,4-dihydroxybenzaldehyde (20 mg, 0.143 mmol), and NEt$_3$ (21 µL, 0.15 mmol) in EtOH (1 mL); the reaction time was 3 h. The solvent was evaporated in vacuo and the resulting solid was stirred in CH$_3$CN (2 mL) at 25° C. for 48 h. The solid was collected by filtration, washed with diethyl ether (3×1 mL) and dried under vacuum. The product was obtained as an orange-solid (30 mg, 51%).

$^1$H NMR (500 MHz, DMSO-d$_6$) δ (ppm) 8.28 (s, 1H), 7.86 (d, J=8.7 Hz, 2H), 7.65-7.56 (m, 1H), 7.49 (s, 1H), 7.37 (d, J=8.4 Hz, 1H), 7.00 (d, J=8.7 Hz, 2H), 6.92 (d, J=8.4 Hz, 1H), 3.80 (s, 1H);
$^{13}$C NMR (126 MHz, DMSO-d$_6$) δ (ppm) 162.4, 159.0, 151.7, 148.3, 145.8, 127.1, 126.8, 125.9, 123.1, 116.7, 116.4, 116.1, 114.1, 106.5, 55.1;
HRMS calcd for C$_{20}$H$_{14}$N$_3$O$_4$S [M−H]$^−$ 392.0711, found 392.0712.

Preparative Example 163

(E)-2-cyano-3-(3,4-dihydroxyphenyl)-N-(4-(naphthalen-2-yl)thiazol-2-yl)acrylamide

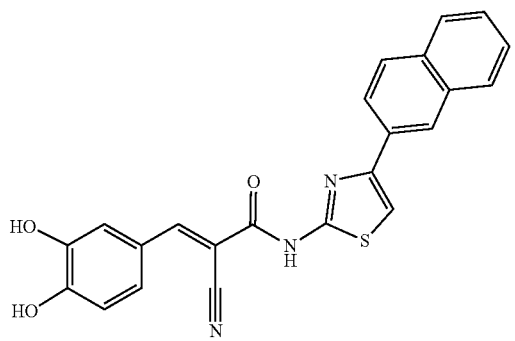 [SMILES: N#C/C(=C\c1ccc(O)c(O)c1)C(=O)Nc1nc(-c2ccc3ccccc3c2)cs1]

The compound was prepared according to General procedure D1 from 2-cyano-N-(4-(naphthalen-2-yl)thiazol-2-yl)acetamide (56 mg, 0.191 mmol), 3,4-dihydroxybenzaldehyde (25 mg, 0.181 mmol), and NEt$_3$ (27 µL, 0.191 mmol) in EtOH (1 mL); the reaction time was 4 h. The solvent was evaporated in vacuo and the residue was stirred in a mixture of CH$_2$Cl$_2$ and CH$_3$CN (1.5 mL+1.5 mL) at 25° C. for 2 h. The solid was collected by filtration and dried under vacuum. The product was obtained as an orange-brown solid (34 mg, 43%).

$^1$H NMR (500 MHz, DMSO-d$_6$) δ (ppm) 8.49 (s, 1H), 8.33 (s, 1H), 8.08 (d, J=8.5, 1.7 Hz, 1H), 8.04-7.90 (m, 3H), 7.83 (s, 1H), 7.63 (d, J=2.4 Hz, 1H), 7.58-7.49 (m, 1H), 7.40 (dd, J=8.3, 2.4 Hz, 1H), 6.94 (d, J=8.2 Hz, 1H);
$^{13}$C NMR (126 MHz, DMSO-d$_6$) δ (ppm) 162.1, 152.0, 151.6, 149.0, 145.8, 133.1, 132.5, 128.3, 128.1, 127.6, 126.5, 126.2, 125.9, 124.3, 124.0, 123.1, 116.5, 116.1, 109.3;
HRMS calcd for C$_{23}$H$_{14}$N$_3$O$_3$S [M−H]$^−$ 412.0761, found 412.0761.

Preparative Example 164

(E)-N-(4-([1,1'-biphenyl]-4-yl)thiazol-2-yl)-2-cyano-3-(3,4-dihydroxyphenyl)acrylamide

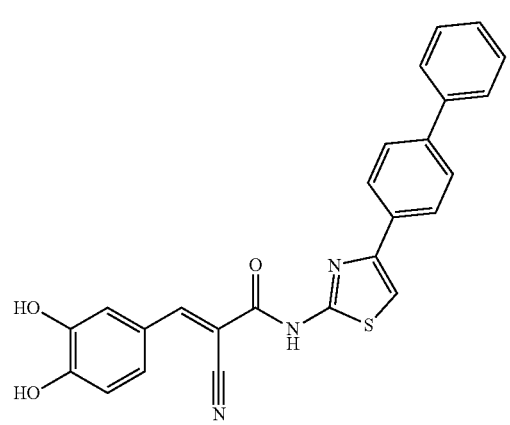 [SMILES: N#C/C(=C\c1ccc(O)c(O)c1)C(=O)Nc1nc(-c2ccc(-c3ccccc3)cc2)cs1]

The compound was prepared according to General procedure D2 from N-(4-([1,1'-biphenyl]4-yl)thiazol-2-yl)-2-cyanoacetamide (58 mg, 0.182 mmol), 3,4-dihydroxybenzaldehyde (24 mg, 0.173 mmol), and piperidine (3 μL, 0.027 mmol) in CH₃CN (2 mL); the reaction time was 2 h. Work-up 1 of General procedure D2. The product was obtained as a yellow solid (48 mg, 60%).

$^1$H NMR (500 MHz, DMSO-d$_6$) δ (ppm) 8.30 (s, 1H), 8.03 (d, J=8.5 Hz, 3H), 7.80-7.67 (m, 5H), 7.62 (d, J=2.3 Hz, 1H), 7.53-7.44 (m, 2H), 7.41-7.34 (m, 2H), 6.95-6.87 (m, 1H);

$^{13}$C NMR (126 MHz, DMSO-d$_6$) δ (ppm) 162.5, 151.6, 145.9, 139.6, 139.3, 133.2, 128.9, 127.5, 126.9, 126.5, 126.3, 116.8, 116.2, 116.1, 108.6;

HRMS calcd for C$_{25}$H$_{16}$N$_3$O$_3$S [M−H]⁻ 438.0918, found 438.0919.

Preparative Example 165

(E)-N-(4-(4-bromophenyl)thiazol-2-yl)-2-cyano-3-(3,5-dichloro-4-hydroxyphenyl)acrylamide

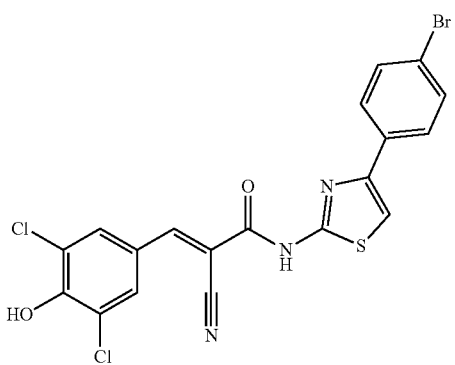 [SMILES: N#C/C(=C\c1cc(Cl)c(O)c(Cl)c1)C(=O)Nc1nc(-c2ccc(Br)cc2)cs1]

The compound was prepared according to General procedure D1 from N-(4-(4-bromophenyl)thiazol-2-yl)-2-cyanoacetamide (50 mg, 0.16 mmol), 3,5-dichloro-4-hydroxy benzaldehyde (28 mg, 0.15 mmol) and NEt₃ (20 μL, 0.15 mmol) in EtOH (3 mL); the reaction time was 4 h. Work-up 1 of General procedure D1. The product was obtained as a yellow solid (15 mg, 20%).

$^1$H NMR (500 MHz, DMSO-d$_6$) δ (ppm) 12.39 (s, 1H), 8.18 (s, 1H), 7.96 (s, 2H), 7.91-7.86 (m, 2H), 7.73 (s, 1H), 7.67-7.61 (m, 2H);

$^{13}$C NMR (126 MHz, DMSO-d$_6$) δ (ppm) 162.5, 158.8, 149.1, 147.1, 133.3, 131.6, 131.4, 127.7, 124.0, 120.9, 117.4, 109.3, 103.0;

HRMS calcd for C$_{19}$H$_{14}$BrN$_3$O$_3$S [M−H]⁻ 493.8958, found 493.8960.

Preparative Example 166

(E)-2-cyano-3-(3,4-dihydroxyphenyl)-N-(4-(3-hydroxy-4-methoxyphenyl)thiazol-2-yl)acrylamide

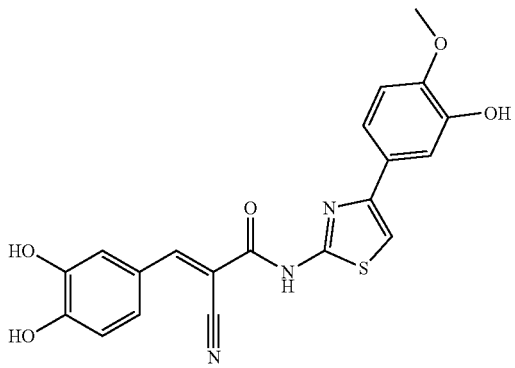 [SMILES: COc1ccc(-c2csc(NC(=O)/C(C#N)=C/c3ccc(O)c(O)c3)n2)cc1O]

The compound was prepared according to General procedure D1 from 2-cyano-N-(4-(3-hydroxy-4-methoxyphenyl)thiazol-2-yl)acetamide (41 mg, 0.14 mmol), 3,4-dihydroxybenzaldehyde (18 mg, 0.13 mmol) and NEt₃ (20 μL, 0.14 mmol) in EtOH (1.5 mL); the reaction time was 4 h. Work-up 1 of General procedure D1. The product was obtained as a yellow solid (25 mg, 45%).

$^1$H NMR (500 MHz, DMSO-d$_6$) δ (ppm) 12.55 (s, 1H), 9.81 (s, 2H), 9.03 (s, 1H), 8.29 (s, 1H), 7.61 (d, J=2.3 Hz, 1H), 7.41 (s, 1H), 7.38 (dd, J=8.5, 2.2 Hz, 1H), 7.37-7.31 (m, 2H), 6.97 (d, J=9.0 Hz, 1H), 6.93 (d, J=8.3 Hz, 1H), 3.81 (s, 3H);

$^{13}$C NMR (126 MHz, DMSO-d$_6$) δ (ppm) 151.9, 151.5, 147.7, 146.5, 145.8, 125.8, 123.2, 117.0, 116.5, 116.1, 113.2, 112.2, 106.5, 55.6;

HRMS calcd for C$_{20}$H$_{14}$N$_3$O$_5$S [M−H]⁻ 408.0660, found 408.0659.

Preparative Example 167

(E)-2-cyano-3-(3,4-dihydroxyphenyl)-N-(4-(2-hydroxypropan-2-yl)thiazol-2-yl)acrylamide

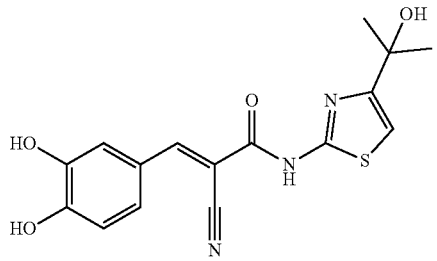 [SMILES: CC(C)(O)c1csc(NC(=O)/C(C#N)=C/c2ccc(O)c(O)c2)n1]

The compound was prepared according to General procedure D1 from 2-cyano-N-(4-(2-hydroxypropan-2-yl)thiazol-2-yl)acetamide (59 mg, 0.26 mmol), 3,4-dihydroxybenzaldehyde (32 mg, 0.23 mmol) and NEt₃ (36 μL, 0.26 mmol) in EtOH (1.5 mL); the reaction time was 4 h. Work-up 1 of General procedure D1. The product was obtained as a yellow solid (33 mg, 40%).

¹H NMR (500 MHz, DMSO-d₆) δ (ppm) 12.47 (s, 1H), 10.22 (s, 1H), 9.61 (s, 1H), 8.25 (s, 1H), 7.59 (d, J=2.1 Hz, 1H), 7.35 (d, J=8.4 Hz, 1H), 6.91 (d, J=8.3 Hz, 2H), 5.05 (s, 1H), 1.45 (s, 6H);
¹³C NMR (126 MHz, DMSO-d₆) δ (ppm) 151.6, 151.2, 145.7, 125.6, 123.3, 116.5, 116.0, 70.0, 30.2;
HRMS calcd for $C_{16}H_{14}N_3O_4S$ [M+H]⁻ 344.0711, found 344.0711.

Preparative Example 168

(E)-2-cyano-3-(3,5-dichloro-4-hydroxyphenyl)-N-(4-p-tolyl)thiazol-2-yl)acrylamide

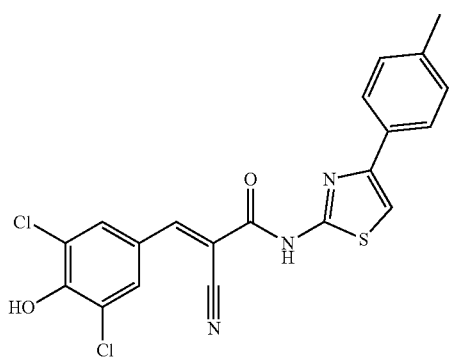 [SMILES: Cc1ccc(-c2csc(NC(=O)/C(C#N)=C/c3cc(Cl)c(O)c(Cl)c3)n2)cc1]

The compound was prepared according to General procedure D1 from 2-cyano-N-(4-(p-tolyl)thiazol-2-yl)acetamide (50 mg, 0.19 mmol), 3,5-dichloro-4-hydroxybenzaldehyde (35 mg, 0.18 mmol) and NEt₃ (26 μL, 0.19 mmol) in EtOH (3 mL); the reaction time was 4 h. Work-up 1 of General procedure D1. The product was obtained as a brown-red solid (35 mg, 43%).
¹H NMR (500 MHz, DMSO-d₆) δ (ppm) 12.24 (s, 1H), 8.14 (s, 1H), 7.95 (s, 2H), 7.86-7.77 (m, 2H), 7.55 (s, 1H), 7.25 (d, J=7.9 Hz, 2H), 2.33 (s, 3H);
¹³C NMR (126 MHz, DMSO-d₆) δ (ppm) 197.3, 162.4, 148.9, 137.1, 129.2, 125.6, 125.2, 124.2, 117.8, 107.4, 20.7;
HRMS calcd for $C_{20}H_{12}Cl_2N_3O_2S$ [M−H]⁻ 428.0033, found 428.0035.

Preparative Example 169

(E)-N-(4-(3-bromophenyl)thiazol-2-yl)-2-cyano-3-(3,4-dihydroxyphenyl)acrylamide

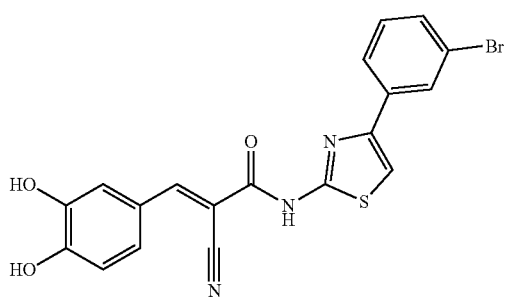 [SMILES: N#C/C(=C\c1ccc(O)c(O)c1)C(=O)Nc1nc(-c2cccc(Br)c2)cs1]

The compound was prepared according to General procedure D1 from N-(4-(3-bromophenyl)thiazol-2-yl)-2-cyanoacetamide (80 mg, 0.24 mmol), 3,4-dihydroxybenzaldehyde (31 mg, 0.23 mmol) and NEt₃ (33 μL, 0.24 mmol) in EtOH (3 mL); the reaction time was 4 h. Work-up 2 of General procedure D1. The residue was purified by column chromatography (hexane:EtOAc; 2:1). The so obtained semi-pure product was sonicated in CH₃CN (4 mL) and the solid was collected by filtration. The product was obtained as a yellow solid (40 mg, 40%).
¹H NMR (500 MHz, DMSO-d₆) δ (ppm) 12.67 (s, 1H), 10.29 (s, 1H), 9.66 (s, 1H), 8.32 (s, 1H), 8.17-8.15 (m, 1H), 7.97-7.92 (m, 1H), 7.85 (s, 1H), 7.62 (d, J=2.3 Hz, 1H), 7.57-7.48 (m, 1H), 7.44-7.39 (m, 1H), 7.40-7.36 (m, 1H), 6.94 (d, J=8.3 Hz, 1H);
¹³C NMR (126 MHz, DMSO-d₆) δ (ppm) 161.9, 158.2, 152.2, 151.6, 147.4, 145.8, 136.4, 130.9, 130.4, 128.4, 125.9, 124.6, 123.1, 122.2, 116.5, 116.3, 116.1, 110.2, 99.5;
HRMS calcd for $C_{19}H_{11}BrN_3O_3S$ [M−H]⁻ 441.9691, found 441.9689.

Preparative Example 170

(E)-N-(4-(2-bromophenyl)thiazol-2-yl)-2-cyano-3-(3,4-dihydroxyphenyl)acrylamide

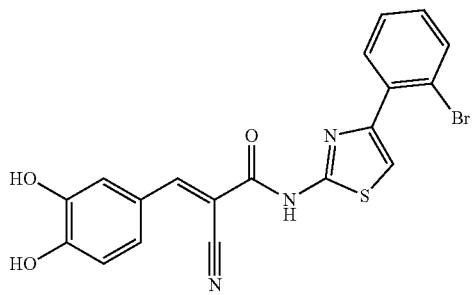 [SMILES: N#C/C(=C\c1ccc(O)c(O)c1)C(=O)Nc1nc(-c2ccccc2Br)cs1]

The compound was prepared according to General procedure D1 from N-(4-(2-bromophenyl)thiazol-2-yl)-2-cyanoacetamide (100 mg, 0.3 mmol), 3,4-dihydroxybenzaldehyde (41 mg, 0.28 mmol) and NEt₃ (42 μL, 0.3 mmol) in EtOH (3 mL); the reaction time was 4 h. Work-up 2 of general procedure D1. The residue was purified by column chromatography (toluene:EtOAc; 1:1). The resulting semi-pure product was sonicated in CH₃CN (4 mL) and the solid was collected by filtration. The product was obtained as a yellow solid (40 mg, 30%).
¹H NMR (500 MHz, DMSO-d₆) δ (ppm) 12.70 (s, 1H), 10.27 (s, 1H), 9.65 (s, 1H), 8.30 (s, 1H), 7.77-7.71 (m, 2H), 7.61 (d, J=2.2 Hz, 2H), 7.49-7.46 (m, 1H), 7.37 (dd, J=8.4, 2.3 Hz, 1H), 7.36-7.29 (m, 1H), 6.93 (d, J=8.2 Hz, 1H);
¹³C NMR (126 MHz, DMSO-d₆) δ (ppm) 161.8, 152.1, 151.5, 145.8, 133.4, 131.5, 129.8, 127.7, 125.8, 123.1, 121.2, 116.5, 116.4, 116.1, 113.1;
HRMS calcd for $C_{19}H_{11}BrN_3O_3S$ [M−H]⁻ 441.9691, found 441.9692.

Preparative Example 171

(E)-2-cyano-3-(3,4-dihydroxyphenyl)-N-(4-(3-(trifluoromethoxy)phenyl)thiazol-2-yl)acrylamide

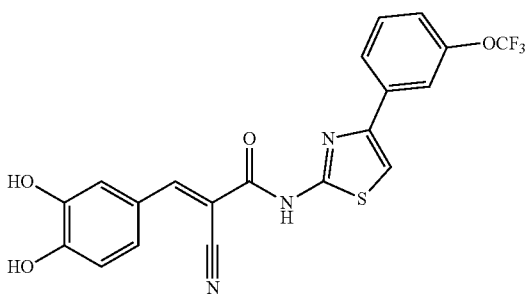 [SMILES: N#C/C(=C\c1ccc(O)c(O)c1)C(=O)Nc1nc(-c2cccc(OC(F)(F)F)c2)cs1]

The compound was prepared according to General procedure D2 from 2-cyano-N-(4-(3-(trifluoromethoxy)phenyl)thiazol-2-yl)acetamide (70 mg, 0.22 mmol), 3,4-dihydroxybenzaldehyde (30 mg, 0.22 mmol) and piperidine (2.0 µL, 0.02 mmol) in $CH_2Cl_2$ (2 mL); the reaction time was 4 h at reflux and then 16 h at 25° C. The product, purified by reverse phase column chromatography ($H_2O$:MeOH:AcOH; 45:55:0.05 to 10:90:0.05), was obtained as a yellow solid (60 mg, 60%).

$^1$H NMR (500 MHz, DMSO-$d_6$) δ (ppm) 12.68 (s, 1H), 10.29 (s, 1H), 9.67 (s, 1H), 8.32 (s, 1H), 8.01-7.95 (m, 1H), 7.93-7.87 (m, 2H), 7.62 (d, J=2.2 Hz, 1H), 7.60-7.58 (m, 1H), 7.39 (dd, J=8.4, 2.2 Hz, 1H), 7.37-7.31 (m, 1H), 6.94 (d, J=8.3 Hz, 1H);

$^{13}$C NMR (126 MHz, DMSO-$d_6$) δ (ppm) 162.0, 158.4, 152.2, 151.6, 148.9, 147.4, 145.8, 136.4, 130.8, 128.7, 125.9, 124.6, 123.1, 120.2, 120.1 (q, J=256.4 Hz), 117.9, 116.6, 116.4, 116.9, 110.5;

$^{19}$F NMR (471 MHz, DMSO-$d_6$) δ (ppm) −56.61;

HRMS calcd for $C_{20}H_{11}F_3N_3O_4S$ [M−H]$^−$ 446.0428, found 446.0428.

Preparative Example 172

(E)-2-cyano-3-(3,4-dihydroxyphenyl)-N-(4-(4-phenoxyphenyl)thiazol-2-yl)acrylamide

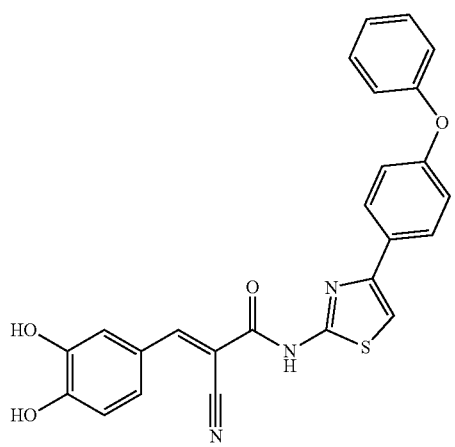 [SMILES: N#C/C(=C\c1ccc(O)c(O)c1)C(=O)Nc1nc(-c2ccc(Oc3ccccc3)cc2)cs1]

The compound was prepared according to General procedure D2 from 2-cyano-N-(4-(4-phenoxyphenyl)thiazol-2-yl)acetamide (68 mg, 0.2 mmol), 3,4-dihydroxybenzaldehyde (28 mg, 0.2 mmol) and piperidine (2.0 µL, 0.02 mmol) in $CH_2Cl_2$ (2 mL); the reaction time was 4 h at reflux and then 16 h at 25° C. The precipitate was collected by filtration and washed with $CH_2Cl_2$ (2 mL). The solid was mixed with a saturated aqueous solution of $NH_4Cl$ (15 mL) and the mixture was extracted with EtOAc (3×15 mL). The combined organic extracts were dried over $MgSO_4$, filtered, and the solvent was evaporated in vacuo. The product was obtained as a yellow solid (45 mg, 40%).

$^1$H NMR (500 MHz, DMSO-$d_6$) δ (ppm) 12.67 (s, 1H), 10.24 (s, 1H), 9.66 (s, 1H), 8.31 (s, 1H), 7.97-7.95 (m, 2H), 7.68-7.56 (m, 3H), 7.48-7.41 (m, 1H), 7.39 (dd, J=8.5, 2.2 Hz, 1H), 7.22-7.16 (m, 1H), 7.14-7.01 (m, 4H), 6.94 (d, J=8.4 Hz, 1H);

$^{13}$C NMR (126 MHz, DMSO-$d_6$) δ (ppm) 156.6, 156.3, 156.0, 155.9, 151.5, 145.8, 132.8, 130.1, 127.4, 125.7, 123.7, 123.1, 121.0, 119.0, 118.8, 118.5, 116.5, 116.9, 116.1, 115.3, 107.8;

HRMS calcd for $C_{25}H_{16}N_3O_4S$ [M−H]$^−$ 454.0867, found 454.0868.

Preparative Example 173

(E)-N-(4-(benzofuran-2-yl)thiazol-2-yl)-2-cyano-3-(3,4-dihydroxyphenyl)acrylamide

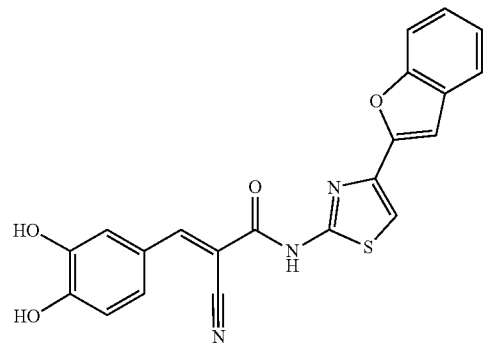 [SMILES: N#C/C(=C\c1ccc(O)c(O)c1)C(=O)Nc1nc(-c2cc3ccccc3o2)cs1]

The compound was prepared according to General procedure D2 from N-(4-(benzofuran-2-yl)thiazol-2-yl)-2-cyanoacetamide (53 mg, 0.187 mmol), 3,4-dihydroxybenzaldehyde (25 mg, 0.183 mmol) and piperidine (3 µL, 0.027 mmol) in $CH_2Cl_2$ (25 mL); the reaction time was 2 h at reflux. The product, purified by column chromatography (hexane:EtOAc; 1:1 to 0:1) followed by reverse phase column chromatography ($H_2O$:MeOH:AcOH; 60:40:0.05 to 10:90:0.05), was obtained as an orange solid (50 mg, 66%).

$^1$H NMR (500 MHz, DMSO-$d_6$) δ (ppm) 8.35-8.28 (m, 1H), 7.74-7.66 (m, 2H), 7.65-7.59 (m, 2H), 7.40-7.36 (m, 1H), 7.36-7.31 (m, 1H), 7.31-7.26 (m, 1H), 7.18 (s, 1H), 6.93 (d, J=8.4 Hz, 1H);

$^{13}$C NMR (126 MHz, DMSO-$d_6$) δ (ppm) 162.6, 154.1, 151.6, 145.8, 140.4, 128.4, 125.9, 124.7, 123.3, 123.1, 121.4, 116.6, 116.4, 116.1, 111.0, 110.8, 102.4;

HRMS calcd for $C_{21}H_{12}N_3O_4S$ [M−H]$^−$ 402.0554, found 402.0552.

Preparative Example 174

(E)-N-(4-((1S,3s)-adamantan-1-yl)thiazol-2-yl)-2-cyano-3-(3,4-dihydroxyphenyl)acrylamide

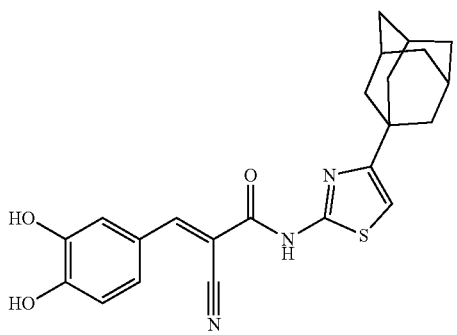 [SMILES: N#C/C(=C\c1ccc(O)c(O)c1)C(=O)Nc1nc(C23CC4CC(CC(C4)C2)C3)cs1]

The compound was prepared according to General procedure D1 from N-(4-adamantan-1-yl)thiazol-2-yl)-2-cyanoacetamide (65 mg, 0.216 mmol), 3,4-dihydroxybenzaldehyde (28 mg, 0.205 mmol) and NEt$_3$ (30 µL, 0.216 mmol) in EtOH (2 mL). The reaction time was 5 h. The solvent was evaporated in vacuo and the residue was purified by column chromatography (hexane:EtOAc; 1:0 to 1:1) followed by reverse phase column chromatography (H$_2$O:MeOH:AcOH; 60:40:0.05 to 10:90:0.05). The product was obtained as a brown-yellow solid (17 mg, 19%).

$^1$H NMR (500 MHz, DMSO-d$_6$) δ (ppm) 8.18 (s, 1H), 7.58 (d, J=2.3 Hz, 1H), 7.32 (dd, J=8.4, 2.3 Hz, 1H), 6.85 (s, 1H), 6.67 (s, 1H), 2.04 (s, 3H), 1.91 (d, J=3.7 Hz, 6H), 1.79-1.68 (m, 6H);

HRMS calcd for C$_{22}$H$_{22}$N$_3$O$_3$S [M–H]$^-$ 420.1387, found 420.1385.

Preparative Example 175

(E)-2-cyano-N-(5-cyclohexyl-4-(4-(trifluoromethoxy)phenyl)thiazol-2-yl)-3-(3,4-dihydroxyphenyl)acrylamide

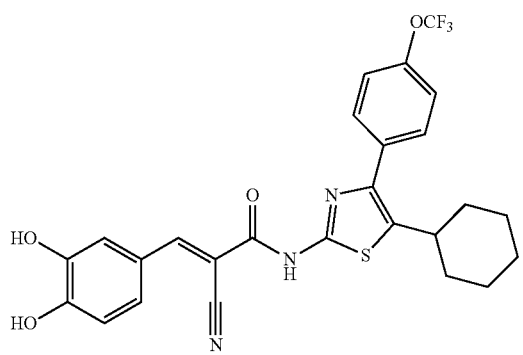 [SMILES: N#C/C(=C\c1ccc(O)c(O)c1)C(=O)Nc1nc(-c2ccc(OC(F)(F)F)cc2)c(C2CCCCC2)s1]

The compound was prepared according to General procedure D2 from 2-cyano-N-(5-cyclohexyl-4-(4-(trifluoromethoxy)phenyl)thiazol-2-yl)acetamide (70 mg, 0.17 mmol), 3,4-dihydroxybenzaldehyde (25 mg, 0.17 mmol) and piperidine (2.0 µL, 0.02 mmol) in CH$_2$Cl$_2$ (3 mL); the reaction time was 4 h at reflux and then 16 h at 25° C. The product, purified by reverse phase column chromatography (H$_2$O:MeOH:AcOH; 45:55:0.05 to 10:90:0.05), was obtained as an orange solid (55 mg, 60%).

$^1$H NMR (500 MHz, DMSO-d$_6$) δ 12.52 (s, 1H), 10.20 (s, 1H), 9.97-9.47 (m, 1H), 8.25 (s, 1H), 7.71-7.66 (m, 2H), 7.59 (d, J=2.2 Hz, 1H), 7.47 (d, J=8.3 Hz, 2H), 7.38-7.33 (m, 1H), 6.92 (d, J=8.3 Hz, 1H), 3.09-2.87 (m, 1H), 2.01-1.92 (m, 2H), 1.83-1.75 (m, 2H), 1.73-1.63 (m, 1H), 1.52-1.38 (m, 2H), 1.39-1.20 (m, 3H);

$^{13}$C NMR (126 MHz, DMSO-d$_6$) δ 151.8, 151.5, 145.8, 142.0, 134.4, 130.2, 125.8, 123.1, 122.8, 122.7, 122.7, 120.9, 120.1 (q, J=256.6 Hz) 117.0, 116.5, 116.0, 36.3, 35.7, 26.0, 25.1;

HRMS calcd for C$_{26}$H$_{23}$F$_3$N$_3$O$_4$S [M+H]$^+$ 530.1356, found 530.1350.

Preparative Example 176

(E)-2-cyano-3-(3,4-dihydroxyphenyl)-N-(4,5-diphenylthiazol-2-yl)acrylamide

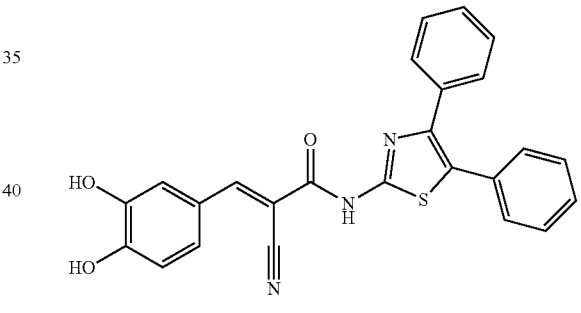

The compound was prepared according to General procedure D1 from 2-cyano-N-(4,5-diphenylthiazol-2-yl)acetamide (53 mg, 0.166 mmol), 3,4-dihydroxybenzaldehyde (22 mg, 0.158 mmol) and NEt$_3$ (23 µL, 0.166 mmol) in EtOH (1 mL); the reaction time was 2 h. The solvent was evaporated in vacuo and the residue was purified by column chromatography (hexane:EtOAc; 1:0 to 0:1) followed by reverse phase column chromatography (H$_2$O:MeOH:AcOH; 70:30:0.05 to 10:90:0.05). The product was obtained as a yellow solid (21 mg, 29%).

$^1$H NMR (500 MHz, DMSO-d$_6$) δ (ppm) 12.70 (s, 1H), 10.19 (s, 1H), 9.67 (s, 1H), 8.31 (s, 1H), 7.62 (d, J=2.3 Hz, 1H), 7.49-7.44 (m, 2H), 7.41-7.30 (m, 9H), 6.93 (d, J=8.2 Hz, 1H);

$^{13}$C NMR (126 MHz, DMSO-d$_6$) δ (ppm) 152.0, 151.6, 145.8, 131.6, 129.2, 128.9, 128.5, 128.3, 128.0, 125.9, 123.1, 116.5, 116.1;

HRMS calcd for C$_{25}$H$_{16}$N$_3$O$_3$S [M–H]$^-$ 438.0918, found 438.0920.

Preparative Example 177

(E)-2-cyano-3-(3,5-dimethyl-4-hydroxyphenyl)-N-(4-(4-(trifluoromethoxy)phenyl)thiazol-2-yl)acrylamide

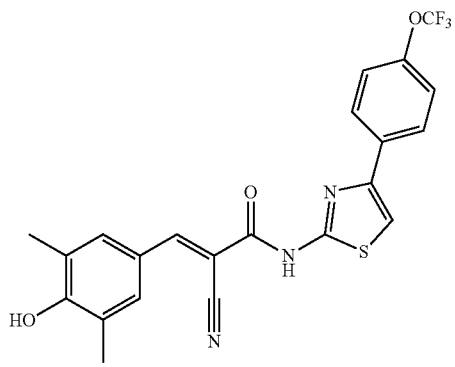 [SMILES: Cc1cc(/C=C(\C#N)C(=O)Nc2nc(-c3ccc(OC(F)(F)F)cc3)cs2)cc(C)c1O]

The compound was prepared according to General procedure D2 from 2-cyano-N-(4-(4-(trifluoromethoxy)phenyl)thiazol-2-yl)acetamide (80 mg, 0.25 mmol), 3,5-dimethyl-4-hydroxybenzaldehyde (37 mg, 0.25 mmol), and piperidine (3 μL, 0.027 mmol) in anhydrous $CH_2Cl_2$ (3 mL). The reaction time was 2 h at reflux. The product, purified by reverse phase column chromatography ($H_2O$:MeOH:AcOH; 60:40:0.05 to 5:95:0.05), was obtained as a yellow solid (80 mg, 70%).

$^1$H NMR (500 MHz, DMSO-$d_6$) δ (ppm) 12.71 (s, 1H), 9.61 (s, 1H), 8.34 (s, 1H), 8.10-8.03 (m, 2H), 7.78 (s, 1H), 7.71 (s, 2H), 7.50-7.42 (m, 2H), 2.24 (s, 6H);

$^{13}$C NMR (126 MHz, DMSO-$d_6$) δ (ppm) 161.8, 158.8, 152.0, 147.8, 133.4, 131.9, 127.5, 125.1, 122.7, 121.3, 120.1 (q, J=256.2 Hz), 109.7, 16.6;

$^{19}$F NMR (471 MHz, DMSO-$d_6$) δ (ppm) −56.68;

HRMS calcd for $C_{22}H_{17}F_3N_3O_3S$ $[M+H]^+$ 460.0937, found 460.0940.

Preparative Example 178

(E)-2-cyano-3-(3,4-dihydroxyphenyl-N-(4-(4-morpholinophenyl)thiazol-2-yl)acrylamide

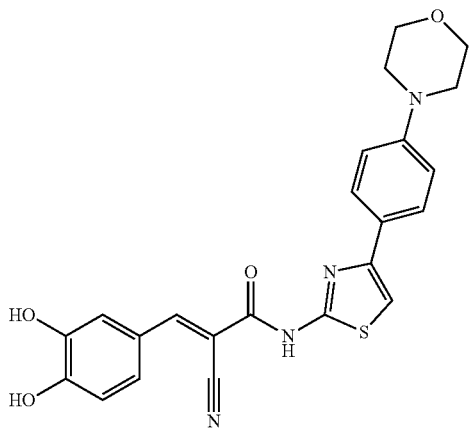 [SMILES: N#C/C(=C\c1ccc(O)c(O)c1)C(=O)Nc1nc(-c2ccc(N3CCOCC3)cc2)cs1]

The compound was prepared according to General procedure D2 from 2-cyano-N-(4-(4-morpholinophenyl)thiazol-2-yl)acetamide (26 mg, 0.079 mmol), 3,4-dihydroxybenzaldehyde (12 mg, 0.087 mmol), and piperidine (1 μL, 0.009 mmol,) in $CH_2Cl_2$ (3 mL); the reaction time was 4 h at 55° C. The product, purified by reverse phase column chromatography ($H_2O$:MeOH:AcOH; 70:30:0.05 to 0:100:0.05), was obtained as a yellow solid (5 mg, 0.011 mmol, 14%).

$^1$H NMR (500 MHz, DMSO-$d_6$) δ (ppm) 12.57 (s, 1H), 10.26 (s, 1H), 9.63 (s, 1H), 8.29 (s, 1H), 7.79 (d, J=8.9 Hz, 2H), 7.61 (d, J=2.1 Hz, 1H), 7.45 (s, 1H), 7.38 (dd, J=8.5, 2.4 Hz, 1H), 7.00 (d, J=9.0 Hz, 2H), 6.93 (d, J=8.2 Hz, 1H), 3.80-3.70 (m, 4H), 3.19-3.13 (m, 4H);

$^{13}$C NMR (126 MHz, DMSO-$d_6$) δ (ppm) 151.7, 126.4, 125.5, 116.3, 115.8, 114.5, 65.7, 47.7;

HRMS calcd for $C_{23}H_{19}N_4O_4S$ $[M−H]^−$ 447.1132, found 447.1135.

Preparative Example 179

(E)-2-cyano-3-(3,4-dihydroxyphenyl)-N-(4-(5-(trifluoromethyl)pyridin-2-yl)thiazol-2-yl)acrylamide

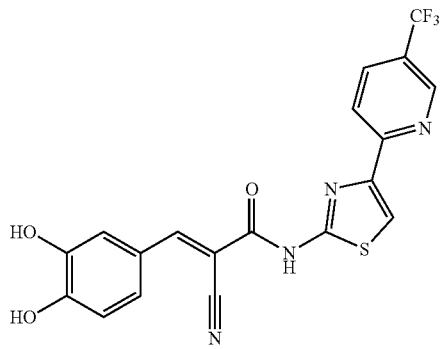 [SMILES: N#C/C(=C\c1ccc(O)c(O)c1)C(=O)Nc1nc(-c2ccc(C(F)(F)F)cn2)cs1]

2-cyano-N-(4-(5-(trifluoromethyl)pyridin-2-yl)thiazol-2-yl)acetamide was prepared according to General procedure C3 from 4-(5-(trifluoromethyl)pyridin-2-yl)thiazol-2-amine (321 mg, 1.31 mmol), NaH (35 mg, 1.44 mmol), ethyl cyanoacetate (0.222 mg, 209 μL, 1.96 mmol) in THF (5 mL) and MeOH (1 mL) at reflux for 2 h. Ethyl cyanoacetate (0.222 mg, 209 μL, 1.96 mmol) was added and the mixture was refluxed for additional 16 h. After the purification by column chromatography (hexane:EtOAc; 1:0 to 1:2), a mixture of the corresponding acetamide with the starting material (ca. 5/3) was obtained as a pale yellow solid (335 mg), which was used as such in the next step.

(E)-2-cyano-3-(3,4-dihydroxyphenyl)-N-(4-(5-(trifluoromethyl)pyridin-2-yl)thiazol-2-yl)acrylamide was prepared according to General procedure D2 from the mixture containing 2-cyano-N-(4-(5-(trifluoromethyl)pyridin-2-yl)thiazol-2-yl)acetamide (113 mg of the mixture corresponding to 71 mg of the pure acetamide intermediate, 0.226 mmol), 3,4-dihydroxybenzaldehyde (34 mg, 0.249 mmol), and piperidine (2 μL, 0.023 mmol,) in anhydrous $CH_2Cl_2$ (5 mL). The product, purified by reverse phase column chromatography ($H_2O$:MeOH:AcOH; 50:50:0.05 to 10:90:0.05), was obtained as a dark orange solid (80 mg, 82%).

$^1$H NMR (500 MHz, DMSO-$d_6$) δ (ppm) 8.99 (s, 1H), 8.35-8.29 (m, 2H), 8.18 (d, J=8.2 Hz, 1H), 8.08 (s, 1H), 7.62 (d, J=2.3 Hz, 1H), 7.38 (dd, J=8.4, 2.3 Hz, 1H), 6.94 (d, J=8.2 Hz, 1H);

$^{13}$C NMR (126 MHz, DMSO-d$_6$) δ (ppm) 162.9, 155.8, 152.5, 152.1, 151.9, 147.07-146.64 (m), 146.3, 135.5 (d, J=3.6 Hz), 126.4, 124.1 (q, J=31.8 Hz), 123.6, 123.3, 120.5, 117.0, 116.6, 115.6;
$^{19}$F NMR (471 MHz, DMSO-d$_6$) δ (ppm) −60.07;
HRMS calcd for C$_{19}$H$_{12}$F$_3$N$_4$O$_3$S [M+H]$^+$ 433.0577, found 433.0578.

Preparative Example 180

(E)-2-cyano-N-(4-(3-cyanophenyl)thiazol-2-yl)-3-(3,4-dihydroxyphenyl)acrylamide

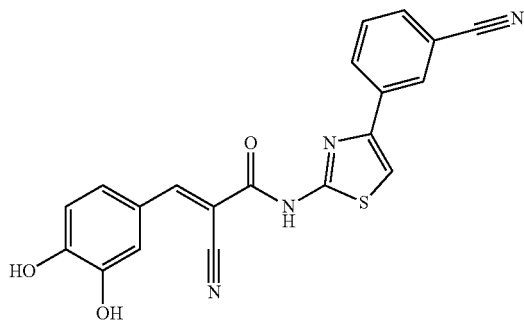 [SMILES: N#C/C(=C\c1ccc(O)c(O)c1)C(=O)Nc1nc(-c2cccc(C#N)c2)cs1]

The compound was prepared according to General procedure D2 from 2-cyano-N-(4-(3-cyanophenyl)thiazol-2-yl)acetamide (100 mg, 0.37 mmol), 3,4-dihydroxybenzaldehyde (51 mg, 0.37 mmol), and piperidine (3 μL, 0.027 mmol) in CH$_2$Cl$_2$ (3 mL); the reaction time was 2 h at reflux. The precipitate was collected by filtration, washed with CH$_2$Cl$_2$ (3 mL), MeOH (3 mL) and dried under vacuum. Product was obtained as a yellow solid (80 mg, 55%).
$^1$H NMR (500 MHz, DMSO-d$_6$) δ (ppm) 12.68 (s, 1H), 10.27 (s, 1H), 9.68 (s, 1H), 8.37 (d, J=1.7 Hz, 1H), 8.32 (s, 1H), 8.29-8.24 (m, 1H), 7.94 (s, 1H), 7.80 (d, J=7.6 Hz, 1H), 7.72-7.65 (m, 1H), 7.62 (d, J=2.2 Hz, 1H), 7.39 (dd, J=8.4, 2.3 Hz, 1H), 6.94 (d, J=8.3 Hz, 1H);
$^{13}$C NMR (126 MHz, DMSO-d$_6$) δ (ppm) 162.3, 159.5, 152.0, 151.6, 146.7, 145.8, 135.2, 131.2, 130.1, 130.1, 129.1, 125.9, 123.1, 118.6, 116.5, 116.5, 116.1, 111.9, 110.7;
HRMS calcd for C$_{20}$H$_{13}$N$_4$O$_3$S [M+H]$^+$ 389.0703, found 389.0704.

Preparative Example 181

(E)-4(2-(2-cyano-3-(3,4-dihydroxyphenyl)acrylamido)thiazol-4-yl)-N,N-dimethylbenzamide

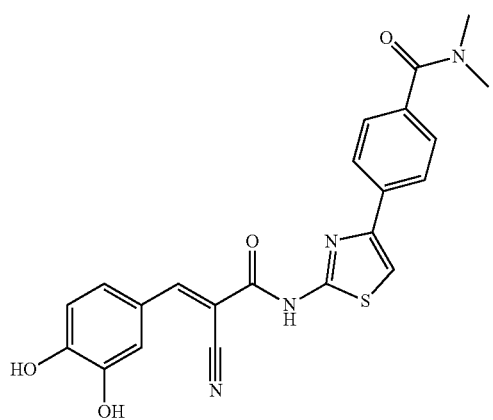 [SMILES: CN(C)C(=O)c1ccc(-c2csc(NC(=O)/C(C#N)=C/c3ccc(O)c(O)c3)n2)cc1]

The compound was prepared according to General procedure D2 from 4-(2-(2-cyanoacetamido)thiazol-4-yl)-N,N-dimethylbenzamide (70 mg, 0.22 mmol), 3,4-dihydroxybenzaldehyde (31 mg, 0.22 mmol), and piperidine (3 μL, 0.027 mmol) in CH$_2$Cl$_2$ (3 mL); the reaction time was 2 h at reflux. The precipitate was collected by filtration and washed with CH$_2$Cl$_2$ (3 mL). The product was obtained as a yellow solid (73 mg, 75%).
$^1$H NMR (500 MHz, DMSO-d$_6$) δ (ppm) 12.5 (s, 1H), 9.87 (s, 2H), 8.31 (s, 1H), 7.98 (d, J=7.9 Hz, 2H), 7.78 (s, 1H), 7.62 (d, J=2.2 Hz, 1H), 7.48 (d, 2H), 7.38 (dd, J=8.4, 2.3 Hz, 1H), 6.94 (d, J=8.3 Hz, 1H), 2.98 (s, 6H);
$^{13}$C NMR (126 MHz, DMSO-d$_6$) δ (ppm) 169.8, 162.1, 158.2, 152.0, 151.6, 148.2, 145.8, 135.6, 134.9, 127.6, 125.9, 125.4, 123.1, 116.5, 116.1, 109.7, 34.7;
HRMS calcd for C$_{22}$H$_{19}$N$_4$O$_4$S [M+H]$^+$ 435.1122, found 435.1126.

Preparative Example 182

(E)-2-cyano-3-(3,4-dihydroxyphenyl)-N-(4-(4-(2-hydroxypropan-2-yl)phenyl)thiazol-2-yl)acrylamide

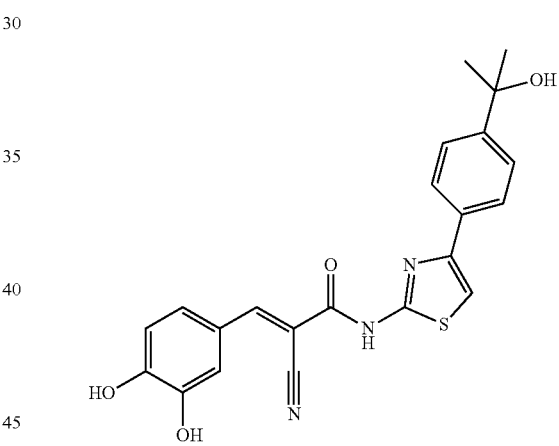

The compound was prepared according to General procedure D2 from 2-cyano-N-(4-(4-(2-hydroxypropan-2-yl)phenyl)thiazol-2-yl)acetamide (50 mg, 0.17 mmol), 3,4-dihydroxy benzaldehyde (23 mg, 0.17 mmol), and piperidine (3 μL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (45 mg, 60%).
$^1$H NMR (500 MHz, DMSO-d$_6$) δ (ppm) 12.62 (s, 1H), 9.82 (s, 2H), 8.31 (s, 1H), 7.86 (dd, J=8.4, 1.9 Hz, 2H), 7.61 (d, J=2.3 Hz, 2H), 7.56-7.50 (m, 2H), 7.38 (dd, J=8.4, 2.3 Hz, 1H), 6.93 (d, J=8.3 Hz, 1H), 5.01 (s, 1H), 1.45 (s, 6H);
$^{13}$C NMR (126 MHz, DMSO-d$_6$) δ (ppm) 162.2, 151.9, 151.6, 150.3, 145.8, 131.7, 125.8, 125.2, 124.9, 123.1, 116.6, 116.5, 116.1, 107.8, 70.5, 31.8;
HRMS calcd for C$_{22}$H$_{20}$N$_3$O$_4$S [M+H]$^+$ 422.1169, found 422.1167.

Preparative Example 183

(E)-2-cyano-N-(4-(5-cyanothiophen-2-yl)thiazol-2-yl)-3-(3,4-dihydroxyphenyl)acrylamide

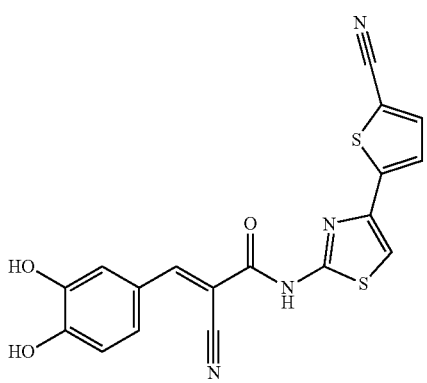 [SMILES: N#C/C(=C\c1ccc(O)c(O)c1)C(=O)Nc1nc(-c2ccc(C#N)s2)cs1]

The compound was prepared according to General procedure D2 from 2-cyano-N-(4-(5-cyanothiophen-2-yl)thiazol-2-yl)acetamide (50 mg, 0.18 mmol), 3,4-dihydroxybenzaldehyde (25 mg, 0.18 mmol) and piperidine (3 μL, 0.027 mmol) in CH$_2$Cl$_2$ (2 mL); the reaction time was 2 h at reflux. The product, purified by reverse phase column chromatography (H$_2$O:MeOH:AcOH; 60:40:0.05 to 5:95:0.05), was obtained as a yellow solid (40 mg, 55%).

$^1$H NMR (500 MHz, DMSO-d$_6$) δ (ppm) 12.87 (s, 1H), 10.30 (s, 1H), 9.66 (s, 1H), 8.33 (s, 1H), 7.96 (d, J=4.0 Hz, 1H), 7.93 (s, 1H), 7.73 (d, J=4.0 Hz, 1H), 7.61 (d, J=2.3 Hz, 1H), 7.38 (dd, J=8.4, 2.3 Hz, 1H), 6.94 (d, J=8.3 Hz, 1H);

$^{13}$C NMR (126 MHz, DMSO-d$_6$) δ (ppm) 162.1, 158.9, 152.4, 151.7, 145.8, 145.7, 142.0, 140.1, 126.0, 124.2, 123.0, 116.6, 116.3, 116.1, 114.6, 111.3, 106.4, 105.1;

HRMS calcd for C$_{18}$H$_9$N$_4$O$_3$S$_2$[M−H]$^−$ 393.0122, found 393.0121.

Preparative Example 184

(E)-2-cyano-3-(3,4-dihydroxyphenyl)-N-(4-(thiophen-2-yl)thiazol-2-yl)acrylamide

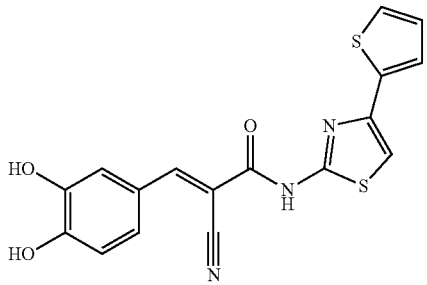 [SMILES: N#C/C(=C\c1ccc(O)c(O)c1)C(=O)Nc1nc(-c2cccs2)cs1]

The compound was prepared according to general procedure D1 from 2-cyano-N-(4-(thiophen-2-yl)thiazol-2-yl)acetamide (41 mg, 0.164 mmol), 3,4-dihydroxybenzaldehyde (22 mg, 0.156 mmol), and NEt$_3$ (23 μL, 0.164 mmol) in EtOH (1.5 mL); the reaction time was 4 h. The solvent was evaporated in vacuo and the resulting solid was triturated with a mixture of CH$_2$Cl$_2$ (2 mL) and EtOH (0.1 mL). The solid was collected by filtration and dried under vacuum. The product was obtained as an orange solid (22 mg, 36%).

$^1$H NMR (500 MHz, DMSO-d$_6$) δ (ppm) 8.31 (s, 1H), 7.61 (s, 1H), 7.58-7.46 (m, 3H), 7.38 (d, J=8.0 Hz, 1H), 7.19-7.05 (m, 1H), 6.93 (d, J=8.3 Hz, 1H);

$^{13}$C NMR (126 MHz, DMSO-d$_6$) δ (ppm) 162.0, 152.1, 151.6, 145.8, 138.2, 128.0, 125.9, 125.6, 123.9, 123.1, 116.5, 116.4, 116.1, 107.1, 99.7;

HRMS calcd for C$_7$H$_{10}$N$_3$O$_3$S$_2$ [M−H]$^−$ 368.0169, found 368.0169.

Preparative Example 185

(E)-2-cyano-N-(4-(3,5-difluorophenyl)thiazol-2-yl)-3-(3,4-dihydroxyphenyl)acrylamide

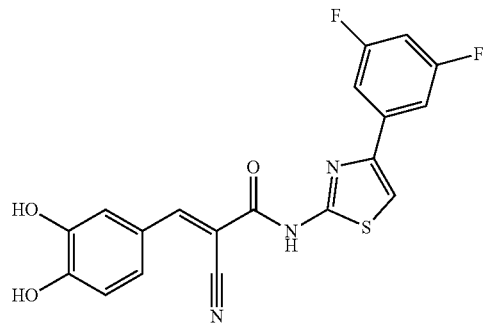 [SMILES: N#C/C(=C\c1ccc(O)c(O)c1)C(=O)Nc1nc(-c2cc(F)cc(F)c2)cs1]

The compound was prepared according to General procedure D2 from 2-cyano-N-(4-(3,5-difluorophenyl)thiazol-2-yl)acetamide (102 mg, 0.365 mmol), 3,4-dihydroxybenzaldehyde (50 mg, 0.365 mmol), and piperidine (3.3 mg, 0.037 mmol, 4 μL) in CH$_2$Cl$_2$ (6 mL). The precipitate was collected by filtration and washed with CH$_2$Cl$_2$ (3 mL). The solid was mixed with a saturated aqueous solution of NaHCO$_3$ (15 mL) and EtOAc (25 mL). The phases were separated, the organic phase was washed with brine (15 mL), dried over MgSO$_4$, filtered, and the solvent was evaporated in vacuo. The product was obtained as a dark orange solid (79 mg, 50%).

$^1$H NMR (500 MHz, DMSO-d$_6$) δ (ppm) 8.31 (s, 1H), 7.93 (s, 1H), 7.68-7.62 (m, 2H), 7.61 (d, J=2.3 Hz, 1H), 7.39 (dd, J=8.4, 2.3 Hz, 1H), 7.24-7.16 (m, 1H), 6.94 (d, J=8.4 Hz, 1H);

$^{13}$C NMR (126 MHz, DMSO-d$_6$) δ (ppm) 163.8 (d, J=13.6 Hz), 162.1, 161.8 (d, J=13.6 Hz), 158.5, 151.9 (d, J=71.8 Hz), 146.7, 145.8, 137.6, 125.9, 123.1, 116.5, 116.1, 111.4, 108.8-108.4 (m), 103.0 (dd, J=25.9 Hz);

$^{19}$F NMR (471 MHz, DMSO-d$_6$) δ (ppm) −109.5;

HRMS calcd for C$_{19}$H$_{12}$F$_2$N$_3$O$_3$S [M+H]$^+$ 400.0562, found 400.0559.

Preparative Example 186

(E)-2-cyano-3-(3,4-dihydroxyphenyl-N-(4-(pyridazin-3-yl)thiazol-2-yl)acrylamide

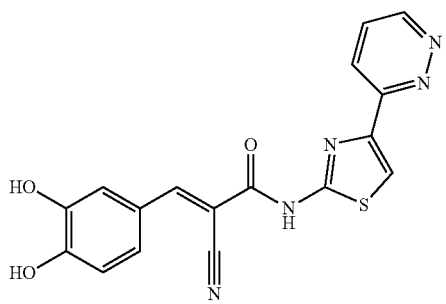 [SMILES: N#C/C(=C\c1ccc(O)c(O)c1)C(=O)Nc1nc(-c2cccnn2)cs1]

The compound was prepared according to General procedure D2 from 2-cyano-N-(4-(pyridazin-3-yl)thiazol-2-yl)acetamide (8 mg, 0.033 mmol), 3,4-dihydroxybenzaldehyde (5 mg, 0.036 mmol), and piperidine (0.3 μL, 0.004 mmol) in CH$_2$Cl$_2$ (1 mL) and DMSO (0.5 mL); the reaction time was 4 h at 55° C. The product, purified by reverse phase column chromatography (H$_2$O:MeOH:AcOH; 70:30:0.05% to 0:100:0.05%), was obtained as a yellow solid (3 mg, 25%).

$^1$H NMR (500 MHz, DMSO-d$_6$) δ (ppm) 9.23-9.16 (m, 1H), 8.28 (s, 1H), 8.20-8.08 (m, 2H), 7.80 (dd, J=8.5, 4.9 Hz, 1H), 7.61 (d, J=2.3 Hz, 1H), 7.37 (dd, J=8.4, 2.3 Hz, 1H), 6.92 (d, J=8.2 Hz, 1H);

$^{13}$C NMR (126 MHz, DMSO-d$_6$) δ (ppm) 150.1, 127.6, 125.3, 123.6, 116.0, 115.7;

HRMS calcd for C$_{17}$H$_{10}$N$_5$O$_3$S [M−H]$^−$ 364.0510, found 364.0513.

Preparative Example 187

(E)-2-cyano-3-(3,4-dihydroxyphenyl)-N-(4-(4-fluorophenyl)thiazol-2-yl)acrylamide

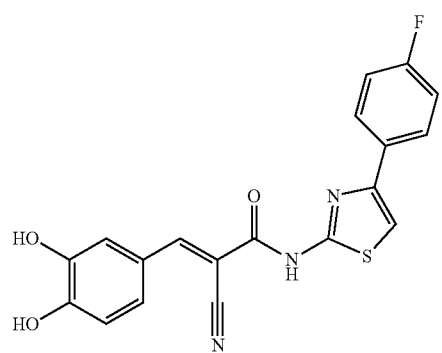 [SMILES: N#C/C(=C\c1ccc(O)c(O)c1)C(=O)Nc1nc(-c2ccc(F)cc2)cs1]

The compound was prepared according to General procedure D2 from 2-cyano-N-(4-(4-fluorophenyl)thiazol-2-yl)acetamide (108 mg, 0.413 mmol), 3,4-dihydroxybenzaldehyde (57 mg, 0.413 mmol), and piperidine (4 μL, 0.041 mmol) in CH$_2$Cl$_2$ (6 mL). The precipitate was collected by filtration and washed with CH$_2$Cl$_2$ (3 mL). The solid was mixed with a saturated aqueous solution of NaHCO$_3$ (15 mL) and EtOAc (25 mL), the phases were separated, the organic phase was washed with brine (15 mL), dried over MgSO$_4$, filtered, and the solvent was evaporated in vacuo. The product was obtained as an orange solid (143 mg, 91%).

$^1$H NMR (500 MHz, DMSO-d$_6$) δ (ppm) 8.31 (s, 1H), 8.01-7.93 (m, 2H), 7.66 (s, 1H), 7.61 (d, J=2.1 Hz, 1H), 7.38 (dd, J=8.5, 2.3 Hz, 1H), 7.32-7.24 (m, 2H), 6.94 (d, J=8.2 Hz, 1H);

$^{13}$C NMR (126 MHz, DMSO-d$_6$) δ (ppm) 162.8, 160.8, 151.8 (d, J=63.6 Hz), 145.8, 130.6, 127.8 (d, J=8.2 Hz), 125.9, 123.1, 116.5, 116.1, 115.6 (d, J=20.9 Hz), 108.5;

$^{19}$F NMR (471 MHz, DMSO-d$_6$) δ (ppm) −114.2;

HRMS calcd for C$_{19}$H$_{13}$FN$_3$O$_3$S [M+H]$^+$ 382.0656, found 382.0656.

Preparative Example 188

(E)-2-cyano-3-(3,4-dihydroxyphenyl)-N-(4-(pyridin-4-yl)thiazol-2-yl)acrylamide

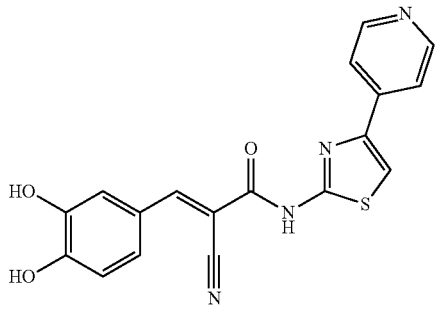 [SMILES: N#C/C(=C\c1ccc(O)c(O)c1)C(=O)Nc1nc(-c2ccncc2)cs1]

The compound was prepared according to general procedure D1 from 2-cyano-N-(4-(pyridin-4-yl)thiazol-2-yl)acetamide (37 mg, 0.151 mmol), 3,4-dihydroxybenzaldehyde (20 mg, 0.144 mmol), and NEt$_3$ (21 μL, 0.151 mmol) in EtOH (2 mL); the reaction time was for 4 h. The precipitate was collected by filtration, washed with ethyl ether (2×2 mL) and dried under vacuum. The product was obtained as yellow solid (14 mg, 25%).

$^1$H NMR (500 MHz, DMSO-d$_6$) δ (ppm) 12.77 (bs, 1H), 10.29 (bs, 1H), 9.66 (s, 1H), 8.64 (d, J=6.3 Hz, 2H), 8.32 (s, 1H), 8.06 (s, 1H), 7.88 (d, J=6.3 Hz, 2H), 7.62 (d, J=2.3 Hz, 1H), 7.39 (dd, J=8.3, 2.4 Hz, 1H), 6.94 (d, J=8.4 Hz, 1H);

$^{13}$C NMR (126 MHz, DMSO-d$_6$) δ (ppm) 162.2, 158.9, 152.3, 151.6, 150.3, 146.5, 145.8, 140.8, 126.0, 123.1, 120.0, 116.6, 116.4, 116.1, 112.9, 99.6;

HRMS calcd for C$_{18}$H$_{11}$N$_4$O$_3$S [M−H]$^−$ 363.0557, found 363.0558.

Preparative Example 189

Methyl (E)-4-(2-(2-cyano-3-(3,4-dihydroxyphenyl)acrylamido)thiazol-4-yl)benzoate

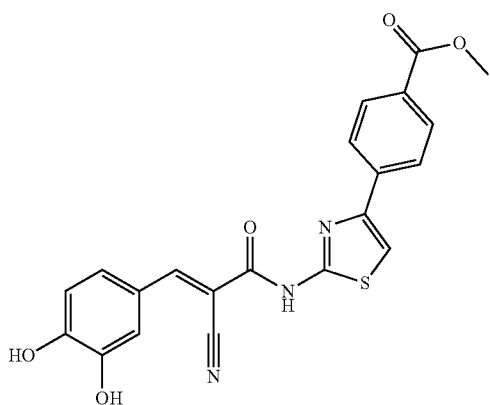 [SMILES: COC(=O)c1ccc(-c2csc(NC(=O)/C(C#N)=C/c3ccc(O)c(O)c3)n2)cc1]

The compound was prepared according to General procedure D2 from methyl 4-(2-(2-cyanoacetamido)thiazol-4-yl)benzoate (25 mg, 0.08 mmol), 3,4-dihydroxybenzaldehyde (15 mg, 0.08 mmol), and piperidine (3 μL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (22 mg, 70%).

$^1$H NMR (500 MHz, DMSO-d$_6$) δ (ppm) 12.74 (s, 1H), 10.29 (s, 1H), 9.66 (s, 1H), 8.33 (s, 1H), 8.12-8.02 (m, 4H), 7.91 (s, 1H), 7.62 (d, J=2.2 Hz, 1H), 7.39 (dd, J=8.4, 2.2 Hz, 1H), 6.94 (d, J=8.3 Hz, 1H), 3.87 (s, 3H);

$^{13}$C NMR (126 MHz, DMSO-d$_6$) δ (ppm) 170.3, 165.9, 161.9, 158.4, 152.1, 151.6, 147.9, 145.8, 138.4, 129.7, 128.6, 125.9, 125.8, 123.1, 116.5, 116.3, 116.1, 111.3, 52.1;

HRMS calcd for C$_{21}$H$_{16}$N$_3$O$_5$S [M+H]$^-$ 422.0805, found 422.0803.

Preparative Example 190

(E/Z)-2-cyano-3-(3,4-dihydroxyphenyl)-3-phenyl-N-(4-phenylthiazol-2-yl)acrylamide

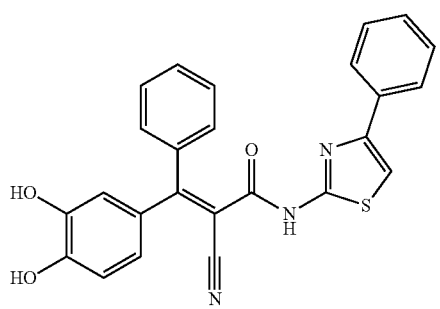

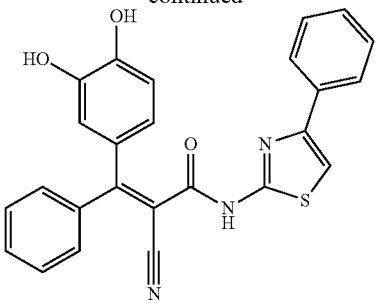

A mixture of 2-cyano-N-(4-phenylthiazol-2-yl)acetamide (201 mg, 0.826 mmol), (3,4-dihydroxyphenyl)phenylmethanone (177 mg, 0.826 mmol), and NH$_4$OAc (191 mg, 2.48 mmol) in toluene (6 mL) was heated to reflux for 24 h with azeotropic removal of water by a Dean-Stark trap. The solvent was evaporated in vacuo, the residue was dissolved in EtOAc (50 mL) and the solution was washed with a saturated aqueous solution of NH$_4$Cl (25 mL), H$_2$O (25 mL), and brine (25 mL). The organic phase was dried over MgSO$_4$, filtered, and the solvent was evaporated in vacuo. The residue was purified by column chromatography (toluene:EtOAc; 1:0 to 2:1). The fractions containing the product were concentrated to the residual volume of 20 mL and the mixture was allowed to stand at 25° C. The precipitate was collected by filtration and dried under vacuum. The product (a 1:0.8 mixture of E and Z isomers) was obtained as a yellow solid (80 mg, 22%).

$^1$H NMR (500 MHz, DMSO-d$_6$) δ (ppm) 12.80 (s, 1H, major isomer), 12.72 (s, 0.8H, minor isomer), 9.70 (s, 0.8H, minor isomer), 9.59 (s, 1H, major isomer), 9.36 (s, 0.8H, minor isomer), 9.23 (s, 1H, major isomer), 7.90-7.78 (m, 3.6H), 7.70 (s, 1H, major isomer), 7.65 (s, 0.8H, minor isomer), 7.57-7.52 (m, 2.8H), 7.44-7.36 (m, 8H), 7.35-7.29 (m, 1.8H), 7.23-7.18 (m, 1.8H), 6.88-6.82 (m, 1.8H), 6.77 (dd, J=8.2, 2.3 Hz, 0.8H, minor isomer), 6.69 (d, J=8.7 Hz, 1H, major isomer), 6.59-6.54 (m, 1.8H);

$^{13}$C NMR (126 MHz, DMSO-d$_6$) δ (ppm) 163.9, 163.8, 161.8, 161.6, 157.4, 157.2, 149.2, 149.2, 148.8, 148.6, 145.1, 138.6, 138.0, 134.0, 133.9, 130.5, 130.4, 129.8, 129.7, 128.7, 128.6, 128.5, 128.2, 127.9, 125.7, 122.5, 122.0, 117.4, 117.3, 117.1, 115.4, 115.3, 108.9, 108.9, 102.7, 102.7;

HRMS calcd for C$_{25}$H$_{18}$N$_3$O$_3$S [M+H]$^-$ 440.1063, found 440.1061.

Preparative Example 191

(E)-2-cyano-3-(3,4-dihydroxyphenyl-N-(4,5,6,7-tetrahydrobenzo[d]thiazol-2-yl)acrylamide

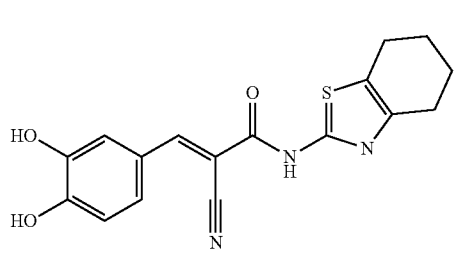

The compound was prepared according to General procedure D1 from 2-cyano-N-(4,5,6,7-tetrahydrobenzo[d]thiazol-2-yl)acetamide (45 mg, 0.2 mmol), 3,4-dihydroxybenzaldehyde (26 mg, 0.2 mmol) and NEt$_3$ (30 μL, 0.20 mmol) in EtOH (3 mL); the reaction time was 2.5 h at 50° C. and then 16 h at 25° C. Work-up 1 of General procedure D1. The product was obtained as a yellow solid (73 mg, 77%).

$^1$H NMR (500 MHz, DMSO-d$_6$) δ (ppm) 12.81 (s, 1H), 10.19 (s, 1H), 9.63 (s, 1H), 8.22 (s, 1H), 7.67 (d, J=2.2 Hz, 1H), 7.41 (dd, J=8.4, 2.2 Hz, 1H), 6.97 (d, J=8.2 Hz, 1H), 2.69-2.59 (m, 4H), 1.86 (p, J=3.3 Hz, 4H);

$^{13}$C NMR (126 MHz, DMSO-d$_6$) δ (ppm) 151.1, 150.8, 145.7, 125.3, 123.6, 117.5, 116.4, 116.0, 23.6, 22.5, 22.2, 21.8;

HRMS calcd for C$_{17}$H$_{14}$N$_3$O$_3$S [M–H]$^-$ 340.0761, found 340.0760.

Preparative Example 192

(E)-2-cyano-3-(3,5-dibromo-4-hydroxyphenyl)-N-(4-phenylthiazol-2-yl)acrylamide

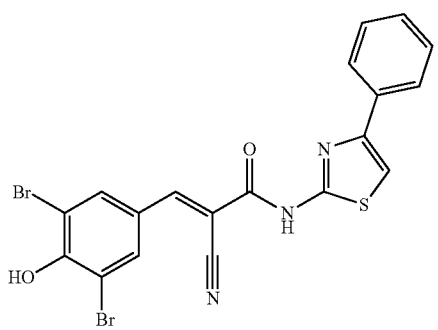 [SMILES: N#C/C(=C\c1cc(Br)c(O)c(Br)c1)C(=O)Nc1nc(-c2ccccc2)cs1]

The compound was prepared according to General procedure D1 from 2-cyano-N-(4-phenylthiazol-2-yl)acetamide (60 mg, 0.247 mmol), 3,5-dibromo-4-hydroxybenzaldehyde (66 mg, 0.234 mmol), and NEt$_3$ (34 μL, 0.247 mmol) in EtOH (1 mL); the reaction time was 2 h. The solvent was evaporated in vacuo and the residue was purified by column chromatography (hexane:EtOAc; 1:0 to 0:1). The product was obtained as a yellow solid (74 mg, 59%).

$^1$H NMR (500 MHz, DMSO-d$_6$) δ (ppm) 12.38 (s, 1H), 8.19 (s, 1H), 8.17 (s, 2H), 7.95-7.90 (m, 2H), 7.65 (s, 1H), 7.48-7.41 (m, 2H), 7.38-7.31 (m, 1H);

$^{13}$C NMR (126 MHz, DMSO-d$_6$) δ (ppm) 162.5, 148.7, 135.1, 134.0, 128.7, 127.9, 125.7, 117.3, 114.1, 108.4;

HRMS calcd for C$_{19}$H$_{10}$Br$_2$N$_3$O$_2$S [M–H]$^-$ 503.8846, found 503.8846.

Preparative Example 193

(E)-2-cyano-3-(3,5-dichloro-4-hydroxyphenyl)-N-(4-phenylthiazol-2-yl)acrylamide

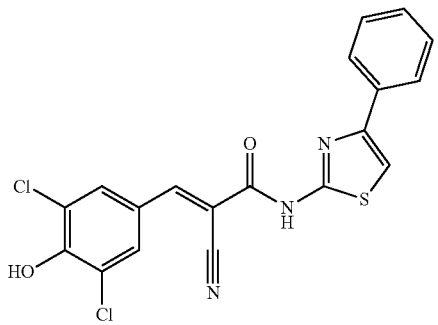 [SMILES: N#C/C(=C\c1cc(Cl)c(O)c(Cl)c1)C(=O)Nc1nc(-c2ccccc2)cs1]

The compound was prepared according to General procedure D1 from 2-cyano-N-(4-phenylthiazol-2-yl)acetamide (30 mg, 0.123 mmol), 3,5-dichloro-4-hydroxybenzaldehyde (22 mg, 0.117 mmol), and NEt$_3$ (17 μL, 0.123 mmol) in EtOH (2 mL); the reaction time was 4 h. Work-up 2 of General procedure D1. The product, purified by preparative TLC (EtOAc), was obtained as an orange-brown solid (32 mg, 62%).

$^1$H NMR (500 MHz, DMSO-d$_6$) δ (ppm) 12.34 (s, 1H), 8.20 (s, 1H), 8.05-7.90 (m, 5H), 7.65 (s, 1H), 7.45 (t, J=7.7 Hz, 2H), 7.37-7.31 (m, 1H);

$^{13}$C NMR (126 MHz, DMSO-d$_6$) δ (ppm) 151.6, 149.1, 131.4, 128.7, 127.9, 125.7, 123.9, 108.4;

HRMS calcd for C$_{19}$H$_{10}$Cl$_2$N$_3$O$_2$S [M–H]$^-$ 413.9876, found 413.9880.

Preparative Example 194

(E)-2-cyano-3-(3,4-dihydroxyphenyl)-N-(5-methyl-4-phenylthiazol-2-yl)acrylamide

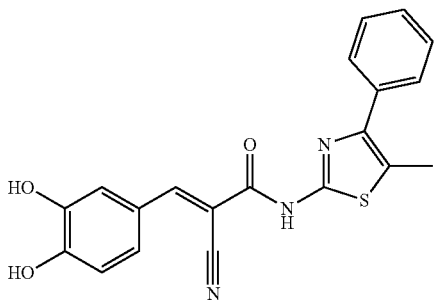 [SMILES: Cc1sc(NC(=O)/C(C#N)=C/c2ccc(O)c(O)c2)nc1-c1ccccc1]

The compound was prepared according to General procedure D1 from 2-cyano-N-(5-methyl-4-phenylthiazol-2-yl)acetamide (63 mg, 0.229 mmol), 3,4-dihydroxybenzaldehyde (30 mg, 0.217 mmol), and NEt$_3$ (32 μL, 0.229 mmol) in EtOH (1 mL); the reaction time was 2 h. The solvent was evaporated in vacuo and the residue was purified by column chromatography (hexane:EtOAc; 1:0 to 0:1) followed by reverse phase column chromatography (H$_2$O:MeOH:AcOH; 70:30:0.05 to 10:90:0.05). The product was obtained as an orange solid (37 mg, 43%).

¹H NMR (500 MHz, DMSO-d₆) δ (ppm) 12.49 (s, 1H), 10.24 (s, 1H), 9.62 (s, 1H), 7.66 (d, J=7.5 Hz, 2H), 7.60 (d, J=2.3 Hz, 1H), 7.50-7.44 (m, 2H), 7.41-7.34 (m, 2H), 6.92 (d, J=8.4 Hz, 1H), 2.47 (s, 3H);
¹³C NMR (126 MHz, DMSO-d₆) δ (ppm) 151.8, 151.3, 145.8, 128.4, 128.1, 127.5, 125.7, 123.2, 116.5, 116.0, 11.8;
HRMS calcd for $C_{20}H_{14}N_3O_3S$ [M–H]⁻ 376.0761, found 376.0760.

Preparative Example 195

(E)-N-(5-chloro-4-phenylthiazol-2-yl)-2-cyano-3-(3,4-dihydroxyphenyl)acrylamide

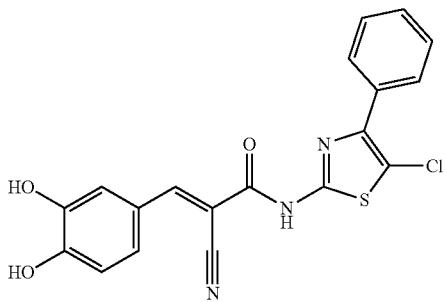 [SMILES: N#C/C(=C\c1ccc(O)c(O)c1)C(=O)Nc1nc(-c2ccccc2)c(Cl)s1]

The compound was prepared according to General procedure D2 from N-(5-chloro-4-phenylthiazol-2-yl)-2-cyanoacetamide (56 mg, 0.2 mmol), 3,4-dihydroxybenzaldehyde (27 mg, 0.2 mmol), and piperidine (2.0 μL, 0.02 mmol) in CH₂Cl₂ (3 mL); the reaction time was 4 h at 50° C. and then 16 h at 25° C. The product was obtained as a yellow solid (30 mg, 40%).
¹H NMR (500 MHz, DMSO-d₆) δ (ppm) 12.96 (s, 1H), 10.33 (s, 1H), 9.67 (s, 1H), 8.32 (s, 1H), 7.91 (d, J=6.9 Hz, 2H), 7.61 (d, J=2.2 Hz, 1H), 7.51 (t, J=7.5 Hz, 2H), 7.47-7.40 (m, 1H), 7.38 (dd, J=8.4, 2.2 Hz, 1H), 6.94 (d, J=8.3 Hz, 1H);
¹³C NMR (126 MHz, DMSO-d₆) δ (ppm) 162.0, 152.5, 151.8, 145.8, 132.3, 128.5, 127.7, 126.1, 123.0, 116.6, 116.2, 116.1;
HRMS calcd for $C_{19}H_{11}ClN_3O_3S$ [M–H]⁻ 396.0215, found 396.0213.

Preparative Example 196

(E)-N-(5-bromo-4-phenylthiazol-2-yl)-2-cyano-3-(3,4-dihydroxyphenyl)acrylamide

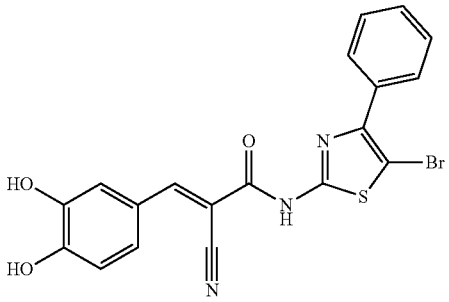 [SMILES: N#C/C(=C\c1ccc(O)c(O)c1)C(=O)Nc1nc(-c2ccccc2)c(Br)s1]

The compound was prepared according to General procedure D1 from N-(5-bromo-4-phenylthiazol-2-yl)-2-cyanoacetamide (53 mg, 0.164 mmol), 3,4-dihydroxybenzaldehyde (22 mg, 0.156 mmol), and NEt₃ (23 μL, 0.164 mmol) in EtOH (2 mL); the reaction time was 2 h. The solvent was evaporated in vacuo and the residue was purified by column chromatography (hexane:EtOAc; 1:0 to 0:1) followed by reverse phase column chromatography (H₂O:MeOH:AcOH; 50:50:0.05 to 0:100:0.05). The product was obtained as a yellow-orange solid (14 mg, 19%).
¹H NMR (500 MHz, DMSO-d₆) δ (ppm) 12.97 (s, 1H), 10.32 (s, 1H), 9.67 (s, 1H), 8.32 (s, 1H), 7.89 (d, J=7.2 Hz, 2H), 7.61 (d, J=2.3 Hz, 1H), 7.55-7.47 (m, 2H), 7.47-7.41 (m, 1H), 7.38 (dd, J=8.4, 2.3 Hz, 1H), 6.94 (d, J=8.4 Hz, 1H);
¹³C NMR (126 MHz, DMSO-d₆) δ (ppm) 162.5, 152.5, 151.8, 145.8, 133.0, 128.5, 128.4, 128.0, 126.1, 123.1, 116.6, 116.1;
HRMS calcd for $C_{19}H_{12}BrN_3O_3S$ [M–H]⁻ 439.9710, found 439.9709.

Preparative Example 197

(E)-2-cyano-3-(3,4-dihydroxyphenyl)-N-(4-(4-ethynylphenyl)thiazol-2-yl)acrylamide

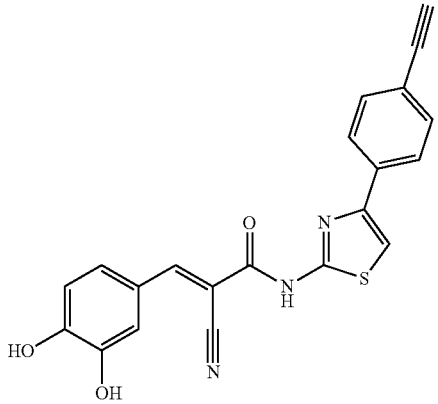 [SMILES: C#Cc1ccc(-c2csc(NC(=O)/C(C#N)=C/c3ccc(O)c(O)c3)n2)cc1]

The compound was prepared according to General procedure D2 from 2-cyano-N-(4-(4-ethynylphenyl)thiazol-2-yl)acetamide (80 mg, 0.25 mmol), 3,4-dihydroxybenzaldehyde (13 mg, 0.09 mmol), and piperidine (3 μL, 0.027 mmol) in CH₂Cl₂ (3 mL); the reaction time was 2 h at reflux. The product, purified by reverse phase column chromatography (H₂O:MeOH:AcOH; 60:40:0.05 to 5:95:0.05), was obtained as a yellow solid (21 mg, 60%).
¹H NMR (500 MHz, DMSO-d₆) δ (ppm) 12.69 (s, 1H), 10.27 (s, 1H), 9.68 (s, 1H), 8.31 (s, 1H), 7.98-7.92 (m, 2H), 7.79 (s, 1H), 7.61 (d, J=2.3 Hz, 1H), 7.58-7.53 (m, 2H), 7.38 (dd, J=8.4, 2.2 Hz, 1H), 6.94 (d, J=8.3 Hz, 1H), 4.24 (s, 1H);
¹³C NMR (126 MHz, DMSO-d₆) δ (ppm) 161.9, 158.4, 152.0, 151.6, 148.1, 145.8, 134.4, 132.1, 125.9, 125.8, 123.1, 120.9, 116.5, 116.1, 110.0, 83.4, 81.5;
HRMS calcd for $C_{21}H_{14}N_3O_3S$ [M+H]⁺ 388.0750, found 388.0752.

Preparative Example 198

(E)-2-cyano-N-(4-(3-cyclopropyl-4-methoxyphenyl)thiazol-2-yl)-3-(3,4-dihydroxyphenyl)acrylamide

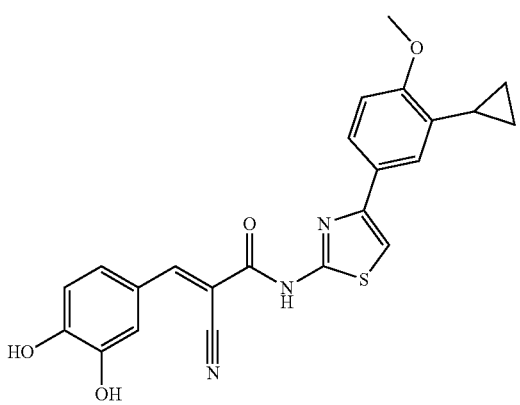 [SMILES: COc1ccc(-c2csc(NC(=O)/C(C#N)=C/c3ccc(O)c(O)c3)n2)cc1C1CC1]

The compound was prepared according to General procedure D2 from 2-cyano-N-(4-(3-cyclopropyl-4-methoxyphenyl)thiazol-2-yl)acetamide (70 mg, 0.22 mmol), 3,4-dihydroxybenzaldehyde (30 mg, 0.22 mmol), and piperidine (3 μL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (50 mg, 50%).

$^1$H NMR (500 MHz, DMSO-d$_6$) δ (ppm) 12.6 (s, 1H), 9.6 (s, 2H), 8.28 (s, 1H), 7.69 (dd, J=8.5, 2.2 Hz, 1H), 7.61 (d, J=2.3 Hz, 1H), 7.51 (s, 1H), 7.41-7.34 (m, 2H), 7.01 (d, J=8.5 Hz, 1H), 6.92 (d, J=8.3 Hz, 1H), 3.85 (s, 3H), 2.21-2.10 (m, 1H), 0.99-0.88 (m, 2H), 0.76-0.61 (m, 2H);

$^{13}$C NMR (126 MHz, DMSO-d$_6$) δ (ppm) 162.1, 157.7, 151.9, 151.4, 145.8, 131.4, 126.5, 125.8, 123.9, 123.2, 122.0, 116.5, 116.0, 110.6, 55.5, 9.2, 7.9;

HRMS calcd for C$_{23}$H$_{20}$N$_3$O$_4$S [M+H]$^+$ 434.1169, found 434.1172.

Preparative Example 199

(E)-N-(4-(tert-butyl)thiazol-2-yl)-2-cyano-3-(3,4-dihydroxyphenyl)acrylamide

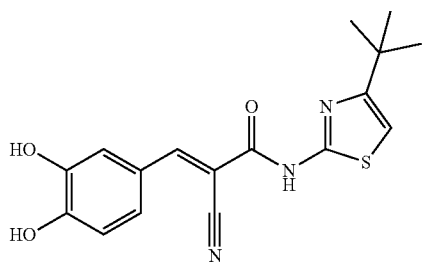 [SMILES: CC(C)(C)c1csc(NC(=O)/C(C#N)=C/c2ccc(O)c(O)c2)n1]

The compound was prepared according to General procedure D1 from N-(4-(tert-butyl)thiazol-2-yl)-2-cyanoacetamide (60 mg, 0.269 mmol), 3,4-dihydroxybenzaldehyde (35 mg, 0.255 mmol), and NEt$_3$ (38 μL, 0.269 mmol) in EtOH (1 mL); the reaction time was 3 h. The solvent was evaporated in vacuo and the residue was purified by column chromatography (hexane:EtOAc; 1:0 to 1:1) followed by reverse phase column chromatography (H$_2$O:MeOH:AcOH; 70:30:0.05 to 10:90:0.05). The product was obtained as a yellow solid (14 mg, 15%).

$^1$H NMR (500 MHz, DMSO-d$_6$) δ (ppm) 8.22 (s, 1H), 7.59 (d, J=2.3 Hz, 1H), 7.34 (dd, J=8.2, 2.3 Hz, 1H), 6.89 (d, J=8.4 Hz, 1H), 6.75 (s, 1H), 1.29 (s, 9H);

$^{13}$C NMR (126 MHz, DMSO-d$_6$) δ (ppm) 151.4, 145.8, 125.7, 123.2, 117.1, 116.3, 116.0, 104.6, 33.7, 29.4;

HRMS calcd for C$_{17}$H$_{16}$N$_3$O$_3$S [M−H]$^−$ 342.0918, found 342.0919.

Preparative Example 200

(E)-2-cyano-3-(5,6-dihydroxypyridin-3-yl)-N-(4-phenylthiazol-2-yl)acrylamide

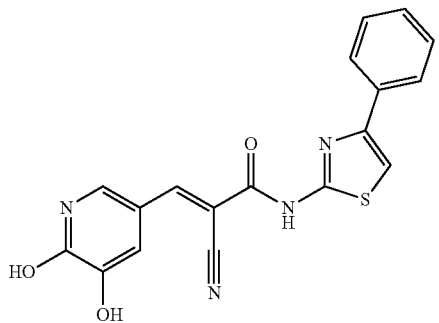 [SMILES: N#C/C(=C\c1cnc(O)c(O)c1)C(=O)Nc1nc(-c2ccccc2)cs1]

To 5,6-dimethoxynicotinaldehyde (50 mg, 0.299 mmol) was added AcOH (1 mL) and HBr (47% in H$_2$O, 1 mL). The mixture was microwaved for 30 min at 150° C. The residue was diluted with water (5 mL) and the pH was adjusted to 7 with a saturated aqueous solution of NaHCO$_3$. The mixture was extracted with EtOAc (3×50 mL). The organic phases were combined, dried over MgSO$_4$, filtered, and the solvent was evaporated in vacuo. 5,6-dihydroxynicotinaldehyde, purified by column chromatography (EtOAc:MeOH:7M NH$_3$ in MeOH; 4:1:0.1 to 0:1:0.1), was obtained as an off-white solid (10 mg, 24%) and used as such in the next step.

$^1$H NMR (300 MHz, DMSO-d$_6$) δ 9.54 (s, 1H), 7.80 (s, 1H), 6.91 (s, 1H).

(E)-2-cyano-3-(5,6-dihydroxypyridin-3-yl)-N-(4-phenylthiazol-2-yl)acrylamide was prepared according to General procedure D2 from 2-cyano-N-(4-(6-methoxypyridin-2-yl)thiazol-2-yl)acetamide (80 mg, 0.3 mmol), 5,6-dihydroxynicotinaldehyde (10 mg, 0.072 mmol), and piperidine (8 μL, 0.083 mmol) in CH$_2$Cl$_2$ (3 mL) and MeOH (2 mL); the reaction time was 5 h at 55° C. The product, purified by reverse phase column chromatography (H$_2$O:MeOH:AcOH; 60:40:0.05 to 10:90:0.05), was obtained as a yellow solid (2 mg, 8%).

$^1$H NMR (500 MHz, acetone-d$_6$) δ (ppm) 8.23 (s, 1H), 7.97-7.90 (m, 2H), 7.82 (s, 1H), 7.55 (s, 1H), 7.47-7.39 (m, 2H), 7.37-7.30 (m, 1H);

HRMS calcd for C$_{18}$H$_{11}$N$_4$O$_3$S [M−H]$^−$ 363.0557, found 363.0557.

Preparative Example 201

(E)-3-(3-chloro-4-hydroxyphenyl)-2-cyano-N-(4-phenylthiazol-2-yl)acrylamide

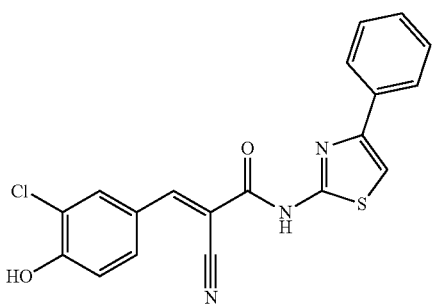 [SMILES: N#C/C(=C\c1ccc(O)c(Cl)c1)C(=O)Nc1nc(-c2ccccc2)cs1]

The compound was prepared according to General procedure D1 from 2-cyano-N-(4-phenylthiazol-2-yl)acetamide (51 mg, 0.21 mmol), 3,4-dihydroxybenzaldehyde (31 mg, 0.20 mmol), and NEt$_3$ (29 μL, 0.21 mmol) in EtOH (1 mL); the reaction time was 2 h. The solvent was evaporated in vacuo and the residue was purified by column chromatography (hexane:EtOAc; 1:0 to 1:1). The product was obtained as a pale-yellow solid (50 mg, 62%).

$^1$H NMR (500 MHz, DMSO-d$_6$) δ (ppm) 12.74 (bs, 1H), 11.53 (s, 1H), 8.39 (s, 1H), 8.09 (d, J=2.3 Hz, 1H), 7.93 (d, J=7.0 Hz, 2H), 7.89 (dd, J=8.7, 2.3 Hz, 1H), 7.70 (s, 1H), 7.45 (dd, J=7.7 Hz, 2H), 7.39-7.31 (m, 1H), 7.18 (d, J=8.5 Hz, 1H);

$^{13}$C NMR (126 MHz, DMSO-d$_6$) δ (ppm) 157.6, 150.6, 132.4, 131.5, 128.7, 128.0, 125.7, 123.8, 120.7, 117.2, 108.8;

HRMS calcd for C$_{19}$H$_{11}$ClN$_3$O$_2$S [M–H]$^-$ 380.0266, found 380.0266.

Preparative Example 202

(E)-3-(3-bromo-4-hydroxyphenyl)-2-cyano-N-(4-phenylthiazol-2-yl)acrylamide

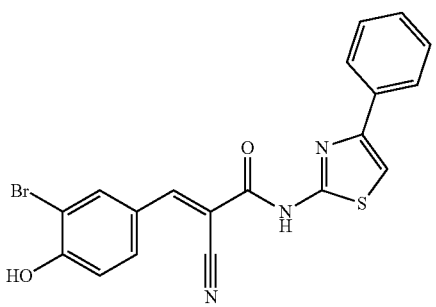 [SMILES: N#C/C(=C\c1ccc(O)c(Br)c1)C(=O)Nc1nc(-c2ccccc2)cs1]

The compound was prepared according to General procedure D1 from 2-cyano-N-(4-phenylthiazol-2-yl)acetamide (75 mg, 0.308 mmol), 3-bromo-4-hydroxybenzaldehyde (59 mg, 0.293 mmol), and NEt$_3$ (43 μL, 0.308 mmol) in EtOH (5 mL); the reaction time was 4 h. Work-up 2 of General procedure D1. The product, purified by column chromatography (hexane:EtOAc; 1:0 to 1:1), was obtained as a yellow solid (32 mg, 24%).

$^1$H NMR (500 MHz, DMSO-d$_6$) δ (ppm) 12.74 (s, 1H), 11.60 (s, 1H), 8.39 (s, 1H), 8.24 (d, J=2.3 Hz, 1H), 8.00-7.87 (m, 3H), 7.70 (s, 1H), 7.45 (t, J=7.7 Hz, 2H), 7.35 (t, J=7.4 Hz, 1H), 7.17 (d, J=8.7 Hz, 1H);

$^{13}$C NMR (126 MHz, DMSO-d$_6$) δ (ppm) 158.6, 150.4, 135.6, 132.0, 128.7, 128.0, 125.7, 124.2, 116.9, 110.1, 108.8;

HRMS calcd for C$_{19}$H$_{11}$BrN$_3$O$_2$S [M–H]$^-$ 423.9761, found 423.9769.

Preparative Example 203

(E)-2-cyano-3-(3-fluoro-4-hydroxy-5-methoxyphenyl)-N-(4-phenylthiazol-2-yl)acrylamide

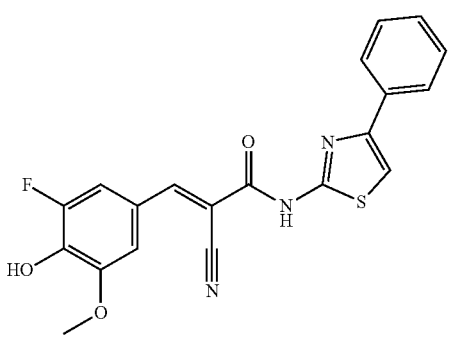 [SMILES: COc1cc(/C=C(\C#N)C(=O)Nc2nc(-c3ccccc3)cs2)cc(F)c1O]

The compound was prepared according to General procedure D1 from 2-cyano-N-(4-phenylthiazol-2-yl)acetamide (80 mg, 0.33 mmol) in EtOH (3 mL), 3-fluoro-4-hydroxy-5-methoxybenzaldehyde (53 mg, 0.31 mmol), and NEt$_3$ (46 μL, 0.33 mmol); the reaction time was 4 h. Work-up 1 of General procedure D1. The product was obtained as a yellow solid (50 mg, 40%).

$^1$H NMR (500 MHz, DMSO-d$_6$) δ (ppm) 12.79 (s, 1H), 10.70 (s, 1H), 8.40 (s, 1H), 8.00-7.86 (m, 2H), 7.70 (s, 1H), 7.56 (dd, J=9.7, 2.0 Hz, 2H), 7.45 (t, J=7.7 Hz, 2H), 7.38-7.32 (m, 1H), 3.90 (s, 3H);

$^{13}$C NMR (126 MHz, DMSO-d$_6$) δ (ppm) 161.6, 151.8, 151.2, 149.9, 149.5 (d, J=6.4 Hz), 139.8 (d, J=14.4 Hz), 136.4, 133.7, 128.7, 128.0, 125.7, 121.7 (d, J=9.5 Hz), 116.3, 111.7 (d, J=20.1 Hz), 110.4, 108.7, 56.3;

$^{19}$F NMR (471 MHz, DMSO-d$_6$) δ (ppm) –134.29;

HRMS calcd for C$_{20}$H$_{13}$FN$_3$O$_3$S [M–H]$^-$ 394.0667, found 394.0666.

Preparative Example 204

(E)-4-(2-cyano-3-oxo-3-((4-phenylthiazol-2-yl)amino)prop-1-en-1-yl)benzoic acid

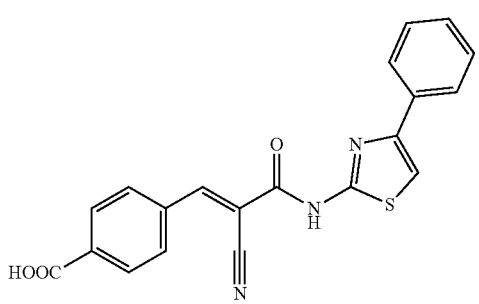 [SMILES: N#C/C(=C\c1ccc(C(=O)O)cc1)C(=O)Nc1nc(-c2ccccc2)cs1]

The compound was prepared according to General procedure D1 from 2-cyano-N-(4-phenylthiazol-2-yl)acetamide (80 mg, 0.33 mmol), 4-formylbenzoic acid (47 mg, 0.31 mmol), and NEt₃ (92 μL, 0.66 mmol) in EtOH (3 mL); the reaction time was 4 h at 50° C. and then 16 h at 25° C. Work-up 2 of General procedure D1. The crude product was purified by column chromatography (hexane:EtOAc; 1:1). The fractions containing the product were combined, the solvent was evaporated in vacuo, and the solid product was triturated with a mixture of toluene (3 mL) and EtOAc (0.3 mL). The solid was collected by filtration, washed with a mixture of toluene and EtOAc (10:1; 2 mL) and dried under vacuum. The product was obtained as a yellow solid (55 mg, 45%).

¹H NMR (500 MHz, DMSO-d₆) δ (ppm) 8.19 (s, 1H), 7.99 (d, J=8.2 Hz, 2H), 7.97-7.89 (m, 4H), 7.37 (t, J=7.6 Hz, 2H), 7.25 (s, 1H), 7.23 (t, J=7.3 Hz, 1H);

¹³C NMR (126 MHz, DMSO-d₆) δ (ppm) 169.1, 167.9, 164.4, 148.2, 145.7, 138.4, 136.1, 135.0, 129.4, 129.0, 128.7, 128.3, 126.6, 125.6, 125.5, 118.4, 114.5, 106.5;

HRMS calcd for C₂₀H₁₂N₃O₃S [M−H]⁻ 374.0605, found 374.0606.

Preparative Example 205

(E)-2-cyano-3-(1H-indazol-6-yl)-N-(4-phenylthiazol-2-yl)acrylamide

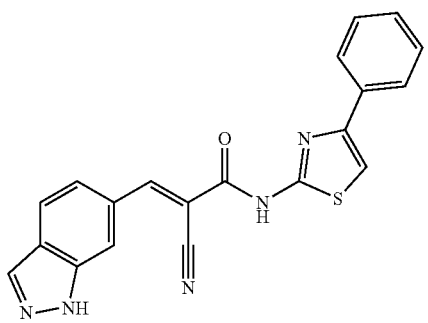 [SMILES: N#C/C(=C\c1ccc2cn[nH]c2c1)C(=O)Nc1nc(-c2ccccc2)cs1]

The compound was prepared according to General procedure D1 from 2-cyano-N-(4-phenylthiazol-2-yl)acetamide (60 mg, 0.247 mmol), 1H-indazole-6-carboxaldehyde (34 mg, 0.234 mmol), and NEt₃ (34 μL, 0.247 mmol) in EtOH (1 mL); the reaction time was 3 h. The solvent was evaporated in vacuo and the residue was triturated with a mixture of CH₂Cl₂ and CH₃CN (1.5 mL+1.5 mL). The solid was collected by filtration and dried under vacuum. The product was obtained as a yellow solid (74 mg, 81%).

¹H NMR (500 MHz, DMSO-d₆) δ (ppm) 13.55 (s, 1H), 12.90 (s, 1H), 8.67 (s, 1H), 8.28 (s, 1H), 8.23 (s, 1H), 7.98 (d, J=8.4 Hz, 1H), 7.95 (d, J=7.3 Hz, 2H), 7.76 (d, J=8.5, 1.6 Hz, 1H), 7.73 (s, 1H), 7.46 (dd, J=7.7 Hz, 2H), 7.36 (dd, J=7.3 Hz, 1H);

¹³C NMR (126 MHz, DMSO-d₆) δ (ppm) 161.3, 152.8, 149.4, 139.6, 133.9, 129.2, 128.8, 128.0, 125.7, 124.9, 121.5, 121.5, 116.0, 113.4, 108.9;

HRMS calcd for C₂₀H₁₂N₅OS [M−H]⁻ 370.0768, found 370.0767.

Preparative Example 206

(E)-2-cyano-3-(2-fluorophenyl)-N-(4-phenylthiazol-2-yl)acrylamide

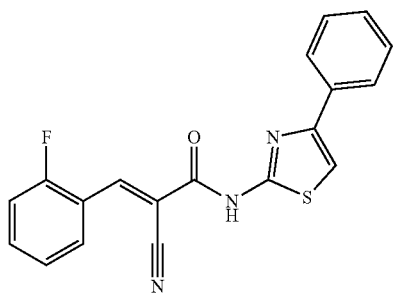 [SMILES: N#C/C(=C\c1ccccc1F)C(=O)Nc1nc(-c2ccccc2)cs1]

The compound was prepared according to General procedure D1 from 2-cyano-N-(4-phenylthiazol-2-yl)acetamide (50 mg, 0.206 mmol), 2-fluorobenzaldehyde (24 mg, 0.195 mmol), and NEt₃ (29 μL, 0.206 mmol) in EtOH (1 mL); the reaction time was for 2 h. Work-up 2 of General procedure D1. The product, purified by column chromatography (hexane:EtOAc; 1:0 to 1:1), was obtained as a yellow solid (42 mg, 59%).

¹H NMR (500 MHz, DMSO-d₆) δ (ppm) 13.13 (s, 1H), 8.59 (s, 1H), 8.19 (t, J=7.8 Hz, 1H), 7.94 (d, J=7.8 Hz, 2H), 7.79-7.64 (m, 2H), 7.52-7.41 (m, 4H), 7.36 (t, J=7.5 Hz, 1H);

¹³C NMR (126 MHz, DMSO-d₆) δ (ppm) 161.6, 159.6, 143.8, 135.0, 129.0, 128.8, 128.1, 125.8, 125.2, 125.2, 120.0, 119.9, 116.5, 116.3, 115.2, 108.9;

¹⁹F NMR (471 MHz, DMSO-d₆) δ (ppm) −111.17;

HRMS calcd for C₁₉H₁₃FN₃OS [M+H]⁺ 350.0758, found 350.0759.

Preparative Example 207

3-(3-acetamidophenyl)-2-cyano-N-(4-phenylthiazol-2-yl)acrylamide

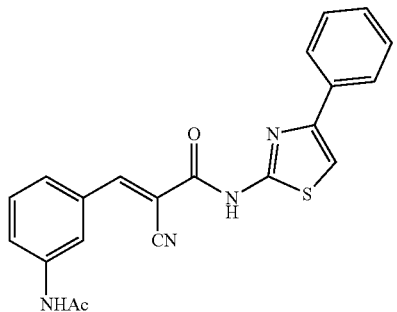 [SMILES: CC(=O)Nc1cccc(/C=C(\C#N)C(=O)Nc2nc(-c3ccccc3)cs2)c1]

The compound was prepared according to General procedure D2 from N-(3-formylphenyl)acetamide (76 mg, 0.3 mmol), 2-cyano-N-(4-phenylthiazol-2-yl)acetamide (50 mg, 0.3 mmol), and piperidine (3 μL, 0.027 mmol) in CH₂Cl₂ (5 mL); the reaction time was 2 h at reflux. The product, purified by reverse phase column chromatography (H₂O: MeOH:AcOH; 60:40:0.05 to 5:95:0.05), was obtained as a yellow solid (40 mg, 35%).

¹H NMR (500 MHz, DMSO-d₆) δ (ppm) 12.93 (s, 1H), 10.21 (s, 1H), 8.49 (s, 1H), 8.30 (s, 1H), 7.99-7.92 (m, 2H), 7.80-7.69 (m, 3H), 7.56-7.51 (m, 1H), 7.49-7.43 (m, 2H), 7.35 (t, J=7.4 Hz, 1H), 2.09 (s, 3H);

¹³C NMR (126 MHz, DMSO-d₆) δ (ppm) 168.7, 161.1, 152.0, 147.2, 140.0, 133.4, 132.1, 129.6, 128.7, 128.0, 125.7, 124.5, 123.2, 120.7, 115.4, 108.8, 24.0;

HRMS calcd for $C_{21}H_{17}N_4O_2S$ [M+H]⁺ 389.1067, found 389.1069.

Preparative Example 208

(E)-2-cyano-3-(4-hydroxy-3-nitrophenyl)-N-(4-phenylthiazol-2-yl)acrylamide

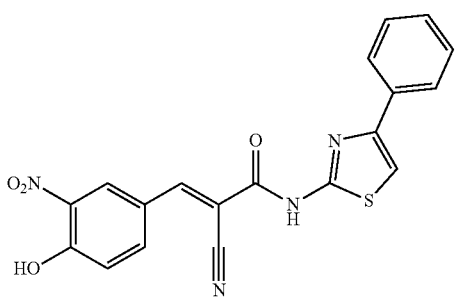 [SMILES: N#C/C(=C\c1ccc(O)c([N+](=O)[O-])c1)C(=O)Nc1nc(-c2ccccc2)cs1]

The compound was prepared according to General procedure D1 from 2-cyano-N-(4-phenylthiazol-2-yl)acetamide (69 mg, 0.284 mmol), 4-hydroxy-3-nitrobenzaldehyde (45 mg, 0.269 mmol), and NEt₃ (40 μL, 0.284 mmol) in EtOH (1 mL); the reaction time was 3 h. The solvent was evaporated in vacuo and the residue was purified by column chromatography (hexane:EtOAc:MeOH; 1:1:0 to 0:9:1). The product was obtained as an orange solid (65 mg, 58%).

¹H NMR (500 MHz, DMSO-d₆) δ (ppm) 12.72 (s, 1H), 8.54 (d, J=2.4 Hz, 1H), 8.44 (s, 1H), 8.13 (dd, J=9.0, 2.4 Hz, 1H), 7.97-7.91 (m, 2H), 7.69 (s, 1H), 7.45 (dd, J=7.7, 7.7 Hz, 2H), 7.38-7.32 (m, 1H), 7.15 (d, J=8.9 Hz, 1H);

¹³C NMR (126 MHz, DMSO-d₆) δ (ppm) 162.0, 159.0, 150.1, 148.3, 137.5, 135.4, 133.8, 129.8, 128.7, 128.0, 125.7, 121.9, 120.0, 116.3, 108.7;

HRMS calcd for $C_{19}H_{11}N_4O_4S$ [M−H]⁻ 391.0506, found 391.0505.

Preparative Example 209

(E)-2-cyano-3-(4-nitrophenyl)-N-(4-phenylthiazol-2-yl)acrylamide

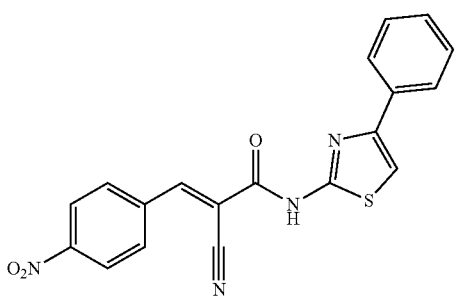 [SMILES: N#C/C(=C\c1ccc([N+](=O)[O-])cc1)C(=O)Nc1nc(-c2ccccc2)cs1]

The compound was prepared according to General procedure D1 from 2-cyano-N-(4-phenylthiazol-2-yl)acetamide (51 mg, 0.209 mmol), 4-nitrobenzaldehyde (30 mg, 0.198 mmol), and NEt₃ (29 μL, 0.209 mmol) in EtOH (2 mL); the reaction time was 2 h. The solvent was evaporated in vacuo and the residue was triturated with CH₃CN (0.7 mL). The solid was collected by filtration and washed with diethyl ether (2 mL). After drying under vacuum, the product was obtained as an orange-solid (47 mg, 63%).

¹H NMR (500 MHz, DMSO-d₆) δ (ppm) 13.14 (s, 1H), 8.61 (s, 1H), 8.43 (d, J=8.7 Hz, 2H), 8.19 (d, J=8.7 Hz, 2H), 7.94 (d, J=7.8 Hz, 2H), 7.72 (s, 1H), 7.46 (t, J=7.6 Hz, 2H), 7.36 (t, J=7.3 Hz, 1H);

¹³C NMR (126 MHz, DMSO-d₆) δ (ppm) 160.8, 149.6, 149.0, 137.8, 131.1, 130.6, 128.8, 128.1, 125.8, 124.2, 115.1, 108.9;

HRMS calcd for $C_{19}H_{13}N_4O_3S$ [M+H]⁺ 377.0703, found 377.0701.

Preparative Example 210

(E)-3-(2-cyano-3-oxo-3-((4-phenylthiazol-2-yl)amino)prop-1-en-1-yl)benzoic acid

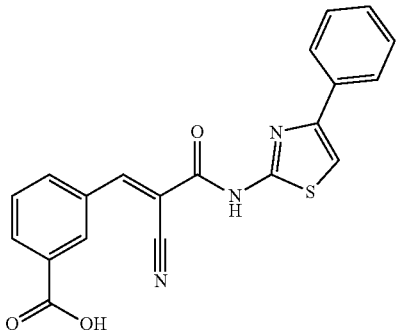 [SMILES: N#C/C(=C\c1cccc(C(=O)O)c1)C(=O)Nc1nc(-c2ccccc2)cs1]

The compound was prepared according to General procedure D1 from 2-cyano-N-(4-phenylthiazol-2-yl)acetamide (61 mg, 0.251 mmol), 3-formylbenzoic acid (36 mg, 0.238 mmol), and NEt₃ (35 μL, 0.251 mmol) in EtOH (1 mL); the reaction time was 3 h. The solvent was evaporated in vacuo and the residue was triturated with a mixture of CH₂Cl₂ and CH₃CN (1.5 mL+1.5 mL). The solid was collected by filtration and dried under vacuum. The product was obtained as a yellow solid (47 mg, 52%).

¹H NMR (500 MHz, DMSO-d₆) δ (ppm) 13.18 (s, 2H), 8.61 (s, 2H), 8.21 (d, J=7.9 Hz, 1H), 8.16 (d, J=7.8 Hz, 1H), 7.99-7.90 (m, 2H), 7.81-7.66 (m, 2H), 7.46 (dd, J=7.7 Hz, 2H), 7.36 (dd, J=7.4 Hz, 1H);

¹³C NMR (126 MHz, DMSO-d₆) δ (ppm) 166.4, 151.1, 134.1, 133.0, 132.1, 131.8, 130.8, 129.8, 128.8, 128.0, 125.7, 115.4, 108.9;

HRMS calcd for $C_{20}H_{12}N_3O_3S$ [M−H]⁻ 374.0605, found 374.0604.

Preparative Example 211

(E)-2-cyano-3-(6-hydroxy-[1,1'-biphenyl]-3-yl)-N-(4-phenylthiazol-2-yl)acrylamide

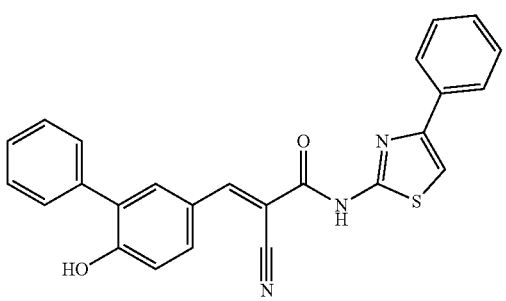 [SMILES: N#C/C(=C\c1ccc(O)c(-c2ccccc2)c1)C(=O)Nc1nc(-c2ccccc2)cs1]

The compound was prepared according to General procedure D2 from 2-cyano-N-(4-phenylthiazol-2-yl)acetamide (62 mg, 0.25 mmol), 6-hydroxy-[1,1'-biphenyl]-3-carbaldehyde (50 mg, 0.25 mmol) and piperidine (3 µL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (70 mg, 65%).

$^1$H NMR (500 MHz, DMSO-d$_6$) δ (ppm) 11.66 (s, 2H), 8.47 (s, 1H), 8.06 (d, J=2.3 Hz, 1H), 7.96-7.90 (m, 3H), 7.67 (s, 1H), 7.62-7.57 (m, 2H), 7.49-7.41 (m, 4H), 7.40-7.31 (m, 2H), 7.17 (d, J=8.5 Hz, 1H);
$^{13}$C NMR (126 MHz, DMSO-d$_6$) δ (ppm) 162.2, 159.4, 151.6, 148.7, 137.1, 134.0, 133.7, 132.1, 128.9, 128.7, 128.7, 128.1, 127.9, 127.2, 125.7, 123.2, 117.0, 116.6, 108.6;
HRMS calcd for C$_{25}$H$_{18}$N$_3$O$_2$S [M+H]$^+$ 424.1114, found 424.1112.

Preparative Example 212

(E)-2-cyano-3-(3,5-difluoro-4-hydroxyphenyl)-N-(4-phenylthiazol-2-yl)acrylamide

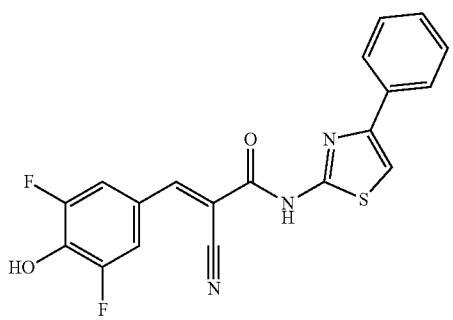 [SMILES: N#C/C(=C\c1cc(F)c(O)c(F)c1)C(=O)Nc1nc(-c2ccccc2)cs1]

The compound was prepared according to General procedure D1 from 2-cyano-N-(4-phenylthiazol-2-yl)acetamide (80 mg, 0.33 mmol), 3,5-difluoro-4-hydroxybenzaldehyde (50 mg, 0.31 mmol), and NEt$_3$ (46 µL, 0.33 mmol) in EtOH (3 mL); the reaction time was 4 h. Work-up 1 of General procedure D1. The product was obtained as a yellow solid (90 mg, 71%).

$^1$H NMR (500 MHz, DMSO-d$_6$) δ (ppm) 12.87 (s, 1H), 11.66 (s, 1H), 8.37 (s, 1H), 7.97-7.90 (m, 2H), 7.79-7.71 (m, 2H), 7.71 (s, 1H), 7.46 (t, J=7.7 Hz, 2H), 7.36 (t, J=7.4 Hz, 1H);
$^{13}$C NMR (126 MHz, DMSO-d$_6$) δ (ppm) 152.8 (d, J=7.6 Hz), 150.9 (d, J=7.5 Hz), 149.9, 138.8, 128.8, 128.0, 125.7, 121.5, 115.8, 115.2-113.3 (m), 108.8;
HRMS calcd for C$_{19}$H$_{10}$F$_2$N$_3$O$_2$S [M−H]$^-$ 382.0467, found 382.0469.

Preparative Example 213

(E)-2-cyano-3-(3,4-difluorophenyl)-N-(4-phenylthiazol-2-yl)acrylamide

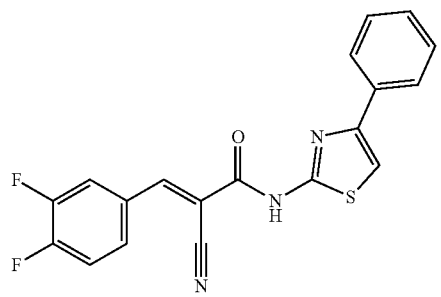 [SMILES: N#C/C(=C\c1ccc(F)c(F)c1)C(=O)Nc1nc(-c2ccccc2)cs1]

The compound was prepared according to General procedure D1 from 2-cyano-N-(4-phenylthiazol-2-yl)acetamide (80 mg, 0.33 mmol), 3,4-difluorobenzaldehyde (44 mg, 0.31 mmol), and NEt$_3$ (46 µL, 0.33 mmol) in EtOH (3 mL); the reaction time was 4 h. Work-up 1 of General procedure D1. The product was obtained as a yellow solid (65 mg, 55%).

$^1$H NMR (500 MHz, DMSO-d$_6$) δ (ppm) 13.03 (s, 1H), 8.47 (s, 1H), 8.03 (ddd, J=11.6, 7.8, 2.2 Hz, 1H), 7.95-7.91 (m, 2H), 7.90-7.86 (m, 1H), 7.77-7.65 (m, 2H), 7.45 (t, J=7.7 Hz, 2H), 7.39-7.29 (m, 1H);
$^{13}$C NMR (126 MHz, DMSO-d$_6$) δ (ppm) 161.7, 153.2 (d, J=12.4 Hz), 151.2 (d, J=12.8 Hz), 151.0 (d, J=13.5 Hz), 150.2, 149.0 (d, J=13.4 Hz), 134.1, 129.9 (dd, J=3.8 Hz), 129.3, 128.7 (dd, J=7.4, 3.4 Hz), 128.6, 126.3, 119.3 (dd, J=17.7, 15.8 Hz), 116.0, 109.4;
$^{19}$F NMR (471 MHz, DMSO-d$_6$) δ (ppm) −136.40, −136.45;
HRMS calcd for C$_{19}$H$_{10}$F$_2$N$_3$OS [M−H]$^-$ 366.0518, found 366.0520.

Preparative Example 214

(E)- and (Z)-2-cyano-3-(1H-imidazol-4-yl)-N-(4-phenylthiazol-2-yl)acrylamide

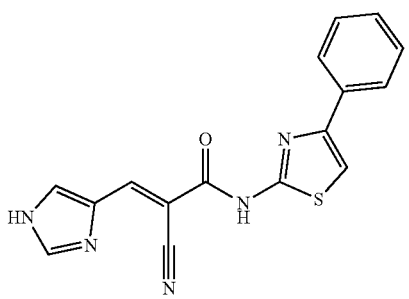

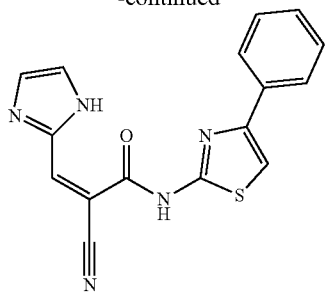

The compounds were prepared according to General procedure D1 from 2-cyano-N-(4-phenylthiazol-2-yl)acetamide (59 mg, 0.242 mmol), 4-imidazolecarboxaldehyde (22 mg, 0.23 mmol), and NEt$_3$ (34 μL, 0.242 mmol) in EtOH (1 mL); the reaction time was 3 h. The solvent was evaporated in vacuo and the residue was purified by reverse phase column chromatography (H$_2$O:MeOH:AcOH; 70:30:0.05 to 10:90:0.05). The product, a mixture of isomers (E)- and (Z)-, was obtained as a yellow solid (14 mg, 18%).

$^1$H NMR (500 MHz, DMSO-d$_6$) δ (ppm) 2.92 (s, 1H), 12.67 (s, 1H), 8.46 (s, 0.15H), 8.37 (s, 0.85H), 8.09 (s, 0.15H), 8.05 (s, 0.85H), 8.03-7.91 (m, 3H), 7.70 (s, 0.15H), 7.68 (s, 0.85H), 7.50-7.41 (m, 2H), 7.34 (t, J=7.3 Hz, 1H);

HRMS calcd for C$_{16}$H$_{10}$N$_5$OS [M−H]$^-$ 320.0612, found 320.0614.

Preparative Example 215

(E)-2-cyano-3-(2,3-dihydroxyphenyl)-N-(4-phenylthiazol-2-yl)acrylamide

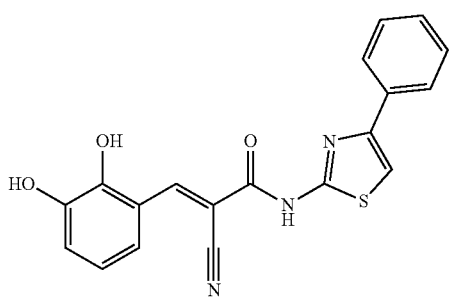 [SMILES: N#C/C(=C\c1cccc(O)c1O)C(=O)Nc1nc(-c2ccccc2)cs1]

The compound was prepared according to General procedure D2 from 2-cyano-N-(4-phenylthiazol-2-yl)acetamide (87 mg, 0.358 mmol), 2,3-dihydroxybenzaldehyde (49 mg, 0.358 mmol), and piperidine (4 μL, 0.036 mmol) in CH$_2$Cl$_2$ (3 mL). The precipitate was collected by filtration and washed with CH$_2$Cl$_2$ (3 mL). The solid was mixed with a saturated aqueous solution of NaHCO$_3$ (15 mL) and EtOAc (25 mL). The phases were separated and the organic phase was washed with brine (15 mL), dried over MgSO$_4$, filtered, and the solvent was evaporated in vacuo. The product was obtained as a pale green solid (120 mg, 91%).

$^1$H NMR (500 MHz, DMSO-d$_6$) δ (ppm) 14.46 (s, 1H), 10.27 (s, 1H), 9.29 (s, 1H), 8.61 (s, 1H), 7.99-7.87 (m, 2H), 7.73 (s, 1H), 7.47-7.39 (m, 2H), 7.36-7.31 (m, 1H), 7.28 (dd, J=7.3, 2.1 Hz, 1H), 7.18-7.09 (m, 2H);

$^{13}$C NMR (126 MHz, DMSO-d$_6$) δ (ppm) 160.0, 156.9, 155.6, 149.4, 144.1, 143.4, 142.1, 134.0, 128.7, 127.9, 125.8, 124.3, 120.4, 120.3, 119.2, 117.8, 108.9;

HRMS calcd for C$_{19}$H$_{14}$N$_3$O$_3$S [M+H]$^+$ 364.0750, found 364.0748.

Preparative Example 216

(E)-2-cyano-3-(2-oxo-2,3-dihydro-1H-benzo[d]imidazol-5-yl)-N-(4-phenylthiazol-2-yl)acrylamide

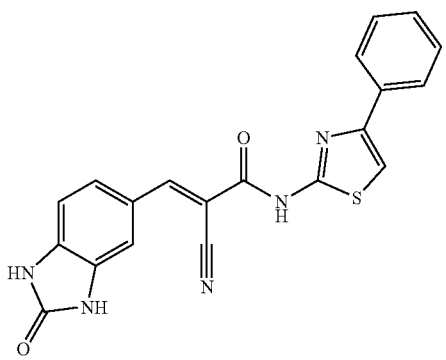 [SMILES: N#C/C(=C\c1ccc2[nH]c(=O)[nH]c2c1)C(=O)Nc1nc(-c2ccccc2)cs1]

The compound was prepared according to General procedure D1 from 2-cyano-N-(4-phenylthiazol-2-yl)acetamide (49 mg, 0.201 mmol), 2-oxo-2,3-dihydro-1H-benzodiazole-5-carbaldehyde (31 mg, 0.191 mmol), and NEt$_3$ (28 μL, 0.201 mmol) in EtOH (2 mL); the reaction time was 3 h. The solvent was evaporated in vacuo, the residue was mixed with a mixture of CH$_3$CN and EtOH (1 mL+1 mL) and stirred for 16 h at 60° C. The solid was collected by filtration and dried under vacuum. The product was obtained as a yellow-solid (39 mg, 53%).

$^1$H NMR (500 MHz, DMSO-d$_6$) δ (ppm) 12.71 (bs, 1H), 11.21 (s, 1H), 11.02 (s, 1H), 8.48 (s, 1H), 7.94 (d, J=7.5 Hz, 2H), 7.80 (s, 1H), 7.70 (s, 1H), 7.62 (dd, J=8.2, 1.8 Hz, 1H), 7.45 (t, J=7.7 Hz, 2H), 7.35 (t, J=7.4 Hz, 1H), 7.15 (d, J=8.2 Hz, 1H);

$^{13}$C NMR (126 MHz, DMSO-d$_6$) δ (ppm) 161.7, 155.2, 152.7, 134.6, 134.1, 130.4, 128.7, 127.9, 127.0, 125.7, 124.1, 116.5, 109.0, 108.8;

HRMS calcd for C$_{20}$H$_{12}$N$_5$O$_2$S [M−H]$^-$ 386.0717, found 386.0716.

Preparative Example 217

(E)-2-cyano-3-(4-hydroxy-3-methylphenyl)-N-(4-phenylthiazol-2-yl)acrylamide

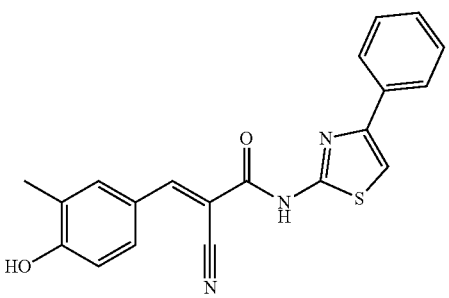 [SMILES: Cc1cc(/C=C(\C#N)C(=O)Nc2nc(-c3ccccc3)cs2)ccc1O]

The compound was prepared according to General procedure D1 from 2-cyano-N-(4-phenylthiazol-2-yl)acetamide (60 mg, 0.247 mmol), 4-hydroxy-3-methylbenzaldehyde (32 mg, 0.234 mmol), and NEt₃ (34 µL, 0.247 mmol) in EtOH (2 mL); the reaction time was 4 h. The reaction mixture was cooled to 25° C. and sonicated for 10 min. The precipitate was collected by filtration, washed with cold EtOH (1 mL) and diethyl ether (1 mL), and dried under vacuum. The product was obtained as a yellow solid (45 mg, 50%).

$^1$H NMR (500 MHz, DMSO-d₆) δ (ppm) 12.68 (s, 1H), 10.70 (s, 1H), 8.37 (s, 1H), 7.94 (d, J=7.3 Hz, 2H), 7.84 (s, 1H), 7.81 (dd, J=8.5, 2.4 Hz, 1H), 7.69 (s, 1H), 7.49-7.41 (m, 2H), 7.39-7.29 (m, 1H), 6.99 (d, J=8.4 Hz, 1H), 2.19 (s, 3H);

$^{13}$C NMR (126 MHz, DMSO-d₆) δ (ppm) 161.8, 160.8, 151.9, 141.9, 134.2, 133.9, 131.1, 128.7, 127.9, 125.7, 125.2, 122.6, 115.4, 108.7, 15.9;

HRMS calcd for $C_{20}H_{14}N_3O_2S$ [M−H]⁻ 360.0812, found 360.0812.

Preparative Example 218

(E)-2-cyano-3-(2,4-dihydroxyphenyl)-N-(4-phenylthiazol-2-yl)acrylamide

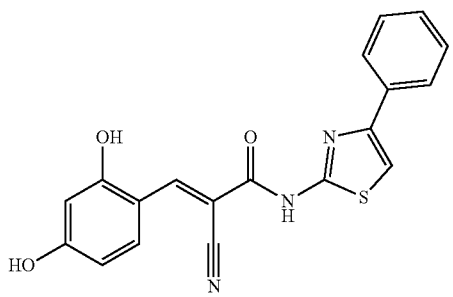

The compound was prepared according to General procedure D2 from 2-cyano-N-(4-phenylthiazol-2-yl)acetamide (242 mg, 1 mmol), 2,4-dihydroxybenzaldehyde (138 mg, 1 mmol) and piperidine (3 µL, 0.027 mmol) in CH₂Cl₂ (3 mL); the reaction time was 2 h at reflux. The precipitate was collected by filtration, washed with CH₂Cl₂ (5 mL) and dried under vacuum. The product was obtained as a yellow solid (150 mg, 40%).

$^1$H NMR (500 MHz, DMSO-d₆) δ (ppm) 14.32 (s, 1H), 10.91 (s, 1H), 9.24-9.02 (m, 1H), 8.57 (s, 1H), 7.96-7.89 (m, 2H), 7.71-7.65 (m, 2H), 7.47-7.40 (m, 2H), 7.37-7.29 (m, 1H), 6.76 (dd, J=8.5, 2.3 Hz, 1H), 6.65 (d, J=2.1 Hz, 1H);

$^{13}$C NMR (126 MHz, DMSO-d₆) δ (ppm) 163.4, 160.4, 157.0, 156.0, 155.7, 149.2, 143.4, 134.0, 132.1, 128.7, 127.8, 125.7, 113.2, 113.1, 110.7, 108.7, 101.4;

HRMS calcd for $C_{19}H_{14}N_3O_3S$ [M+H]⁺ 364.0750, found 364.0757.

Preparative Example 219

(E)-N-(4-(5-bromothiophen-2-yl)thiazol-2-yl)-2-cyano-3-(3,4-dihydroxyphenyl) acrylamide

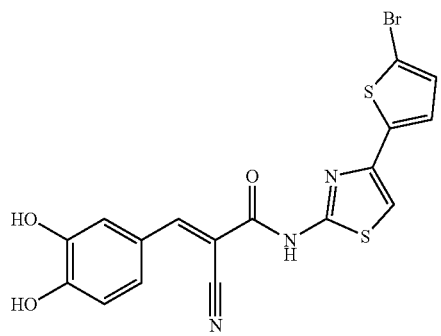 [SMILES: N#C/C(=C\c1ccc(O)c(O)c1)C(=O)Nc1nc(-c2ccc(Br)s2)cs1]

The compound was prepared according to General procedure D2 from N-(4-(5-bromothiophen-2-yl)thiazol-2-yl)-2-cyanoacetamide (300 mg, 0.914 mmol), 3,4-dihydroxybenzaldehyde (126 mg, 0.914 mmol), and piperidine (9.0 µL, 0.091 mmol) in CH₂Cl₂ (8 mL) and THF (3 mL); the reaction time was 3 h. The product, purified by reverse phase column chromatography (H₂O:MeOH:AcOH; 50:50:0.05 to 10:90:0.05), was obtained as a dark yellow solid (50 mg, 12%).

$^1$H NMR (500 MHz, DMSO-d₆) δ (ppm) 12.72 (brs, 1H), 10.28 (brs, 1H), 9.67 (brs, 1H), 8.31 (s, 1H), 7.60 (d, J=2.69 Hz, 2H), 7.42-7.36 (m, 2H), 7.24 (d, J=3.88 Hz, 1H), 6.94 (d, J=8.28 Hz, 1H);

$^{13}$C NMR (126 MHz, DMSO-d₆) δ (ppm) 152.2, 151.6, 145.8, 131.4, 125.9, 124.3, 123.0, 116.6, 116.4, 116.0, 110.9, 107.7;

HRMS calcd for $C_{17}H_{11}BrN_3O_3S_2$[M+H]⁺ 449.9399, found 449.9401.

Preparative Example 220

(E)-2-cyano-3-(3-oxo-3,4-dihydro-2H-benzo[b][1,4]oxazin-7-yl)-N-(4-phenylthiazol-2-yl)acrylamide

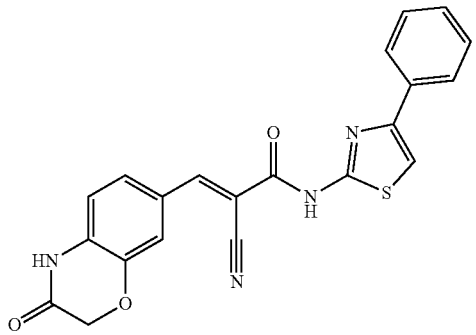 [SMILES: N#C/C(=C\c1ccc2c(c1)OCC(=O)N2)C(=O)Nc1nc(-c2ccccc2)cs1]

The compound was prepared according to General procedure D2 from 2-cyano-N-(4-phenylthiazol-2-yl)acetamide (42 mg, 0.17 mmol), 3-oxo-3,4-dihydro-2H-benzo[b][1,4]oxazine-7-carbaldehyde (30 mg, 0.17 mmol), and piperidine (3 µL, 0.027 mmol) in CH₂Cl₂ (3 mL); the reaction time was 2 h at reflux. The precipitate was collected by filtration and washed with CH₂Cl₂ (2 mL). The solid was mixed with a saturated aqueous solution of NH₄Cl (10 mL) and the mixture was extracted with EtOAc (3×10 mL). The combined organic extracts were dried over MgSO₄, filtered, and the solvent was evaporated in vacuo. The product was obtained as a yellow solid (60 mg, 85%).

¹H NMR (500 MHz, DMSO-d₆) δ (ppm) 12.72 (s, 1H), 11.15 (s, 1H), 8.35 (s, 1H), 7.95-7.91 (m, 2H), 7.69 (d, J=1.9 Hz, 1H), 7.63 (s, 1H), 7.61 (dd, J=8.3, 2.0 Hz, 1H), 7.48-7.41 (m, 2H), 7.37-7.30 (m, 1H), 7.08 (d, J=8.2 Hz, 1H), 4.70 (s, 2H);

¹³C NMR (126 MHz, DMSO-d₆) δ (ppm) 164.8, 150.3, 143.1, 131.5, 128.7, 126.6, 126.5, 125.7, 116.9, 116.5, 116.2, 108.44, 66.6;

HRMS calcd for C₂₁H₁₅N₄O₃S [M+H]⁺ 403.0859, found 403.0863.

Preparative Example 221

(E)-2-cyano-3-(3,5-di-tert-butyl-4-hydroxyphenyl)-N-(4-(4-(trifluoromethoxy)phenylthiazol-2-yl)acrylamide

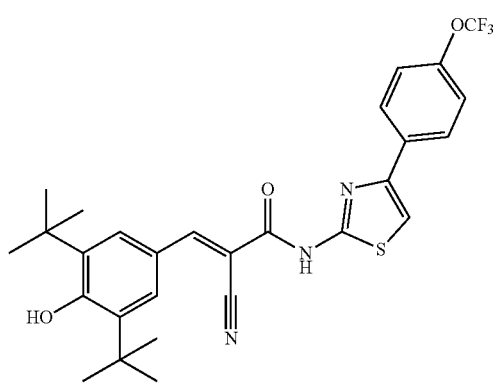 [SMILES: CC(C)(C)c1cc(/C=C(\C#N)C(=O)Nc2nc(-c3ccc(OC(F)(F)F)cc3)cs2)cc(C(C)(C)C)c1O]

The compound was prepared according to General procedure D2 from 2-cyano-N-(4-(4-(trifluoromethoxy)phenyl)thiazol-2-yl)acetamide (80 mg, 0.25 mmol), 3,5-di-tert-butyl-4-hydroxybenzaldehyde (60 mg, 0.25 mmol), and piperidine (3 μL, 0.027 mmol) in CH₂Cl₂ (3 mL); the reaction time was 2 h at reflux. The product, purified by reverse phase column chromatography (H₂O:MeOH:AcOH; 60:40:0.05 to 5:95:0.05), was obtained as a yellow solid (80 mg, 60%).

¹H NMR (500 MHz, DMSO-d₆) δ (ppm) 12.71 (s, 1H), 8.50 (s, 1H), 8.17 (s, 1H), 8.09-8.02 (m, 2H), 7.94 (s, 2H), 7.79 (s, 1H), 7.45 (d, J=8.3 Hz, 2H), 1.43 (s, 18H);

¹³C NMR (126 MHz, DMSO-d₆) δ (ppm) 161.8, 159.2, 158.3, 153.0, 147.8, 139.0, 133.4, 128.7, 127.5, 122.9, 121.3, 120.1 (q, J=256.3 Hz), 116.5, 109.7, 100.2, 34.7, 29.9;

¹⁹F NMR (471 MHz, DMSO-d₆) δ (ppm) -56.68;

HRMS calcd for C₂₈H₂₉F₃N₃O₃S [M+H]⁺ 544.1876, found 544.1876.

Preparative Example 222

(E)-3-(4-acetamido-3-((tert-butyldimethylsilyl)oxy)phenyl)-2-cyano-N-(4-phenylthiazol-2-yl)acrylamide

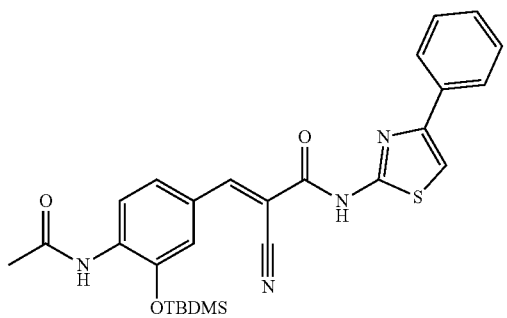 [SMILES: CC(=O)Nc1ccc(/C=C(\C#N)C(=O)Nc2nc(-c3ccccc3)cs2)cc1O[Si](C)(C)C(C)(C)C]

The compound was prepared according to General procedure D2 from 2-cyano-N-(4-phenylthiazol-2-yl)acetamide (40 mg, 0.22 mmol), N-(2-((tert-butyldimethylsilyl)oxy)-4-formylphenyl)acetamide (65 mg, 0.22 mmol), and piperidine (3 μL, 0.027 mmol) in CH₂Cl₂ (3 mL); the reaction time was 2 h at reflux. The product, purified by column chromatography (hexane:EtOAc; 1:1), was obtained as a yellow solid (65 mg, 60%).

¹H NMR (500 MHz, CDCl₃) δ (ppm) 9.61 (s, 1H), 8.53 (d, J=8.5 Hz, 1H), 8.34 (s, 1H), 8.00 (s, 1H), 7.90-7.83 (m, 2H), 7.76 (d, J=2.1 Hz, 1H), 7.49-7.40 (m, 3H), 7.38-7.32 (m, 1H), 7.23 (s, 1H), 2.24 (s, 3H), 1.09 (s, 9H), 0.40 (s, 6H);

¹³C NMR (126 MHz, CDCl₃) δ (ppm) 168.4, 159.0, 157.0, 154.6, 150.8, 144.2, 135.6, 134.3, 129.1, 129.0, 128.5, 126.7, 126.3, 119.7, 117.3, 116.8, 108.9, 26.0, 25.2, 18.4, -4.2;

HRMS calcd for C₂₇H₃₁N₄O₃SSi [M+H]⁺ 519.1881, found 519.1880.

Preparative Example 223

(E)-3-(4-acetamido-3-hydroxyphenyl)-2-cyano-N-(4-phenylthiazol-2-yl)acrylamide

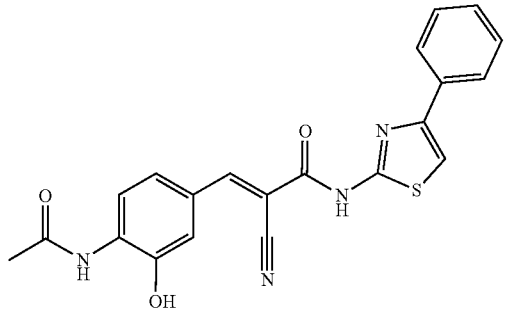 [SMILES: CC(=O)Nc1ccc(/C=C(\C#N)C(=O)Nc2nc(-c3ccccc3)cs2)cc1O]

3-(4-acetamido-3-((tert-butyldimethylsilyl)oxy)phenyl)-2-cyano-N-(4-phenylthiazol-2-yl)acrylamide was dissolved in anhydrous THF (2 mL), the solution was cooled to 0° C. and TBAF (1M in THF, 0.15 mL, 0.15 mmol) was added. The mixture was stirred for 1 h, the solvent was evaporated and the residue was purified by column chromatography (hexane:EtOAc; 1:1 to 0:1). The product was obtained as a yellow solid (33 mg, 65%).

¹H NMR (500 MHz, DMSO-d₆) δ (ppm) 12.78 (s, 1H), 10.59 (s, 1H), 9.47 (s, 1H), 8.36 (s, 1H), 8.20 (d, J=8.5 Hz, 1H), 7.98-7.90 (m, 2H), 7.76-7.67 (m, 2H), 7.48-7.43 (m, 2H), 7.41 (dd, J=8.5, 2.1 Hz, 1H), 7.38-7.32 (m, 1H), 2.17 (s, 3H);

¹³C NMR (126 MHz, DMSO-d₆) δ (ppm) 169.4, 161.6, 151.6, 149.3, 146.9, 134.1, 131.9, 128.7, 127.9, 126.8, 125.7, 124.4, 120.5, 115.1, 108.8, 24.0;

HRMS calcd for $C_{21}H_{17}N_4O_3S$ [M+H]⁺ 405.1016, found 405.1020.

Preparative Example 224

(E)-N-(4-(4-(tert-butyl)phenyl)thiazol-2-yl)-2-cyano-3-(3,5-dichloro-4-hydroxyphenyl)acrylamide

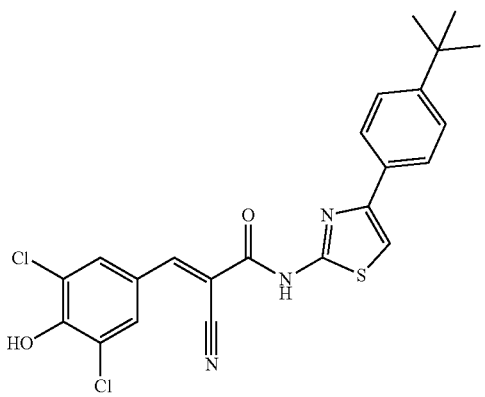 [SMILES: CC(C)(C)c1ccc(-c2csc(NC(=O)/C(C#N)=C/c3cc(Cl)c(O)c(Cl)c3)n2)cc1]

The compound was prepared according to General procedure D2 from N-(4-(4-(tert-butyl)phenyl)thiazol-2-yl)-2-cyanoacetamide ((50 mg, 0.167 mmol), 3,5-dichloro-4-hydroxybenzaldehyde (32 mg, 0.167 mmol), and piperidine (2 μL, 0.017 mmol) in CH₂Cl₂ (4 mL); the reaction time was 3 h at reflux. The product, purified by column chromatography (hexane:EtOAc; 1:1), was obtained as a yellow solid (52 mg, 66% yield).

¹H NMR (500 MHz, DMSO-d₆) δ (ppm) 12.80 (s, 1H), 8.35 (s, 1H), 8.05 (s, 2H), 7.85 (d, J=8.5 Hz, 2H), 7.62 (s, 1H), 7.47 (d, J=8.6 Hz, 2H), 1.31 (s, 9H);

¹³C NMR (126 MHz, DMSO-d₆) δ 153.4, 150.6, 149.2, 130.8, 125.5, 122.7, 116.0, 34.3, 31.0;

HRMS calcd for $C_{23}H_{20}Cl_2N_3O_2S$ [M+H]⁺ 472.0648, found 472.0646.

Preparative Example 225

(E)-2-cyano-3-(4-hydroxy-2-methylphenyl)-N-(4-phenylthiazol-2-yl)acrylamide

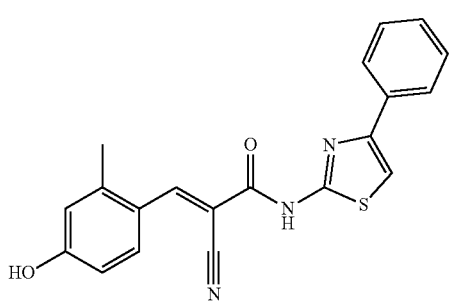 [SMILES: Cc1cc(O)ccc1/C=C(\C#N)C(=O)Nc1nc(-c2ccccc2)cs1]

The compound was prepared according to General procedure D2 from 2-cyano-N-(4-phenylthiazol-2-yl)acetamide (80 mg, 0.329 mmol), 4-hydroxy-2-methylbenzaldehyde (45 mg, 0.329 mmol), and piperidine (3 μL, 0.033 mmol) in CH₂Cl₂ (4 mL); the reaction time was 3 h at reflux. The product, purified by column chromatography (hexane:EtOAc; 10:1 to 1:2), was obtained as a yellow solid (112 mg, 94% yield).

¹H NMR (500 MHz, DMSO-d₆) δ (ppm) 12.87 (s, 1H), 10.48 (s, 1H), 8.51 (s, 1H), 8.11 (d, J=8.4 Hz, 1H), 7.94 (d, J=7.2 Hz, 2H), 7.70 (s, 1H), 7.45 (dd, J=7.7 Hz, 2H), 7.34 (dd, J=7.3 Hz, 1H), 6.83-6.77 (m, 2H), 2.45 (s, 3H);

¹³C NMR (126 MHz, DMSO-d₆) δ (ppm) 161.8, 149.4, 143.5, 134.2, 130.3, 128.7, 127.9, 125.8, 121.6, 117.8, 116.6, 113.8, 108.8, 19.7;

HRMS calcd for $C_{20}H_{16}N_3O_2S$ [M+H]⁺ 362.0958, found 362.0955.

Preparative Example 226

(E)-2-cyano-3-(2-fluoro-4-hydroxyphenyl)-N-(4-phenylthiazol-2-yl)acrylamide

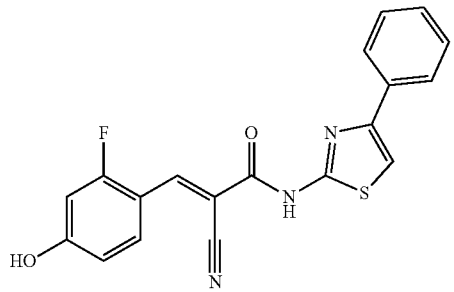

The compound was prepared according to General procedure D2 from 2-cyano-N-(4-phenylthiazol-2-yl)acetamide (80 mg, 0.329 mmol), 2-fluoro-4-hydroxybenzaldehyde (46 mg, 0.329 mmol), and piperidine (3 μL, 0.033 mmol) in CH₂Cl₂ (4 mL); the reaction time was 2 h at reflux. The product, purified by column chromatography (hexane:EtOAc; 10:1 to 1:4), was obtained as a yellow solid (108 mg, 90%).

¹H NMR (500 MHz, DMSO-d₆) δ (ppm) 12.94 (s, 1H), 11.19 (s, 1H), 8.46 (s, 1H), 8.23 (dd, J=8.9 Hz, 1H), 7.93 (d, J=7.0 Hz, 2H), 7.69 (s, 1H), 7.45 (dd, J=7.7 Hz, 2H), 7.35 (dd, J=7.4 Hz, 1H), 6.87 (dd, J=8.9, 2.4 Hz, 1H), 6.78 (dd, J=12.5, 2.3 Hz, 1H);

¹³C NMR (126 MHz, DMSO-d₆) δ (ppm) 164.9, 163.4 (d, J=256.1 Hz), 143.5, 130.4, 129.3, 128.5, 126.3, 116.7, 113.7, 111.2 (d, J=10.9 Hz), 109.3, 103.7 (d, J=23.6 Hz);

¹⁹F NMR (471 MHz, DMSO-d₆) δ (ppm) -109.0;

HRMS calcd for $C_{19}H_{13}FN_3O_2S$ [M+H]⁺ 366.0707, found 366.0704.

Preparative Example 227

(E)-2-cyano-3-(4-hydroxynaphthalen-1-yl)-N-(4-phenylthiazol-2-yl)acrylamide

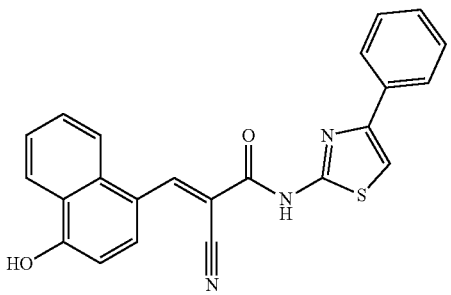 [SMILES: N#C/C(=C\c1ccc(O)c2ccccc12)C(=O)Nc1nc(-c2ccccc2)cs1]

The compound was prepared according to General procedure D2 from 2-cyano-N-(4-phenylthiazol-2-yl)acetamide (81 mg, 0.331 mmol), 4-hydroxy-1-naphthaldehyde (57 mg, 0.331 mmol), and piperidine (3 µL, 0.033 mmol) in CH$_2$Cl$_2$ (5 mL); the reaction time was 4 h at reflux. The product, purified by column chromatography (hexane:EtOAc; 10:1 to 1:3), was obtained as an orange solid (118 mg, 90%).

$^1$H NMR (500 MHz, DMSO-d$_6$) δ (ppm) 13.10 (s, 1H), 11.42 (s, 1H), 9.14 (s, 1H), 8.46 (d, J=8.7 Hz, 1H), 8.33 (d, J=8.2 Hz, 1H), 8.28 (dd, J=8.4, 1.5 Hz, 1H), 7.97 (d, J=7.8 Hz, 2H), 7.73 (ddd, J=8.4, 5.0, 1.5 Hz, 2H), 7.65-7.58 (m, 1H), 7.46 (dd, J=7.7 Hz, 2H), 7.35 (dd, J=7.4 Hz, 1H), 7.08 (d, J=8.2 Hz, 1H);

$^{13}$C NMR (126 MHz, DMSO-d$_6$) δ (ppm) 161.6, 158.7, 158.1, 149.3, 148.8, 134.2, 133.4, 130.1, 128.7, 128.1, 127.9, 125.8, 125.7, 124.4, 123.7, 122.8, 119.1, 116.6, 108.7, 108.2;

HRMS calcd for C$_{23}$H$_{16}$N$_3$O$_2$S [M+H]$^+$ 398.0958, found 398.0956.

Preparative Example 228

2-cyano-3-(3-cyano-4-hydroxyphenyl)-N-(4-phenylthiazol-2-yl)propanamide

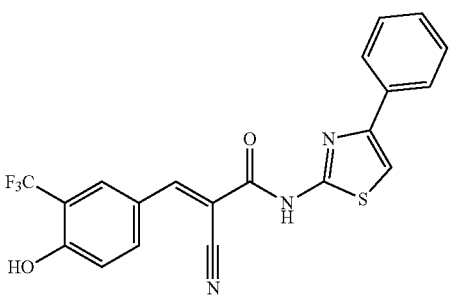 [SMILES: N#C/C(=C\c1ccc(O)c(C(F)(F)F)c1)C(=O)Nc1nc(-c2ccccc2)cs1]

The compound was prepared according to General procedure D2 from 2-cyano-N-(4-phenylthiazol-2-yl)acetamide (70 mg, 0.4 mmol), 4-hydroxy-3-(trifluoromethyl)benzaldehyde (75 mg, 0.4 mmol) and piperidine (3 µL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (100 mg, 70%).

$^1$H NMR (500 MHz, DMSO-d$_6$) δ (ppm) 12.80 (s, 1H), 11.90 (s, 1H), 8.50 (s, 1H), 8.28-8.23 (m, 1H), 8.18 (dd, J=8.8, 2.2 Hz, 1H), 7.96-7.90 (m, 2H), 7.70 (s, 1H), 7.49-7.42 (m, 2H), 7.39-7.32 (m, 1H), 7.24 (d, J=8.7 Hz, 1H);

$^{13}$C NMR (126 MHz, DMSO-d$_6$) δ (ppm) 170.3, 160.1, 150.7, 136.0, 130.2 (q, J=3.8 Hz), 128.7, 128.0, 125.7, 123.4 (q, J=272.3 Hz), 122.2, 118.1, 116.3 (q, J=30.3 Hz), 116.1, 108.7;

$^{19}$F NMR (471 MHz, DMSO-d$_6$) δ (ppm) −61.76;

HRMS calcd for C$_{20}$H$_{13}$F$_3$N$_3$O$_2$S [M+H]$^+$ 416.0675, found 416.0678.

Preparative Example 229

(E)-2-cyano-3-(3,4-dihydroxyphenyl)-N-(4-(5-methylthiophen-2-yl)thiazol-2-yl)acrylamide

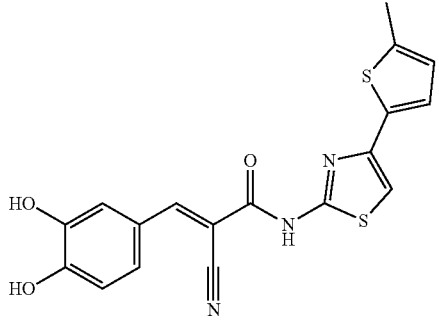 [SMILES: Cc1ccc(-c2csc(NC(=O)/C(C#N)=C/c3ccc(O)c(O)c3)n2)s1]

The compound was prepared according to General procedure D2 from 2-cyano-N-(4-(5-methylthiophen-2-yl)thiazol-2-yl)acetamide (60 mg, 0.23 mmol), 3,4-dihydroxybenzaldehyde (32 mg, 0.23 mmol) and piperidine (3 µL, 0.027 mmol) in CH$_2$Cl$_2$ (2 mL); the reaction time was 2 h at reflux. The product, purified by reverse phase column chromatography (H$_2$O:MeOH:AcOH; 60:40:0.05 to 5:95:0.05), was obtained as a yellow solid (70 mg, 80%).

$^1$H NMR (500 MHz, DMSO-d$_6$) δ (ppm) 10.01 (s, 2H), 8.30 (s, 1H), 7.60 (d, J=2.3 Hz, 1H), 7.40 (s, 1H), 7.37 (dd, J=8.5, 2.3 Hz, 1H), 7.32 (d, J=3.5 Hz, 1H), 6.94 (d, J=8.3 Hz, 1H), 6.79 (dd, J=3.5, 1.3 Hz, 1H), 2.46 (s, 3H);

$^{13}$C NMR (126 MHz, DMSO-d$_6$) δ (ppm) 162.1, 158.4, 151.9, 151.6, 145.8, 144.0, 138.9, 135.9, 126.3, 125.8, 123.8, 123.1, 116.6, 116.5, 116.1, 106.2, 15.0;

HRMS calcd for C$_{18}$H$_{14}$N$_3$O$_3$S$_2$[M+H]$^+$ 384.0471, found 384.0469.

Preparative Example 230

(E)-2-cyano-3-(3,4-dihydroxyphenyl)-N-methyl-N-(4-phenylthiazol-2-yl)acrylamide

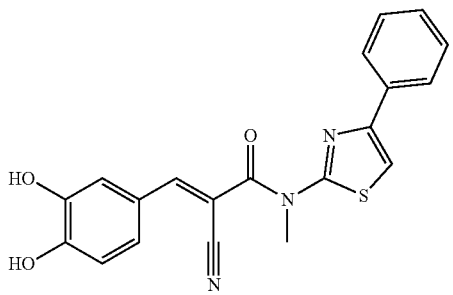 [SMILES: CN(C(=O)/C(C#N)=C/c1ccc(O)c(O)c1)c1nc(-c2ccccc2)cs1]

The compound was prepared according to General procedure D2 from 2-cyano-N-methyl-N-(4-phenylthiazol-2-yl)acetamide (53 mg, 0.28 mmol), 3,4-dihydroxybenzaldehyde (38 mg, 0.28 mmol), and piperidine (2 μL, 0.02 mmol) in CH$_2$Cl$_2$ (2 mL). The mixture was stirred for 4 h at reflux and then 16 h at 25° C. The product, purified by reverse phase column chromatography (H$_2$O:MeOH:AcOH; 60:40:0.05 to 5:95:0.05), was obtained as a yellow solid (50 mg, 60%).

$^1$H NMR (500 MHz, DMSO-d$_6$) δ (ppm) 10.14 (s, 1H), 9.70 (s, 1H), 8.00-7.94 (m, 2H), 7.93 (s, 1H), 7.80 (s, 1H), 7.61 (d, J=2.3 Hz, 1H), 7.48-7.41 (m, 2H), 7.40-7.30 (m, 2H), 6.91 (d, J=8.3 Hz, 1H), 3.85 (s, 3H);

$^{13}$C NMR (126 MHz, DMSO-d$_6$) δ (ppm) 164.2, 159.7, 153.3, 151.3, 148.6, 145.7, 134.1, 128.7, 127.9, 125.7, 125.5, 123.4, 116.3, 116.2, 115.9, 110.4, 99.0, 38.1;

HRMS calcd for C$_{20}$H$_{16}$N$_3$O$_3$S [M+H]$^+$ 378.0907, found 378.0910.

Preparative Example 231

(E)-2-cyano-N-(4-phenylthiazol-2-yl)-3-(3-(trifluoromethyl)phenyl)acrylamide

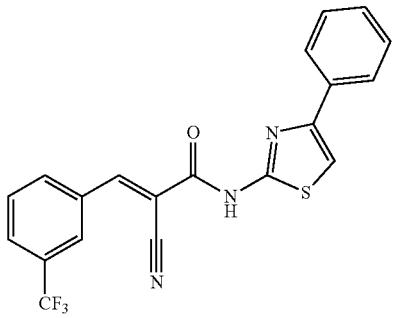 [SMILES: N#C/C(=C\c1cccc(C(F)(F)F)c1)C(=O)Nc1nc(-c2ccccc2)cs1]

The compound was prepared according to General procedure D2 from 2-cyano-N-(4-phenylthiazol-2-yl)acetamide (220 mg, 0.9 mmol), 3-(trifluoromethyl)benzaldehyde (157 mg, 0.9 mmol), and piperidine (3 μL, 0.027 mmol) in CH$_2$Cl$_2$ (3 mL); the reaction time was 2 h at reflux. The residue was purified by column chromatography (hexane:EtOAc; 10:1 to 10:3). The fractions containing the product were combined, the solvent was evaporated and the residue was suspended in a mixture of hexane (5 mL) and EtOAc (0.5 mL). The mixture was sonicated for 10 min, the solid was collected by filtration and dried under vacuum. The product was obtained as a yellow solid (200 mg, 55%).

$^1$H NMR (500 MHz, DMSO-d$_6$) δ (ppm) 12.97 (s, 1H), 8.62 (s, 1H), 8.32 (s, 1H), 8.28 (d, J=8.0 Hz, 1H), 8.00 (d, J=7.9 Hz, 1H), 7.94 (d, J=7.7 Hz, 2H), 7.91-7.84 (m, 1H), 7.74 (s, 1H), 7.50-7.44 (m, 2H), 7.39-7.33 (m, 1H);

$^{13}$C NMR (126 MHz, DMSO-d$_6$) δ (ppm) 160.7, 150.5, 149.2, 133.6, 132.7 (q, J=4.7 Hz), 132.6, 130.6, 129.9 (q, J=32.7 Hz), 128.8, 128.0, 126.5 (q, J=4.7 Hz), 125.8, 123.7 (q, J=273.2 Hz), 115.2;

$^{19}$F NMR (471 MHz, DMSO-d$_6$) δ (ppm) −61.53;

HRMS calcd for C$_{20}$H$_{13}$F$_3$N$_3$OS [M+H]$^+$ 400.0726, found 400.0722.

Preparative Example 232

(E)-2-cyano-3-(3,4-dihydroxyphenyl)-N-(4-(6-methylpyridin-3-yl)thiazol-2-yl)acrylamide

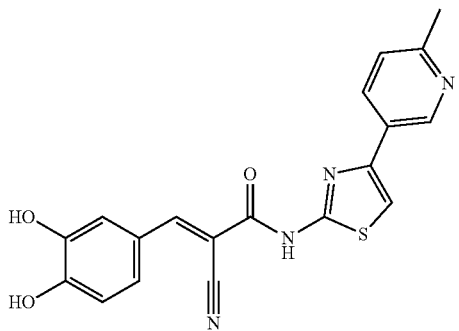 [SMILES: Cc1ccc(-c2csc(NC(=O)/C(C#N)=C/c3ccc(O)c(O)c3)n2)cn1]

The compound was prepared according to General procedure D2 from 2-cyano-N-(4-(6-methylpyridin-3-yl)thiazol-2-yl)acetamide (100 mg, 0.39 mmol), 3,4-dihydroxybenzaldehyde (55 mg, 0.39 mmol) and piperidine (3 μL, 0.027 mmol) in CH$_2$Cl$_2$ (3 mL); the reaction time was 2 h at reflux. The product, purified by reverse phase column chromatography (H$_2$O:MeOH:AcOH; 60:40:0.05 to 5:95:0.05), was obtained as a yellow solid (97 mg, 65%).

$^1$H NMR (500 MHz, DMSO-d$_6$) δ (ppm) 12.51 (s, 1H), 10.82-9.33 (m, 2H), 9.02 (d, J=2.3 Hz, 1H), 8.31 (s, 1H), 8.15 (dd, J=8.1, 2.4 Hz, 1H), 7.77 (s, 1H), 7.62 (d, J=2.2 Hz, 1H), 7.38 (dd, J=8.4, 2.2 Hz, 1H), 7.33 (d, J=8.1 Hz, 1H), 6.94 (d, J=8.3 Hz, 1H), 2.46 (s, 3H);

$^{13}$C NMR (126 MHz, DMSO-d$_6$) δ (ppm) 157.2, 152.2, 151.6, 146.2, 145.8, 136.1, 133.3, 127.0, 125.9, 123.1, 123.1, 116.6, 116.4, 116.1, 109.3, 99.8, 23.7;

HRMS calcd for C$_{19}$H$_{15}$N$_4$O$_3$S [M+H]$^+$ 379.0859, found 379.0854.

Preparative Example 233

(E)-2-cyano-3-(3,4-dihydroxyphenyl)-N-(4-phenyl-5-(tetrahydro-2H-pyran-4-yl)thiazol-2-yl)acrylamide

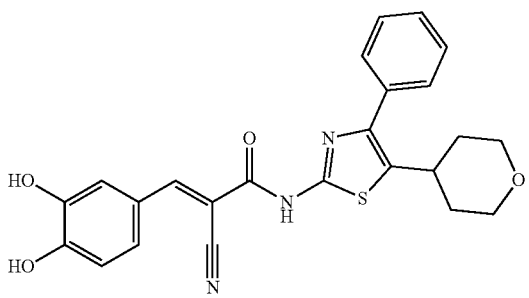 [SMILES: N#C/C(=C\c1ccc(O)c(O)c1)C(=O)Nc1nc(-c2ccccc2)c(C2CCOCC2)s1]

The compound was prepared according to General procedure D2 from 2-cyano-N-(4-phenyl-5-(tetrahydro-2H-pyran-4-yl)thiazol-2-yl)acetamide (37 mg, 0.11 mmol), 3,4-dihydroxybenzaldehyde (15 mg, 0.11 mmol) and piperidine (3 µL, 0.027 mmol) in $CH_2Cl_2$ (2 mL); the reaction time was 2 h at reflux. The product, purified by reverse phase column chromatography ($H_2O$:MeOH:AcOH; 60:40:0.05 to 5:95:0.05), was obtained as a yellow solid (30 mg, 60%).

$^1$H NMR (500 MHz, DMSO-$d_6$) δ (ppm) 12.54 (s, 1H), 10.25 (s, 1H), 9.63 (s, 1H), 8.26 (s, 1H), 7.60 (d, J=2.3 Hz, 1H), 7.59-7.54 (m, 2H), 7.52-7.46 (m, 2H), 7.44-7.38 (m, 1H), 7.36 (dd, J=8.4, 2.2 Hz, 1H), 6.92 (d, J=8.3 Hz, 1H), 3.97-3.86 (m, 2H), 3.44-3.34 (m, 2H), 3.30-3.33 (m, 1H), 1.86 (d, J=12.9 Hz, 2H), 1.68 (qd, J=12.2, 4.4 Hz, 2H);

$^{13}$C NMR (126 MHz, DMSO-$d_6$) δ (ppm) 151.9, 145.8, 144.0, 134.7, 128.5, 127.7, 125.7, 123.1, 116.5, 116.0, 67.0, 35.4, 33.7;

HRMS calcd for $C_4H_{22}N_3O_4S$ [M+H]$^+$ 448.1326, found 448.1321.

Preparative Example 234

(E)-3-(3-(tert-butyl)-4-hydroxy-5-methylphenyl)-2-cyano-N-(4-phenylthiazol-2-yl)acrylamide

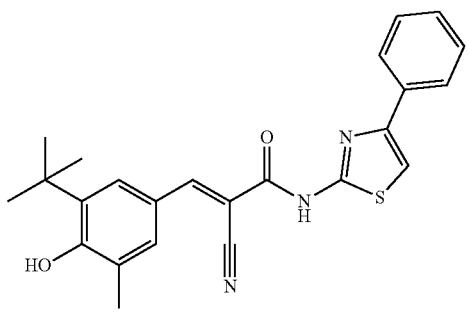 [SMILES: Cc1cc(/C=C(\C#N)C(=O)Nc2nc(-c3ccccc3)cs2)cc(C(C)(C)C)c1O]

The compound was prepared according to General procedure D2 from 2-cyano-N-(4-(6-methoxypyridin-2-yl)thiazol-2-yl)acetamide (96 mg, 0.395 mmol), 3-(tert-butyl)-4-hydroxy-5-methylbenzaldehyde (76 mg, 0.395 mmol), and piperidine (4 µL, 0.039 mmol) in $CH_2Cl_2$ (3 mL). The product, purified by column chromatography (hexane:EtOAc; 10:1 to 1:1), was obtained as a yellow solid (137 mg, 83%).

$^1$H NMR (500 MHz, DMSO-$d_6$) δ (ppm) 12.65 (s, 1H), 9.51 (s, 1H), 8.41 (s, 1H), 8.02-7.88 (m, 3H), 7.78-7.62 (m, 2H), 7.50-7.39 (m, 2H), 7.41-7.26 (m, 1H), 2.27 (s, 3H), 1.42 (s, 9H);

$^{13}$C NMR (126 MHz, DMSO-$d_6$) δ (ppm) 161.9, 159.2, 152.4, 149.1, 137.3, 134.1, 132.4, 128.7, 128.2, 127.9, 125.7, 122.6, 116.6, 108.7, 34.8, 29.3, 17.1;

HRMS calcd for $C_{24}H_{24}N_3O_2S$ [M+H]$^+$ 418.1584, found 418.1585.

Preparative Example 235

(E)-3-(3-(tert-butyl)-4-hydroxyphenyl)-2-cyano-N-(4-phenylthiazol-2-yl)acrylamide

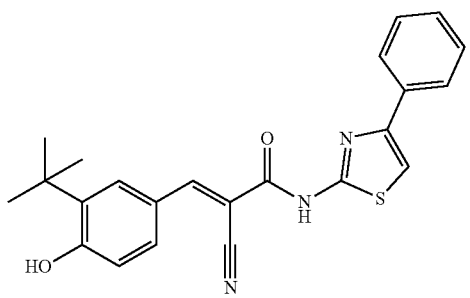 [SMILES: CC(C)(C)c1cc(/C=C(\C#N)C(=O)Nc2nc(-c3ccccc3)cs2)ccc1O]

The compound was prepared according to General procedure D2 from 2-cyano-N-(4-(6-methoxypyridin-2-yl)thiazol-2-yl)acetamide (102 mg, 0.421 mmol), 3-(tert-butyl)-4-hydroxybenzaldehyde (75 mg, 0.421 mmol), and piperidine (4 µL, 0.041 mmol) in $CH_2Cl_2$ (4 mL). The product, purified by column chromatography (hexane:EtOAc; 10:1 to 1:1), was obtained as a yellow solid (138 mg, 81%).

$^1$H NMR (500 MHz, DMSO-$d_6$) δ (ppm) 12.66 (s, 1H), 10.77 (s, 1H), 8.44 (s, 1H), 8.03 (d, J=2.4 Hz, 1H), 7.94 (d, J=7.6 Hz, 2H), 7.79 (dd, J=8.5, 2.3 Hz, 1H), 7.70 (s, 1H), 7.48-7.42 (m, 2H), 7.38-7.32 (m, 1H), 7.00 (d, J=8.4 Hz, 1H), 1.40 (s, 9H);

$^{13}$C NMR (126 MHz, DMSO-$d_6$) δ (ppm) 161.8, 161.4, 158.1, 152.4, 149.1, 136.4, 134.2, 131.2, 130.4, 128.7, 127.9, 125.7, 122.4, 117.1, 116.6, 108.7, 34.7, 29.0;

HRMS calcd for $C_{23}H_{22}N_3O_2S$ [M+H]$^+$ 404.1427, found 404.1429.

Preparative Example 236

(E)-2-cyano-3-(3,4-dihydroxyphenyl)-N-(4-(3-fluorophenyl)thiazol-2-yl)acrylamide

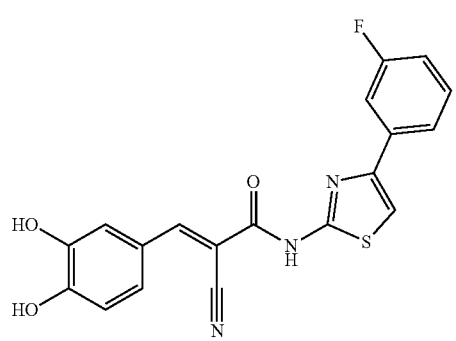 [SMILES: N#C/C(=C\c1ccc(O)c(O)c1)C(=O)Nc1nc(-c2cccc(F)c2)cs1]

The compound was prepared according to General procedure D2 from 2-cyano-N-(4-(3-fluorophenyl)thiazol-2-yl)acetamide (106 mg, 0.406 mmol), 3,4-dihydroxybenzaldehyde (56 mg, 0.406 mmol), and piperidine (3 μL, 0.041 mmol) in $CH_2Cl_2$ (4 mL). The product, purified by column chromatography (hexane:EtOAc; 10:1 to 1:2) followed by reverse phase column chromatography ($H_2O$:MeOH:AcOH; 50:50:0.05 to 10:90:0.05), was obtained as an orange solid (132 mg, 85%).

$^1$H NMR (500 MHz, DMSO-$d_6$) δ (ppm) 8.20 (s, 1H), 7.82-7.76 (m, 1H), 7.75-7.68 (m, 2H), 7.59 (d, J=2.3 Hz, 1H), 7.51-7.43 (m, 1H), 7.34 (dd, J=8.4, 2.4 Hz, 1H), 7.14 (ddd, J=8.8, 3.5 Hz, 1H), 6.85 (d, J=7.8 Hz, 1H);

$^{13}$C NMR (126 MHz, DMSO-$d_6$) δ (ppm) 163.0, 162.57 (d, J=243.4 Hz), 150.9, 147.3, 146.1, 137.0 (d, J=8.1 Hz), 130.6 (d, J=9.1 Hz), 121.7, 117.4, 116.2, 114.2 (d, J=20.9 Hz), 112.2 (d, J=22.7 Hz), 109.5;

$^{19}$F NMR (471 MHz, DMSO-$d_6$) δ (ppm) −113.1;

HRMS calcd for $C_{19}H_{13}FN_3O_3S$ [M+H]$^+$ 382.0656, found 382.0653.

Preparative Example 237

(E)-2-cyano-3-(4-hydroxy-3,5-diisopropylphenyl)-N-(4-phenylthiazol-2-yl)acrylamide

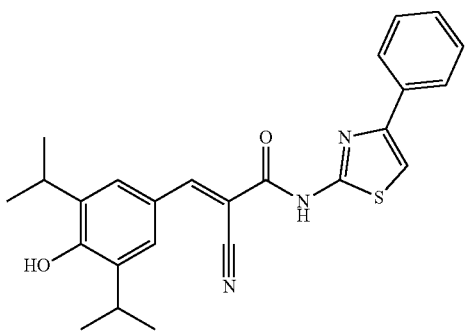 [SMILES: CC(C)c1cc(/C=C(\C#N)C(=O)Nc2nc(-c3ccccc3)cs2)cc(C(C)C)c1O]

The compound was prepared according to General procedure D2 from 2-cyano-N-(4-(6-methoxypyridin-2-yl)thiazol-2-yl)acetamide (96 mg, 0.395 mmol), 4-hydroxy-3,5-diisopropylbenzaldehyde (81 mg, 0.395 mmol), and piperidine (4 μL, 0.039 mmol) in $CH_2Cl_2$ (3 mL). The product, purified by column chromatography (hexane:EtOAc; 10:1 to 1:1), was obtained as a yellow solid (121 mg, 71%).

$^1$H NMR (500 MHz, DMSO-$d_6$) δ (ppm) 12.65 (s, 1H), 9.47 (s, 1H), 8.47 (s, 1H), 7.94 (dd, J=8.4, 1.4 Hz, 2H), 7.84 (s, 2H), 7.69 (s, 1H), 7.45 (t, J=7.7 Hz, 2H), 7.39-7.31 (m, 1H), 3.36 (hept, J=6.8 Hz, 2H), 1.21 (d, J=6.7 Hz, 12H);

$^{13}$C NMR (126 MHz, DMSO-$d_6$) δ (ppm) 161.9, 158.0, 156.4, 152.6, 149.1, 135.8, 134.2, 128.7, 127.9, 127.3, 125.7, 123.2, 116.7, 108.6, 26.1, 22.7;

HRMS calcd for $C_{25}H_{26}N_3O_2S$ [M+H]$^+$ 432.1740, found 432.1739.

Preparative Example 238

(E)-2-cyano-3-(3,4-dihydroxyphenyl)-N-(4-phenyl-5-pyrazin-2-yl)thiazol-2-yl)acrylamide

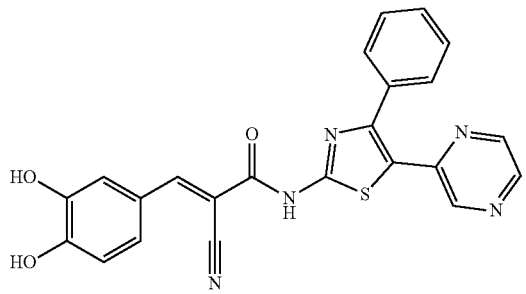 [SMILES: N#C/C(=C\c1ccc(O)c(O)c1)C(=O)Nc1nc(-c2ccccc2)c(-c2cnccn2)s1]

The compound was prepared according to General procedure D2 from 2-cyano-N-(4-phenyl-5-(pyrazin-2-yl)thiazol-2-yl)acetamide (75 mg, 0.23 mmol), 3,4-dihydroxybenzaldehyde (33 mg, 0.23 mmol), and piperidine (3 μL, 0.027 mmol) in $CH_2Cl_2$ (3 mL); the reaction time was 2 h at reflux. The precipitate was collected by filtration, washed with $CH_2Cl_2$ (3 mL) and dried under vacuum. The product was obtained as a yellow solid (90 mg, 90%).

$^1$H NMR (500 MHz, DMSO-$d_6$) δ (ppm) 12.84 (s, 1H), 10.23 (s, 1H), 9.67 (s, 1H), 8.68-8.62 (m, 1H), 8.45 (d, J=2.6 Hz, 1H), 8.33 (s, 1H), 8.27 (s, 1H), 7.62 (d, J=2.2 Hz, 1H), 7.59-7.53 (m, 2H), 7.52-7.46 (m, 3H), 7.38 (dd, J=8.4, 2.3 Hz, 1H), 6.93 (d, J=8.3 Hz, 1H);

$^{13}$C NMR (126 MHz, DMSO-$d_6$) δ (ppm) 162.2, 152.3, 151.6, 147.6, 145.8, 144.4, 142.3, 142.2, 134.6, 131.7, 128.9, 126.0, 123.1, 116.5, 116.1;

HRMS calcd for $C_{23}H_{16}N_5O_3S$ [M+H]$^+$ 442.0968, found 442.0967.

Preparative Example 239

(E)-2-cyano-3-(3,4-dihydroxyphenyl)-N-(4-(3-methylpyridin-2-yl)thiazol-2-yl)acrylamide

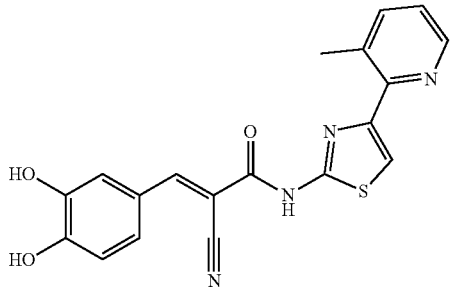 [SMILES: Cc1cccnc1-c1csc(NC(=O)/C(C#N)=C/c2ccc(O)c(O)c2)n1]

The compound was prepared according to General procedure D2 from 2-cyano-N-(4-(3-methylpyridin-2-yl)thiazol-2-yl)acetamide (74 mg, 0.29 mmol), 3,4-dihydroxybenzaldehyde (40 mg, 0.29 mmol), and piperidine (3 μL, 0.027 mmol) in $CH_2Cl_2$ (3 mL); the reaction time was 2 h at reflux. The precipitate was collected by filtration, washed with $CH_2Cl_2$ (5 mL) and dried under vacuum. The product was obtained as a yellow solid (88 mg, 80%).

¹H NMR (500 MHz, DMSO-d₆) δ (ppm) 8.46 (dd, J=4.7, 1.6 Hz, 1H), 8.27 (s, 1H), 7.71 (d, J=7.6 Hz, 1H), 7.65-7.58 (m, 2H), 7.38 (dd, J=8.4, 2.3 Hz, 1H), 7.29 (dd, J=7.7, 4.7 Hz, 1H), 6.92 (d, J=8.3 Hz, 1H), 2.57 (s, 3H);

¹³C NMR (126 MHz, DMSO-d₆) δ (ppm) 162.7, 151.9, 151.6, 150.8, 146.6, 145.8, 139.2, 131.1, 125.9, 123.1, 122.8, 116.7, 116.4, 116.0, 113.8, 20.0;

HRMS calcd for $C_{19}H_{15}N_4O_3S$ [M+H]⁺ 379.0859, found 379.0865.

Preparative Example 240

(E)-2-cyano-3-(2,6-di-tert-butylpyridine-4-yl)-N-(4-phenylthiazol-2-yl)acrylamide

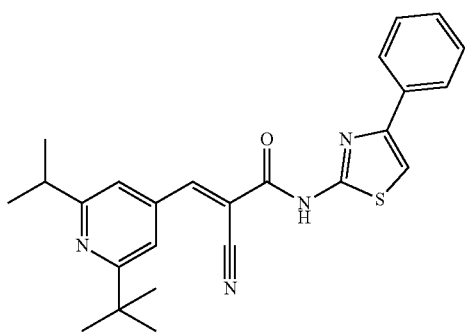 [SMILES: CC(C)c1cc(/C=C(\C#N)C(=O)Nc2nc(-c3ccccc3)cs2)cc(C(C)(C)C)n1]

The compound was prepared according to General procedure D2 from 2-cyano-N-(4-(6-methoxypyridin-2-yl)thiazol-2-yl)acetamide (44 mg, 0.182 mmol), 2,6-di-tert-butylisonicotinaldehyde (40 mg, 0.182 mmol), and piperidine (2 μL, 0.018 mmol) in CH₂Cl₂ (2 mL). The product, purified by column chromatography (hexane:EtOAc; 10:1 to 1:1), was obtained as a yellow solid (64 mg, 79%).

¹H NMR (500 MHz, CDCl₃) δ (ppm) 8.45 (s, 1H), 7.88-7.82 (m, 2H), 7.57 (s, 2H), 7.47-7.41 (m, 2H), 7.38-7.33 (m, 1H), 1.41 (s, 18H);

¹³C NMR (126 MHz, CDCl₃) δ (ppm) 170.0, 157.8, 156.8, 155.0, 150.8, 138.3, 134.0, 129.0, 128.5, 126.3, 115.6, 109.1, 106.1, 38.2, 30.2;

HRMS calcd for $C_{26}H_{29}N_4OS$ [M+H]⁺ 445.2057, found 445.2060.

Preparative Example 241

(E)-2-cyano-3-(3,4-dihydroxyphenyl)-N-(4-(6-methoxypyridin-3-yl)thiazol-2-yl)acrylamide

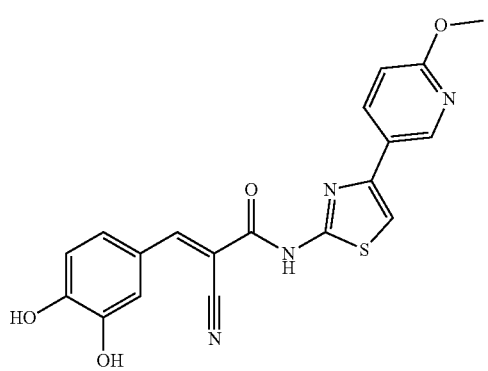 [SMILES: COc1ccc(-c2csc(NC(=O)/C(C#N)=C/c3ccc(O)c(O)c3)n2)cn1]

The compound was prepared according to General procedure D2 from 2-cyano-N-(4-(6-methoxypyridin-3-yl)thiazol-2-yl)acetamide (150 mg, 0.54 mmol), 3,4-dihydroxybenzaldehyde (76 mg, 0.56 mmol), and piperidine (3 μL, 0.027 mmol) in CH₂Cl₂ (3 mL); the reaction time was 2 h at reflux. The precipitate was collected by filtration, suspended in CH₂Cl₂ (5 mL), and the mixture was stirred for 2 h. The solid was collected by filtration and dried under vacuum. The product was obtained as a yellow solid (120 mg, 60%).

¹H NMR (500 MHz, DMSO-d₆) δ (ppm) 10.65 (s, 3H), 8.73 (d, J=2.4 Hz, 1H), 8.29 (s, 1H), 8.19 (dd, J=8.7, 2.5 Hz, 1H), 7.62 (s, 1H), 7.61 (d, J=2.3 Hz, 1H), 7.38 (dd, J=8.4, 2.2 Hz, 1H), 6.96-6.88 (m, 2H), 3.90 (s, 3H);

¹³C NMR (126 MHz, DMSO-d₆) δ (ppm) 163.1, 162.3, 159.5, 151.8, 151.7, 145.8, 144.2, 136.6, 125.9, 123.9, 123.1, 116.6, 116.4, 116.1, 110.5, 107.8, 53.3;

HRMS calcd for $C_{19}H_{15}N_4O_4S$ [M+H]⁺ 395.0809, found 395.0810.

Preparative Example 242

(E)-2-cyano-3-(3,4-dihydroxyphenyl)-N-(4-(3-methoxypyridin-2-yl)thiazol-2-yl)acrylamide

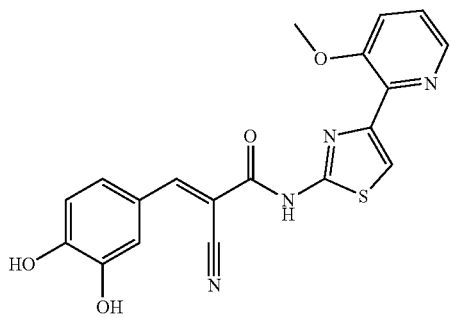 [SMILES: COc1cccnc1-c1csc(NC(=O)/C(C#N)=C/c2ccc(O)c(O)c2)n1]

The compound was prepared according to General procedure D2 from 2-cyano-N-(4-(3-methoxypyridin-2-yl)thiazol-2-yl)acetamide (76 mg, 0.27 mmol), 3,4-dihydroxybenzaldehyde (38 mg, 0.27 mmol), and piperidine (3 μL, 0.027 mmol) in CH₂Cl₂ (5 mL); the reaction time was 2 h at reflux. The precipitate was collected by filtration, washed with CH₂Cl₂ (5 mL) and dried under vacuum. The product was obtained as a yellow solid (94 mg, 90%).

¹H NMR (500 MHz, DMSO-d₆) δ (ppm) 10.14 (s, 2H), 8.31 (s, 1H), 8.24 (dd, J=4.5, 1.2 Hz, 1H), 7.78 (s, 1H), 7.63-7.56 (m, 2H), 7.39 (dd, J=8.4, 4.6 Hz, 1H), 7.36 (dd, J=8.4, 2.2 Hz, 1H), 6.92 (d, J=8.3 Hz, 1H), 3.95 (s, 3H);

¹³C NMR (126 MHz, DMSO-d₆) δ (ppm) 164.5, 160.3, 153.4, 151.6, 151.4, 145.8, 140.5, 139.4, 125.7, 123.9, 123.3, 119.3, 117.0, 116.4, 116.0, 114.2, 55.7;

HRMS calcd for $C_{19}H_{15}N_4O_4S$ [M+H]⁺ 395.0809, found 395.0807.

Preparative Example 243

(E)-2-cyano-3-(3,5-dichloro-4-hydroxyphenyl)-N-(4-(pyridin-2-yl)thiazol-2-yl)acrylamide

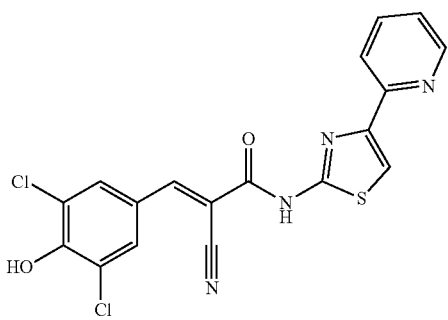 [SMILES: N#C/C(=C\c1cc(Cl)c(O)c(Cl)c1)C(=O)Nc1nc(-c2ccccn2)cs1]

The compound was prepared according to General procedure D2 from 2-cyano-N-(4-(pyridin-2-yl)thiazol-2-yl)acetamide (80 mg, 0.33 mmol), 3,5-dichloro-4-hydroxybenzaldehyde (63 mg, 0.33 mmol), and piperidine (3 μL, 0.027 mmol) in CH$_2$Cl$_2$ (3 mL); the reaction time was 16 h at reflux. The precipitate was collected by filtration, washed with CH$_2$Cl$_2$ (5 mL) and dried under vacuum. The product was obtained as a yellow solid (95 mg, 70%).

$^1$H NMR (500 MHz, DMSO-d$_6$) δ (ppm) 12.58 (s, 1H), 8.65-8.59 (m, 1H), 8.25 (s, 1H), 8.03-7.97 (m, 3H), 7.95-7.86 (m, 2H), 7.38-7.32 (m, 1H);

$^{13}$C NMR (126 MHz, DMSO-d$_6$) δ (ppm) 162.2, 159.0, 158.3, 151.7, 149.5, 149.2, 137.3, 136.0, 131.2, 126.3, 123.5, 122.9, 120.0, 116.9, 112.2;

HRMS calcd for C$_{18}$H$_{11}$Cl$_2$N$_4$O$_2$S [M+H]$^+$ 416.9974, found 416.9970.

Preparative Example 244

(E)-2-cyano-3-(3,4-dihydroxyphenyl-N-(4-(4-methylsulfonyl)phenyl)thiazol-2-yl)acrylamide

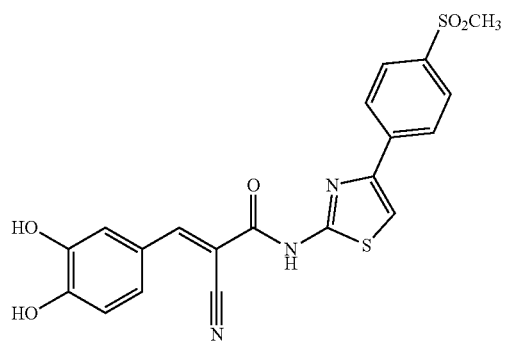 [SMILES: CS(=O)(=O)c1ccc(-c2csc(NC(=O)/C(C#N)=C/c3ccc(O)c(O)c3)n2)cc1]

The compound was prepared according to General procedure D2 from 2-cyano-N-(4-(4-(methylsulfonyl)phenyl)thiazol-2-yl)acetamide (100 mg, 0.311 mmol), 3,4-dihydroxybenzaldehyde (43 mg, 0.31 mmol), and piperidine (3 μL, 0.027 mmol) in CH$_2$Cl$_2$ (5 mL); the reaction time was 2 h at reflux. The precipitate was collected by filtration, washed with a mixture of CH$_2$Cl$_2$ and MeOH (5 mL+0.5 mL) and dried under vacuum. The product was obtained as a yellow solid (90 mg, 65%).

$^1$H NMR (500 MHz, DMSO-d$_6$) δ (ppm) 10.39 (s, 3H), 8.27 (s, 1H), 8.19 (d, J=8.1 Hz, 2H), 7.99 (d, J=8.1 Hz, 2H), 7.91 (s, 1H), 7.61 (d, J=2.3 Hz, 1H), 7.37 (dd, J=8.4, 2.3 Hz, 1H), 6.92 (d, J=8.3 Hz, 1H), 3.24 (s, 3H);

$^{13}$C NMR (126 MHz, DMSO-d$_6$) δ (ppm) 162.6, 160.2, 151.6, 151.5, 147.1, 145.8, 139.4, 138.9, 133.1, 127.6, 126.2, 125.8, 123.1, 116.8, 116.3, 116.0, 111.7, 43.6;

HRMS calcd for C$_{20}$H$_{16}$N$_3$O$_5$S$_2$ [M+H]$^+$ 442.0526, found 442.0528.

Preparative Example 245

(E)-2-cyano-3-(3,4-dihydroxyphenyl)-N-(5-phenylthiazol-2-yl)acrylamide

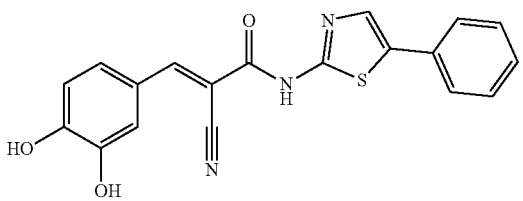 [SMILES: N#C/C(=C\c1ccc(O)c(O)c1)C(=O)Nc1ncc(-c2ccccc2)s1]

The compound was prepared according to General procedure D2 from 2-cyano-N-(5-phenylthiazol-2-yl)acetamide (66 mg, 0.271 mmol), 3,4-dihydroxybenzaldehyde (0.244 mg, 33 mmol), and piperidine (2 μL, 0.03 mmol) in CH$_2$Cl$_2$ (3 mL); the reaction time was 4 h at reflux. The product, purified by reverse phase column chromatography (H$_2$O:MeOH:AcOH; 60:40:0.05 to 5:95:0.05), was obtained as a yellow solid (66 mg, 67%).

$^1$H NMR (500 MHz, acetone-d$_6$) δ (ppm) 8.29 (s, 1H), 7.82 (s, 1H), 7.79 (s, 1H), 7.66 (d, J=7.9 Hz, 2H), 7.52-7.42 (m, 3H), 7.34 (dd, J=14.8, 7.7 Hz, 1H), 7.03 (d, J=8.3 Hz, 1H);

$^{13}$C NMR (126 MHz, acetone-d$_6$) δ (ppm) 153.4, 151.9, 146.6, 132.8, 130.19, 128.8, 127.7, 126.9, 125.4, 117.4, 117.2, 116.9, 79.7, 79.1, 78.9;

HRMS calcd for C$_{19}$H$_{14}$N$_3$O$_3$S [M+H]$^+$ 364.0750, found [M+H]$^+$:364.0752.

Preparative Example 246

(E)-N-(4-(4-(tert-butyl)-2,6-dimethylphenyl)thiazol-2-yl)-2-cyano-3-(3,4-dihydroxyphenyl)acrylamide

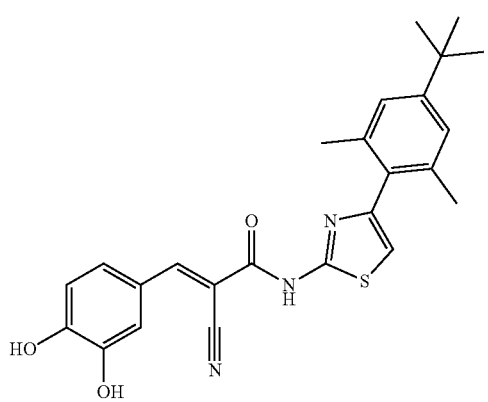 [SMILES: Cc1cc(C(C)(C)C)cc(C)c1-c1csc(NC(=O)/C(C#N)=C/c2ccc(O)c(O)c2)n1]

The compound was prepared according to General procedure D2 from N-(4-(4-(tert-butyl)-2,6-dimethylphenyl)thiazol-2-yl)-2-cyanoacetamide (80 mg, 0.24 mmol), 3,4-dihydroxybenzaldehyde (33 mg, 0.24 mmol), and piperidine (3 μL, 0.02 mmol) in CH₂Cl₂ (2 mL); the reaction time was 4 h at reflux. The product, purified by reverse phase column chromatography (H₂O:MeOH:AcOH; 60:40:0.05 to 5:95:0.05), was obtained as a yellow solid (65 mg, 65%).

$^1$H NMR (500 MHz, acetone-d₆) δ (ppm) 8.25 (s, 1H), 7.77 (s, 1H), 7.47 (d, J=8.2 Hz, 1H), 7.16 (s, 2H), 7.02 (d, J=8.3 Hz, 1H), 6.95 (s, 1H), 2.13 (s, 6H), 1.32 (s, 10H);

$^{13}$C NMR (126 MHz, acetone-d₆) δ (ppm) 163.3, 153.2, 151.9, 151.8, 146.5, 137.8, 132.7, 127.6, 125.5, 125.4, 117.5, 117.2, 116.8, 112.0, 102.3, 79.39, 79.1, 35.1, 31.7, 20.9;

HRMS calcd for $C_{25}H_{26}N_3O_3S$ [M+H]⁺ 448.1689, found 448.1691.

Preparative Example 247

(E)-N-(4-(3-(tert-butyl)phenyl)thiazol-2-yl)-2-cyano-3-(3,4-dihydroxyphenyl)acrylamide

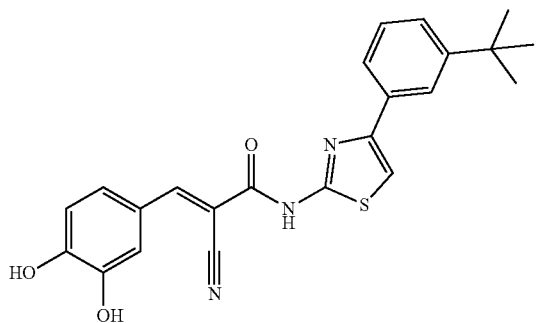 [SMILES: CC(C)(C)c1cccc(-c2csc(NC(=O)/C(C#N)=C/c3ccc(O)c(O)c3)n2)c1]

The compound was prepared according to General procedure D2 from N-(4-(2-(tert-butyl)phenyl)thiazol-2-yl)-2-cyanoacetamide (100 mg, 0.33 mmol), 3,4-dihydroxybenzaldehyde (46 mg, 0.33 mmol), and piperidine (3 μL, 0.03 mmol) in CH₂Cl₂ (3 mL); the reaction time was 4 h at reflux. The product, purified by reverse phase column chromatography (H₂O:MeOH:AcOH; 60:40:0.05 to 5:95:0.05), was obtained as a yellow solid (83 mg, 60%).

$^1$H NMR (500 MHz, acetone-d₆) δ (ppm) 8.31 (s, 1H), 8.02 (s, 1H), 7.80 (s, 1H), 7.74 (d, J=7.5 Hz, 1H), 7.56 (s, 1H), 7.51 (d, J=8.1 Hz, 1H), 7.38 (dd, J=24.3, 11.6 Hz, 2H), 7.04 (d, J=8.3 Hz, 1H), 1.37 (s, 9H);

$^{13}$C NMR (126 MHz, acetone-d₆) δ (ppm) 172.1, 162.1, 159.1, 153.7, 152.41, 152.1, 151.0, 146.6, 135.1, 129.4, 129.2, 127.9, 126.2, 125.9, 125.3, 124.2, 124.0, 117.2, 116.9, 109.1, 101.2, 31.8, 30.9;

HRMS calcd for $C_{23}H_{2}N_3O_3S$ [M+H]⁺ 420.1376, found 420.1379.

Preparative Example 248

(E)-2-cyano-3-(4-hydroxy-3,5-dimethylphenyl)-N-(4-(pyridin-2-yl)thiazol-2-yl)acrylamide

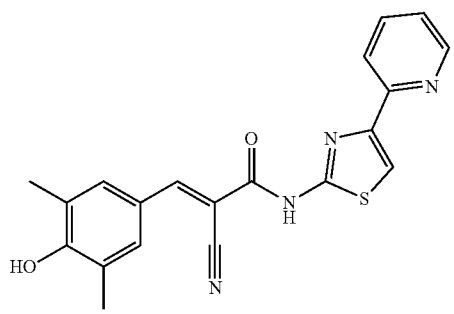 [SMILES: Cc1cc(/C=C(\C#N)C(=O)Nc2nc(-c3ccccn3)cs2)cc(C)c1O]

The compound was prepared according to General procedure D2 from 2-cyano-N-(4-(pyridin-2-yl)thiazol-2-yl)acetamide (70 mg, 0.29 mmol), 4-hydroxy-3,5-dimethylbenzaldehyde (45 mg, 0.29 mmol), and piperidine (3 μL, 0.029 mmol) in CH₂Cl₂ (3 mL); the reaction time was 16 h at reflux. The precipitate was collected by filtration, washed with CH₂Cl₂ (5 mL) and dried under vacuum. The product was obtained as a yellow solid (60 mg, 55%).

$^1$H NMR (500 MHz, DMSO-d₆) δ (ppm) 8.62 (d, J=3.3 Hz, 1H), 8.34 (s, 1H), 8.00 (d, J=7.8 Hz, 1H), 7.93-7.86 (m, 2H), 7.71 (s, 2H), 7.35 (dd, J=4.8, 7.5 Hz, 1H), 2.24 (s, 6H);

$^{13}$C NMR (126 MHz, DMSO-d₆) δ (ppm) 162.0, 158.8, 152.0, 151.8, 149.5, 137.3, 131.9, 125.1, 122.9, 122.7, 120.0, 116.5, 112.3, 100.0, 16.6;

HRMS calcd for $C_{20}H_{15}N_4O_2S$ [M−H]⁻ 375.0921, found 375.0918.

Preparative Example 249

(E)-2-cyano-3-(3,5-dibromo-4-hydroxyphenyl)-N-(4-(pyridin-2-yl)thiazol-2-yl)acrylamide

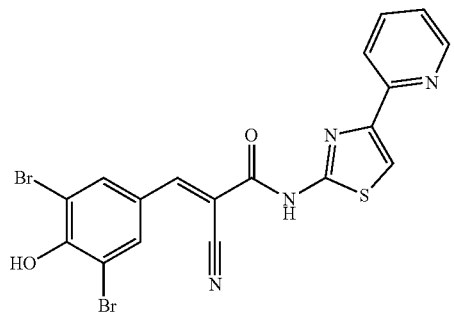 [SMILES: N#C/C(=C\c1cc(Br)c(O)c(Br)c1)C(=O)Nc1nc(-c2ccccn2)cs1]

The compound was prepared according to General procedure D2 from 2-cyano-N-(4-(pyridin-2-yl)thiazol-2-yl)acetamide (70 mg, 0.29 mmol), 3,5-dibromo-4-hydroxybenzaldehyde (82 mg, 0.29 mmol), and piperidine (3 μL, 0.029 mmol) in CH₂Cl₂ (3 mL); the reaction time was 16 h at reflux. The product was purified by reverse phase column chromatography (H₂O:MeOH:7M NH₃ in MeOH; 60:40:0.05 gradually to 5:95:0.05). All fractions containing the product were combined, MeOH was evaporated, and the remaining aqueous phase was neutralized with HCl (2 M) to neutral pH. The solid was collected by filtration, washed with EtOAc (3 mL) and dried under vacuum. The product was obtained as a yellow solid (30 mg, 20%).

$^1$H NMR (500 MHz, DMSO-d$_6$) δ (ppm) 12.88 (s, 1H), 8.67 (d, J=4.9 Hz, 1H), 8.38 (s, 1H), 8.24 (s, 2H), 8.07 (q, J=8.0 Hz, 3H), 7.47 (t, J=6.3 Hz, 1H);

$^{13}$C NMR (126 MHz, DMSO-d$_6$) δ (ppm) 161.5, 158.8, 154.9, 150.3, 149.2, 148.2, 139.0, 134.5, 125.6, 123.5, 120.7, 115.6, 113.8, 112.0, 103.9;

HRMS calcd for C$_{18}$H$_9$Br$_2$N$_4$O$_2$S [M−H]$^−$ 502.8818, found 502.8814.

Preparative Example 250

(E)-2-cyano-N-(4-(3-fluoropyridin-2-yl)thiazol-2-yl)-3-(4-hydroxy-3,5-dimethylphenyl)acrylamide

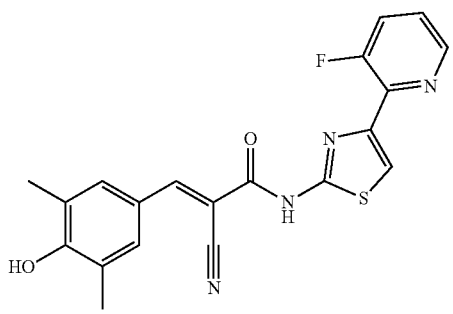 [SMILES: Cc1cc(/C=C(\C#N)C(=O)Nc2nc(-c3ncccc3F)cs2)cc(C)c1O]

The compound was prepared according to General procedure D2 from 2-cyano-N-(4-(3-fluoropyridin-2-yl)thiazol-2-yl)acetamide (40 mg, 0.15 mmol), 4-hydroxy-3,5-dimethylbenzaldehyde (25 mg, 0.15 mmol), and piperidine (3 μL, 0.029 mmol) in CH$_2$Cl$_2$ (3 mL); the reaction time was 16 h at reflux. The precipitate was collected by filtration, washed with CH$_2$Cl$_2$ (5 mL) and dried under vacuum. The product was obtained as a yellow solid (60 mg, 55%).

$^1$H NMR (500 MHz, DMSO-d$_6$) δ (ppm) 8.49-8.43 (m, 1H), 8.10 (s, 1H), 7.77 (ddd, J=1.4, 8.3, 11.5 Hz, 1H), 7.65 (s, 2H), 7.59 (s, 1H), 7.46-7.38 (m, 1H), 2.20 (s, 6H);

$^{13}$C NMR (126 MHz, DMSO-d$_6$) δ (ppm) 164.3, 156.2 (d, J=261.6 Hz), 148.3, 145.1 (d, J=5.1 Hz), 144.5, 141.2, 131.2, 125.0, 124.4 (d, J=20.0 Hz), 123.8 (d, J=3.9 Hz), 122.7, 118.5, 114.0, 16.6;

HRMS calcd for C$_{20}$H$_{14}$FN$_4$O$_2$S [M−H]$^−$ 393.0827, found 393.0823.

Preparative Example 251

(E)-2-cyano-3-(3,5-dibromo-4-hydroxyphenyl)-N-(4-(3-fluoropyridin-2-yl)thiazol-2-yl)acrylamide

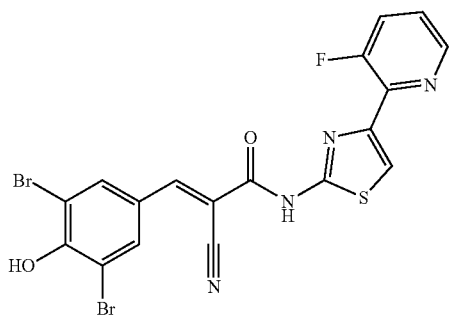 [SMILES: N#C/C(=C\c1cc(Br)c(O)c(Br)c1)C(=O)Nc1nc(-c2ncccc2F)cs1]

The compound was prepared according to General procedure D2 from 2-cyano-N-(4-(3-fluoropyridin-2-yl)thiazol-2-yl)acetamide (40 mg, 0.15 mmol), 3,5-dibromo-4-hydroxybenzaldehyde (45 mg, 0.15 mmol), and piperidine (3 μL, 0.029 mmol) in CH$_2$Cl$_2$ (3 mL); the reaction time was 16 h at reflux. The precipitate was collected by filtration, washed with CH$_2$Cl$_2$ (5 mL) and dried under vacuum. The product was obtained as a yellow solid (60 mg, 55%).

$^1$H NMR (500 MHz, DMSO-d$_6$) δ (ppm) 12.77 (s, 1H), 8.53-8.49 (m, 1H), 8.33 (s, 1H), 8.21 (s, 2H), 7.88-7.83 (m, 2H), 7.53-7.47 (m, 1H);

$^{13}$C NMR (126 MHz, DMSO-d$_6$) δ (ppm) 166.6, 163.4, 158.5, 156.4 (d, J=261.7 Hz), 148.4, 145.3 (d, J=5.1 Hz), 140.3, 135.6, 124.6 (d, J=14.0 Hz), 124.5, 118.6, 115.8, 115.2 (d, J=8.2 Hz), 113.8;

$^{19}$F NMR (471 MHz, DMSO-d$_6$) δ (ppm) −121.0;

HRMS calcd for C$_{18}$H$_8$Br$_2$FN$_4$O$_2$S [M−H]$^−$ 520.8724, found 520.8723.

Preparative Example 252

(E)-2-cyano-3-(3,5-dichloro-4-hydroxyphenyl)-N-(4-(3-fluoropyridin-2-yl)thiazol-2-yl)acrylamide

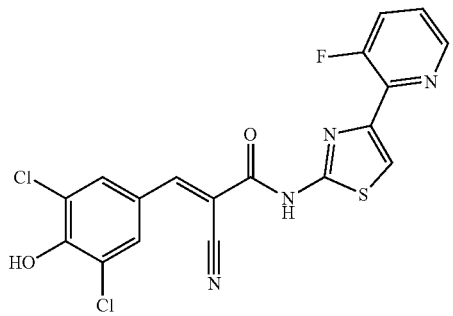 [SMILES: N#C/C(=C\c1cc(Cl)c(O)c(Cl)c1)C(=O)Nc1nc(-c2ncccc2F)cs1]

The compound was prepared according to General procedure D2 from 2-cyano-N-(4-(3-fluoropyridin-2-yl)thiazol-2-yl)acetamide (40 mg, 0.15 mmol), 3,5-dichloro-4-hydroxybenzaldehyde (30 mg, 0.15 mmol), and piperidine (3 μL, 0.029 mmol) in CH$_2$Cl$_2$ (3 mL); the reaction time was 16 h at reflux. The product, purified by reverse phase column chromatography (H$_2$O:MeOH:AcOH; 60:40:0.05 to 5:95:0.05), was obtained as a yellow solid (10 mg, 15%).

$^1$H NMR (500 MHz, DMSO-d$_6$) δ (ppm) 12.98 (s, 1H), 8.55-8.48 (m, 1H), 8.38 (s, 1H), 8.05 (s, 2H), 7.90-7.81 (m, 2H), 7.55-7.46 (m, 1H);

$^{13}$C NMR (126 MHz, DMSO-d$_6$) δ (ppm) 156.5 (d, J=262.2 Hz), 154.2, 149.3, 145.4 (d, J=5.3 Hz), 130.8, 124.8, 124.7 (d, J=19.5 Hz), 122.7;

$^{19}$F NMR (471 MHz DMSO-d$_6$) δ (ppm) −121.1;

HRMS calcd for C$_{18}$H$_8$Cl$_2$FN$_4$O$_2$S [M−H]$^−$ 432.9735, found 432.9733.

Preparative Example 253 methyl (E)-5-(2-cyano-3-oxo-3-((4-phenylthiazol-2-yl)amino)prop-1-en-1-yl)-2-hydroxybenzoate

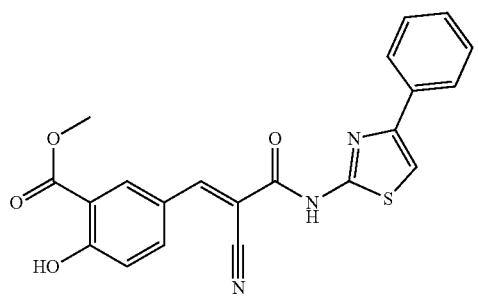 [SMILES: COC(=O)c1cc(/C=C(\C#N)C(=O)Nc2nc(-c3ccccc3)cs2)ccc1O]

The compound was prepared according to General procedure D2 from 2-cyano-N-(4-phenylthiazol-2-yl)acetamide (169 mg, 0.695 mmol), methyl 5-formyl-2-hydroxybenzoate (125 mg, 0.695 mmol), and piperidine (7 μL, 0.07 mmol) in $CH_2Cl_2$ (6 mL); the reaction time was 24 h at reflux. The yellow precipitate was filtered, washed with $CH_2Cl_2$ (3×2 mL) and dried in a vacuum oven at 50° C. The product was obtained as a yellow solid (237 mg, 84%).

$^1$H NMR (701 MHz, DMSO-$d_6$) δ (ppm) 12.74 (s, 1H), 11.20 (s, 1H), 8.51 (s, 1H), 8.48 (d, J=2.4 Hz, 1H), 8.20 (dd, J=8.8, 2.4 Hz, 1H), 7.94 (d, J=7.6 Hz, 2H), 7.70 (s, 1H), 7.45 (t, J=7.7 Hz, 2H), 7.35 (t, J=7.3 Hz, 1H), 7.22 (d, J=8.7 Hz, 1H), 3.92 (s, 3H);

$^{13}$C NMR (176 MHz, DMSO-$d_6$) δ (ppm) 167.5, 162.8, 150.7, 136.3, 134.5, 128.8, 127.9, 125.7, 122.9, 118.8, 115.1, 108.8, 52.7;

HRMS calcd for $C_{21}H_{14}N_3O_4S$ [M−H]$^-$ 404.0711, found 404.0711.

Preparative Example 254

(E)-5-(2-cyano-3-oxo-3-((4-phenylthiazol-2-yl)amino)prop-1-en-1-yl)-2-hydroxybenzoic acid

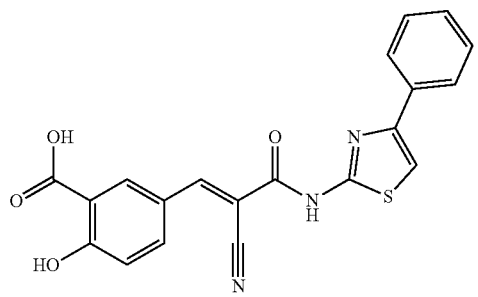 [SMILES: N#C/C(=C\c1ccc(O)c(C(=O)O)c1)C(=O)Nc1nc(-c2ccccc2)cs1]

To a solution of methyl (E)-5-(2-cyano-3-oxo-3-((4-phenylthiazol-2-yl)amino)prop-1-en-1-yl)-2-hydroxybenzoate (61 mg, 0.15 mmol) in THF (3 mL), MeOH (1 mL) and $H_2O$ (1 mL) was added LiOH (14 mg, 0.6 mmol). The mixture was stirred at 25° C. for 24 h. LiOH (14 mg, 0.6 mmol) was added and the mixture was stirred for additional 6 h. Then, the pH was adjusted to ca. 2 with 1M aqueous HCl. The precipitate was collected by filtration, washed with $H_2O$ (3 mL), then with diethyl ether (2×2 mL), and dried in a vacuum oven at 50° C. The product was obtained as a yellow solid (48 mg, 82%).

$^1$H NMR (500 MHz, DMSO-$d_6$) δ (ppm) 12.75 (s, 1H), 8.57 (d, J=2.5 Hz, 1H), 8.50 (s, 1H), 8.18 (dd, J=8.8, 2.5 Hz, 1H), 7.94 (d, J=7.1 Hz, 2H), 7.70 (s, 1H), 7.45 (t, J=7.6 Hz, 2H), 7.35 (t, J=7.4 Hz, 1H), 7.19 (d, J=8.7 Hz, 1H);

$^{13}$C NMR (126 MHz, DMSO-$d_6$) δ (ppm) 170.8, 164.7, 150.9, 136.9, 134.2, 128.8, 128.0, 125.7, 122.7, 118.6, 116.0, 114.4, 108.8;

HRMS calcd for $C_{20}H_{12}N_3O_4S$ [M−H]$^-$ 390.0554, found 390.0554.

Preparative Example 255

(E)-5-(2-cyano-3-oxo-3-((4-phenylthiazol-2-yl)amino)prop-1-en-1-yl)-2-hydroxybenzamide

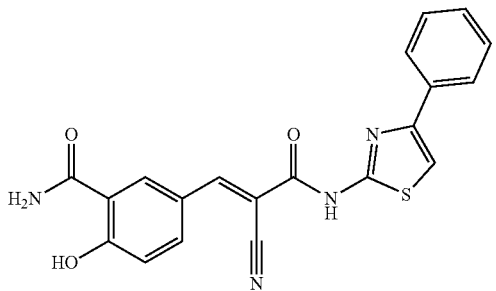 [SMILES: N#C/C(=C\c1ccc(O)c(C(N)=O)c1)C(=O)Nc1nc(-c2ccccc2)cs1]

The compound was prepared according to General procedure D2 from 2-cyano-N-(4-phenylthiazol-2-yl)acetamide (50 mg, 0.2 mmol), 5-formyl-2-hydroxybenzamide (33 mg, 0.2 mmol), and piperidine (3 μL, 0.029 mmol) in $CH_2Cl_2$ (3 mL); the reaction time was 16 h at reflux. The precipitate was collected by filtration, washed with $CH_2Cl_2$ (5 mL) and dried under vacuum. The product was obtained as a yellow solid (73 mg, 93%).

$^1$H NMR (500 MHz, DMSO-$d_6$) δ (ppm) 13.44 (s, 1H), 12.82 (s, 1H), 8.43 (d, J=2.3 Hz, 1H), 8.40 (s, 1H), 8.37 (s, 1H), 8.22 (dd, J=2.3, 8.8 Hz, 1H), 8.06 (s, 1H), 7.96-7.92 (m, 2H), 7.70 (s, 1H), 7.46 (t, J=7.7 Hz, 2H), 7.40-7.31 (m, 1H), 7.15 (d, J=8.8 Hz, 1H);

$^{13}$C NMR (126 MHz, DMSO-$d_6$) δ (ppm) 169.9, 163.9, 161.3, 151.4, 149.3, 134.2, 134.1, 128.7, 128.0, 125.7, 122.5, 118.6, 116.4, 116.0, 108.8;

HRMS calcd for $C_{20}H_{13}N_4O_3S$ [M−H]$^-$ 389.0714, found 389.0715.

Preparative Example 256

(E)-3-(2-bromo-4-hydroxyphenyl)-2-cyano-N-(4-phenylthiazol-2-yl)acrylamide

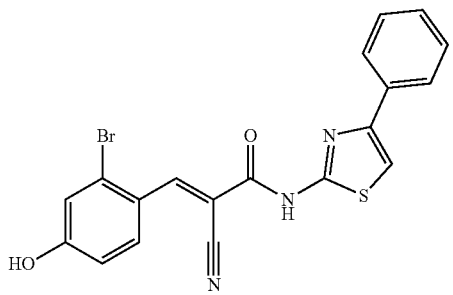 [SMILES: N#C/C(=C\c1ccc(O)cc1Br)C(=O)Nc1nc(-c2ccccc2)cs1]

The compound was prepared according to General procedure D2 from 2-cyano-N-(4-phenylthiazol-2-yl)acetamide (120 mg, 0.49 mmol), 2-bromo-4-hydroxybenzaldehyde (100 mg, 0.49 mmol), and piperidine (3 μL, 0.03 mmol) in $CH_2Cl_2$ (5 mL); the reaction time was 16 h at reflux. The precipitate was collected by filtration, washed with $CH_2Cl_2$ (5 mL) and dried under vacuum. The product was obtained as a yellow solid (160 mg, 75%).

$^1$H NMR (500 MHz, DMSO-$d_6$) δ (ppm) 12.99 (s, 1H), 11.01 (s, 1H), 8.52 (s, 1H), 8.13 (d, J=8.7 Hz, 1H), 7.96-7.91 (m, 2H), 7.70 (s, 1H), 7.50-7.41 (m, 2H), 7.40-7.32 (m, 1H), 7.24 (d, J=2.4 Hz, 1H), 7.02 (dd, J=2.5, 8.7 Hz, 1H);

$^{13}$C NMR (126 MHz, DMSO-$d_6$) δ (ppm) 162.2, 161.2, 134.2, 131.3, 128.7, 128.0, 127.7, 125.8, 122.1, 120.2, 115.7, 108.9, 105.1;

HRMS calcd for $C_{19}H_{11}BrN_3O_2S$ [M–H]$^-$ 423.9761, found 423.9764.

Preparative Example 257

(E)-2-cyano-3-(3,4-dihydroxy-5-nitrophenyl)-N-(4-phenylthiazol-2-yl)acrylamide

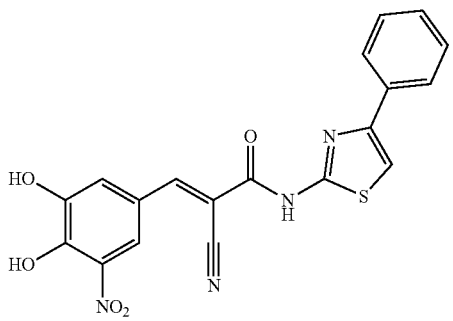 [SMILES: N#C/C(=C\c1cc(O)c(O)c([N+](=O)[O-])c1)C(=O)Nc1nc(-c2ccccc2)cs1]

The compound was prepared according to General procedure D2 from 2-cyano-N-(4-phenylthiazol-2-yl)acetamide (103 mg, 0.423 mmol), 3,4-dihydroxy-5-nitrobenzaldehyde (78 mg, 0.423 mmol), and piperidine (4 μL, 0.04 mmol) in $CH_2Cl_2$ (5 mL); the reaction time was 48 h at reflux. The precipitate was collected by filtration, washed with $CH_2Cl_2$ (2×2 mL), then with pentane (2×2 mL), and dried in a vacuum oven at 50° C. The product was obtained as a yellow solid (78 mg, 45%).

$^1$H NMR (500 MHz, DMSO-$d_6$) δ (ppm) 12.74 (s, 1H), 10.86 (s, 1H), 8.40 (s, 1H), 8.01 (d, J=2.2 Hz, 1H), 7.93 (d, J=7.1 Hz, 2H), 7.84 (d, J=2.2 Hz, 1H), 7.70 (s, 1H), 7.45 (t, J=7.7 Hz, 2H), 7.35 (t, J=7.3 Hz, 1H);

$^{13}$C NMR (126 MHz, DMSO-$d_6$) δ (ppm) 161.5, 150.3, 148.3, 146.4, 137.2, 133.8, 128.8, 128.0, 125.7, 121.6, 120.1, 117.9, 115.7, 108.8, 103.3;

HRMS calcd for $C_{19}H_{11}N_4OS$ [M–H]$^-$ 407.0456, found 407.0456.

Preparative Example 258

Methyl (E)$_4$-(2-cyano-3-oxo-3-((4-phenylthiazol-2-yl)amino)prop-1-en-1-yl)-2-hydroxybenzoate

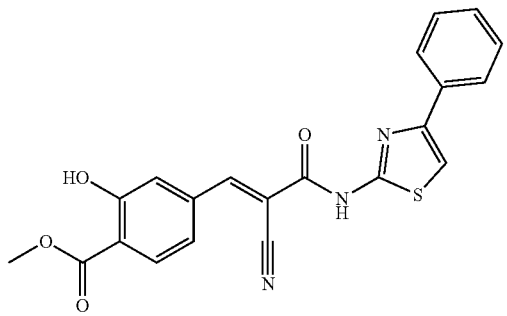 [SMILES: COC(=O)c1ccc(/C=C(\C#N)C(=O)Nc2nc(-c3ccccc3)cs2)cc1O]

The compound was prepared according to General procedure D2 from 2-cyano-N-(4-phenylthiazol-2-yl)acetamide (136 mg, 0.55 mmol), methyl 4-formyl-2-hydroxybenzoate (100 mg, 0.55 mmol), and piperidine (3 μL, 0.029 mmol) in $CH_2Cl_2$ (5 mL); the reaction time was 16 h at reflux. The product was purified by reverse phase column chromatography ($H_2O$:MeOH:AcOH; 60:40:0.05 to 5:95:0.05). The product was triturated with $CH_2Cl_2$:MeOH (3:0.1; 3.1 mL). The solid was washed with $CH_2Cl_2$ (1 mL) and dried under vacuum. The product was obtained as a yellow solid (150 mg, 67%).

$^1$H NMR (500 MHz, DMSO-$d_6$) δ (ppm) 12.97 (s, 1H), 10.64 (s, 1H), 8.46 (s, 1H), 7.96-7.90 (m, 3H), 7.72 (s, 1H), 7.56 (s, 1H), 7.50 (dd, J=1.8, 8.3 Hz, 1H), 7.48-7.43 (m, 2H), 7.39-7.33 (m, 1H), 3.91 (s, 3H);

$^{13}$C NMR (126 MHz, DMSO-$d_6$) δ (ppm) 167.8, 160.8, 159.1, 150.5, 137.4, 133.8, 130.9, 128.8, 128.0, 125.7, 120.6, 118.4, 117.1, 115.2, 108.9, 52.6;

HRMS calcd for $C_{21}H_{16}N_3O_4S$ [M+H]$^+$ 406.0856, found 406.0859.

Preparative Example 259

(E)-4-(2-cyano-3-oxo-3-((4-phenylthiazol-2-yl)amino)prop-1-en-1-yl)-2-hydroxybenzoic acid

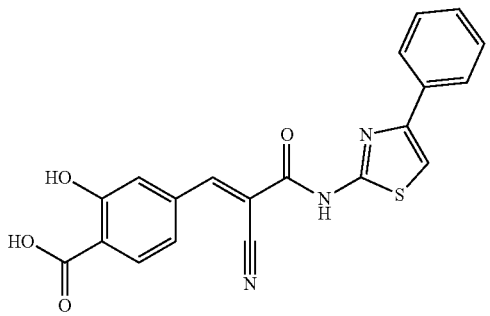 [SMILES: N#C/C(=C\c1ccc(C(=O)O)c(O)c1)C(=O)Nc1nc(-c2ccccc2)cs1]

Methyl 4-formyl-2-hydroxybenzoate (100 mg, 0.55 mmol) and NaOH (66 mg, 1.65 mmol) were dissolved in MeOH:H$_2$O (3+3 mL) and stirred at 25° C. for 3 h. The mixture was poured into 1 M HCl (5 mL) and extracted with EtOAc (3×5 mL). The organic fractions were combined, washed with brine (15 mL), dried over MgSO$_4$, filtered, and the solvent was evaporated. So obtained 4-formyl-2-hydroxybenzoic acid was directly used in the next step without further purification.

The compound was prepared according to General procedure D2 from 2-cyano-N-(4-phenylthiazol-2-yl)acetamide (120 mg, 0.48 mmol), 4-formyl-2-hydroxybenzoic acid (80 mg, 0.48 mmol), and piperidine (3 μL, 0.029 mmol) in CH$_2$Cl$_2$ (5 mL); the reaction time was 16 h at reflux. The precipitate was collected by filtration, washed with CH$_2$Cl$_2$ (5 mL) and dried under vacuum. The product was obtained as a yellow solid (70 mg, 37%).

$^1$H NMR (500 MHz, DMSO-d$_6$) δ (ppm) 13.03 (s, 1H), 8.47 (s, 1H), 7.96 (d, J=8.2 Hz, 1H), 7.95-7.92 (m, 2H), 7.73 (s, 1H), 7.54 (d, J=1.7 Hz, 1H), 7.52-7.45 (m, 1H), 7.48-7.44 (m, 2H), 7.40-7.31 (m, 1H);

$^{13}$C NMR (126 MHz, DMSO-d$_6$) δ (ppm) 170.7, 160.6, 150.6, 137.6, 133.5, 131.1, 128.8, 128.0, 125.8, 120.5, 118.1, 116.6, 115.3, 108.9;

HRMS calcd for C$_{20}$H$_{12}$N$_3$O$_4$S [M–H]$^-$ 390.0554, found 390.0556.

Preparative Example 260

(E)-2-cyano-3-(4-hydroxy-3-(hydroxymethyl)phenyl)-N-(4-phenylthiazol-2-yl)acrylamide

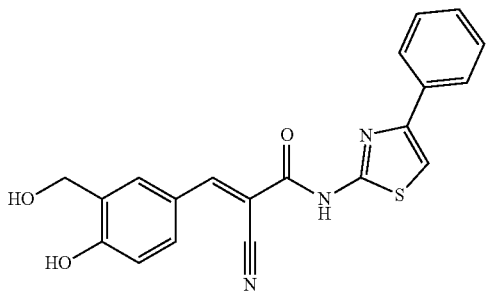 [SMILES: N#C/C(=C\c1ccc(O)c(CO)c1)C(=O)Nc1nc(-c2ccccc2)cs1]

The compound was prepared according to General procedure D2 from 2-cyano-N-(4-phenylthiazol-2-yl)acetamide (80 mg, 0.33 mmol), 4-hydroxy-3-(hydroxymethyl)benzaldehyde (50 mg, 0.33 mmol), and piperidine (3 μL, 0.029 mmol) in CH$_2$Cl$_2$ (5 mL); the reaction time was 16 h at reflux. The precipitate was collected by filtration, washed with CH$_2$Cl$_2$ (3 mL) and dried under vacuum. The product was obtained as a yellow solid (90 mg, 73%).

$^1$H NMR (500 MHz, DMSO-d$_6$) δ (ppm) 12.64 (s, 1H), 10.77 (s, 1H), 8.45 (s, 1H), 8.12 (d, J=2.3 Hz, 1H), 7.97-7.91 (m, 2H), 7.87 (dd, J=2.4, 8.5 Hz, 1H), 7.68 (s, 1H), 7.49-7.42 (m, 2H), 7.40-7.29 (m, 1H), 6.99 (d, J=8.5 Hz, 1H), 5.19 (s, 1H), 4.53 (s, 2H);

$^{13}$C NMR (126 MHz, DMSO-d$_6$) δ (ppm) 161.9, 159.3, 152.1, 149.1, 134.1, 131.3, 130.9, 130.1, 128.7, 127.9, 125.7, 122.6, 116.5, 115.4, 108.6, 57.6;

HRMS calcd for C$_{20}$H$_{16}$N$_3$O$_3$S [M+H]$^+$ 378.0907, found 378.0910.

Preparative Example 261

(E)-N-(4-benzothiazol-2-yl)-2-cyano-3-(3,4-dihydroxyphenyl)acrylamide

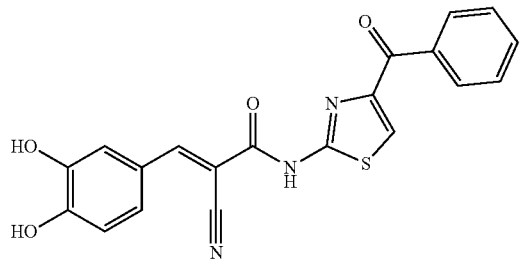 [SMILES: N#C/C(=C\c1ccc(O)c(O)c1)C(=O)Nc1nc(C(=O)c2ccccc2)cs1]

The compound was prepared according to General procedure D2 from N-(4-benzoylthiazol-2-yl)-2-cyanoacetamide (27 mg, 0.1 mmol), 3,4-dihydroxybenzaldehyde (14 mg, 0.1 mmol), and piperidine (3 μL, 0.029 mmol) in CH$_2$Cl$_2$ (3 mL); the reaction time was 16 h at reflux. The product, purified by reverse phase column chromatography (H$_2$O:MeOH:7M NH$_3$ in MeOH; 60:40:0.05 to 5:95:0.05), was obtained as a yellow solid (30 mg, 77%).

$^1$H NMR (500 MHz, DMSO-d$_6$) δ (ppm) 12.85 (s, 1H), 10.32 (s, 1H), 9.67 (s, 1H), 8.33 (s, 1H), 8.12 (s, 1H), 8.03 (d, J=7.5 Hz, 2H), 7.72-7.64 (m, 1H), 7.61 (d, J=2.3 Hz, 1H), 7.60-7.52 (m, 2H), 7.38 (dd, J=2.3, 8.4 Hz, 1H), 6.94 (d, J=8.3 Hz, 1H);

$^{13}$C NMR (126 MHz, DMSO-d$_6$) δ (ppm) 191.0, 186.9, 162.5, 158.3, 152.4, 151.7, 148.1, 145.8, 137.3, 132.7, 129.7, 128.4, 126.0, 124.6, 123.0, 116.6, 116.3, 116.1;

HRMS calcd for C$_{20}$H$_{12}$N$_3$O$_4$S [M–H]$^-$ 390.0554, found 390.0553.

Preparative Example 262

(E)-2-cyano-3-(3,4-dihydroxyphenyl)-N-(5-(pyrazin-2-yl)thiazol-2-yl)acrylamide

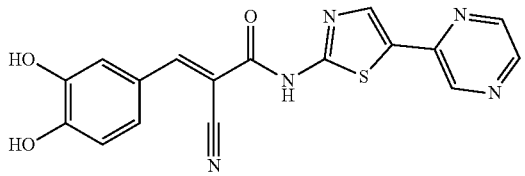 [SMILES: N#C/C(=C\c1ccc(O)c(O)c1)C(=O)Nc1ncc(-c2cnccn2)s1]

The compound was prepared according to General procedure D2 from 2-cyano-N-(5-(pyrazin-2-yl)thiazol-2-yl)acetamide (61 mg, 0.25 mmol), 3,4-dihydroxybenzaldehyde (35 mg, 0.25 mmol), and piperidine (3 μL, 0.029 mmol) in $CH_2Cl_2$ (5 mL); the reaction time was 16 h at reflux. The precipitate was collected by filtration, washed with $CH_2Cl_2$:MeOH (10:1; 2.2 mL) and dried under vacuum. The product was obtained as a yellow solid (75 mg, 82%).

$^1$H NMR (500 MHz, DMSO-$d_6$) δ (ppm) 9.23 (d, J=1.6 Hz, 1H), 8.64-8.56 (m, 1H), 8.48 (d, J=2.6 Hz, 1H), 8.43 (s, 1H), 8.25 (s, 1H), 7.62 (d, J=2.2 Hz, 1H), 7.37 (dd, J=2.2, 8.4 Hz, 1H), 6.92 (d, J=8.2 Hz, 1H);

$^{13}$C NMR (126 MHz, DMSO-$d_6$) δ (ppm) 151.8, 151.3, 146.9, 145.8, 144.1, 142.4, 141.0, 127.8, 125.8, 123.3, 117.0, 116.4, 116.0;

HRMS calcd for $C_{17}H_{10}N_5O_3S$ [M-H]$^-$ 364.0510, found 364.0507.

Preparative Example 263

(E)-2-cyano-3-(3,4-dihydroxyphenyl)-N-(5-(pyrazin-2-yl)-4-pyridin-2-yl)thiazol-2-yl)acrylamide

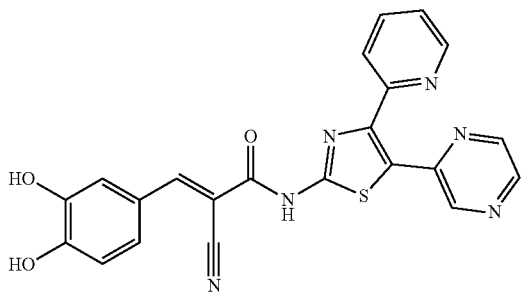 [SMILES: N#C/C(=C\c1ccc(O)c(O)c1)C(=O)Nc1nc(-c2ccccn2)c(-c2cnccn2)s1]

The compound was prepared according to General procedure D2 from 2-cyano-N-(5-(pyrazin-2-yl)$_4$-(pyridin-2-yl)thiazol-2-yl)acetamide (50 mg, 0.15 mmol), 3,4-dihydroxybenzaldehyde (22 mg, 0.15 mmol), and piperidine (3 μL, 0.029 mmol) in $CH_2Cl_2$ (5 mL); the reaction time was 16 h at reflux. The product was purified by reverse phase column chromatography ($H_2O$:MeOH:7M $NH_3$ in MeOH; 60:40:0.05 to 5:95:0.05). All fractions with the product were combined, methanol was evaporated, and the remaining aqueous phase was neutralized with AcOH to neutral pH. The solid was collected by filtration, washed with water (2 mL), then with $CH_2Cl_2$:MeOH (1:0.1; 2.2 mL), and dried under vacuum. The product was obtained as a yellow solid (20 mg, 30%).

$^1$H NMR (700 MHz, DMSO-$d_6$) δ 12.91 (s, 1H), 10.34 (s, 1H), 9.69 (s, 1H), 8.69 (s, 1H), 8.67-8.63 (m, 1H), 8.53 (d, J=4.7 Hz, 1H), 8.49 (d, J=2.6 Hz, 1H), 8.35 (s, 1H), 8.03-7.97 (m, 1H), 7.95 (d, J=7.8 Hz, 1H), 7.63 (d, J=2.2 Hz, 1H), 7.50-7.42 (m, 1H), 7.39 (dd, J=2.3, 8.4 Hz, 1H), 6.95 (d, J=8.3 Hz, 1H);

$^{13}$C NMR (176 MHz DMSO-$d_6$) δ (ppm) 162.2, 158.5, 152.9, 152.5, 151.7, 148.9, 147.6, 146.0, 145.8, 144.2, 143.7, 142.3, 137.4, 126.9, 126.1, 124.0, 123.6, 123.1, 116.6, 116.3, 116.1;

HRMS calcd for $C_{22}H_{13}N_6O_3S$ [M-H]$^-$ 441.0775, found 441.0777.

Preparative Example 264

(E)-2-cyano-3-(3,4-dihydroxyphenyl)-N-(4-(6-morpholinopyridin-2-yl)thiazol-2-yl)acrylamide

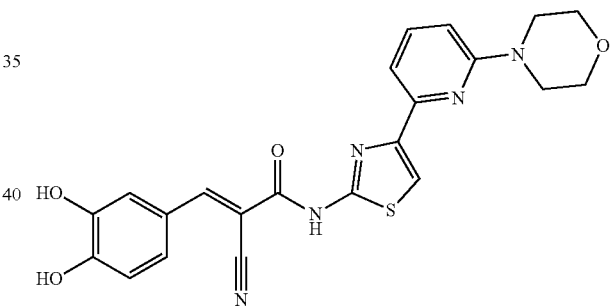

The compound was prepared according to General procedure D2 from 2-cyano-N-(4-(6-morpholinopyridin-2-yl)thiazol-2-yl)acetamide (65 mg, 0.197 mmol), 3,4-dihydroxybenzaldehyde (27 mg, 0.197 mmol), and piperidine (2 μL, 0.02 mmol) in $CH_2Cl_2$ (3 mL); the reaction time was 48 h at reflux. To the cooled reaction mixture was added MeOH (0.5 mL), the precipitate was collected by filtration, washed with $CH_2Cl_2$ (1 mL), then with pentane (2×2 mL), and dried in a vacuum oven at 50° C. The product was obtained as a yellow solid (51 mg, 57%).

$^1$H NMR (500 MHz, DMSO-$d_6$) δ (ppm) 8.30 (s, 1H), 7.79 (s, 1H), 7.65 (dd, J=8.5, 7.4 Hz, 1H), 7.61 (d, J=2.2 Hz, 1H), 7.38 (dd, J=8.4, 2.3 Hz, 1H), 7.34 (d, J=7.3 Hz, 1H), 6.93 (d, J=8.3 Hz, 1H), 6.80 (d, J=8.5 Hz, 1H), 3.76-3.70 (m, 4H), 3.57-3.52 (m, 4H);

$^{13}$C NMR (126 MHz, acetone-$d_6$) δ (ppm) 162.1, 158.6, 151.9, 151.6, 150.0, 145.8, 138.5, 125.9, 123.1, 116.5, 116.1, 111.6, 109.7, 106.4, 66.0, 45.0;

HRMS calcd for $C_{22}H_{20}N_5O_4S$ [M+H]$^+$ 450.1231, found 450.1235.

Preparative Example 265

(E)-2-cyano-3-(3,4-dihydroxyphenyl-N-(4-(6-morpholinopyridin-3-yl)thiazol-2-yl)acrylamide

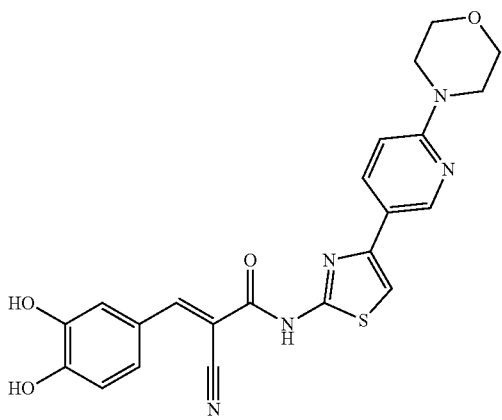

The compound was prepared according to General procedure D2 from 2-cyano-N-(4-(6-morpholinopyridin-3-yl)thiazol-2-yl)acetamide (48 mg, 0.14 mmol), 3,4-dihydroxybenzaldehyde (20 mg, 0.14 mmol), and piperidine (3 μL, 0.029 mmol) in CH$_2$Cl$_2$ (5 mL); the reaction time was 16 h at reflux. MeOH (0.2 mL) was added and the solid was collected by filtration. The solid was mixed with EtOAc (5 mL) and saturated aqueous solution of NH$_4$Cl (10 mL). The mixture was extracted with EtOAc (3×10 mL). The organic fractions were combined, washed with brine (20 mL), dried over MgSO$_4$, filtered, and the solvent was evaporated in vacuo. The product was obtained as a yellow solid (20 mg, 30%).

$^1$H NMR (500 MHz, DMSO-d$_6$) δ (ppm) 12.64 (s, 1H), 10.26 (s, 1H), 9.64 (s, 1H), 8.70 (d, J=2.5 Hz, 1H), 8.30 (s, 1H), 8.05 (dd, J=2.5, 8.9 Hz, 1H), 7.61 (d, J=2.2 Hz, 1H), 7.52 (s, 1H), 7.38 (dd, J=2.3, 8.4 Hz, 1H), 6.99-6.83 (m, 2H), 3.75-3.68 (m, 4H), 3.56-3.48 (m, 4H);

$^{13}$C NMR (126 MHz, DMSO-d$_6$) δ (ppm) 162.1, 158.4, 152.0, 151.5, 145.8, 145.1, 135.0, 125.8, 123.1, 116.5, 116.0, 106.7, 65.9, 45.0;

HRMS calcd for C$_{22}$H$_{18}$N$_5$O$_4$S [M−H]$^-$ 448.1085, found 448.1089.

Preparative Example 266

(E)-3-(3-bromo-4,5-dihydroxyphenyl)-2-cyano-N-(4-phenylthiazol-2-yl)acrylamide

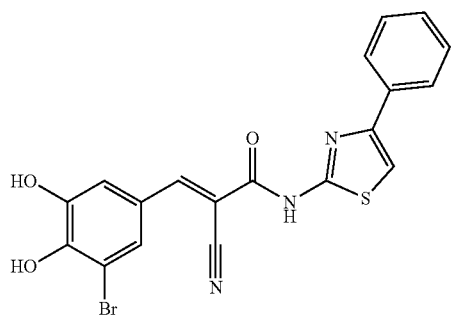 [SMILES: N#C/C(=C\c1cc(O)c(O)c(Br)c1)C(=O)Nc1nc(-c2ccccc2)cs1]

The compound was prepared according to General procedure D2 from from 2-cyano-N-(4-phenylthiazol-2-yl)acetamide (112 mg, 0.46 mmol), 3-bromo-4,5-dihydroxybenzaldehyde (100 mg, 0.46 mmol), and piperidine (6 μL, 0.06 mmol) in CH$_2$Cl$_2$ (5 mL); the reaction time was 16 h at reflux. After completion of the reaction, MeOH (0.2 mL) was added and the solid was collected by filtration. The solid was mixed with EtOAc (5 mL) and saturated aqueous solution of NH$_4$Cl (10 mL). The mixture was extracted with EtOAc (3×10 mL). The organic fractions were combined, washed with brine (20 mL), dried over MgSO$_4$, filtered, and the solvent was evaporated in vacuo. The product was obtained as a yellow solid (80 mg, 40%).

$^1$H NMR (500 MHz, DMSO-d$_6$) δ (ppm) 10.91 (s, 3H), 8.23 (s, 1H), 7.96-7.91 (m, 2H), 7.67 (s, 1H), 7.65 (d, J=2.2 Hz, 1H), 7.59 (d, J=2.2 Hz, 1H), 7.48-7.40 (m, 2H), 7.38-7.29 (m, 1H);

$^{13}$C NMR (126 MHz, DMSO-d$_6$) δ (ppm) 162.3, 158.8, 150.4, 148.5, 146.8, 133.9, 129.4, 128.7, 127.9, 125.7, 116.8, 113.4, 110.0, 108.5;

HRMS calcd for C$_{19}$H$_{11}$BrN$_3$O$_3$S [M−H]$^-$ 439.9710, found 439.9706.

Preparative Example 267

(E)-2-cyano-3-(3-fluoro-4,5-dihydroxyphenyl)-N-(4-phenylthiazol-2-yl)acrylamide

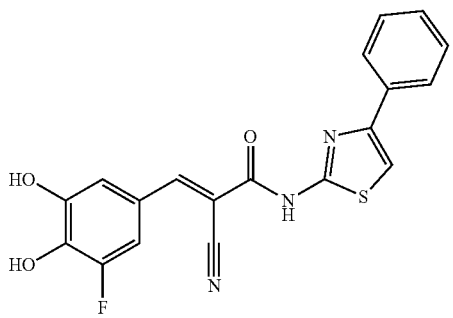 [SMILES: N#C/C(=C\c1cc(O)c(O)c(F)c1)C(=O)Nc1nc(-c2ccccc2)cs1]

The compound was prepared according to General procedure D2 from 2-cyano-N-(4-phenylthiazol-2-yl)acetamide (172 mg, 0.7 mmol), 3-fluoro-4,5-dihydroxybenzaldehyde (110 mg, 0.7 mmol), and piperidine (3 μL, 0.029 mmol) in CH$_2$Cl$_2$ (3 mL); the reaction time was 16 h at reflux. The product, purified by reverse phase column chromatography (H$_2$O:MeOH:AcOH; 45:55:0.05 to 5:95:0.05), was obtained as a yellow solid (45 mg, 17%).

$^1$H NMR (500 MHz, DMSO-d$_6$) δ (ppm) 12.73 (s, 1H), 10.41 (s, 1H), 10.26 (s, 1H), 8.30 (s, 1H), 7.97-7.91 (m, 2H), 7.70 (s, 1H), 7.45 (t, J=7.7 Hz, 2H), 7.43-7.42 (m, 1H), 7.38 (dd, J=2.1, 11.4 Hz, 1H), 7.37-7.33 (m, 1H);

$^{13}$C NMR (126 MHz, DMSO-d$_6$) δ (ppm) 161.5, 158.0, 151.2, 151.2 (d, J=239.4 Hz), 149.3, 147.7 (d, J=6.3 Hz), 139.0 (d, J=14.3 Hz), 134.1, 128.7, 127.9, 125.7, 121.7 (d, J=9.1 Hz), 116.0, 113.5, 108.8, 101.8;

$^{19}$F NMR (471 MHz, DMSO-d$_6$) δ (ppm) −134.3;

HRMS calcd for C$_{19}$H$_{11}$FN$_3$O$_3$S [M−H]$^-$ 380.0511, found 380.0509.

Preparative Example 268

(E)-2-cyano-3-(3-cyano-4-hydroxy-5-methoxyphenyl)-N-(4-phenylthiazol-2-yl)acrylamide

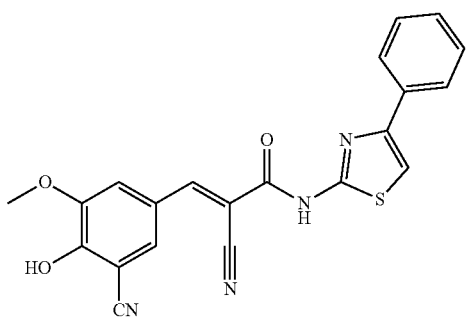 [SMILES: COc1cc(/C=C(\C#N)C(=O)Nc2nc(-c3ccccc3)cs2)cc(C#N)c1O]

The compound was prepared according to General procedure D2 from 2-cyano-N-(4-phenylthiazol-2-yl)acetamide (120 mg, 0.47 mmol), 5-formyl-2-hydroxy-3-methoxybenzonitrile (85 mg, 0.47 mmol), and piperidine (3 µL, 0.029 mmol) in CH$_2$Cl$_2$ (5 mL); the reaction time was 16 h at reflux. The product, purified by reverse phase column chromatography (H$_2$O:MeOH:AcOH; 45:55:0.05 to 5:94.8:0.05), was obtained as a yellow solid (50 mg, 26%).

$^1$H NMR (500 MHz, DMSO-d$_6$) δ (ppm) 12.64 (s, 1H), 11.95 (s, 1H), 8.40 (s, 1H), 7.96-7.90 (m, 3H), 7.82 (d, J=2.0 Hz, 1H), 7.70 (s, 1H), 7.50-7.41 (m, 2H), 7.38-7.32 (m, 1H), 3.93 (s, 3H);

$^{13}$C NMR (126 MHz, DMSO-d$_6$) δ (ppm) 161.8, 154.6, 152.1, 150.4, 148.2, 133.6, 128.7, 128.0, 125.7, 115.8, 115.8, 108.7, 99.9, 56.2;

HRMS calcd for C$_{21}$H$_{13}$N$_4$O$_3$S [M−H]$^-$ 401.0714, found 401.0711.

Preparative Example 269

(E)-2-cyano-3-(3-cyano-4,5-dihydroxyphenyl)-N-(4-phenylthiazol-2-yl)acrylamide

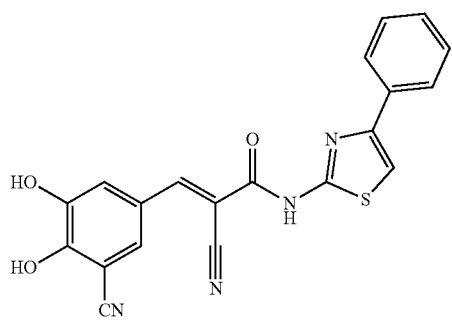 [SMILES: N#C/C(=C\c1cc(O)c(O)c(C#N)c1)C(=O)Nc1nc(-c2ccccc2)cs1]

The compound was prepared according to General procedure D2 from 2-cyano-N-(4-phenylthiazol-2-yl)acetamide (151 mg, 0.61 mmol), 5-formyl-2,3-dihydroxybenzonitrile (100 mg, 0.61 mmol), and piperidine (3 µL, 0.029 mmol) in CH$_2$Cl$_2$ (5 mL); the reaction time was 16 h at reflux. The product was purified by reverse phase column chromatography (H$_2$O:MeOH:AcOH; 45:55:0.05 to 5:94.8:0.05). All fractions with the product were combined and the solvent was evaporated. Water (20 mL) was added, the solution was neutralized to pH=7 with saturated aqueous solution of NaHCO$_3$, and the mixture was extracted with EtOAc (3×10 mL). The organic fractions were combined, washed with brine (20 mL), dried over MgSO$_4$, filtered, and the solvent was evaporated in vacuo. To the solid residue was added CH$_2$Cl$_2$ (2 mL). The mixture was sonicated, the solid was collected by filtration, washed with CH$_2$Cl$_2$ (0.5 mL) and dried under vacuum. The product was obtained as a yellow solid (30 mg, 13%).

$^1$H NMR (500 MHz, DMSO-d$_6$) δ (ppm) 12.75 (s, 1H), 10.87 (s, 1H), 8.31 (s, 1H), 7.96-7.91 (m, 2H), 7.84 (d, J=2.2 Hz, 1H), 7.70 (s, 1H), 7.66 (d, J=2.1 Hz, 1H), 7.50-7.42 (m, 2H), 7.38-7.30 (m, 1H);

$^{13}$C NMR (126 MHz, DMSO-d$_6$) δ (ppm) 161.6, 154.6, 150.4, 146.6, 133.8, 128.7, 128.5, 128.0, 125.7, 118.1, 116.1, 108.7, 99.8;

HRMS calcd for C$_{20}$H$_{11}$N$_4$O$_3$S [M−H]$^-$ 387.0557, found 387.0556.

Preparative Example 270

(E)-2-cyano-3-(3,4-dihydroxyphenyl)-N-(4-(3-fluoro-5-morpholinopyridin-2-yl)thiazol-2-yl)acrylamide

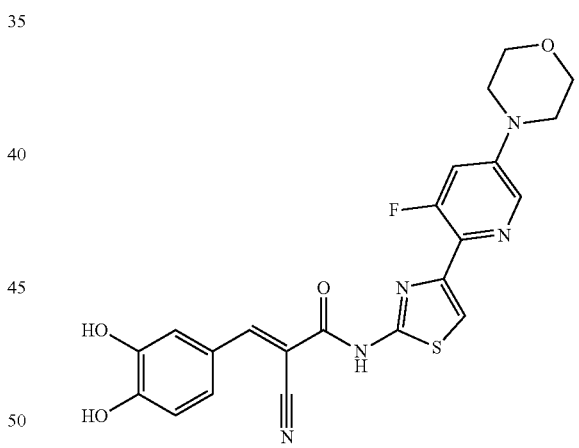

The compound was prepared according to General procedure D2 from 2-cyano-N-(4-(3-fluoro-5-morpholinopyridin-2-yl)thiazol-2-yl)acetamide (40 mg, 0.115 mmol), 3,4-dihydroxybenzaldehyde (17 mg, 0.121 mmol), and piperidine (1 µL, 0.011 mmol) in CH$_2$Cl$_2$ (5 mL); the reaction time was 16 h at reflux. Saturated aqueous solution of NH$_4$Cl (5 mL) was added and the mixture was extracted with EtOAc (3×20 mL). To the combined organic extracts was added EtOAc (40 mL) and the organic phase was washed with water (3×50 mL). MeOH (3 mL) was added to the organic phase, the mixture was sonicated and filtered. The solid was washed with CH$_2$Cl$_2$ (2×5 mL), then with pentane (2×10 mL), and dried in a vacuum oven at 50° C. overnight. The product was obtained as a dark yellow-green solid (29 mg, 54%).

$^1$H NMR (500 MHz, DMSO-d$_6$) δ (ppm) 12.81 (s, 1H), 10.25 (s, 1H), 9.63 (s, 1H), 8.28 (d, J=39.5 Hz, 2H), 7.58 (d, J=28.3 Hz, 2H), 7.45-7.25 (m, 2H), 6.93 (d, J=8.3 Hz, 1H), 3.76 (s, 4H), 3.30 (s, 4H);

$^{13}$C NMR (126 MHz, DMSO-d$_6$) δ (ppm) 157.1 (d, J=260.5 Hz), 151.7 (d, J=63.2 Hz), 147.8, 145.8, 132.3, 125.8, 123.2, 116.5, 116.1, 108.6 (d, J=23.4 Hz), 65.7, 47.1;

$^{19}$F NMR (471 MHz, DMSO-d$_6$) δ (ppm) −121.43;

HRMS calcd for C$_{22}$H$_{17}$FN$_5$O$_4$S [M−H]$^−$ 466.0991, found 466.0991.

Preparative Example 271

(E)-2-cyano-3-(3,5-dibromo-4-hydroxyphenyl)-N-(4-(3-fluoro-5-morpholinopyridin-2-yl)thiazol-2-yl)acrylamide

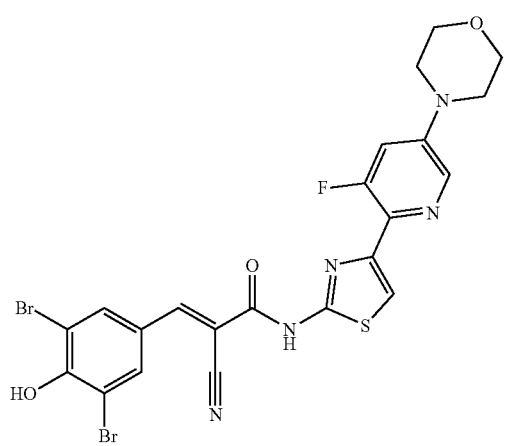 [SMILES: N#C/C(=C\c1cc(Br)c(O)c(Br)c1)C(=O)Nc1nc(-c2ncc(N3CCOCC3)cc2F)cs1]

The compound was prepared according to General procedure D2 from 2-cyano-N-(4-(3-fluoro-5-morpholinopyridin-2-yl)thiazol-2-yl)acetamide (40 mg, 0.115 mmol), 3,5-dibromo-4-hydroxybenzaldehyde (34 mg, 0.121 mmol), and piperidine (1 µL, 0.011 mmol) in CH$_2$Cl$_2$ (5 mL); the reaction time was 16 h at reflux. Purification by column chromatography (CH$_2$Cl$_2$:MeOH; 1:0 to 100:1 to 50:1 to 25:1 to 20:1 to 15:1 to 10:1) afforded a yellow solid, which was sonicated in CH$_2$Cl$_2$:MeOH (5:1, 6 mL), washed with CH$_2$Cl$_2$ (2×5 mL) and then with pentane (2×5 mL), and dried in a vacuum oven at 50° C. overnight. The product was obtained as a yellow solid (37 mg, 53%).

$^1$H NMR (500 MHz, DMSO-d$_6$) δ (ppm) 12.44 (s, 1H), 8.24 (t, J=2.1 Hz, 1H), 8.18 (s, 1H), 8.15 (s, 2H), 7.51 (s, 1H), 7.32 (dd, J=14.5, 2.4 Hz, 1H), 3.82-3.71 (m, 4H), 3.34-3.26 (m, 4H);

$^{13}$C NMR (126 MHz, DMSO-d$_6$) δ (ppm) 157.1 (d, J=260.0 Hz), 148.5, 147.7 (d, J=5.6 Hz), 135.1, 132.3 (d, J=3.4 Hz), 117.5, 114.3, 111.7, 108.6 (d, J=23.4 Hz), 65.7, 47.1;

$^{19}$F NMR (471 MHz, DMSO-d$_6$) δ (ppm) −121.42;

HRMS calcd for C$_{22}$H$_{15}$Br$_2$FN$_5$O$_3$S [M−H]$^−$ 605.9252, found 605.9258.

Preparative Example 272

(E)-3-(3-bromo-4,5-dihydroxyphenyl)-2-cyano-N-(4-(3-fluoro-5-morpholinopyridin-2-yl)thiazol-2-yl)acrylamide

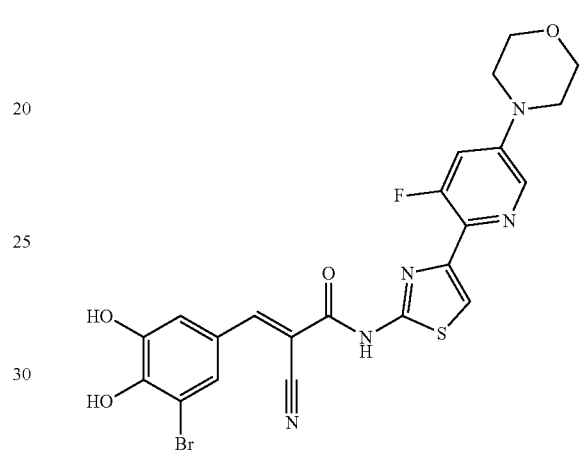

The compound was prepared according to General procedure D2 from 2-cyano-N-(4-(3-fluoro-5-morpholinopyridin-2-yl)thiazol-2-yl)acetamide (42 mg, 0.121 mmol), 3-bromo-4,5-dihydroxybenzaldehyde (28 mg, 0.127 mmol), and piperidine (1 µL, 0.012 mmol) in CH$_2$Cl$_2$ (5 mL); the reaction time was 16 h at reflux. Saturated aqueous solution of NH$_4$Cl (50 mL) was added and the mixture was extracted with EtOAc (4×50 mL). The combined organic extracts were washed with water (3×15 mL) and brine (20 mL). The organic phase was concentrated in vacuo to afford a solid. The aqueous phase was filtered to afford another part of the solid. Both solids were combined and sonicated in a solution of MeOH (10 mL), acetone (10 mL) and CH$_2$Cl$_2$ (10 mL). The solid was collected by filtration, washed with CH$_2$Cl$_2$ (2×5 mL), then with pentane (2×10 mL), and dried in a vacuum oven at 50° C. overnight. The product was obtained as a dark yellow-green solid (38 mg, 57%).

$^1$H NMR (500 MHz, DMSO-d$_6$) δ (ppm) 12.83 (s, 1H), 10.54 (s, 2H), 8.27 (d, J=27.8 Hz, 2H), 7.63 (d, J=13.5 Hz, 2H), 7.56 (s, 1H), 7.33 (d, J=14.4 Hz, 1H), 3.89-3.69 (m, 4H), 3.30 (s, 4H);

$^{13}$C NMR (126 MHz, DMSO-d$_6$) δ (ppm) 157.1 (d, J=259.9 Hz), 150.6, 148.1 (d, J=76.3 Hz), 147.8, 146.4, 132.3, 127.9, 123.8, 116.1, 114.9, 109.7, 108.6 (d, J=23.4 Hz), 65.7, 47.0;

$^{19}$F NMR (282 MHz, DMSO-d$_6$) δ (ppm) −121.40;

HRMS calcd for C$_{22}$H$_{16}$BrFN$_5$O$_4$S [M−H]$^−$ 544.0096, found 544.0091.

Preparative Example 273

(E)-N-(4-benzylthiazol-2-yl)-2-cyano-3-(3,4-dihydroxyphenyl)acrylamide

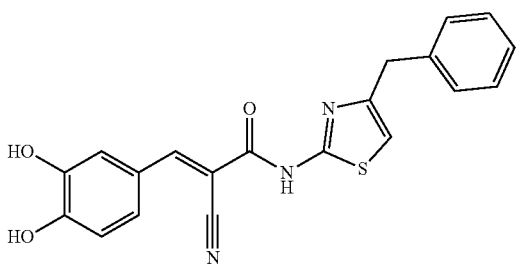 [SMILES: N#C/C(=C\c1ccc(O)c(O)c1)C(=O)Nc1nc(Cc2ccccc2)cs1]

The compound was prepared according to General procedure D2 from N-(4-benzylthiazol-2-yl)-2-cyanoacetamide (78 mg, 0.303 mmol), 3,4-dihydroxybenzaldehyde (42 mg, 0.303 mmol), and piperidine (3 μL, 0.03 mmol) in CH$_2$Cl$_2$ (10 mL); the reaction time was 4 h at reflux. The precipitate was collected by filtration, washed with pentane (2×2 mL) and dried in a vacuum oven at 50° C. The product was obtained as a yellow solid (63 mg, 55%).

$^1$H NMR (500 MHz, DMSO-d$_6$) δ (ppm) 8.19 (s, 1H), 7.57 (d, J=2.3 Hz, 1H), 7.35-7.25 (m, 5H), 7.24-7.18 (m, 1H), 6.89 (d, J=8.4 Hz, 1H), 6.82 (s, 1H), 3.96 (s, 2H);

$^{13}$C NMR (126 MHz, DMSO-d$_6$) δ (ppm) 151.5, 145.8, 138.9, 128.7, 128.3, 126.3, 125.7, 123.2, 116.4, 116.0, 108.5;

HRMS calcd for C$_{20}$H$_{14}$N$_3$O$_3$S [M–H]$^-$ 376.0761, found 376.0761.

Preparative Example 274

(E)-N-(4-benzylthiazol-2-yl)-3-(3-bromo-4,5-dihydroxyphenyl)-2-cyanoacrylamide

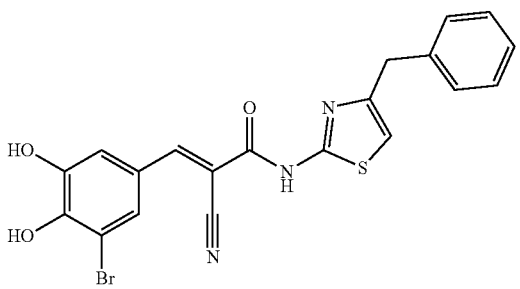 [SMILES: N#C/C(=C\c1cc(O)c(O)c(Br)c1)C(=O)Nc1nc(Cc2ccccc2)cs1]

The compound was prepared according to General procedure D2 from N-(4-benzylthiazol-2-yl)-2-cyanoacetamide (40 mg, 0.16 mmol), 3-bromo-4,5-dihydroxybenzaldehyde (34 mg, 0.16 mmol), and piperidine (3 μL, 0.029 mmol) in CH$_2$Cl$_2$ (5 mL); the reaction time was 16 h at reflux. The product was purified by reverse phase column chromatography (H$_2$O:MeOH:AcOH; 45:55:0.05 to 5:94.8:0.05). All fractions containing the product were combined, methanol was evaporated, and the remaining aqueous phase was neutralized with saturated aqueous solution of NaHCO$_3$ to neutral pH. The solution was extracted with EtOAc (3×10 mL). The organic fractions were combined, washed with brine (20 mL), dried over MgSO$_4$, filtered, and the solvent was evaporated in vacuo. The product was obtained as a yellow solid (36 mg, 50%).

$^1$H NMR (500 MHz, DMSO-d$_6$) δ (ppm) 12.52 (s, 1H), 10.37 (s, 1H), 8.13 (s, 1H), 7.61 (d, J=2.2 Hz, 1H), 7.55 (d, J=2.2 Hz, 1H), 7.34-7.25 (m, 4H), 7.25-7.18 (m, 1H), 6.83 (s, 1H), 3.96 (s, 2H);

$^{13}$C NMR (126 MHz, DMSO-d$_6$) δ (ppm) 150.0, 146.6, 138.8, 128.7, 128.3, 126.2, 117.0, 113.8, 109.8, 108.4, 35.8;

HRMS calcd for C$_{20}$H$_{13}$BrN$_3$O$_3$S [M–H]$^-$ 453.9866, found 453.9864.

Preparative Example 275

(E)-N-(4-benzylthiazol-2-yl)-2-cyano-3-(3,5-dichloro-4-hydroxyphenyl)acrylamide

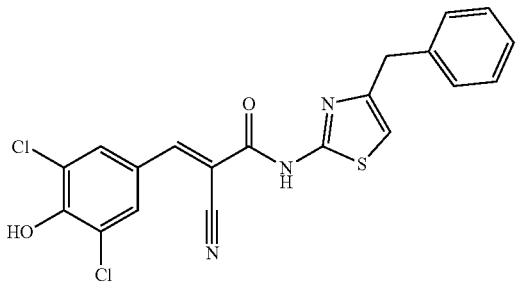 [SMILES: N#C/C(=C\c1cc(Cl)c(O)c(Cl)c1)C(=O)Nc1nc(Cc2ccccc2)cs1]

The compound was prepared according to General procedure D2 from N-(4-benzylthiazol-2-yl)-2-cyanoacetamide (40 mg, 0.16 mmol), 3,5-dichloro-4-hydroxybenzaldehyde (31 mg, 0.16 mmol), and piperidine (3 μL, 0.029 mmol) in CH$_2$Cl$_2$ (5 mL); the reaction time was 16 h at reflux. The product was purified by reverse phase column chromatography (H$_2$O:MeOH:AcOH; 45:55:0.05 to 5:94.8:0.05). All fractions with the product were combined, MeOH was evaporated, the precipitate was washed with Et$_2$O (2 mL) and dried under vacuum. The product was obtained as a yellow solid (13 mg, 20%).

$^1$H NMR (500 MHz, DMSO-d$_6$) δ (ppm) 8.24 (s, 1H), 8.05 (s, 2H), 7.37-7.26 (m, 4H), 7.25-7.20 (m, 1H), 6.83 (s, 1H), 3.96 (s, 2H);

$^{13}$C NMR (126 MHz, DMSO-d$_6$) δ (ppm) 152.9, 148.5, 138.2, 135.5, 130.6, 128.7, 128.4, 126.4, 122.6, 108.6, 35.3;

HRMS calcd for C$_{20}$H$_{12}$Cl$_2$N$_3$O$_2$S [M–H]$^-$ 428.0033, found 428.0033.

Preparative Example 276

(E)-N-(4-benzylthiazol-2-yl)-2-cyano-3-(3,5-dibromo-4-hydroxyphenyl)acrylamide

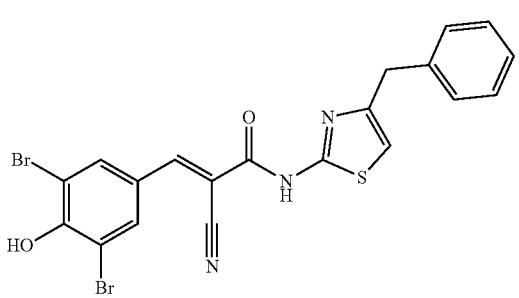 [SMILES: N#C/C(=C\c1cc(Br)c(O)c(Br)c1)C(=O)Nc1nc(Cc2ccccc2)cs1]

The compound was prepared according to General procedure D2 from N-(4-benzylthiazol-2-yl)-2-cyanoacetamide (41 mg, 0.159 mmol), 3,5-dibromo-4-hydroxybenzaldehyde (49 mg, 0.175 mmol), and piperidine (2 µL, 0.016 mmol) in $CH_2Cl_2$ (5 mL); the reaction time was 16 h at reflux. The product, purified by column chromatography (hexane:EtOAc; 1:1 to 1:2 to 1:3 to 1:4 to 1:8 to 0:1), was obtained as a yellow solid (41 mg, 50%).

$^1$H NMR (500 MHz, DMSO-$d_6$) δ (ppm) 8.22 (s, 3H), 7.35-7.25 (m, 4H), 7.25-7.19 (m, 1H), 6.83 (s, 1H), 3.96 (s, 2H);

$^{13}$C NMR (126 MHz, DMSO-$d_6$) δ (ppm) 148.2, 134.4, 128.7, 128.4, 126.4, 112.2;

HRMS calcd for $C_{20}H_{12}Br_2N_3O_2S$ [M–H]$^-$ 515.9022, found 515.9022.

Assays:
HTS Assay
DNA Substrate Preparation

The DNA substrate is prepared by mixing the oligonucleotides listed below in a 1:1 ratio to reach a final concentration of 6 µM in a buffer containing 50 mM Tris pH 7.5, 100 mM NaCl and 8 mM $MgCl_2$.

```
Oligo 1:
                                        (SEQ ID NO. 1)
5' CY5-CTAAGTTCGTCAGGATTCCAGC Oligo 2:
                                        (SEQ ID NO. 2)
5' CTCTATCACTGTTACAATGCTGGAATCCTGACGAACTTAG-
BBQ[650]
```

This substrate is a 5' overhang, which is a preferred substrate of MRE11. The CY5 fluorescent label is quenched by the quencher BBQ [650] and therefore it shows no or very low fluorescence. The fluorescence increases upon substrate cleavage by MRE11, when separation of the two labels occur.

Setup
The conditions of the assay are as follows:
Microplate type: 1536 Well Black Round Bottom Polystyrene Not Treated (Corning cat no. 3936)
Total reaction volume: 5 µL
MRE11 concentration in the reaction: 18 nM
DNA substrate concentration in the reaction: 40 nM
Number of compounds to test: 257
Inhibitor concentration range tested: 7 nM-50 µM
Multiplicates: 3
Concentration points: 13
Dilution step: 2.1

Each plate contains a series of high and low signal control wells, where no compound is added:
High signal: MRE11+DNA substrate
Low signal: DNA substrate only
These are used during data evaluation.

Two extra assay controls:
1) To check whether unwinding of DNA by the compounds alone occurs.
The DNA substrate [CY5+BBQ(650)] is mixed with the compounds with no protein present.
This is done as a single measurement at 25 µM inhibitor concentration.
2) To check whether the compounds are able to quench the CY5.
The CY5 single stranded oligo is mixed with the compounds with no protein present. This is done as a single measurement at 25 µM inhibitor concentration.

The layout of the plates is created by the in-house software (CZ-Openscreen Prague) and this information is transferred to the robotic HTS station.

Assay Steps
1) Prepare 50 mL of master mix:
   16.7 mL 5× reaction buffer (150 mM Bis Tris pH 7; 5 mM DTT)
   1042 µL 400 mM $MnCl_2$
   32.3 mL $H_2O$
2) Fill the plates with 3 µL of master mix per well using MultiDrop (Thermo Scientific)
3) Transfer of compounds to the plates at the robotic station with the contactless Echo dispenser (Labcyte)
4) Measurement of autofluorescence with the EnVision reader (PerkinElmer)
5) Prepare 20 mL of 90 nM MRE11 in T+50 buffer (25 mM Tris-HCl pH7.5, 50 mM KCl 8.7% glycerol, 0.5 mM EDTA)
6) Add 1 µL of 90 nM MRE11 to the corresponding wells using MultiDrop
7) Preincubation at RT for 30 min
8) Prepare 20 mL of a 200 nM solution of 5' overhang DNA substrate:
   480 µL 6 µM DNA+19.52 mL $H_2O$
9) Prepare 4 mL of a 200 nM solution of the single stranded DNA (oligo 1):
   8 µL 100 µM DNA+4 mL $H_2O$
10) Add 1 µL of each 200 nM DNA solution to the corresponding wells with the MultiDrop
11) Fluorescence measurement with the EnVision reader every 45 minutes Fluorescence readout: CY5 $\lambda_{ex/em}$=620/665 nm Analysis The reaction is started by the addition of DNA and the reaction time is counted from that moment, including a 15 min delay. Ten timepoints are measured:

|    | min | h   |
|----|-----|-----|
| 1  | 15  | 0.3 |
| 2  | 60  | 1.0 |
| 3  | 105 | 1.8 |
| 4  | 150 | 2.5 |
| 5  | 195 | 3.3 |
| 6  | 240 | 4.0 |
| 7  | 285 | 4.8 |
| 8  | 330 | 5.5 |
| 9  | 375 | 6.3 |
| 10 | 420 | 7.0 |

The assay data analysis was performed at t=4 h. This corresponds to the time when the reaction is close to its maximum.

The data analysis was performed using the in-house software to obtain $IC_{50}$ for each compound.

HR Assay

DR-GFP U2OS cells (*Methods in Molecular Biology* 2012, 920, 379.) were transfected with 2.5 µg of I-SceI-expressing pCAGGS vector and treated with the inhibitors at 25 µM concentration. 72 hours after the transfection, the cells were trypsinized and resuspended in 3% BSA in PBS. GFP fluorescence detection was carried out using a BD FACSVerse flow cytometer and data analyzed with FlowJo software.

RPA Assay

U2OS cells were pre-treated for 1 h with MRE11 inhibitors followed by addition of 1 uM camptothecin for 1 h. Cells were lysed in SDS-PAGE loading buffer, sonicated and boiled at 70° C. for 10 min. Equal amounts of protein (50-100 μg) were analysed by Tris-glycine gel electrophoresis Expression levels were quantified using Multi Gauge software and expressed relative to loading control. Phosphorylated RPA32 S4/S8 (A300-245A, Bethyl Laboratories) 1:1000 dilution was used.

Results

Table 1 summarizes the inhibitory activities of indicated compounds tested in the in vitro HTS nuclease assay ($IC_{50}$), HR assay (inhibition of HR @ 25 μM) and RPA assay (% of inhibition of RPA phosphorylation at [10 μM] or [25 μM] (concentration of the inhibitor)).

HTS nuclease assay: ($IC_{50}$)
A: $IC_{50}$<2 μM
B: 2 μM<$IC_{50}$<10 μM
C: 10 μM<$IC_{50}$<90 μM
HR assay: inhibition of HR @ 25 μM
A: HR inhibition >75%
B: 75%>HR inhibition>50%
C: 50%>HR inhibition

TABLE 1

| compound | HTS $IC_{50}$ (μM) | HR assay | RPA assay |
|---|---|---|---|
| Preparative Example 162 (E)-2-cyano-3-(3,4-dihydroxyphenyl)-N-(4-(4-methoxyphenyl)thiazol-2-yl)acrylamide | A | A | N.A. |
| Preparative Example 163 (E)-2-cyano-3-(3,4-dihydroxyphenyl)-N-(4-(naphthalen-2-yl)thiazol-2-yl)acrylamide | A | A | N.A. |
| Preparative Example 164 (E)-N-(4-([1,1'-biphenyl]-4-yl)thiazol-2-yl)-2-cyano-3-(3,4-dihydroxyphenyl)acrylamide | B | A | N.A. |
| Preparative Example 165 (E)-N-(4-(4-bromophenyl)thiazol-2-yl)-2-cyano-3-(3,5-dichloro-4-hydroxyphenyl)acrylamide | A | B | N.A. |
| Preparative Example 166 (E)-2-cyano-3-(3,4-dihydroxyphenyl)-N-(4-(3-hydroxy-4-methoxyphenyl)thiazol-2-yl)acrylamide | A | A | N.A. |
| Preparative Example 167 (E)-2-cyano-3-(3,4-dihydroxyphenyl)-N-(4-(2-hydroxypropan-2-yl)thiazol-2-yl)acrylamide | B | C | N.A. |
| Preparative Example 168 (E)-2-cyano-3-(3,5-dichloro-4-hydroxyphenyl)-N-(4-(p-tolyl)thiazol-2-yl)acrylamide | A | A | N.A. |
| Preparative Example 169 (E)-N-(4-(3-bromophenyl)thiazol-2-yl)-2-cyano-3-(3,4-dihydroxyphenyl)acrylamide | A | A | N.A. |
| Preparative Example 170 (E)-N-(4-(2-bromophenyl)thiazol-2-yl)-2-cyano-3-(3,4-dihydroxyphenyl)acrylamide | A | B | N.A. |
| Preparative Example 171 (E)-2-cyano-3-(3,4-dihydroxyphenyl)-N-(4-(3-(trifluoromethoxy)phenyl)thiazol-2-yl)acrylamide | B | B | N.A. |
| Preparative Example 172 (E)-2-cyano-3-(3,4-dihydroxyphenyl)-N-(4-(4-phenoxyphenyl)thiazol-2-yl)acrylamide | B | A | N.A. |
| Preparative Example 173 (E)-N-(4-(benzofuran-2-yl)thiazol-2-yl)-2-cyano-3-(3,4-dihydroxyphenyl)acrylamide | A | A | N.A. |
| Preparative Example 174 (E)-N-(4-((1S,3s)-adamantan-1-yl)thiazol-2-yl)-2-cyano-3-(3,4-dihydroxyphenyl)acrylamide | B | B | N.A. |
| Preparative Example 175 (E)-2-cyano-N-(5-cyclohexyl-4-(4-(trifluoromethoxy)phenyl)thiazol-2-yl)-3-(3,4-dihydroxyphenyl)acrylamide | B | A | N.A. |
| Preparative Example 176 (E)-2-cyano-3-(3,4-dihydroxyphenyl)-N-(4,5-diphenylthiazol-2-yl)acrylamide | A | A | N.A. |
| Preparative Example 177 (E)-2-cyano-3-(3,5-dimethyl-4-hydroxyphenyl)-N-(4-(4-(trifluoromethoxy)phenyl)thiazol-2-yl)acrylamide | N.A. | A | N.A. |
| Preparative Example 178 (E)-2-cyano-3-(3,4-dihydroxyphenyl)-N-(4-(4-morpholinophenyl)thiazol-2-yl)acrylamide | A | B | N.A. |
| Preparative Example 179 (E)-2-cyano-3-(3,4-dihydroxyphenyl)-N-(4-(5-(trifluoromethyl)pyridin-2-yl)thiazol-2-yl)acrylamide | A | A | N.A. |
| Preparative Example 180 (E)-2-cyano-N-(4-(3-cyanophenyl)thiazol-2-yl)-3-(3,4-dihydroxyphenyl)acrylamide | A | B | N.A. |
| Preparative Example 181 (E)-4-(2-(2-cyano-3-(3,4-dihydroxyphenyl)acrylamido)thiazol-4-yl)-N,N-dimethylbenzamide | A | C | N.A. |

TABLE 1-continued

| compound | HTS IC$_{50}$ (μM) | HR assay | RPA assay |
|---|---|---|---|
| Preparative Example 182 (E)-2-cyano-3-(3,4-dihydroxyphenyl)-N-(4-(4-(2-hydroxypropan-2-yl)phenyl)thiazol-2-yl)acrylamide | A | B | N.A. |
| Preparative Example 183 (E)-2-cyano-N-(4-(5-cyanothiophen-2-yl)thiazol-2-yl)-3-(3,4-dihydroxyphenyl)acrylamide | A | C | N.A. |
| Preparative Example 184 (E)-2-cyano-3-(3,4-dihydroxyphenyl)-N-(4-(thiophen-2-yl)thiazol-2-yl)acrylamide | A | A | N.A. |
| Preparative Example 185 (E)-2-cyano-N-(4-(3,5-difluorophenyl)thiazol-2-yl)-3-(3,4-dihydroxyphenyl)acrylamide | A | B | N.A. |
| Preparative Example 186 (E)-2-cyano-3-(3,4-dihydroxyphenyl)-N-(4-(pyridazin-3-yl)thiazol-2-yl)acrylamide | A | C | N.A. |
| Preparative Example 187 (E)-2-cyano-3-(3,4-dihydroxyphenyl)-N-(4-(4-fluorophenyl)thiazol-2-yl)acrylamide | A | A | N.A. |
| Preparative Example 188 (E)-2-cyano-3-(3,4-dihydroxyphenyl)-N-(4-(pyridin-4-yl)thiazol-2-yl)acrylamide | A | B | N.A. |
| Preparative Example 189 methyl (E)-4-(2-(2-cyano-3-(3,4-dihydroxyphenyl)acrylamido)thiazol-4-yl)benzoate | A | B | N.A. |
| Preparative Example 190 (E/Z)-2-cyano-3-(3,4-dihydroxyphenyl)-3-phenyl-N-(4-phenylthiazol-2-yl)acrylamide | A | A | N.A. |
| Preparative Example 191 (E)-2-cyano-3-(3,4-dihydroxyphenyl)-N-(4,5,6,7-tetrahydrobenzo[d]thiazol-2-yl)acrylamide | A | C | N.A. |
| Preparative Example 192 (E)-2-cyano-3-(3,5-dibromo-4-hydroxyphenyl)-N-(4-phenylthiazol-2-yl)acrylamide | A | B | N.A. |
| Preparative Example 193 (E)-2-cyano-3-(3,5-dichloro-4-hydroxyphenyl)-N-(4-phenylthiazol-2-yl)acrylamide | A | N.A. | N.A. |
| Preparative Example 194 (E)-2-cyano-3-(3,4-dihydroxyphenyl)-N-(5-methyl-4-phenylthiazol-2-yl)acrylamide | A | B | N.A. |
| Preparative Example 195 (E)-N-(5-chloro-4-phenylthiazol-2-yl)-2-cyano-3-(3,4-dihydroxyphenyl)acrylamide | A | B | N.A. |
| Preparative Example 196 (E)-N-(5-bromo-4-phenylthiazol-2-yl)-2-cyano-3-(3,4-dihydroxyphenyl)acrylamide | A | B | N.A. |
| Preparative Example 197 (E)-2-cyano-3-(3,4-dihydroxyphenyl)-N-(4-(4-ethynylphenyl)thiazol-2-yl)acrylamide | A | A | N.A. |
| Preparative Example 198 (E)-2-cyano-N-(4-(3-cyclopropyl-4-methoxyphenyl)thiazol-2-yl)-3-(3,4-dihydroxyphenyl)acrylamide | A | A | N.A. |
| Preparative Example 199 (E)-N-(4-(tert-butyl)thiazol-2-yl)-2-cyano-3-(3,4-dihydroxyphenyl)acrylamide | A | B | N.A. |
| Preparative Example 200 (E)-2-cyano-3-(5,6-dihydroxypyridin-3-yl)-N-(4-phenylthiazol-2-yl)acrylamide | B | C | N.A. |
| Preparative Example 201 (E)-3-(3-chloro-4-hydroxyphenyl)-2-cyano-N-(4-phenylthiazol-2-yl)acrylamide | B | B | N.A. |
| Preparative Example 202 (E)-3-(3-bromo-4-hydroxyphenyl)-2-cyano-N-(4-phenylthiazol-2-yl)acrylamide | B | N.A. | N.A. |
| Preparative Example 203 (E)-2-cyano-3-(3-fluoro-4-hydroxy-5-methoxyphenyl)-N-(4-phenylthiazol-2-yl)acrylamide | B | C | N.A. |
| Preparative Example 204 (E)-4-(2-cyano-3-oxo-3-((4-phenylthiazol-2-yl)amino)prop-1-en-1-yl)benzoic acid | B | C | N.A. |
| Preparative Example 205 (E)-2-cyano-3-(1H-indazol-6-yl)-N-(4-phenylthiazol-2-yl)acrylamide | B | C | N.A. |
| Preparative Example 206 (E)-2-cyano-3-(2-fluorophenyl)-N-(4-phenylthiazol-2-yl)acrylamide | B | C | N.A. |

TABLE 1-continued

| compound | HTS IC$_{50}$ (µM) | HR assay | RPA assay |
|---|---|---|---|
| Preparative Example 207<br>3-(3-acetamidophenyl)-2-cyano-N-(4-phenylthiazol-2-yl)acrylamide | B | B | N.A. |
| Preparative Example 208<br>(E)-2-cyano-3-(4-hydroxy-3-nitrophenyl)-N-(4-phenylthiazol-2-yl)acrylamide | C | B | N.A. |
| Preparative Example 209<br>(E)-2-cyano-3-(4-nitrophenyl)-N-(4-phenylthiazol-2-yl)acrylamide | C | B | N.A. |
| Preparative Example 210<br>(E)-3-(2-cyano-3-oxo-3-((4-phenylthiazol-2-yl)amino)prop-1-en-1-yl)benzoic acid | C | C | N.A. |
| Preparative Example 211<br>(E)-2-cyano-3-(6-hydroxy-[1,1'-biphenyl]-3-yl)-N-(4-phenylthiazol-2-yl)acrylamide | C | C | N.A. |
| Preparative Example 212<br>(E)-2-cyano-3-(3,5-difluoro-4-hydroxyphenyl)-N-(4-phenylthiazol-2-yl)acrylamide | C | C | N.A. |
| Preparative Example 213<br>(E)-2-cyano-3-(3,4-difluorophenyl)-N-(4-phenylthiazol-2-yl)acrylamide | C | C | N.A. |
| Preparative Example 214<br>(E)- and (Z)-2-cyano-3-(1H-imidazol-4-yl)-N-(4-phenylthiazol-2-yl)acrylamide | C | C | N.A. |
| Preparative Example 215<br>(E)-2-cyano-3-(2,3-dihydroxyphenyl)-N-(4-phenylthiazol-2-yl)acrylamide | C | B | N.A. |
| Preparative Example 216<br>(E)-2-cyano-3-(2-oxo-2,3-dihydro-1H-benzo[d]imidazol-5-yl)-N-(4-phenylthiazol-2-yl)acrylamide | C | C | N.A. |
| Preparative Example 217<br>(E)-2-cyano-3-(4-hydroxy-3-methylphenyl)-N-(4-phenylthiazol-2-yl)acrylamide | N.A. | B | N.A. |
| Preparative Example 218<br>(E)-2-cyano-3-(2,4-dihydroxyphenyl)-N-(4-phenylthiazol-2-yl)acrylamide | N.A. | B | N.A. |
| Preparative Example 219<br>(E)-N-(4-(5-bromothiophen-2-yl)thiazol-2-yl)-2-cyano-3-(3,4-dihydroxyphenyl) acrylamide | A | A | N.A. |
| Preparative Example 220<br>(E)-2-cyano-3-(3-oxo-3,4-dihydro-2H-benzo[b][1,4]oxazin-7-yl)-N-(4-phenylthiazol-2-yl)acrylamide | C | B | N.A. |
| Preparative Example 221<br>(E)-2-cyano-3-(3,5-di-tert-butyl-4-hydroxyphenyl)-N-(4-(4-(trifluoromethoxy)phenyl)thiazol-2-yl)acrylamide | N.A. | C | N.A. |
| Preparative Example 223<br>(E)-3-(4-acetamido-3-hydroxyphenyl)-2-cyano-N-(4-phenylthiazol-2-yl)acrylamide | C | C | N.A. |
| Preparative Example 224<br>(E)-N-(4-(4-(tert-butyl)phenyl)thiazol-2-yl)-2-cyano-3-(3,5-dichloro-4-hydroxyphenyl)acrylamide | B | N.A. | N.A. |
| Preparative Example 225<br>(E)-2-cyano-3-(4-hydroxy-2-methylphenyl)-N-(4-phenylthiazol-2-yl)acrylamide | C | C | N.A. |
| Preparative Example 226<br>(E)-2-cyano-3-(2-fluoro-4-hydroxyphenyl)-N-(4-phenylthiazol-2-yl)acrylamide | C | A | N.A. |
| Preparative Example 227<br>(E)-2-cyano-3-(4-hydroxynaphthalen-1-yl)-N-(4-phenylthiazol-2-yl)acrylamide | B | A | N.A. |
| Preparative Example 228<br>2-cyano-3-(3-cyano-4-hydroxyphenyl)-N-(4-phenylthiazol-2-yl)propanamide | A | A | N.A. |
| Preparative Example 229<br>(E)-2-cyano-3-(3,4-dihydroxyphenyl)-N-(4-(5-methylthiophen-2-yl)thiazol-2-yl)acrylamide | A | B | N.A. |
| Preparative Example 230<br>(E)-2-cyano-3-(3,4-dihydroxyphenyl)-N-methyl-N-(4-phenylthiazol-2-yl)acrylamide | A | C | N.A. |
| Preparative Example 231<br>(E)-2-cyano-N-(4-phenylthiazol-2-yl)-3-(3-(trifluoromethyl)phenyl)acrylamide | B | C | N.A. |
| Preparative Example 232<br>(E)-2-cyano-3-(3,4-dihydroxyphenyl)-N-(4-(6-methylpyridin-3-yl)thiazol-2-yl)acrylamide | A | C | N.A. |

TABLE 1-continued

| compound | HTS IC$_{50}$ (μM) | HR assay | RPA assay |
| --- | --- | --- | --- |
| Preparative Example 233 (E)-2-cyano-3-(3,4-dihydroxyphenyl)-N-(4-phenyl-5-(tetrahydro-2H-pyran-4-yl)thiazol-2-yl)acrylamide | A | B | N.A. |
| Preparative Example 234 (E)-3-(3-(tert-butyl)-4-hydroxy-5-methylphenyl)-2-cyano-N-(4-phenylthiazol-2-yl)acrylamide | N.A. | A | N.A. |
| Preparative Example 235 (E)-3-(3-(tert-butyl)-4-hydroxyphenyl)-2-cyano-N-(4-phenylthiazol-2-yl)acrylamide | N.A. | A | N.A. |
| Preparative Example 236 (E)-2-cyano-3-(3,4-dihydroxyphenyl)-N-(4-(3-fluorophenyl)thiazol-2-yl)acrylamide | A | B | N.A. |
| Preparative Example 237 (E)-2-cyano-3-(4-hydroxy-3,5-diisopropylphenyl)-N-(4-phenylthiazol-2-yl)acrylamide | N.A. | A | N.A. |
| Preparative Example 238 (E)-2-cyano-3-(3,4-dihydroxyphenyl)-N-(4-phenyl-5-(pyrazin-2-yl)thiazol-2-yl)acrylamide | A | B | N.A. |
| Preparative Example 239 (E)-2-cyano-3-(3,4-dihydroxyphenyl)-N-(4-(3-methylpyridin-2-yl)thiazol-2-yl)acrylamide | A | A | N.A. |
| Preparative Example 240 (E)-2-cyano-3-(2,6-di-tert-butylpyridin-4-yl)-N-(4-phenylthiazol-2-yl)acrylamide | N.A. | A | N.A. |
| Preparative Example 241 (E)-2-cyano-3-(3,4-dihydroxyphenyl)-N-(4-(6-methoxypyridin-3-yl)thiazol-2-yl)acrylamide | A | C | 75% at 25 μM |
| Preparative Example 242 (E)-2-cyano-3-(3,4-dihydroxyphenyl)-N-(4-(3-methoxypyridin-2-yl)thiazol-2-yl)acrylamide | A | A | 95% at 10 μM |
| Preparative Example 243 (E)-2-cyano-3-(3,5-dichloro-4-hydroxyphenyl)-N-(4-(pyridin-2-yl)thiazol-2-yl)acrylamide | A | B | 100% at 10 μM |
| Preparative Example 244 (E)-2-cyano-3-(3,4-dihydroxyphenyl)-N-(4-(4-(methylsulfonyl)phenyl)thiazol-2-yl)acrylamide | A | C | N.A. |
| Preparative Example 245 (E)-2-cyano-3-(3,4-dihydroxyphenyl)-N-(5-phenylthiazol-2-yl)acrylamide | A | B | N.A. |
| Preparative Example 246 (E)-N-(4-(4-(tert-butyl)-2,6-dimethylphenyl)thiazol-2-yl)-2-cyano-3-(3,4-dihydroxyphenyl)acrylamide | A | A | N.A. |
| Preparative Example 247 (E)-N-(4-(3-(tert-butyl)phenyl)thiazol-2-yl)-2-cyano-3-(3,4-dihydroxyphenyl)acrylamide | B | B | N.A. |
| Preparative Example 248 (E)-2-cyano-3-(4-hydroxy-3,5-dimethylphenyl)-N-(4-(pyridin-2-yl)thiazol-2-yl)acrylamide | C | N.A. | N.A. |
| Preparative Example 249 (E)-2-cyano-3-(3,5-dibromo-4-hydroxyphenyl)-N-(4-(pyridin-2-yl)thiazol-2-yl)acrylamide | A | N.A. | N.A. |
| Preparative Example 250 (E)-2-cyano-N-(4-(3-fluoropyridin-2-yl)thiazol-2-yl)-3-(4-hydroxy-3,5-dimethylphenyl)acrylamide | C | N.A. | N.A. |
| Preparative Example 251 (E)-2-cyano-3-(3,5-dibromo-4-hydroxyphenyl)-N-(4-(3-fluoropyridin-2-yl)thiazol-2-yl)acrylamide | A | N.A. | N.A. |
| Preparative Example 252 (E)-2-cyano-3-(3,5-dichloro-4-hydroxyphenyl)-N-(4-(3-fluoropyridin-2-yl)thiazol-2-yl)acrylamide | A | N.A. | N.A. |
| Preparative Example 254 (E)-5-(2-cyano-3-oxo-3-((4-phenylthiazol-2-yl)amino)prop-1-en-1-yl)-2-hydroxybenzoic acid | C | N.A. | N.A. |
| Preparative Example 255 (E)-5-(2-cyano-3-oxo-3-((4-phenylthiazol-2-yl)amino)prop-1-en-1-yl)-2-hydroxybenzamide | C | N.A. | N.A. |
| Preparative Example 256 (E)-3-(2-bromo-4-hydroxyphenyl)-2-cyano-N-(4-phenylthiazol-2-yl)acrylamide | C | N.A. | N.A. |
| Preparative Example 257 (E)-2-cyano-3-(3,4-dihydroxy-5-nitrophenyl)-N-(4-phenylthiazol-2-yl)acrylamide | A | N.A. | N.A. |
| Preparative Example 258 Methyl (E)-4-(2-cyano-3-oxo-3-((4-phenylthiazol-2-yl)amino)prop-1-en-1-yl)-2-hydroxybenzoate | B | N.A. | N.A. |

TABLE 1-continued

| compound | HTS IC$_{50}$ (μM) | HR assay | RPA assay |
|---|---|---|---|
| Preparative Example 259 (E)-4-(2-cyano-3-oxo-3-((4-phenylthiazol-2-yl)amino)prop-1-en-1-yl)-2-hydroxybenzoic acid | B | N.A. | N.A. |
| Preparative Example 260 (E)-2-cyano-3-(4-hydroxy-3-(hydroxymethyl)phenyl)-N-(4-phenylthiazol-2-yl)acrylamide | B | N.A. | N.A. |
| Preparative Example 261 (E)-N-(4-benzoylthiazol-2-yl)-2-cyano-3-(3,4-dihydroxyphenyl)acrylamide | A | N.A. | N.A. |
| Preparative Example 262 (E)-2-cyano-3-(3,4-dihydroxyphenyl)-N-(5-(pyrazin-2-yl)thiazol-2-yl)acrylamide | C | N.A. | N.A. |
| Preparative Example 263 (E)-2-cyano-3-(3,4-dihydroxyphenyl)-N-(5-(pyrazin-2-yl)-4-(pyridin-2-yl)thiazol-2-yl)acrylamide | A | N.A. | N.A. |
| Preparative Example 264 (E)-2-cyano-3-(3,4-dihydroxyphenyl)-N-(4-(6-morpholinopyridin-2-yl)thiazol-2-yl)acrylamide | B | N.A. | N.A. |
| Preparative Example 265 (E)-2-cyano-3-(3,4-dihydroxyphenyl)-N-(4-(6-morpholinopyridin-3-yl)thiazol-2-yl)acrylamide | B | N.A. | N.A. |
| Preparative Example 266 (E)-3-(3-bromo-4,5-dihydroxyphenyl)-2-cyano-N-(4-phenylthiazol-2-yl)acrylamide | A | N.A. | N.A. |
| Preparative Example 267 (E)-2-cyano-3-(3-fluoro-4,5-dihydroxyphenyl)-N-(4-phenylthiazol-2-yl)acrylamide | A | N.A. | N.A. |
| Preparative Example 268 (E)-2-cyano-3-(3-cyano-4-hydroxy-5-methoxyphenyl)-N-(4-phenylthiazol-2-yl)acrylamide | C | N.A. | N.A. |
| Preparative Example 269 (E)-2-cyano-3-(3-cyano-4,5-dihydroxyphenyl)-N-(4-phenylthiazol-2-yl)acrylamide | A | N.A. | N.A. |
| Preparative Example 270 (E)-2-cyano-3-(3,4-dihydroxyphenyl)-N-(4-(3-fluoro-5-morpholinopyridin-2-yl)thiazol-2-yl)acrylamide | A | N.A. | N.A. |
| Preparative Example 271 (E)-2-cyano-3-(3,5-dibromo-4-hydroxyphenyl)-N-(4-(3-fluoro-5-morpholinopyridin-2-yl)thiazol-2-yl)acrylamide | A | N.A. | N.A. |
| Preparative Example 272 (E)-3-(3-bromo-4,5-dihydroxyphenyl)-2-cyano-N-(4-(3-fluoro-5-morpholinopyridin-2-yl)thiazol-2-yl)acrylamide | A | N.A. | N.A. |
| Preparative Example 273 (E)-N-(4-benzylthiazol-2-yl)-2-cyano-3-(3,4-dihydroxyphenyl)acrylamide | A | N.A. | N.A. |
| Preparative Example 274 (E)-N-(4-benzylthiazol-2-yl)-3-(3-bromo-4,5-dihydroxyphenyl)-2-cyanoacrylamide | A | N.A. | N.A. |
| Preparative Example 275 (E)-N-(4-benzylthiazol-2-yl)-2-cyano-3-(3,5-dichloro-4-hydroxyphenyl)acrylamide | C | N.A. | N.A. |
| Preparative Example 276 (E)-N-(4-benzylthiazol-2-yl)-2-cyano-3-(3,5-dibromo-4-hydroxyphenyl)acrylamide | B | N.A. | N.A. |

The invention claimed is:

1. A compound of general formula (1):

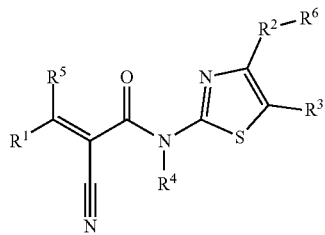

(1)

or a pharmaceutically acceptable salt, or solvate thereof, wherein:

$R^1$ is selected from $C_6$-$C_{12}$ aryl and heteroaryl having 5 to 12 ring atoms, wherein the aryl or heteroaryl is substituted with two to three OH groups, and the aryl or heteroaryl may optionally be further substituted by one or more substituents, independently selected from the group consisting of F, Cl, Br, $C_1$-$C_6$ alkyl, O($C_1$-$C_4$ alkyl), phenyl, O-phenyl, $NH_2$, N($C_1$-$C_4$ alkyl)$_2$, $NO_2$, NHCO($C_1$-$C_4$ alkyl), $CF_3$, $OCF_3$, CN, S(O)$_2$$C_1$-$C_6$-alkyl, SO$_2$NH($C_1$-$C_6$-alkyl), SO$_2$N($C_1$-$C_6$-alkyl)$_2$;

or wherein the aryl or heteroaryl is substituted with one OH group and one group selected from CN, Cl, Br, F, and the aryl or heteroaryl may optionally be further substituted by one or more substituents, independently selected from the group consisting of F, Cl, Br, $C_1$-$C_6$ alkyl, O($C_1$-$C_4$ alkyl), phenyl, O-phenyl, $NH_2$, N($C_1$-$C_4$ alkyl)$_2$, $NO_2$, NHCO($C_1$-$C_4$ alkyl), $CF_3$, $OCF_3$, CN, S(O)$_2$$C_1$-$C_6$-alkyl, SO$_2$NH($C_1$-$C_6$-alkyl), SO$_2$N($C_1$-$C_6$-alkyl)$_2$;

$R^2$ is selected from the group consisting of aryl; heteroaryl; cycloalkyl; heterocyclyl; and hydroxyalkyl residues;

wherein aryl is substituted with one or more moieties which can be the same or different, independently selected from the group consisting of F, Cl, Br, I, OH, CN, $N_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, $CF_3$, $C_2F_5$, $OCF_3$, $OC_2F_5$, $NH_2$, NH($C_1$-$C_6$-alkyl), N($C_1$-$C_6$-alkyl)$_2$, =N—OH, =N—O($C_1$-$C_6$-alkyl), $NO_2$, COOH, COO($C_1$-$C_6$-alkyl), CO($C_1$-$C_6$-alkyl), $CONH_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, $NH_2$—CO—NH—, ($C_1$-$C_6$-alkyl)-NH—CO—NH—, ($C_1$-$C_6$-alkyl)$_2$N—CO—NH—, $NH_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, $NH_2$—S(O)$_2$—NH—, ($C_1$-$C_6$-alkyl)-NH—S(O)$_2$—NH—, ($C_1$-$C_6$-alkyl)$_2$N—S(O)$_2$—NH—, $NH_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

wherein each of the hydroxyalkyl, cycloalkyl, heterocyclyl, heteroaryl, can be unsubstituted or optionally substituted with one or more moieties which can be the same or different, independently selected from the group consisting of F, Cl, Br, I, OH, CN, $N_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, $CF_3$, $C_2F_5$, $OCF_3$, $OC_2F_5$, $NH_2$, NH($C_1$-$C_6$-alkyl), N($C_1$-$C_6$-alkyl)$_2$, =N—OH, =N—O($C_1$-$C_6$-alkyl), $NO_2$, COOH, COO($C_1$-$C_6$-alkyl), CO($C_1$-$C_6$-alkyl), $CONH_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, $NH_2$—CO—NH—, ($C_1$-$C_6$-alkyl)-NH—CO—NH—, ($C_1$-$C_6$-alkyl)$_2$N—CO—NH—, $NH_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, $NH_2$—S(O)$_2$—NH—, ($C_1$-$C_6$-alkyl)-NH—S(O)$_2$—NH—, ($C_1$-$C_6$-alkyl)$_2$N—S(O)$_2$—NH—, $NH_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

whereas the $C_1$-$C_6$-alkyl, O-phenyl, phenyl in these moieties can optionally be further substituted by one or more substituents selected independently from: F, Cl, Br, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$, $NO_2$, COOH, COO($C_1$-$C_6$-alkyl), $CONH_2$, CONH($C_1$-$C_6$-alkyl), CON($C_1$-$C_6$-alkyl)$_2$, NHC(O)$C_1$-$C_6$-alkyl, or NHC(O)$NH_2$ $R^6$ is selected from the group consisting of H; heterocyclyl; cycloalkyl; heteroaryl; aryl; heteraryl; wherein each of the aryl, cycloalkyl, heterocyclyl, heteroaryl, can be unsubstituted or optionally substituted with one or more moieties which can be the same or different, independently selected from the group consisting of F, Cl, Br, $C_1$-$C_6$-alkyl, OH, O—$C_1$-$C_6$-alkyl, SH, $SCH_3$, S(O)$C_1$-$C_6$-alkyl, S(O)$_2$$C_1$-$C_6$-alkyl, $CF_3$, $OCF_3$, $NH_2$, NH($C_1$-$C_6$-alkyl), N($C_1$-$C_6$-alkyl)$_2$, $NO_2$, COOH, COO($C_1$-$C_6$-alkyl), CONH$_2$, CONH($C_1$-$C_6$-alkyl), CON($C_1$-$C_6$-alkyl)$_2$, NHC(O)$C_1$-$C_6$-alkyl, or NHC(O)NH$_2$;

$R^3$ is selected from the group consisting of H; aryl; heteroaryl; heterocyclyl; cycloalkyl; alkyl; and halogen;

wherein each of the aryl, cycloalkyl, alkyl or heteroaryl can be unsubstituted or optionally substituted with one or more moieties which can be the same or different, each moiety being independently selected from the group consisting of F, Cl, Br, I, OH, CN, N$_3$, =O, O($C_1$-$C_6$-alkyl), =S, SH, S($C_1$-$C_6$-alkyl), S(O)$C_1$-$C_6$-alkyl, S(O)$_2$$C_1$-$C_6$-alkyl, CF$_3$, C$_2$F$_5$, OCF$_3$, OC$_2$F$_5$, NH$_2$, NH($C_1$-$C_6$-alkyl), N($C_1$-$C_6$-alkyl)$_2$, =N—OH, =N—O($C_1$-$C_6$-alkyl), NO$_2$, COOH, COO($C_1$-$C_6$-alkyl), CO($C_1$-$C_6$-alkyl), CONH$_2$, CONH($C_1$-$C_6$-alkyl), CON($C_1$-$C_6$-alkyl)$_2$, ($C_1$-$C_6$-alkyl)-S(O)$_2$—NH—, ($C_1$-$C_6$-alkyl)-S(O)$_2$—N($C_1$-$C_6$-alkyl)-, ($C_1$-$C_6$-alkyl)-NH—(SO)$_2$—, ($C_1$-$C_6$-alkyl)$_2$N—(SO)$_2$—, ($C_1$-$C_6$-alkyl)-CO—NH—, ($C_1$-$C_6$-alkyl)-CO—N($C_1$-$C_6$-alkyl)-, ($C_1$-$C_6$-alkyl)-OCO—NH—, ($C_1$-$C_6$-alkyl)-OCO—N($C_1$-$C_6$-alkyl)-, ($C_1$-$C_6$-alkyl)-CO—NH—CO—, ($C_1$-$C_6$-alkyl)-CO—N($C_1$-$C_6$-alkyl)-CO—, NH$_2$—CO—NH—, ($C_1$-$C_6$-alkyl)-NH—CO—NH—, ($C_1$-$C_6$-alkyl)$_2$N—CO—NH—, NH$_2$—CO—N($C_1$-$C_6$-alkyl)-, ($C_1$-$C_6$-alkyl)-NH—CO—N($C_1$-$C_6$-alkyl)-, ($C_1$-$C_6$-alkyl)$_2$N—CO—N($C_1$-$C_6$-alkyl)-, NH$_2$—S(O)$_2$—NH—, ($C_1$-$C_6$-alkyl)-NH—S(O)$_2$—NH—, ($C_1$-$C_6$-alkyl)$_2$N—S(O)$_2$—NH—, NH$_2$—S(O)$_2$—N($C_1$-$C_6$-alkyl)-, ($C_1$-$C_6$-alkyl)-NH—S(O)$_2$—N($C_1$-$C_6$-alkyl)-, ($C_1$-$C_6$-alkyl)$_2$N—S(O)$_2$—N($C_1$-$C_6$-alkyl)-, $C_1$-$C_6$-alkyl, O—$C_1$-$C_6$-alkyl, O-phenyl, phenyl;

whereas the $C_1$-$C_6$-alkyl, O-phenyl, phenyl in these moieties can optionally be further substituted by one or more substituents selected independently from: F, Cl, Br, $C_1$-$C_6$-alkyl, OH, O—$C_1$-$C_6$-alkyl, SH, SCH$_3$, S(O)$C_1$-$C_6$-alkyl, S(O)$_2$$C_1$-$C_6$-alkyl, CF$_3$, OCF$_3$, NH$_2$, NH($C_1$-$C_6$-alkyl), N($C_1$-$C_6$-alkyl)$_2$, NO$_2$, COOH, COO($C_1$-$C_6$-alkyl), CONH$_2$, CONH($C_1$-$C_6$-alkyl), CON($C_1$-$C_6$-alkyl)$_2$, NHC(O)$C_1$-$C_6$-alkyl, or NHC(O)NH$_2$, $R^4$ is selected from the group consisting of H and $C_1$-$C_6$-alkyl;

$R^5$ is selected from the group consisting of H and aryl.

2. The compound according to claim 1, wherein $R^1$ is selected from $C_6$-$C_{12}$ aryl and heteroaryl having 5 to 12 ring atoms, wherein the aryl or heteroaryl is substituted with two OH groups, and the aryl or heteroaryl may optionally be further substituted by one or more substituents, independently selected from the group consisting of F, Cl, Br, $C_1$-$C_6$ alkyl, O($C_1$-$C_4$ alkyl), phenyl, O-phenyl, NH$_2$, N($C_1$-$C_4$ alkyl)$_2$, NO$_2$, NHCO($C_1$-$C_4$ alkyl), CF$_3$, OCF$_3$, CN, S(O)$_2$$C_1$-$C_6$-alkyl, SO$_2$NH($C_1$-$C_6$-alkyl), SO$_2$N($C_1$-$C_6$-alkyl)$_2$.

3. The compound according to claim 1, wherein $R^2$ is selected from $C_6$-$C_{12}$ aryl and heteroaryl having 5 to 12 ring atoms, which may optionally be substituted by one or more substituents, independently selected from the group consisting of F, Cl, Br, $C_1$-$C_4$ linear or branched alkyl, $C_3$-$C_5$ cycloalkyl, O($C_1$-$C_4$ alkyl), phenyl, O-phenyl, NH$_2$, N($C_1$-$C_4$ alkyl)$_2$, NO$_2$, NHCO($C_1$-$C_4$ alkyl), CF$_3$, OCF$_3$, CN, S(O)$_2$$C_1$-$C_6$-alkyl, SO$_2$NH($C_1$-$C_6$-alkyl), SO$_2$N($C_1$-$C_6$-alkyl)$_2$.

4. The compound according to claim 1, wherein $R^2$ is selected from phenyl, naphthyl, benzofuranyl, pyridyl, thiophenyl, pyridazinyl, which are unsubstituted or substituted with one to two substituents selected independently from O($C_1$-$C_4$ alkyl), OH, $C_1$-$C_4$ linear or branched alkyl, $C_3$-$C_5$ cycloalkyl, F, Br, Cl, CF$_3$, OCF$_3$.

5. The compound according to claim 1, wherein $R^6$ is selected from H or unsubstituted or optionally substituted phenyl or morpholinyl.

6. The compound according to claim 1, wherein $R^3$ is selected from H, phenyl, methyl, ethyl, propyl, isopropyl, butyl, isobutyl, tert-butyl, F, Cl, Br, cyclopropyl, cyclobutyl, cyclopentyl, cyclohexyl, tetrahydropyranyl, tetrahydrofuranyl, piperidinyl, which are unsubstituted or substituted by one or more substituents, independently selected from the group consisting of F, Cl, Br, OH, $C_1$-$C_6$ alkyl, phenyl, NH$_2$, N($C_1$-$C_4$ alkyl)$_2$, NO$_2$, NHCO($C_1$-$C_4$ alkyl), CF$_3$, OCF$_3$, CN, SO$_2$NH($C_1$-$C_6$-alkyl), SO$_2$N($C_1$-$C_6$-alkyl)$_2$, S(O)$_2$$C_1$-$C_6$-alkyl.

7. A method of treatment of cancer, premature aging or neurological diseases, genome instability-related cancer, genome instability-related premature aging and/or genome instability-related neurological diseases, the method comprising the step of administering the compound according to claim 1 to a subject in need thereof.

8. A method of treatment of breast, colon, prostate, lung, head and neck, hepatic, ovarian, colorectal, gastric, melanoma cancers, leukemias, Nijmegen breakage syndrome and Nijmegen breakage-like syndrome, Ataxia-telangiectasia and Ataxia-telangiectasia-like disorder, and Fanconi anemia, the method comprising the step of administering the compound according to claim 1 to a subject in need thereof.

9. A method of treatment of solid tumors with mutated BRCA-2, the method comprising the step of administering the compound according to claim 1 to a subject in need thereof.

10. A pharmaceutical composition comprising at least one compound of formula (1) according to claim 1 and at least one pharmaceutically acceptable auxiliary compound selected from the group consisting of pharmaceutically acceptable carriers, diluents, fillers, preservatives, stabilisers, binders, wetting agents, emulsifiers, buffers.

11. The compound according to claim 1, wherein $R^1$ is 3,4-dihydroxyphenyl.

* * * * *